(12) United States Patent
Charifson et al.

(10) Patent No.: US 8,871,774 B2
(45) Date of Patent: Oct. 28, 2014

(54) INHIBITORS OF INFLUENZA VIRUSES REPLICATION

(71) Applicant: Vertex Pharmaceuticals Incorporated, Cambridge, MA (US)

(72) Inventors: Paul S. Charifson, Framingham, MA (US); Michael P. Clark, Concord, MA (US); Upul K. Bandarage, Lexington, MA (US); Ioana Davies, Watertown, MA (US); John P. Duffy, Northborough, MA (US); Huai Gao, Arlington, MA (US); Jun Feng, Acton, MA (US); Jianglin Liang, Needham, MA (US); Joseph M. Kennedy, Charlestown, MA (US); Mark W. Ledeboer, Acton, MA (US); Brian Ledford, Norton, MA (US); Francois Maltais, Tewksbury, MA (US); Emanuele Perola, Brookline, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/918,048

(22) Filed: Jun. 14, 2013

(65) Prior Publication Data
US 2014/0005192 A1 Jan. 2, 2014

Related U.S. Application Data

(63) Continuation of application No. PCT/US2011/065371, filed on Dec. 16, 2011.

(60) Provisional application No. 61/527,273, filed on Aug. 25, 2011, provisional application No. 61/423,943, filed on Dec. 16, 2010.

(51) Int. Cl.
| | | |
|---|---|---|
| A01N 43/54 | (2006.01) |
| C07D 239/42 | (2006.01) |
| C07D 401/04 | (2006.01) |
| A61K 31/5377 | (2006.01) |
| A61K 31/506 | (2006.01) |
| A61K 45/06 | (2006.01) |
| C07D 471/04 | (2006.01) |

(52) U.S. Cl.
CPC .......... *C07D 471/04* (2013.01); *A61K 31/5377* (2013.01); *A61K 31/506* (2013.01); *A61K 45/06* (2013.01)
USPC .......................................... 514/256; 544/296

(58) Field of Classification Search
USPC .......................................... 544/296; 514/256
See application file for complete search history.

(56) References Cited

U.S. PATENT DOCUMENTS

| | | | |
|---|---|---|---|
| 3,829,581 A * | 8/1974 | Ellis .............................. 514/633 |
| 5,051,412 A | 9/1991 | Macor |
| 5,304,121 A | 4/1994 | Sahatjian |
| 5,338,849 A | 8/1994 | Festal et al. |
| 5,395,840 A | 3/1995 | Müller et al. |
| 5,886,026 A | 3/1999 | Hunter et al. |
| 6,099,562 A | 8/2000 | Ding et al. |
| 6,169,181 B1 | 1/2001 | Romines et al. |
| 6,265,403 B1 | 7/2001 | Fraley et al. |
| 6,313,126 B1 | 11/2001 | Mewshaw et al. |

(Continued)

FOREIGN PATENT DOCUMENTS

| | | |
|---|---|---|
| EP | 0557171 | 8/1993 |
| EP | 1748829 B1 | 7/2007 |

(Continued)

OTHER PUBLICATIONS

K. Tobita et al., 162 Medical Microbiology and Immunology, 9-14 (1975).*

(Continued)

*Primary Examiner* — James O Wilson
*Assistant Examiner* — Alexander R Pagano
(74) *Attorney, Agent, or Firm* — Booyong S. Lim

(57) ABSTRACT

Methods of inhibiting the replication of influenza viruses in a biological sample or patient, of reducing the amount of influenza viruses in a biological sample or patient, and of treating influenza in a patient, comprises administering to said biological sample or patient an effective amount of a compound represented by Structural Formula (I):

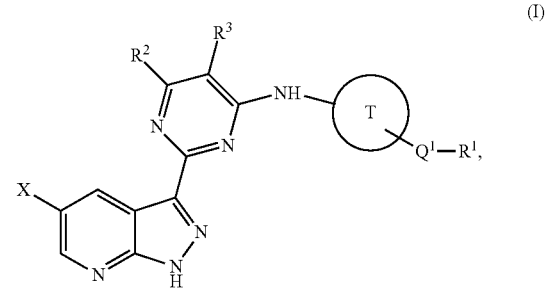

or a pharmaceutically acceptable salt thereof, wherein the values of Structural Formula (I) are as described herein. A compound is represented by Structural Formula (I) or a pharmaceutically acceptable salt thereof, wherein the values of Structural Formula (I) are as described herein. A pharmaceutical composition comprises an effective amount of such a compound or pharmaceutically acceptable salt thereof, and a pharmaceutically acceptable carrier, adjuvant or vehicle.

29 Claims, No Drawings

(56) References Cited

U.S. PATENT DOCUMENTS

| | | |
|---|---|---|
| 6,699,883 B1 | 3/2004 | Doemling et al. |
| 7,135,550 B2 | 11/2006 | Come et al. |
| 7,507,826 B2 | 3/2009 | Salituro et al. |
| 7,645,769 B2 | 1/2010 | Khan et al. |
| 7,767,816 B2 | 8/2010 | Farmer et al. |
| 7,795,259 B2 | 9/2010 | Binch et al. |
| 8,188,281 B2 | 5/2012 | Salituro et al. |
| 8,247,421 B2 | 8/2012 | Mortimore et al. |
| 8,541,445 B2 | 9/2013 | Jimenez et al. |
| 8,563,576 B2 | 10/2013 | Brenchley et al. |
| 8,569,337 B2 | 10/2013 | Jimenez et al. |
| 2002/0147189 A1 | 10/2002 | Cai et al. |
| 2002/0183329 A1 | 12/2002 | Gross et al. |
| 2002/0183352 A1 | 12/2002 | Stack et al. |
| 2002/0183353 A1 | 12/2002 | Stack et al. |
| 2002/0183354 A1 | 12/2002 | Tran et al. |
| 2002/0193400 A1 | 12/2002 | Husbands et al. |
| 2003/0078268 A1 | 4/2003 | Zhao et al. |
| 2003/0100579 A1 | 5/2003 | Gross et al. |
| 2003/0153560 A1 | 8/2003 | Salituro et al. |
| 2003/0166668 A1 | 9/2003 | Zandt et al. |
| 2004/0009968 A1 | 1/2004 | Binch et al. |
| 2004/0009996 A1 | 1/2004 | Moon et al. |
| 2004/0043388 A1 | 3/2004 | Come et al. |
| 2005/0137201 A1 | 6/2005 | Aronov et al. |
| 2005/0148603 A1 | 7/2005 | Jimenez et al. |
| 2006/0003968 A1 | 1/2006 | Green et al. |
| 2006/0122185 A1 | 6/2006 | Green et al. |
| 2006/0122213 A1 | 6/2006 | Pierard et al. |
| 2006/0183761 A1 | 8/2006 | Ledeboer et al. |
| 2006/0183911 A1 | 8/2006 | Charrier et al. |
| 2006/0258662 A1 | 11/2006 | Binch et al. |
| 2007/0043063 A1 | 2/2007 | Salituro et al. |
| 2007/0049615 A1 | 3/2007 | Ibrahim et al. |
| 2007/0066641 A1 | 3/2007 | Ibrahim et al. |
| 2007/0072896 A1 | 3/2007 | Khan et al. |
| 2007/0135466 A1 | 6/2007 | Ledeboer et al. |
| 2007/0203142 A1 | 8/2007 | Farmer et al. |
| 2007/0207995 A1 | 9/2007 | Salituro et al. |
| 2007/0213327 A1 | 9/2007 | Collier et al. |
| 2008/0300267 A1 | 12/2008 | Okram et al. |
| 2009/0048250 A1 | 2/2009 | Aronov et al. |
| 2009/0088445 A1 | 4/2009 | Ledeboer et al. |
| 2009/0118278 A1 | 5/2009 | Forster et al. |
| 2009/0176763 A1 | 7/2009 | Salituro et al. |
| 2009/0291937 A1 | 11/2009 | Jimenez et al. |
| 2010/0099686 A1 | 4/2010 | Charrier et al. |
| 2010/0189773 A1 | 7/2010 | Mortimore et al. |
| 2010/0311743 A1 | 12/2010 | Farmer et al. |
| 2011/0224197 A1 | 9/2011 | Henkle et al. |
| 2011/0263575 A1 | 10/2011 | Pierard et al. |
| 2012/0010197 A1 | 1/2012 | Charrier et al. |
| 2012/0028966 A1 | 2/2012 | Charrier et al. |
| 2012/0165368 A1 | 6/2012 | Brenchley et al. |
| 2012/0184524 A1 | 7/2012 | Boyall et al. |
| 2013/0252939 A1 | 9/2013 | Jimenez et al. |
| 2014/0005197 A1 * | 1/2014 | Charifson et al. ............ 514/242 |

FOREIGN PATENT DOCUMENTS

| | | |
|---|---|---|
| JP | 2003-519143 | 6/2003 |
| JP | 2003-532635 | 11/2003 |
| WO | 88/01997 | 3/1988 |
| WO | 95/33748 | 12/1995 |
| WO | 99/21859 A1 | 5/1999 |
| WO | 00/40554 A1 | 7/2000 |
| WO | 00/40581 | 7/2000 |
| WO | 00/43393 | 7/2000 |
| WO | 00/64898 A1 | 11/2000 |
| WO | 01/01986 A1 | 1/2001 |
| WO | 01/14374 A2 | 3/2001 |
| WO | 01/87887 A2 | 11/2001 |
| WO | 02/14317 A2 | 2/2002 |
| WO | 02/20013 A2 | 3/2002 |
| WO | 02/051837 | 7/2002 |
| WO | 02/072587 | 9/2002 |
| WO | 02/085896 | 10/2002 |
| WO | 02/085911 | 10/2002 |
| WO | 02/088129 A1 | 11/2002 |
| WO | 02/088131 | 11/2002 |
| WO | 02/088135 | 11/2002 |
| WO | 02/088136 A2 | 11/2002 |
| WO | 02/088140 | 11/2002 |
| WO | 02/088144 | 11/2002 |
| WO | 02/088146 A2 | 11/2002 |
| WO | 02/089811 A1 | 11/2002 |
| WO | 02/092602 | 11/2002 |
| WO | 03/000688 A1 | 1/2003 |
| WO | 03/091246 A1 | 11/2003 |
| WO | 03/101968 A1 | 12/2003 |
| WO | 03/101990 A1 | 12/2003 |
| WO | 2004/013140 A1 | 2/2004 |
| WO | 2004/014912 A1 | 2/2004 |
| WO | 2004/016609 A1 | 2/2004 |
| WO | 2004/016610 A1 | 2/2004 |
| WO | 2004/043388 | 5/2004 |
| WO | 2004/076454 | 9/2004 |
| WO | 2004/078756 A2 | 9/2004 |
| WO | 2004/082638 A2 | 9/2004 |
| WO | 2004/089913 A1 | 10/2004 |
| WO | 2004/106298 | 12/2004 |
| WO | 2005/000813 A1 | 1/2005 |
| WO | 2005/028475 A2 | 3/2005 |
| WO | 2005/044181 A2 | 5/2005 |
| WO | 2005/062795 A2 | 7/2005 |
| WO | 2005/085244 | 9/2005 |
| WO | 2005/095400 A1 | 10/2005 |
| WO | 2005/105213 | 11/2005 |
| WO | 2005/123736 A1 | 12/2005 |
| WO | 2006/009755 A1 | 1/2006 |
| WO | 2006/015123 A1 | 2/2006 |
| WO | 2006/030031 A1 | 3/2006 |
| WO | 2006/038001 A1 | 4/2006 |
| WO | 2006/041773 A2 | 4/2006 |
| WO | 2006/050076 A1 | 5/2006 |
| WO | WO 2006052913 A1 * | 5/2006 |
| WO | 2006/063167 A1 | 6/2006 |
| WO | 2006069258 A1 | 6/2006 |
| WO | 2006/124863 A2 | 11/2006 |
| WO | 2006/127587 A1 | 11/2006 |
| WO | 2007/002433 A1 | 1/2007 |
| WO | 2007/084557 A2 | 7/2007 |
| WO | 2007/095188 A2 | 8/2007 |
| WO | 2007/107221 A1 | 9/2007 |
| WO | 2007/117494 A1 | 10/2007 |
| WO | WO 2007129195 A2 * | 11/2007 |
| WO | 2007/146057 A2 | 12/2007 |
| WO | 2008/003958 A2 | 1/2008 |
| WO | 2008/005457 A2 | 1/2008 |
| WO | 2008/076392 A2 | 6/2008 |
| WO | 2008/079346 A1 | 7/2008 |
| WO | 2008/112642 A1 | 9/2008 |
| WO | 2008/112646 A1 | 9/2008 |
| WO | 2008/112651 A2 | 9/2008 |
| WO | 2008/113711 A1 | 9/2008 |
| WO | 2009/023269 A2 | 2/2009 |
| WO | 2009/145814 A2 | 3/2009 |
| WO | 2009/040556 A1 | 4/2009 |
| WO | 2009/046983 A1 | 4/2009 |
| WO | 2010/008454 A1 | 1/2010 |
| WO | 2010/008459 A1 | 1/2010 |
| WO | 2010011756 A1 | 1/2010 |
| WO | 2010148197 A1 | 12/2010 |
| WO | 2011000566 A2 | 1/2011 |
| WO | 2011008915 A1 | 1/2011 |
| WO | 2011130146 A1 | 10/2011 |
| WO | 2011137022 A1 | 11/2011 |
| WO | 2012083121 A1 | 6/2012 |
| WO | 2012083122 A1 | 6/2012 |

OTHER PUBLICATIONS

M. Schmidtke et al., 95 Journal of Virological Methods, 133-143 (2001).*

(56) References Cited

OTHER PUBLICATIONS

Rizki, A., et al., "Polo-like kinase 1 is involved in invasion through extracellular matrix", Cancer Res., 2007, 67(23), pp. 11106-11100.
Sah, V.P., et al., "Rho Is Required for Gαq and α1-Adrenergic Receptor Signaling in Cardiomyocytes", J. Biol. Chem., 271(49), Dec. 6, 1996, pp. 31185-31190.
Sahai, E., et al., "Transformation mediated by RhoA requires activity of ROCK kinases", Curr. Biol., 1999, 9(3), pp. 136-145.
Sato, M., et al., "Involvement of Rho-kinase-mediated phosphorylation of myosin light chain in enhancement of cerebral vasospasm", Circ. Res., 2000, 87(3), pp. 195-200.
Satoh, S., et al., "Augmented agonist-induced Ca(2+)-sensitization of coronary artery contraction in genetically hypertensive rats. Evidence for altered signal transduction in the coronary smooth muscle cells",J. Clin. Invest., 1994, 94(4), pp. 1397-1403.
Satoh, S., et al., "Antiischemic Properties of Fasudil in Experimental Models of Vasospastic Angina", Jpn. J. Pharmacol., 87, 2001, pp. 34-40.
Sawada, N., et al., "Inhibition of Rho-Associated Kinase Results in Suppression of Neointimal Formation of Balloon-Injured Arteries", Circulation, 101(17), May 2, 2000, pp. 2030-2033.
Schwaller, J., et al., "Transformation of hematopoietic cell lines to growth-factor independence and induction of a fatal myelo- and lymphoproliferative disease in mice by retrovirally transduced TEL/JAK2 fusion genes", EMBO J., 1998, 17(18), pp. 5321-5333.
Seasholtz, T.M., et al., "Rho and Rho kinase mediate thrombin-stimulated vascular smooth muscle cell DNA synthesis and migration", Circ. Res., 1999, 84(10), pp. 1186-1193.
Segain, J.P., et al., "Rho Kinase Blockade Prevents Inflammation Via Nuclear Factor kB Inhibition: Evidence in Crohn's Disease and Experimental Colitis", Gastroenterology, 124(5), May 2003, pp. 1180-1187.
Seidel, H.M., et al., "Pharmaceutical intervention in the JAK/STAT signaling pathway", Oncogene 19(21), 2000, pp. 2645-2656.
Shibata, R., et al., Role of Rho-Associated Kinase in Neointima Formation After Vascular Injury, Circulation, 103(2), Jan. 16, 2001, pp. 284-289.
Shimokawa, H., et al., "Cellular and molecular mechanisms of coronary artery spasm: lessons from animal models", Jpn. Cir. J. 2000, 64(1), pp. 1-12.
Shimokawa, H., et al., "Anti-anginal Effect of Fasudil, a Rho-Kinase Inhibitor, in Patients With Stable Effort Angina: A Multicenter Study", J. Cardiovasc. Pharmacol., 40(5), 2002, pp. 751-761.
Shimokawa, H., et al., "Long-term inhibition of Rho-kinase induces a regression of arteriosclerotic coronary lesions in a porcine model in vivo", Cardiovasc. Res., 51(1), 2001, pp. 169-177.
Shimokawa, H., et al., "Rho-kinase as a Novel Therapeutic Target in Treatment of Cardiovascilar Diseases", J. Cardiovasc. Pharmacol., 39(3), 2002, pp. 319-327.
Smith, M.R., et al., "Malignant transformation of mammalian cells initiated by constitutive expression of the polo-like kinase", Biochem. Biophys. Res. Commun.,1997, 234(2), pp. 397-405.
Somlyo, A.V., et al., "Rho-Kinase Inhibitor Retards Migration and in Vivo Dissemination of Human Prostate Cancer Cells", Biochem. Biophys. Res. Commun., 269(3), 2000, pp. 652-659.
Strebhardt, K., et al., "Targeting polo-like kinase 1 for cancer therapy", Nat. Rev. Cancer, Nature Publishing Group, London, GB, 6(4), Apr. 1, 2006, pp. 321-330.
Sudbeck, E.A., et al., "Structure-based design of specific inhibitors of Janus kinase 3 as apoptosis-inducing antileukemic agents", Clin. Cancer Res., 1999, 5(6), 1569-1582.
Suzuki, K., et al., "Role of common cytokine receptor gamma chain (gamma(c))- and Jak3-dependent signaling in the proliferation and survival of murine mast cells", Blood, 2000, 96(6), pp. 2172-2180.
Tachibana, E., et al., "Intra-arterial infusion of fasudil hydrochloride for treating vasospasm following subarachnoid haemorrhage", Acta Neurochir (Wien), 1999, 141(1), pp. 13-19.
Tahara, M., et al., "RhoA/Rho-Kinase Cascade Is Involved in Oxytocin-Induced Rat Uterine Contraction", Endocrinology, 143(3), Mar. 2002, pp. 920-929.
Trieu, V.N., et al., "A specific inhibitor of janus kinase-3 increases survival in a transgenic mouse model of amyotrophic lateral sclerosis", Biochem. Biophys. Res. Commun., 2000, 267(1), pp. 22-25.
Uehata, M., et al., "Calcium sensitization of smooth muscle mediated by a Rho-associated protein kinase in hypertension", Nature, 1997, 389, pp. 990-994.
Utsunomiya, T., et al., "Antianginal effects of hydroxyfasudil, a Rho-kinase inhibitor, in a canine model of effort angina", British Journal of Pharmacology, 134(8), 2001, pp. 1724-1730.
Wada, M., et al., "siRNA targeting PLK-1 induces apoptosis of synoviocytes in rheumatoid arthritis", Biochem. Biophys. Res. Commun., 2007, 357(2), pp. 353-359.
Watanabe, G., et al., "Protein kinase N (PKN) and PKN-related protein rhophilin as targets of small GTPase Rho", Science, 1996, 271, pp. 645-648.
Weichert, W., et al., "Polo-like kinase isoforms in breast cancer: expression patterns and prognostic implications", Virchows. Arch., 2005, 446(4), pp. 442-450.
Weichert, W., et al., "Polo-like kinase isoform expression is a prognostic factor in ovarian carcinoma", Br. J. Cancer, 2004, 90(4), pp. 815-821.
Written Opinion of the International Searching Authority issued for PCT Application No. PCT/US2005/010846 Dated Aug. 19, 2005.
Written Opinion of the International Searching Authority issued for PCT Application No. PCT/US2007/001225 Dated Jul. 20, 2007.
Written Opinion of the International Searching Authority issued for PCT Application No. PCT/US2007/025688 Dated Apr. 6, 2008.
Written Opinion of the International Searching Authority issued for PCT Application No. PCT/US2007/026190 Dated May 20, 2008.
Written Opinion of the International Searching Authority issued for PCT Application No. PCT/US2008/009786 Dated Jan. 19, 2009.
Written Opinion of the International Searching Authority issued for PCT Application No. PCT/US2009/001534 Dated Apr. 2, 2010.
Written Opinion of the International Searching Authority issued for PCT Application No. PCT/US2009/003716 Dated Nov. 20, 2009.
Written Opinion of the International Searching Authority issued for PCT Application No. PCT/US2009/003723 Dated Nov. 20, 2009.
Yanazume, T., et al., "Rho/ROCK Pathway Contributes to the Activation of Extracellular Signal-regulated Kinase/ GTA-4 during Myocardial Cell Hypertrophy", J. Biol. Chem., 277(10), Mar. 8, 2002, pp. 8618-8625.
Yoshii, A., et al., "Relaxation of contracted rabbit tracheal and human bronchial smooth muscle by Y-27632 through inhibition of Ca2+ sensitization", Am. J. Respir. Cell Mol. Biol., 1999, 20(6), pp. 1190-1200.
Yu, C.L., et al., "Constitutive activation of the Janus kinase-STAT pathway in T lymphoma overexpressing the Lck protein tyrosine kinase", J. Immunol.. 1997, 159(11), pp. 5206-5210.
Zhou, Y., et al., "Nonsteroidal Anti-Inflamatory Drugs Can Lower Amyloidogenic Aβ42 by Inhibiting Rho", Science, 2003, 302, pp. 1215-1217.
Ha, H-H, et al., "Novel heterocycle-substituted pyrimidines as inhibitors of NF-κB transcription regulation related to TNF-α cytokine release", Bioorg. Med. Chem. Lett., 2008, 18, pp. 653-656.
Huang, S., et al., "Synthesis of 2-amino-4-(7-azaindol-3-yl)pyrimidiens as cyclin dependent kinase 1 (CDK1) inhibitors", Bioorg. Med. Chem. Lett., 2006, 16, pp. 4818-4821.
International Search Report issued for PCT/US2011/065371 dated Jun. 21, 2012.
International Search Report issued for PCT/US2011/065388 dated Jun. 21, 2012.
International Search Report issued for PCT/US2011/065389 dated Jun. 21, 2012.
Alvarez, Mercedes, et al., "Synthesis of 3-Aryl- and 3-Heteroaryl-7-azaindoles", Synthesis, Thieme Stuttgart, New York, 4, 1999, pp. 615-620.
Amano, M., et al., "Formation of actin stress fibers and focal adhesions enhanced by Rho-kinase", Science, 1997, 275, pp. 1308-1311.
Amano. M., et al., "Identification of a putative target for Rho as the serine-threonine kinase protein kinase N", Science 1996, 271, pp. 648-650.
Berge, Stephen M., et al., "Pharmaceutical Salts" Journal of Pharmaceutical Sciences, 66(1), Jan. 1977, pp. 1-19.

(56) References Cited

OTHER PUBLICATIONS

Bettayeb, Karima, et al., "Meriolins, a New Class of Cell Death-Inducing Kinase Inhbitiors with Enhanced Selectivity for Cyclin-Dependent Kinases", Cancer Research, 67(17), Sep. 1, 2007, pp. 8325-8334.
Burns, T.F. et al., "Silencing of the novel p53 target gene Snk/Plk2 leads to mitotic catastrophe in paclitaxel (Taxol)-exposed cells", Mol. Cell Biol., 2003, 23, pp. 5556-5571.
Catlett-Falcone, R., et al, "Constitutive activation of Stat3 signaling confers resistance to apoptosis in human U266 myeloma cells", Immunity, 1999, 10, pp. 105-115.
Chelucci, G., et al., The chiral version of compound 41 can be prepared using known methods: Tetrahedron Asymmetry 2006, 17(22), pp. 3163-3169.
Chiba, Y., et al., "Characteristics of muscarinic cholilnoceptros in airways of antigen-induced airway hyperresponsive rats", Comp. Biochem. Physiol. C Pharmacol. Toxicol. Endocrinol. 1995, 111C(3), pp. 351-357.
Chiba, Y., et al., "Augmented acetylcholine-induced translocation of RhoA in bronchial smooth muscle from antigen-induced airway hyperresponsive rats", Br. J. Pharmacol. 2001, 133, pp. 886-890.
Chiba, Y., et al., "Augmented acetylcholine-induced, Rho-mediated Ca2+ sensitization of bronchial smooth muscle contraction in antigen-induced airway hyperresponsive rats", Br. J. Pharmacol. 1999, 127, pp. 597-600.
Chitaley, K., et al., "Antagonism of Rho-kinase stimulates rat penile erection via a nitric oxide-independent pathway", Nature Medicine, Nature Publishing Group, 7(1), Jan. 2001, pp. 119-122.
Eto, M., et al., "Thrombin Suppresses Endothelial Nitric Oxide Synthase and Upregulates Endothelin-Converting Enzyme-1 Expression by Distinct Pathways", Circulation Research, 89, 2001, pp. 583-590.
Eto, Y., et al., "Gene transfer of dominant negative Rho kinase suppresses neointimal formation after balloon injury in pigs", Am. J. Physiol. Heart Circ. Physiol., American Physiological Society, 278, 2000, pp. H1744-H1750.
Fan, Y. et al., "Apoptosis induction with polo-like kinase-1 antisense phosph-orothioate oligodeoxynucleotide of colon cancer cell line SW480", World J. Gastroenterol., 2005, 11(29), pp. 4596-4599.
Fernandez, D., et al., "Synthesis of Polyheterocyclic Nitrogen-Containing Marine Natural Products", Monatshefte Fur Chemie, Chemical Monthly, AU, 135, 2004, pp. 615-627.
Fournier, A.E., et al., "Rho Kinase Inhibition Enhances Axonal Regeneration in the Injured CNS", The Journal of Neuroscience, 23(4), Feb. 15, 2003, pp. 1416-1423.
Frank, D.A., "STAT signaling in the pathogenesis and treatment of cancer", Mol. Med. 5, 1999, pp. 432-456.
Fresneda, Pilar M., et al., "Synthesis of the indole alkaloids meridianins from the tunicate *Aplidium meridianum*", Tetrahedron, Pergamon, 57(12), 2001, pp. 2355-2363.
Fu, X., et al., "The effects of the Rho-kinase inhibitor Y-27632 on arachidonic acid-, GTPgammaS-, and phorbol ester-induced Ca2+-sensitization of smooth muscle", FEBS Lett., 440, 1998, pp. 183-187.
Fukata, Y., et al., "Rho-Rho-kinase pathway in smooth muscle contraction and cytoskeletal reorganization of non-muscle cells", Trends Pharmacol Sci., 22(1), 2001, pp. 32-39.
Galli, S.J., "New concepts about the mast cell", N. Engl. J. Med., 328(4), 1993, pp. 257-265.
Garcia-Bustos, J.F., et. al., "PIK1, an essential phosphatidylinositol 4-kinase associated with the yeast nucleus", EMBO J, 13, 1994, pp. 2352-2361.
Genda, T., et al., "Cell Motility Mediated by Rho and Rho-Associated Protein Kinase Plays a Critical Role in Intrahepatic Metastasis of Human Hepatocellular Carcinoma", Hepatology, 30(4), Oct. 1999, pp. 1027-1036.
Gordon, J.R., et al, "Mast cells as a source of both preformed and immunologically inducible TNF-alpha/cachectin", Nature, 1990, 346, pp. 274-276.
Guan, R. et al., "Small Interfering RNA-Mediated Polo-Like Kinase 1 Depletion Preferentially Reduces the Survival of p53-Defective, Oncogenic Transformed Cells and Inhibits Tumor Growth in Animals", Cancer Res., 65(7), 2005, pp. 2698-2704.
Hamanaka, R., et al., "Polo-like kinase is a cell cycle-regulated kinase activated during mitosis", J. Biol. Chem., 1995, 270(36), pp. 21086-21091.
Hanks, S.K. and Hunter, T., "Protein kinases 6. The eukaryotic protein kinase superfamily: kinase (catalytic) domain structure and classification", FASEB J. 1995, 9(8), pp. 576-596.
Harrington, E.A., et al., "VX-680, a potent and selective small-molecule inhibitor of the Aurora kinases, suppresses tumor growth in vivo", Nature Med., 2004, 10(3), pp. 262-267.
Hatanaka, M., et al., "Preparation and antioxidant activity of alpha-pyridoin and its derivatives", Bioorg. Med. Chem., 2005, 13, pp. 6763-6770.
Herbert, R., et al., "1H-Pyrrolo[2,3-b]pyridines. Part II. Fragmentation of Some 1H-Pyrrolo[2,3-b]pyridines induced by Electron Impact", J. Chem. Soc., Phys. Org. (B), 1970, pp. 459-463.
Hernandez-Perera, O., et al., "Involvement of Rho GTPases in the Transcriptional Inhibition of Preproendothelin-1 Gene Expression by Simvastatin in Vascular Endothelial Cells", Circulation Research, 87, 2000, pp. 616-622.
Hiles, I.D., et al., "Phosphatidylinositol 3-kinase: structure and expression of the 110 kd catalytic subunit", Cell, 1992, 70(3), pp. 419-429.
Hirose, M., et al., "Molecular dissection of the Rho-associated protein kinase (p160ROCK)-regulated neurite remodeling in neuroblastoma N1E-115 cells", J. Cell. Biol., 1998, 141(7), pp. 1625-1636.
Honjo, M., et al., "Effects of Protein Kinase Inhibitor, HA1077 on Intraocular Pressure and Outflow Facility in Rabbit Eyes", Arch. Ophthalmol, 119, Aug. 2001, pp. 1171-1178.
Hoshijima, M., et al., "The Low Molecular Weight GTPase Rho Regulates Myofibril Formation and Organization in Neonatal Rat Ventricular Myocytes", The Journal of Biological Chemistry, USA, 273(13), Mar. 27, 1998, pp. 7725-7730.
Hudson, J.W. et al., "Late mitotic failure in mice lacking Sak, a polo-like kinase", Current Biology, 2001, 11(6), pp. 441-446.
Iizuka, K., et al., "Evaluation of Y-27632, a rho-kinase inhibitor, as a bronchodilator in guinea pigs", Eur. J. Pharmacol. 2000, 406(2), pp. 273-279.
Ikeda, F., et al., "Reduction of Hepatic Ischemia/Reperfusion-Induced Injury by a Specific ROCK/Rho Kinase Inhibitor Y-27632", Journal of Surgical Research, Elsevier Science (USA), 109, 2003, pp. 155-160.
International Search Report issued for PCT/US2005/010846 Dated Aug. 19, 2005.
International Search Report issued for PCT/US2007/001225 Dated Jul. 20, 2007.
International Search Report issued for PCT/US2007/026190 Dated Jul. 3, 2008.
International Search Report issued for PCT/US2008/009786 Dated Jan. 19, 2009.
International Search Report issued for PCT/US2009/001534 Dated Apr. 2, 2010.
International Search Report issued for PCT/US2010/038988 dated Dec. 23, 2010.
IPRP issued for PCT/US2005/010846 dated Oct. 4, 2006.
IPRP issued for PCT/US2007/001225 dated Jul. 22, 2008.
IPRP issued for PCT/US2007/026190 dated Jun. 24, 2009.
IPRP issued for PCT/US2008/009786 dated Apr. 2, 2010.
IPRP issued for PCT/US2009/001534 dated Sep. 14, 2010.
IPRP issued for PCT/US2010/038988 dated Dec. 20, 2011.
Ishibashi, Toshiyuki, et al., "Inhibition of Rho/Rho-kinase signaling downregulates plasminogen activator inhibitor-1 synthesis in cultured human monocytes", Biochimica Et Biophysica Acta, Elsevier, 1590, 2002, pp. 123-130.
Ishizaki, T., et al., "The small GTP-binding protein Rho binds to and activates a 160 kDa Ser/Thr protein kinase homologous to myotonic dystrophy kinase", EMBO J., 1996, 15(8), pp. 1885-1893.
Ishizaki, T., et al., "p160ROCK, a Rho-associated coiled-coil forming protein kinase, works downstream of Rho and induces focal adhesions", FEBS Lett. 1997, 404(2-3), pp. 118-124.

(56) References Cited

OTHER PUBLICATIONS

Itoh, Kazuyuki, et al., "An essential part for Rho-associated kinase in the transcellular invasion of tumor cells", Nat. Med., 5(2), Feb. 1999, pp. 221-225.
Kandabashi, T., et al., "Inhibition of myosin phosphatase by upregulated rho-kinase plays a key role for coronary artery spasm in a porcine model with interleukin-1beta", Circulation, 2000, 101(11), pp. 1319-1323.
Karpov, A.S., et al., "Concise Synthesis of Meridianins by Carbonylative Alkynylation and a Four-Component Pyrimidine Synthesis", Angewandte Chemie., International Edition, Wiley VCH Verlag, Weinheim, DE, 44, 2005, pp. 6951-6956.
Katsumata, N., et al., "Enhanced myosin light chain phosphorylations as a central mechanism for coronary artery spasm in a swine model with interleukin-1beta", Circulation, 1997, 96(12), pp. 4357-4363.
Kelly, T.A., et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", J. Med. Chem., 40(15), 1997, pp. 2430-2433.
Kimura, K., et al., "Regulation of myosin phosphatase by Rho and Rho-associated kinase (Rho-kinase)", Science, 1996, 273, pp. 245-248.
Kirken, R.A., "Targeting Jak3 for immune suppression and allograft acceptance", Transplant. Proc. 2001, 33(7-8), pp. 3268-3270.
Klages, B., et al., "Activation of G12/G13 results in shape change and Rho/Rho-kinase-mediated myosin light chain phosphorylation in mouse platelets", J. Cell. Biol., 1999, 144(4), pp. 745-754.
Knighton, D.R., et al., "Crystal structure of the catalytic subunit of cyclic adenosine monophosphate-dependent protein kinase", Science, 1991, 253, pp. 407-414.
Kunz, J., et al., "Target of rapamycin in yeast, TOR2, is an essential phosphatidylinositol kinase homolog required for G1 progression", Cell, 1993, 73(3), pp. 585-596.
Kupittayanant, S., et al., "The effects of inhibiting Rho-associated kinase with Y-27632 on force and intracellular calcium in human myometrium", Pflugers Arch—Eur J Physiol,, 443, 2001, pp. 112-114.
Kuwahara, Koichiro, et al., "The effects of the selective ROCK inhibitor, Y27632, on ET-1-induced hypertrophic response in nenatal rat cardiac myocytes—possible involvement of Rho/ROCK pathway in cardiac muscle cell hypertrophy" Federation of European Biochemical Societies Letters, vol. 452, 1999, pp. 314-318.
Lane, H.A. et al., "Antibody microinjection reveals an essential role for human polo-like kinase 1 (Plk1) in the functional maturation of mitotic centrosomes", J. Cell. Biol., 1996, 135, pp. 1701-1713.
Laufs, Ulrich, et al., "Post-transcriptional Regulation of Endothelial Nitric Oxide Synthase mRNA Stability by Rho GTPase", J. Biol. Chem., 273(37), Sep. 11, 1998, pp. 24266-24271.
Leung, T., et al., "A novel serine/threonine kinase binding the Ras-related RhoA GTPase which translocates the kinase to peripheral membranes", J. Biol. Chem., 1995, 270(49), pp. 29051-29054.
Leung, T., et al., "The p160 RhoA-binding kinase ROK alpha is a member of a kinase family and is involved in the reorganization of the cytoskeleton", Mol. Cell Biol. 1996, 16(10), pp. 5313-5327.
Li, J. et. al., "SAK, A New Polo-Like Kinase, Is Transcriptionally Repressed by p53 and Induces Apoptosis upon RNAi Silencing", Neoplasia, 2005, 7(4), pp. 312-323.
Li, Z., et. al., "Function of polo-like kinase 3 in NF-kappa B-mediated proapoptotic response", J. Biol. Chem., 2005, 280 (17), pp. 16843-16850.
Liu, X., et al., "Polo-like kinase (Plk)1 depletion induces apoptosis in cancer cells", Proc. Nat'l. Acad. Sci. USA, 2003, 100(10), pp. 5789-5794.
Lowery, Drew M., et al., "Structure and function of Polo-like Kinases", Oncogene, Nature Publishing Group, 24, 2005, pp. 248-259.

M.A. MaIikobcknn, "JleKapcTBeHHble cpeAcTBa", 2001, 1, p. 14 (Russian Language).
Ma, S. et al., "Role of Plk2 (Snk) in mouse development and cell proliferation", Mol. Cell Biol., 2003, 23(19), pp. 6936-6943.
MacMillan, J.C., et al., "Comparative expression of the mitotic regulators SAK and PLK in colorectal cancer", Ann. Surg. Oncol., 2001, 8(9), pp. 729-740.
Madaule, P., et al., "Role of citron kinase as a target of the small GTPase Rho in cytokinesis", Nature, 1998, 394, pp. 491-494.
Madaule, P., et al., "A novel partner for the GTP-bound forms of rho and rac", FEBS Lett. 1995, 377(2), pp. 243-248.
Malaviya, R., et al., "Targeting Janus kinase 3 in mast cells prevents immediate hypersensitivity reactions and anaphylaxis", J. Biol. Chem., 1999, 274, pp. 27028-27038.
Malaviya, R., et al., "Genetic and biochemical evidence for a critical role of Janus kinase (JAK)-3 in mast cell-mediated type I hypersensitivity reactions", Biochem. Biophys. Res. Commun., 1999, 257(3), pp. 807-813.
Masumoto, A., et al., "Possible involvement of Rho-kinase in the pathogenesis of hypertension in humans", Hypertension, 2001, 38(6), pp. 1307-1310.
Masumoto, A., et al., "Suppression of Coronary Artery Spasm by the Rho-Kinase Inhibitor Fasudil in Patients With Vasospastic Angina", Circulation, 105(13), 2002, pp. 1545-1547.
Matsui, T., et al., "Rho-associated kinase, a novel serine/threonine kinase, as a putative target for small GTP binding protein Rho", EMBO J. 1996, 15(9), pp. 2208-2216.
Mills, T.M., et al., "Effect of Rho-kinase inhibition on vasoconstriction in the penil circulation", J. Appl. Physiol., 91(3), 2001, pp. 1269-1273.
Miyagi, Y., et al., "Upregulation of rho A and rho kinase messenger RNAs in the basilar artery of a rat model of subarachnoid hemorrhage", J. Neurosurg., 2000, 93(3), pp. 471-476.
Mizunuma, Kazuyuki, et al., "Prevention of ischemia-reperfusion-induced hepatic microcirculatory disruption by inhibiting stellate cell contraction using rock inhibitor", Transplantation, 75(5), Mar. 15, 2003, pp. 579-586.
Morishige, Kunio, et al., "Adenovirus-Mediated Transfer of Dominant-Negative Rho-Kinase Induces a Regression of Coronary Arteriosclerosis in Pigs In Vivo", Arterioscler. Thromb. Vasc. Biol., 21, Apr. 2001, pp. 548-554.
Mukai, Y., et al., "Involvement of Rho-kinase in hypertensive vascular disease: a novel therapeutic target in hypertension", FASEB J., 2001, 15(6), pp. 1062-1064.
Müller-Ladner, U., et al., "Activation of the IL-4 STAT pathway in rheumatoid synovium", J. Immunol., 2000, 164 (7), pp. 3894-3901.
Nakagawa, O., et al., "ROCK-I and ROCK-II, two isoforms of Rho-associated coiled-coil forming protein serine/ threonine kinase in mice", FEBS Lett., 1996, 392(2), pp. 189-193.
Nielsen, M., et al., "Constitutive activation of a slowly migrating isoform of Stat3 in mycosis fungoides: tyrphostin AG490 inhibits Stat3 activation and growth of mycosis fungoides tumor cell lines", Proc. Nat. Acad. Sci., USA, 1997, 94(13), pp. 6764-6769.
Niggli, V., "Rho-kinase in human neutrophils: a role in signalling for myosin light chain phosphorylation and cell migration", FEBS Lett., 1999, 445(1), pp. 69-72.
Niiro, N., et al., "Up-Regulation of rho A and rho-Kinase mRHAs in the Rat Myometrium during Pregnancy", Biochem. Biophys. Res, Commun,, 230(2), 1997, pp. 356-359.
Nilius, B., et al., "Role of Rho and Rho kinase in the activation of volume-regulated anion channels in bovine endothelial cells", J. Physiol., 1999, 516, pp. 67-74.
Nobes, C.D., and Hall, A., "Rho GTPases control polarity, protrusion, and adhesion during cell movement", J. Cell. Biol., 1999, 144(6), pp. 1235-1244.
Pungpo, P., et al., "Three-dimensional quantitative structure-activity relationship study on HIV-1 reverse transcriptase inhibitors in the class of dipyridodiazepinone derivatives, using comparative molecular field analysis", J. Mol. Graph. Model., 18(6), 2000, pp. 581-590.
Rao, P.V., et al., "Modulation of Aqueous Humor Outflow Facility by the Rho Kinase-Specific Inhibitor Y-27632", Invest. Ophthalmol. Vis. Sci., 42(5), Apr. 2001, pp. 1029-1037.

(56) References Cited

OTHER PUBLICATIONS

Rees, R.W., et al., "Y-27632, a Rho-kinase inhibitor, inhibits proliferation and adrenergic contraction of prostatic smooth muscle cells", J. Urol., 170, Dec. 2003, pp. 2517-2522.

Retzer, M., et al., "Mildly oxidised low density lipoprotein induces platelet shape change via Rho-kinase-dependent phosphorylation of myosin light chain and moesin", Federation of European Biochemical Societies Letters, vol. 466, 2000, pp. 70-74.

* cited by examiner

INHIBITORS OF INFLUENZA VIRUSES REPLICATION

CROSS REFERENCE TO RELATED APPLICATIONS

This application is a continuation of PCT Application Number PCT/US2011/065371, filed Dec. 16, 2011, which claims priority to U.S. Provisional Application No. 61/527,273, filed Aug. 25, 2011, and U.S. Provisional Application No. 61/423,943, filed Dec. 16, 2010, the entire contents of which are incorporated herein by reference.

BACKGROUND OF THE INVENTION

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs.

Thus, there is still a need for drugs for treating influenza infections, such as for drugs with expanded treatment window, and/or reduced sensitivity to viral titer.

SUMMARY OF THE INVENTION

The present invention generally relates to methods of treating influenza, to methods of inhibiting the replication of influenza viruses, to methods of reducing the amount of influenza viruses, to compounds and compositions that can be employed for such methods.

In one embodiment, the present invention is directed to a compound represented by Structural Formula (I):

or a pharmaceutically acceptable salt thereof, wherein:

X is —H, —Cl, —Br, —F, —CN, or $C_1$-$C_6$ aliphatic optionally substituted with one or more instances of $J^1$;

Ring T is a $C_3$-$C_{10}$ carbocycle or 4-10 membered heterocycle optionally further substituted with one or more instances of $J^T$;

$Q^1$ is —C(O)—, —$CO_2$—, —OC(O)—, —O($CR^tR^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —P(O)(OR)O—, —OP(O)($OR^a$)O—, —$P(O)_2$O—, —$CO_2SO_2$—, —$B(O)_2$—, or —($CR^tR^s$)$_p$—$Y^1$—;

$Y^1$ is —C(O)—, —$CO_2$—, —OC(O)—, —O($CR^tR^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —P(O)(OR)O—, —OP(O)($OR^a$)O—, —$P(O)_2$O—, —$B(O)_2$—, or —$CO_2SO_2$—; and $R^1$ is: i) —H; ii) a $C_1$-$C_6$ aliphatic group optionally substituted with one or more instances of $J^A$; iii) a $C_3$-$C_{10}$ carbocyclic group or 4-10 membered heterocyclic group, each optionally and independently substituted with one or more instances of $J^B$; or iv) a 6-10 membered aryl group or 5-10 membered heteroaryl group, each optionally and independently substituted with one or more instances of $J^C$;

optionally $R^1$, together with R' and the nitrogen to which they are attached, form a 4-8 membered heterocyclic group optionally substituted with one or more instances of $J^2$; or optionally -$Q^1$-$R^1$ forms, together with Ring T, a 4-10 membered, non-aromatic, spiro ring optionally substituted with one or more instances of $J^4$; and $Y^1$ is —C(O)—, —$CO_2$—, —OC(O)—, —O($CR^tR^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —P(O)(OR)O—, —OP(O)($OR^a$)O—, —$P(O)_2$O—, —$B(O)_2$—, or —$CO_2SO_2$—; and $R^2$ is —H, —OR, —$CO_2$R, —NRR', —CONRR', or $C_1$-$C_6$ aliphatic optionally substituted with one or more instances of $J^1$;

$R^3$ is —H, —F, —Cl, —CN, —$NO_2$, —OR, —$CO_2$R, —CONRR', or $C_1$-$C_6$ aliphatic optionally substituted with one or more instances of $J^1$;

$J^A$, $J^B$, and $J^T$ are each and independently oxo or $J^C$;

$J^C$ are each and independently selected from the group consisting of halogen, cyano, M, $R^a$, or $R^a$-M;

M is independently selected from the group consisting of —$OR^b$, —$SR^b$, —S(O)$R^a$, —$SO_2R^a$, —$NR^bR^c$, —C(O)$R^a$, —C(=NR)$R^c$, —C(=NR)$NR^bR^c$, —NRC(=NR)$NR^bR^c$, —C(O)$OR^b$, —OC(O)$R^b$, —NRC(O)$R^b$, —C(O)$NR^bR^c$, —NRC(O)$NR^bR^c$, —NRC(O)$OR^b$, —OCON$R^bR^c$, —C(O)N$RCO_2R^b$, —NRC(O)NRC(O)$OR^b$, —C(O)NR($OR^b$), —$OSO_2NR^bR^c$, —$SO_2NR^cR^b$, —$NRSO_2R^b$, —$NRSO_2NR^cR^b$, —P(O)($OR^b$)$_2$, —OP(O)($OR^b$)$_2$, —$P(O)_2OR^b$ and —$CO_2SO_2R^b$; or optionally, two $J^T$, two $J^A$, two $J^B$, and two $J^C$, respectively, together with the atom(s) to which they are attached, independently form a 4-10-membered ring that is optionally substituted with one or more instances of $J^4$; and $R^a$ is independently:

i) a $C_1$-$C_6$ aliphatic group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), $C_3$-$C_8$ carbocyclic group optionally substituted with one or more instances of $J^2$, 4-8 membered heterocyclic group optionally substituted with one or more instances of $J^2$, 5-10 membered heteroaryl group optionally substituted with one or more instances of $J^3$, and 6-10 membered aryl group optionally substituted with one or more instances of $J^3$;

ii) a $C_3$-$C_8$ carbocyclic group, or 4-8 membered heterocyclic group, each of which is optionally and independently substituted with one or more instances of $J^2$; or iii) a 5-10 membered heteroaryl group, or 6-10 membered aryl group, each of which is optionally and independently substituted with one or more instances of $J^3$; and $R^b$ and $R^c$ are each independently $R^a$ or —H; or optionally, $R^b$ and $R^c$, together with the nitrogen atom(s) to which they are attached, each independently form a 4-8 membered heterocyclic group optionally substituted with one or more instances of $J^2$;

$R^t$ and $R^s$ are each independently —H, halogen, or $C_1$-$C_6$ alkyl optionally substituted with one or more instances of $J^1$, or optionally, $R^t$ and $R^s$, together with the carbon atom to which they are attached, form a cyclopropane ring optionally substituted with one or more instances of methyl;

R and R' are each independently —H or $C_1$-$C_6$ alkyl optionally and independently substituted with one or more instances of $J^1$, or optionally R and R', together with the nitrogen to which they are attached, form a 4-8 membered heterocyclic group optionally substituted with one or more instances of $J^2$;

each $J^1$ is independently selected from the group consisting of halogen, cyano, hydroxy, oxo, —$NH_2$, —$NH(C_1-C_4$ alkyl), —$N(C_1-C_4$ alkyl$)_2$, —$OCO(C_1-C_4$ alkyl), —$CO(C_1-C_4$ alkyl), —$CO_2H$, —$CO_2(C_1-C_4$ alkyl), —$O(C_1-C_4$ alkyl), and phenyl;

each $J^2$ is independently selected from the group consisting of halogen, cyano, hydroxy, oxo, —$NH_2$, —$NH(C_1-C_4$ alkyl), —$N(C_1-C_4$ alkyl$)_2$, —$OCO(C_1-C_4$ alkyl), —$CO(C_1-C_4$ alkyl), —$CO_2H$, —$CO_2(C_1-C_4$ alkyl), $C_1-C_4$ alkyl, $C_1-C_4$ haloalkyl, and —$O(C_1-C_4$ alkyl);

each of $J^3$ and $J^4$ is independently selected from the group consisting of halogen, cyano, hydroxy, —$NH_2$, —$NH(C_1-C_4$ alkyl), —$N(C_1-C_4$ alkyl$)_2$, —$OCO(C_1-C_4$ alkyl), —$CO(C_1-C_4$ alkyl), —$CO_2H$, —$CO_2(C_1-C_4$ alkyl), $C_1-C_4$ alkyl, $C_1-C_4$ haloalkyl, and —$O(C_1-C_4$ alkyl);

p is 1, 2, 3 or 4; and k is 1, 2, 3 or 4; and provided that $Q^1$-$R^1$ is not at the same carbon atom to which —NH group that is attached to the pyrimidine ring of Structural Formula (I) is attached.

In some embodiments, p is independently 1 or 2; and k is independently 1 or 2.

In another embodiment, the present invention is directed to a pharmaceutical composition comprising a compound disclosed herein (e.g., a compound represented by Structural Formula (I), (II), (IIIA) or (IIIB), or a pharmaceutically acceptable salt thereof) and a pharmaceutically acceptable carrier, adjuvant or vehicle.

In yet another embodiment, the present invention is directed to a method of inhibiting the replication of influenza viruses in a biological sample or patient, comprising the step of administering to said biological sample or patient an effective amount of a compound disclosed herein (e.g., a compound represented by Structural Formula (I), (II), (IIIA) or (IIIB), or a pharmaceutically acceptable salt thereof).

In yet another embodiment, the present invention is directed to a method of reducing the amount of influenza viruses in a biological sample or in a patient, comprising administering to said biological sample or patient an effective amount of a compound disclosed herein (e.g., a compound represented by Structural Formula (I), (II), (IIIA) or (IIIB), or a pharmaceutically acceptable salt thereof).

In yet another embodiment, the present invention is directed to a method of method of treating influenza in a patient, comprising administering to said patient an effective amount of a compound disclosed herein (e.g., a compound represented by Structural Formula (I), (II), (IIIA) or (IIIB), or a pharmaceutically acceptable salt thereof).

The present invention also provides use of the compounds described herein for inhibiting the replication of influenza viruses in a biological sample or patient, for reducing the amount of influenza viruses in a biological sample or patient, or for treating influenza in a patient.

Also provided herein is use of the compounds described herein for the manufacture of a medicament for treating influenza in a patient, for reducing the amount of influenza viruses in a biological sample or in a patient, or for inhibiting the replication of influenza viruses in a biological sample or patient.

Also provided here in are the compounds represented by Structural Formula (XX):

or a pharmaceutically acceptable salt thereof. Without being bound to a particular theory, the compounds of Structural Formula (XX) can be used for synthesizing the compound of Formula (I). The variables of Structural Formula (XX) are each and independently as defined herein; and G is trityl (i.e., $C(Ph)_3$ where Ph is phenyl).

The invention also provides methods of preparing a compound represented by Structural Formula (I) or a pharmaceutically acceptable salt thereof. In one embodiment, the method comprises the steps of: i) reacting compound A:

(A)

with compound (B):

(B)

to form a compound represented by Structural Formula (XX); and ii) deprotecting the G group of the compound of Structural Formula (XX) under suitable conditions to form the compound of Structural Formula (I), wherein: the variables of Structural Formulae (I) and (XX), and compounds (A) and (B) are each independently as defined herein; $L^2$ is a halogen (such as Cl, Br, or I); and each G is independently trityl. In another embodiment, the method comprises the steps of: i) reacting compound (K) or (L):

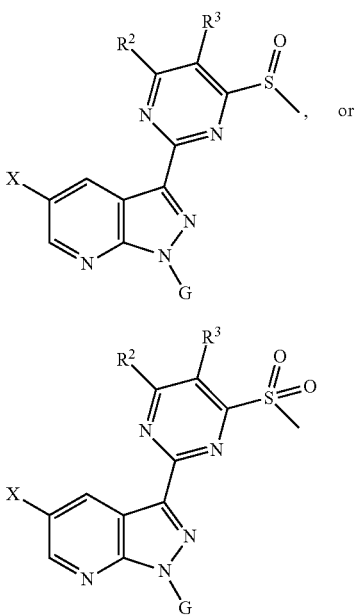

(K)

(L)

with compound (D):

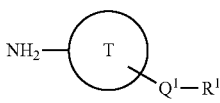

under suitable conditions to form a compound represented by Structural Formula (XX); and
ii) deprotecting the G group of the compound of Structural Formula (XX) under suitable conditions to form the compound of Structural Formula (I), wherein: the variables of Structural Formulae (I) and (XX), and compounds (K), (L), and (D) are each and independently as defined herein; and each G is independently tityl. In another embodiment, the method comprises the steps of: i) reacting Compound (G) with Compound (D):

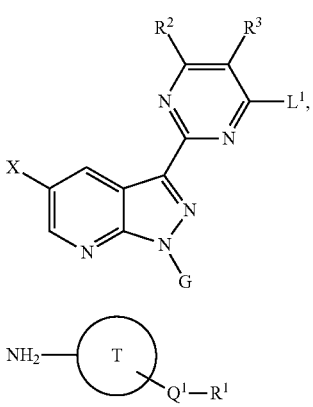

(G)

(D)

under suitable conditions to form a compound represented by Structural Formula (XX); and ii) deprotecting the G group of the compound of Structural Formula (XX) under suitable conditions to form the compound of Structural Formula (I), wherein: the variables of Structural Formulae (I) and (XX), and Compounds (G) and (D) are each and independently as defined herein; $L^1$ is a halogen (such as Cl, Br, or I); and each G is independently tityl.

DETAILED DESCRIPTION OF THE INVENTION

The compounds of the invention are as described in the claims. In some embodiments, the compounds of the invention are represented by any one of Structural Formulae (I), (II), (IIIA) and (IIIB), or pharmaceutically acceptable salts thereof, wherein the variables are each and independently as described herein. In some embodiments, the compounds of the invention are represented by any chemical formulae depicted in Table 1, or pharmaceutically acceptable salts thereof. In some embodiments, the compounds of the invention are represented by any chemical formulae depicted in Table 2, or pharmaceutically acceptable salts thereof. In some embodiments, the compounds of the invention are represented by any one of Structural Formulae (I), (II), (IIIA) and (IIIB), or pharmaceutically acceptable salts thereof, wherein the variables are each and independently as depicted in the chemical formulae in Table 1. In some embodiments, the compounds of the invention are represented by any one of Structural Formulae (I), (II), (IIIA) and (IIIB), or pharmaceutically acceptable salts thereof, wherein the variables are each and independently as depicted in the chemical formulae in Table 2.

In one embodiment, the compounds of the invention are represented by Structural Formula (I) or pharmaceutically acceptable salts thereof, wherein the first set of values of the variables of Structural Formula (I) is as follows:

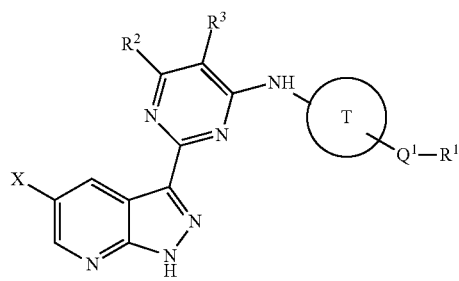

X is —H, —Cl, —Br, —F, —CN, —O($C_{1-4}$ alkyl), or $C_1$-$C_6$ aliphatic optionally substituted with one or more instances of $J^1$. Typically, X is —Cl, —Br, —F, —CN, —O($C_{1-4}$ alkyl), or optionally substituted $C_1$-$C_6$ aliphatic. More typically, X is —Cl, —Br, —F, —CN, —O($C_{1-4}$ alkyl), or optionally substituted $C_1$-$C_6$ alkyl. More typically, X is —Cl, —Br, —F, —CN, or optionally substituted $C_1$-$C_6$ alkyl. More typically, X is —Cl, —Br, —F, —CN, $C_1$-$C_4$ alkyl, or $C_1$-$C_4$ haloalkyl. More typically, X is —Cl, —Br, —F, —CN, or $C_1$-$C_4$ haloalkyl. More typically, X is —Cl, —F, —Br, —CN, or —$CF_3$. More typically, X is —Cl, —F, —CN, or —$CF_3$. More typically, X is —Cl or —F.

Ring T is a $C_3$-$C_{10}$ carbocycle or 4-10 membered heterocycle optionally further substituted with one or more instances of $J^T$. Typically, Ring T is an optionally substituted $C_5$-$C_{10}$ carbocyclic group or an optionally substituted 5-10 membered heterocarbocyclic group. In one aspect, Ring T is an optionally substituted, bridged, $C_5$-$C_{10}$ carbocyclic group. In another aspect, Ring T is an optionally substituted, monocyclic, $C_5$-$C_8$ carbocyclic group.

A typical example of Ring T includes:

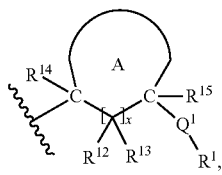

wherein x is 0, 1, or 2. In one specific example, Ring A and $R^{15}$, Ring A and $R^{14}$, or Ring A and $R^{13}$ independently form an optionally substituted, 4-10 membered, bridged ring. Further typical examples of Ring T include:

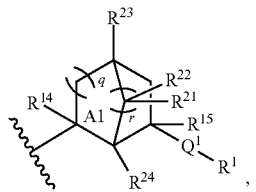 , 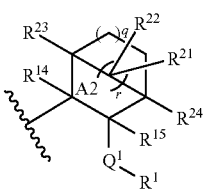 ,

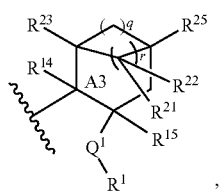 , 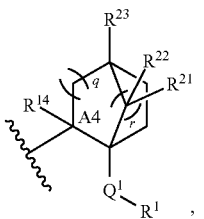 ,

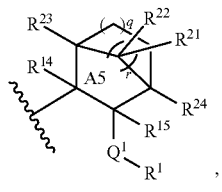 , and 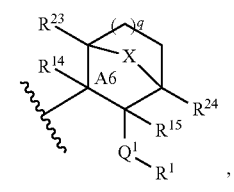 , wherein q is 0, 1 or 2; and r is 1 or 2. Additional typical examples of Ring T include:

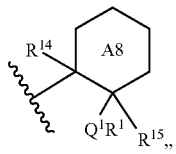 , 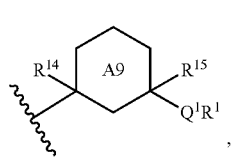 ,

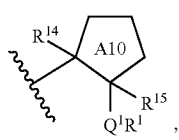 , and 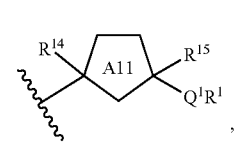 ,

Additional typical examples of Ring T include:

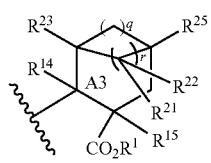 , 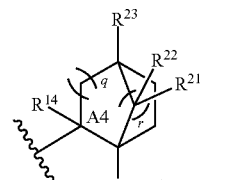 ,

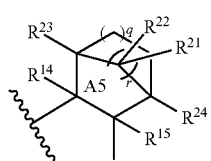 , 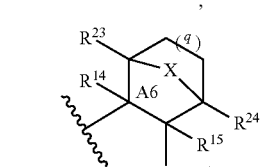 ,

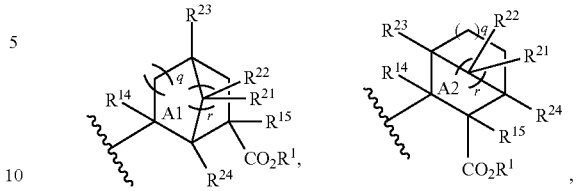 and 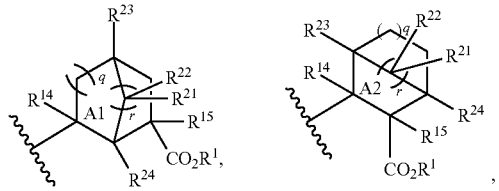 , wherein q is 0, 1 or 2; and
r is 1 or 2.

Ring A (including Rings A1-A6) is a 5-10 membered carbocyclic group optionally further substituted with one or more instances of $J^T$; or optionally Ring A and $R^{15}$, Ring A and $R^{14}$, or Ring A and $R^{13}$ independently and optionally form a 5-10 membered, bridged carbocyclic ring optionally further substituted with one or more instances of $J^T$. In one aspect, Ring A is optionally and independently further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl); or Ring A and $R^{15}$, Ring A and $R^{14}$, or Ring A and $R^{13}$ independently and optionally form a bridged carbocyclic group optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl). In another aspect, Ring A and $R^{15}$, Ring A and $R^{14}$, or Ring A and $R^{13}$ independently form an optionally substituted, bridged carbocyclic group.

Each of Rings A1-A5 is independently a 5-10 membered, bridged carbocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl). Ring A6 is independently a 5-10 membered, bridged heterocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl). Typically, each of Rings A1-A6 is independently and optionally further substituted with one or more substituents selected from the group consisting of halogen, cyano, hydroxy, $C_1$-$C_4$ alkyl, $C_1$-$C_4$ haloalkyl, and —O($C_1$-$C_4$ alkyl).

Z is —O—, —S—, or —NR$^g$—, wherein R$^g$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl).

Each of Rings A8-A11 is independently and optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl).

Q$^1$ is —C(O)—, —CO$_2$—, —OC(O)—, —O(CR$'$R$^s$)$_k$—C(O)O—, —C(O)NR$'$—, —C(O)N(R$'$)—O—, —C(O)NRC(O)O—, —NRC(O)—, —NRC(O)NR$'$—, —NRCO$_2$—, —OC(O)NR$'$—, —OSO$_2$NR$'$—, —S(O)—, —SO$_2$—, —SO$_2$NR$'$—, —NRSO$_2$—, —NRSO$_2$NR$'$—, —P(O)(OR)O—, —OP(O)(OR$^a$)O—, —P(O)$_2$O—, —CO$_2$SO$_2$—, or —(CR$'$R$^s$)$_p$—Y$^1$—. Typically, Q$^1$ is —C(O)—, —CO$_2$—, —OC(O)—, —O(CR$'$R$^s$)$_k$—C(O)O—, —C(O)NR$'$—, —C(O)N(R$'$)—O—, —C(O)NRC(O)O—, —NRC(O)—, —NRC(O)NR$'$—, —NRCO$_2$—, —OC(O)NR$'$—, —OSO$_2$NR$'$—, —S(O)—, —SO$_2$—, —SO$_2$NR$'$—, —NRSO$_2$—, —NRSO$_2$NR$'$—, —B(O)$_2$—, or —(CR$'$R$^s$)$_p$—Y$^1$—. More typically, Q$^1$ is —CO$_2$—, —O(CR$'$R$^s$)$_k$—C(O)O—, —P(O)(OR)O—, —OP(O)(OR$^a$)O—, —P(O)$_2$O—, —CO$_2$SO$_2$—, —B(O)$_2$—, or —(CR$'$R$^s$)$_p$—Y$^1$—. More typically, Q$^1$ is —CO$_2$—, —O(CR$'$R$^s$)$_k$—C(O)O—, —P(O)(OR)O—, —OP(O)(OR$^a$)O—, —P(O)$_2$O—, —CO$_2$SO$_2$—, or —(CR$'$R$^s$)$_p$—Y$^1$—. More typically, Q$^1$ is —C(O)O—, —NRC(O)—, —C(O)NR—, —NRC(O)NR$'$—, or —(CR$'$R$^s$)$_{1,2}$—Y$^1$—. Q$^1$ is —C(O)—, —C(O)O—, —NRC(O)—, —C(O)NR—, —NRC(O)NR$'$—, or —(CH$_2$)$_{1,2}$—Y—. Even more typically, Q$^1$ is independently —C(O)O—, —NRC(O)—, —C(O)NR—, —NRC(O)NR$'$—, or —(CH$_2$)$_{1,2}$—Y—. Even more typically, Q$^1$ is —C(O)O—, —NRC(O)—, —C(O)NR—, or —NRC(O)NR$'$—. Specific examples of Q$^1$ include —C(O)O—, —NHC(O)—, or —C(O)NH—.

Y$^1$ is —C(O)—, —CO$_2$—, —OC(O)—, —O(CR$'$R$^s$)$_k$—C(O)O—, —C(O)NR$'$—, —C(O)N(R$'$)—O—, —C(O)NRC(O)O—, —NRC(O)—, —NRC(O)NR$'$—, —NRCO$_2$—, —OC(O)NR$'$—, —OSO$_2$NR$'$—, —S(O)—, —SO$_2$—, —SO$_2$NR$'$—, —NRSO$_2$—, —NRSO$_2$NR$'$—, —P(O)(OR)O—, —OP(O)(OR$^a$)O—, —P(O)$_2$O—, —B(O)$_2$—, or —CO$_2$SO$_2$—. Typically, Y$^1$ is —C(O)—, —CO$_2$—, —OC(O)—, —O(CR$'$R$^s$)$_k$—C(O)O—, —C(O)NR$'$—, —C(O)N(R$'$)—O—, —C(O)NRC(O)O—, —NRC(O)—, —NRC(O)NR$'$—, —NRCO$_2$—, —OC(O)NR$'$—, —OSO$_2$NR$'$—, —S(O)—, —SO$_2$—, —SO$_2$NR$'$—, —NRSO$_2$—, —B(O)$_2$—, or —NRSO$_2$NR$'$—. More typically, Y$^1$ is —C(O)—, —CO$_2$—, —OC(O)—, —O(CR$'$R$^s$)$_k$—C(O)O—, —C(O)NR$'$—, —C(O)N(R$'$)—O—, —C(O)NRC(O)O—, —NRC(O)—, —NRC(O)NR$'$—, —NRCO$_2$—, —OC(O)NR$'$—, —OSO$_2$NR$'$—, —S(O)—, —SO$_2$—, —SO$_2$NR$'$—, —NRSO$_2$—, or —NRSO$_2$NR$'$—. More typically, Y$^1$ is —CO$_2$—, —O(CR$'$R$^s$)$_k$—C(O)O—, —P(O)(OR)O—, —OP(O)(OR$^a$)O—, —P(O)$_2$O—, or —CO$_2$SO$_2$—. More typically, Y$^1$ is —C(O)—, —C(O)O—, —NRC(O)—, —C(O)NR—, or —NRC(O)NR$'$—. More typically, Y$^1$ is —C(O)O—, —NRC(O)—, —C(O)NR—, or —NRC(O)NR$'$—. Specific examples of Y$^1$ include —C(O)O—, —NHC(O)—, —C(O)NH—, or —NHC(O)NH—.

R$^1$ is: i) —H; ii) a $C_1$-$C_6$ aliphatic group optionally substituted with one or more instances of J$^A$; iii) a $C_3$-$C_{10}$ carbocyclic group or 4-10 membered heterocyclic group, each optionally and independently substituted with one or more instances of J$^B$; or iv) a 6-10 membered aryl group or 5-10 membered heteroaryl group, each optionally and independently substituted with one or more instances of J$^C$; or optionally R$^1$, together with R$'$ and the nitrogen to which they are attached, form a 4-8 membered heterocyclic group optionally substituted with one or more instances of J$^2$; or optionally -Q$^1$-R$^1$ forms, together with Ring T, a 4-10 membered, non-aromatic, spiro ring optionally substituted with one or more instances of J$^4$.

In one aspect, R$^1$ is independently i) H; ii) a $C_1$-$C_6$-aliphatic group optionally substituted with one or more instances of J$^A$; iii) a $C_3$-$C_8$ carbocyclic group or 4-8 membered heterocyclic group, each of which is optionally and independently substituted with one or more instances of J$^B$; iv) a phenyl group or 5-6 membered heteroaryl group, each of which is optionally and independently substituted with one or more instances of J$^C$; optionally R$'$, together with R$'$ and the nitrogen to which they are attached, form an optionally substituted, 4-8 membered heterocyclic group; or optionally -Q$^1$-R$^1$ forms, together with Ring T, an optionally substituted, 4-10 membered, non-aromatic, spiro ring.

In another aspect, R$^1$ is independently i) —H; ii) a $C_1$-$C_6$-aliphatic group optionally substituted with one or more instances of J$^A$; iii) a $C_3$-$C_8$ carbocyclic group or 4-8 membered heterocyclic group, each of which is optionally and independently substituted with one or more instances of J$^B$; iv) a phenyl group or 5-6 membered heteroaryl group, each of which is optionally and independently substituted with one or more instances of J$^C$; or optionally R$^1$, together with R$'$ and the nitrogen to which they are attached, form an optionally substituted, 4-8 membered heterocyclic group.

In yet another aspect, R$^1$ is independently: i) —H; ii) a $C_1$-$C_6$ aliphatic group optionally substituted with one or more substituents independently selected from the group consisting of halogen, cyano, hydroxy, oxo, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), —CO$_2$H, $C_3$-$C_8$ carbocyclic group, 4-8 membered heterocyclic group, phenyl, and 5-6 membered heteroaryl; iii) a $C_3$-$C_7$ carbocyclic group; iv) a 4-7 membered heterocyclic group; v) a phenyl group; or vi) a 5-6 membered heteroaryl group; or optionally R$^1$, together with R$'$ and the nitrogen to which they are attached, form an optionally substituted, 4-8 membered heterocyclic group; and each of said carbocyclic, phenyl, heterocyclic, and heteroaryl groups represented by R$^1$ and for the substituents of the $C_1$-$C_6$-aliphatic group represented by R$^1$, and said heterocyclic group formed with R$^1$ and R$'$ is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl).

In yet another aspect, R$^1$ is independently —H or an optionally substituted $C_1$-$C_6$ aliphatic group, such as —H or optionally substituted $C_{1-6}$ alkyl.

In yet another aspect, R$^1$ is independently a 4-7 membered heterocyclic group, a phenyl group, or a 5-6 membered heteroaryl group, wherein each of said heterocyclic, phenyl and heteroaryl groups is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl);

or optionally $R^1$ and R', together with the nitrogen atom to which they are attached, form an optionally substituted, 4-8 membered heterocyclic group.

$R^2$ is —H, —OR, $CO_2R$, —NRR', —CONRR', or $C_1$-$C_6$ aliphatic optionally substituted with one or more instances of $J^1$. Typically, $R^2$ is —H, —O($C_1$-$C_4$ alkyl), —$NH_2$, —NH($C_1$-$C_4$ alkyl), N($C_1$-$C_4$alkyl)$_2$, —$CO_2$H, —$CO_2$($C_1$-$C_4$ alkyl), —C(O)$NH_2$, —C(O)NH($C_1$-$C_4$ alkyl), —C(O)N($C_1$-$C_4$ alkyl)$_2$, or optionally substituted $C_1$-$C_4$ alkyl. More typically, $R^2$ is —H, —O($C_1$-$C_4$ alkyl), $C_1$-$C_4$ alkyl, or $C_1$-$C_4$ haloalkyl. More typically, $R^2$ is H.

$R^3$ is —H, —F, —Cl, —CN, —$NO_2$, —OR, —$CO_2$R, —CONRR', or $C_1$-$C_6$ aliphatic optionally substituted with one or more instances of $J^1$. Typically, $R^3$ is —H, —F, —Cl, —CN, —$NO_2$, —O($C_1$-$C_4$ alkyl), —$CO_2$H, —$CO_2$($C_1$-$C_4$ alkyl), —C(O)$NH_2$, —C(O)NH($C_1$-$C_4$ alkyl), —C(O)N($C_1$-$C_4$alkyl)$_2$, or optionally substituted $C_1$-$C_4$ alkyl. More typically, $R^3$ is —H, —F, —Cl, —CN, —O($C_1$-$C_4$ alkyl), $C_1$-$C_4$ alkyl, or $C_1$-$C_4$ haloalkyl. More typically, $R^3$ is —F, —Cl, —CN, —O($C_1$-$C_4$ alkyl), $C_1$-$C_4$ alkyl, or $C_1$-$C_4$ haloalkyl. More typically, $R^3$ is —F, —Cl, —CN, or $C_1$-$C_4$ haloalkyl. More typically, $R^3$ is —F, —Cl, —CN, or —$CF_3$. More typically, $R^3$ is —F or —Cl.

Each of $R^{12}$, $R^{13}$, and $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —$CO_2$H, or —$CO_2$($C_1$-$C_6$ alkyl), wherein each said $C_1$-$C_6$ alkyl is optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and —O($C_1$-$C_4$ alkyl). Typically, $R^{12}$, $R^{13}$, and $R^{14}$ are each and independently —H, halogen, cyano, hydroxy, —O($C_1$-$C_6$ alkyl), or optionally substituted $C_1$-$C_6$ alkyl. More typically, $R^{12}$, $R^{13}$, and $R^{14}$ are each and independently —H, halogen, hydroxy, $C_1$-$C_6$ alkyl, $C_1$-$C_6$ haloalkyl, or —O($C_1$-$C_6$ alkyl).

Each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and —O($C_1$-$C_4$ alkyl). Typically, $R^{15}$ is —H or optionally substituted $C_1$-$C_6$ alkyl. More typically, $R^{15}$ are each independently —H, $C_1$-$C_6$ alkyl, or $C_1$-$C_6$ haloalkyl.

In one aspect, $R^{12}$, $R^{13}$, and $R^{14}$ are each and independently —H, halogen, cyano, hydroxy, —O($C_1$-$C_6$ alkyl), or optionally substituted $C_1$-$C_6$ alkyl; and $R^{15}$ is —H or optionally substituted $C_1$-$C_6$ alkyl.

In another aspect, $R^{12}$ and $R^{13}$ are each independently —H, halogen, hydroxy, $C_1$-$C_6$ alkyl, $C_1$-$C_6$ haloalkyl, or —O($C_1$-$C_6$ alkyl); and $R^{14}$ and $R^{15}$ are each independently —H, $C_1$-$C_6$ alkyl, or $C_1$-$C_6$ haloalkyl.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl). Typically, $R^{21}$, $R^{22}$, $R^{23}$, $R^{24}$, and $R^{25}$ are each independently —H, halogen, hydroxy, $C_1$-$C_6$ alkoxy, $C_1$-$C_6$ alkyl, or $C_1$-$C_6$ haloalkyl.

$J^A$, $J^B$, and $J^T$ are each and independently oxo or $J^C$; and $J^C$ are each and independently selected from the group consisting of halogen, cyano, M, $R^a$, or $R^a$-M. Optionally, two $J^T$, two $J^A$, two $J^B$, and two $J^C$, respectively, together with the atom(s) to which they are attached, independently form a 4-10-membered ring (e.g., 5-7-membered or 5-6-membered) that is optionally substituted with one or more instances of $J^A$.

M is independently selected from the group consisting of —$OR^b$, —$SR^b$, —S(O)$R^a$, —$SO_2R^a$, —$NR^bR^c$, —C(O)$R^a$, —C(=NR)$R^c$, —C(=NR)$NR^bR^c$, —NRC(=NR)$NR^bR^c$, —C(O)$OR^b$, —OC(O)$R^b$, —NRC(O)$R^b$, —C(O)$NR^bR^c$, —NRC(O)$NR^bR^c$, —NRC(O)$OR^b$, —OCON$R^bR^c$, —C(O)NR$CO_2R^b$, —NRC(O)NRC(O)$OR^b$, —C(O)NR(O$R^b$), —$OSO_2NR^bR^c$, —$SO_2NR^cR^b$, —$NRSO_2R^b$, —NR$SO_2NR^cR^b$, —P(O)(O$R^b$)$_2$, —OP(O)(O$R^b$)$_2$, —P(O)$_2$ $OR^b$ and —$CO_2SO_2R^b$.

Typically, $J^C$ is selected from the group consisting of halogen, cyano, $R^a$, —$OR^b$, —$SR^b$, —S(O)$R^a$, —$SO_2R^a$, —NH$R^c$, —C(O)$R^b$, —C(O)$OR^b$, —OC(O)$R^b$, —NHC(O)$R^b$, —C(O)NH$R^c$, —NHC(O)NH$R^c$, —NHC(O)$OR^b$, —OCONH$R^c$, —NHC(O)NHC(O)$OR^b$, —N($CH_3$)$R^c$, —N($CH_3$)C(O)$R^b$, —C(O)N($CH_3$)$R^c$, —N($CH_3$)C(O)NH$R^c$, —N($CH_3$)C(O)$OR^b$, —OCON($CH_3$)$R^c$, —C(O)NHCO$_2R^b$, —C(O)N($CH_3$)$CO_2R^b$, —N($CH_3$)C(O)NHC(O)$OR^b$, —NH$SO_2R^b$, —$SO_2$NH$R^b$, —$SO_2$N($CH_3$)$R^b$, and —N($CH_3$)$SO_2R^b$; or two $J^C$, respectively, together with the atom(s) to which they are attached, independently form an optionally substituted, 4-10-membered, non-aromatic ring.

In one aspect, $J^A$, $J^B$, $J^C$, and $J^T$ are each independently selected from the group consisting of halogen, cyano, $R^a$, —$OR^b$, —NH$R^c$, —C(O)$R^b$, —C(O)$OR^b$, —OC(O)$R^b$, —NHC(O)$R^b$, —C(O)NH$R^c$, —NHC(O)NH$R^c$, —NHC(O)$OR^b$, —OCONH$R^c$, —N($CH_3$)$R^c$, —N($CH_3$)C(O)$R^b$, —C(O)N($CH_3$)$R^c$, —N($CH_3$)C(O)NH$R^c$, —N($CH_3$)C(O)$OR^b$, —NH$SO_2R^b$, —$SO_2$NH$R^b$, —$SO_2$N($CH_3$)$R^b$, and —N($CH_3$)$SO_2R^b$; or optionally, two $J^T$, two $J^A$, two $J^B$, and two $J^C$, respectively, together with the atom(s) to which they are attached, independently form a 4-10-membered (or 5-7 membered, or 5-6 membered) ring that is optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and —O($C_1$-$C_4$ alkyl).

Typically, $J^A$ is halogen, cyano, hydroxy, oxo, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), —$CO_2$H, $C_3$-$C_8$ carbocyclic group, 4-8 membered heterocyclic group, phenyl, or 5-6 membered heteroaryl, wherein each of said carbocyclic, phenyl, heterocyclic, and heteroaryl groups is independently and optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl). Optionally, two $J^A$, together with the atom(s) to which they are attached, form an optionally substituted, 4-10-membered (or 5-7 membered, or 5-6 membered) ring.

Typically, $J^B$ and $J^C$ are each and independently halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, or —O($C_1$-$C_4$ alkyl). Optionally, two $J^B$ and two $J^C$, together with the atom(s) to which they are attached, independently form an optionally substituted, 4-10-membered (or 5-7 membered, or 5-6 membered) ring.

Typically, $J^T$ is halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, or —O($C_1$-$C_4$ alkyl). More typically, $J^T$ is halogen, cyano, hydroxy, $C_1$-$C_4$ alkyl, $C_1$-$C_4$ haloalkyl, and —O($C_1$-$C_4$ alkyl). Optionally, two $J^T$, together with the atom(s) to which they are attached, form an optionally substituted, 4-10-membered (or 5-7 membered, or 5-6 membered) ring.

Typically, the ring formed with two $J^T$, two $J^A$, two $J^B$, and two $J^C$ independently is an optionally substituted non-aromatic ring, such as carbocycle or heterocycle. More typically, the ring is an optionally substituted carbocycle.

$R^a$ is independently:

i) a $C_1$-$C_6$ aliphatic group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), $C_3$-$C_8$ carbocyclic group optionally substituted with one or more instances of $J^2$, 4-8 membered heterocyclic group optionally substituted with one or more instances of $J^2$, 5-10 membered heteroaryl group optionally substituted with one or more instances of $J^3$, and 6-10 membered aryl group optionally substituted with one or more instances of $J^3$;

ii) a $C_3$-$C_8$ carbocyclic group, or 4-8 membered heterocyclic group, each of which is optionally and independently substituted with one or more instances of $J^2$; or iii) a 5-10 membered heteroaryl group, or 6-10 membered aryl group, each of which is optionally and independently substituted with one or more instances of $J^3$; and $R^b$ and $R^c$ are each independently $R^a$ or H; or optionally, $R^b$ and $R^c$, together with the nitrogen atom(s) to which they are attached, each independently form a 4-8 membered heterocyclic group optionally substituted with one or more instances of $J^2$.

In one aspect, $R^a$ is independently: i) a $C_1$-$C_6$ alkyl group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), optionally substituted $C_3$-$C_8$ carbocyclic group, optionally substituted 4-8 membered heterocyclic group, optionally substituted 5-6 membered heteroaryl, and optionally substituted phenyl group; ii) an optionally substituted $C_3$-$C_8$ carbocyclic group; iii) optionally substituted 4-8 membered heterocyclic group; iv) an optionally substituted 5-6 membered heteroaryl group; v) or optionally substituted phenyl group; and $R^b$ and $R^c$ are each independently $R^a$ or —H; or optionally, $R^b$ and $R^c$, together with the nitrogen atom(s) to which they are attached, each independently form an optionally substituted, 4-8 membered heterocyclic group.

In another aspect, $R^a$ is independently: i) a $C_1$-$C_6$ alkyl group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), $C_3$-$C_8$ carbocycle, 4-8 membered heterocycle, 5-6 membered heteroaryl, and phenyl; ii) a $C_3$-$C_8$ carbocyclic group or 4-8 membered heterocyclic group, each of which is independently and optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl); or iii) a 5-6 membered heteroaryl group or phenyl group, each of which is independently and optionally substituted with one or more substituents selected from the group consisting of halogen, cyano, hydroxy, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$ ($C_1$-$C_4$ alkyl), $C_1$-$C_4$ alkyl, $C_1$-$C_4$ haloalkyl, and —O($C_1$-$C_4$ alkyl); and $R^b$ and $R^c$ are each independently $R^a$ or —H; or optionally, $R^b$ and $R^c$, together with the nitrogen atom(s) to which they are attached, each independently form a 4-8 membered heterocyclic group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl).

$R^t$ and $R^s$ are each independently —H, halogen, or $C_1$-$C_6$ alkyl optionally substituted with one or more instances of $J^1$, or optionally, $R^t$ and $R^s$, together with the carbon atom to which they are attached, form a cyclopropane ring optionally substituted with one or more instances of methyl. Typically, $R^t$ and $R^s$ are each independently —H, halogen, $C_1$-$C_6$ alkyl, or $C_1$-$C_6$ haloalkyl. More typically, $R^t$ and $R^s$ are each independently —H or $C_1$-$C_6$ alkyl.

R and R' are each independently —H or $C_1$-$C_6$ alkyl optionally and independently substituted with one or more instances of $J^1$, or optionally R and R', together with the nitrogen to which they are attached, form a 4-8 membered heterocyclic group optionally substituted with one or more instances of $J^2$. Typically, R and R' are each and independently —H or $C_{1-4}$ alkyl; or optionally $R^1$, together with R' and the nitrogen to which they are attached, form an optionally substituted, 4-8 membered heterocyclic group. More typically, R and R' are each and independently —H or —$CH_3$; or optionally $R^1$, together with R' and the nitrogen to which they are attached, form an optionally substituted, 4-8 membered heterocyclic group. More typically, R and R' are each and independently —H or —$CH_3$.

Each $J^1$ is independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), and phenyl;

Each $J^2$ is independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl);

Each of $J^3$ and $J^4$ is independently selected from the group consisting of halogen, cyano, hydroxy, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkyl, $C_1$-$C_4$ haloalkyl, and —O($C_1$-$C_4$ alkyl).

Each p is independently 1, 2, 3 or 4, and each k is independently 1, 2, 3 or 4. Typically, each of p and k independently is 1 or 2.

The second set of values of the variables of Structural Formula (I) is as follows:

X is —Cl, —Br, —F, —CN, or optionally substituted $C_1$-$C_6$ alkyl.

The remaining variables of Structural Formula (I) are each and independently as described above in the first set of values of the variables of Structural Formula (I).

The third set of values of the variables of Structural Formula (I) is as follows:

X is —Cl, —Br, —F, —CN, or optionally substituted $C_1$-$C_6$ alkyl.

$R^2$ is —H, —O($C_1$-$C_4$ alkyl), —$NH_2$, —NH($C_1$-$C_4$ alkyl), —N($C_1$-$C_4$alkyl)$_2$, —$CO_2$H, —$CO_2$($C_1$-$C_4$ alkyl), —C(O)

$NH_2$, —C(O)NH($C_1$-$C_4$ alkyl), —C(O)N($C_1$-$C_4$alkyl)$_2$, or optionally substituted $C_1$-$C_4$ alkyl.

The remaining variables of Structural Formula (I) are each and independently as described above in the first set of values of the variables of Structural Formula (I).

The fourth set of values of the variables of Structural Formula (I) is as follows:

Values of X and $R^2$ are each and independently as described above in the second or third set of values of the variables of Structural Formula (I).

$R^3$ is —H, —F, —Cl, —CN, —$NO_2$, —O($C_1$-$C_4$ alkyl), —$CO_2$H, —$CO_2$($C_1$-$C_4$alkyl), —C(O)$NH_2$, —C(O)NH($C_1$-$C_4$ alkyl), —C(O)N($C_1$-$C_4$alkyl)$_2$, or optionally substituted $C_1$-$C_4$ alkyl.

The fifth set of values of the variables of Structural Formula (I) is as follows:

Values of X, $R^2$, and $R^3$ are each and independently as described above in any one of the first through fourth sets of values of the variables of Structural Formula (I).

p and k are each and independently 1 or 2.

$R^t$ and $R^s$ are each independently —H, halogen, or $C_1$-$C_4$ alkyl.

The remaining variables of Structural Formula (I) are each and independently as described above in the first set of values of the variables of Structural Formula (I).

The sixth set of values of the variables of Structural Formula (I) is as follows:

Values of $R^2$, $R^3$, $R^t$, $R^s$, p, and k are each and independently as described above in any one of the first through fifth sets of values of the variables of Structural Formula (I).

X is —Cl, —Br, —F, —CN, $C_{1-4}$ alkyl, or $C_1$-$C_4$ haloalkyl.

The remaining variables of Structural Formula (I) are each and independently as described above in the first set of values of the variables of Structural Formula (I).

The seventh set of values of the variables of Structural Formula (I) is as follows:

Values of X, $R^3$, $R^t$, $R^s$, p, and k are each and independently as described above in any one of the first through sixth sets of values of the variables of Structural Formula (I).

$R^2$ is —H, —O($C_1$-$C_4$ alkyl), $C_1$-$C_4$ allyl, or $C_1$-$C_4$ haloalkyl.

The remaining variables of Structural Formula (I) are each and independently as described above in the first set of values of the variables of Structural Formula (I).

The eighth set of values of the variables of Structural Formula (I) is as follows:

Values of X, $R^2$, $R^t$, $R^s$, p, and k are each and independently as described above in any one of the first through seventh sets of values of the variables of Structural Formula (I).

$R^3$ is —H, —F, —Cl, —CN, —O($C_1$-$C_4$ alkyl), $C_1$-$C_4$ alkyl, or $C_1$-$C_4$ haloalkyl.

The remaining variables of Structural Formula (I) are each and independently as described above in the first set of values of the variables of Structural Formula (I).

The ninth set of values of the variables of Structural Formula (I) is as follows:

Values of X, $R^1$, $R^2$, $R^3$, $R^t$, $R^s$, p, and k are each and independently as described above in any one of the first through eighth sets of values of the variables of Structural Formula (I).

Ring T is an optionally substituted $C_5$-$C_{10}$ carbocyclic group or an optionally substituted 5-10 membered heterocarbocyclic group.

The remaining variables of Structural Formula (I) are each and independently as described above in the first set of values of the variables of Structural Formula (I).

The tenth set of values of the variables of Structural Formula (I) is as follows:

Values of X, Ring T, $R^1$, $R^2$, $R^t$, $R^s$, p, and k are each and independently as described above in any one of the first through ninth sets of values of the variables of Structural Formula (I).

$R^3$ is —F, —Cl, —CN, —O($C_1$-$C_4$ alkyl), $C_1$-$C_4$ alkyl, or $C_1$-$C_4$ haloalkyl.

The remaining variables of Structural Formula (I) are each and independently as described above in the first set of values of the variables of Structural Formula (I).

The eleventh set of values of the variables of Structural Formula (I) is as follows:

Values of Ring T, $R^1$, $R^2$, $R^3$, $R^t$, $R^s$, p, and k are each and independently as described above in any one of the first through tenth sets of values of the variables of Structural Formula (I).

X is —Cl, —F, —Br, —CN, —$CH_3$, or —$CF_3$.

The remaining variables of Structural Formula (I) are each and independently as described above in the first set of values of the variables of Structural Formula (I).

The twelfth set of values of the variables of Structural Formula (I) is as follows:

Values of Ring T, X, $R^1$, $R^2$, $R^t$, $R^s$, p, and k are each and independently as described above in any one of the first through eleventh sets of values of the variables of Structural Formula (I).

$R^3$ is —F, —Cl, —CN, or $C_1$-$C_4$ haloalkyl.

The remaining variables of Structural Formula (I) are each and independently as described above in the first set of values of the variables of Structural Formula (I).

The thirteenth set of values of the variables of Structural Formula (I) is as follows:

Values of Ring T, X, $R^1$, $R^2$, $R^3$, $R^t$, $R^s$, p, and k are each and independently as described above in any one of the first through twelfth sets of values of the variables of Structural Formula (I).

$Q^1$ is —C(O)—, —$CO_2$—, —OC(O)—, —O(CR'R$^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —B(O)$_2$—, or —(CR'R$^s$)$_p$—$Y^1$—.

$Y^1$ is —C(O)—, —$CO_2$—, —OC(O)—, —O(CR'R$^s$)$_k$—C(O)O—, —C(O)NR'—, C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —B(O)$_2$—, or —$NRSO_2$NR'—.

The remaining variables of Structural Formula (I) are each and independently as described above in the first set of values of the variables of Structural Formula (I).

The fourteenth set of values of the variables of Structural Formula (I) is as follows:

Values of Ring T, X, $R^1$, $R^2$, $R^3$, $R^t$, $R^s$, p, and k are each and independently as described above in any one of the first through thirteenth sets of values of the variables of Structural Formula (I).

$Q^1$ is —$CO_2$—, —O(CR'R$^s$)$_k$—C(O)O—, —P(O)(OR)O—, —OP(O)(OR$^a$)O—, —P(O)$_2$O—, —$CO_2SO_2$—, or —(CR'R$^s$)$_p$—$Y^1$—.

$Y^1$ is —$CO_2$—, —O(CR'R$^s$)$_k$—C(O)O—, —P(O)(OR)O—, —OP(O)(OR$^a$)O—, —P(O)$_2$O—, or —$CO_2SO_2$—.

The remaining variables of Structural Formula (I) are each and independently as described above in the first set of values of the variables of Structural Formula (I).

The fifteenth set of values of the variables of Structural Formula (I) is as follows:

Values of Ring T, X, $Q^1$, $Y^1$, $R^2$, $R^3$, $R^t$, $R^s$, p, and k are each and independently as described above in any one of the first through fourteenth sets of values of the variables of Structural Formula (I).

$R^1$ is independently i) —H; ii) a $C_1$-$C_6$-aliphatic group optionally substituted with one or more instances of $J^A$; iii) a $C_3$-$C_8$ carbocyclic group or 4-8 membered heterocyclic group, each of which is optionally and independently substituted with one or more instances of $J^B$; iv) a phenyl group or 5-6 membered heteroaryl group, each of which is optionally and independently substituted with one or more instances off; or optionally $R^1$, together with R' and the nitrogen to which they are attached, form a 4-8 membered heterocyclic group optionally substituted with one or more instances of $J^2$.

$J^A$ and $J^B$ are each independently oxo or $J^C$; and $J^C$ is selected from the group consisting of halogen, cyano, $R^a$, —$OR^b$, —$SR^b$, —$S(O)R^a$, —$SO_2R^a$, —$NHR^c$, —$C(O)R^a$, —$C(O)OR^b$, —$OC(O)R^b$, —$NHC(O)R^b$, —$C(O)NHR^c$, —$NHC(O)NHR^c$, —$NHC(O)OR^b$, —$OCONHR^c$, —$NHC(O)NHC(O)OR^b$, —$N(CH_3)R^c$, —$N(CH_3)C(O)R^b$, —$C(O)N(CH_3)R^c$, —$N(CH_3)C(O)NHR^c$, —$N(CH_3)C(O)OR^b$, —$OCON(CH_3)R^c$, —$C(O)NHCO_2R^b$, —$C(O)N(CH_3)CO_2R^b$, —$N(CH_3)C(O)NHC(O)OR^b$, —$NHSO_2R^b$, —$SO_2NHR^b$, —$SO_2N(CH_3)R^b$, and —$N(CH_3)SO_2R^b$; or optionally, two $J^A$, two $J^B$, and two $J^C$, respectively, together with the atom(s) to which they are attached, independently form an optionally substituted, 4-10-membered, non-aromatic ring.

The remaining variables of Structural Formula (I) are each and independently as described above in the first set of values of the variables of Structural Formula (I).

The sixteenth set of values of the variables of Structural Formula (I) is as follows:

Values of Ring T, X, $Q^1$, $Y^1$, $R^1$, $R^2$, $R^3$, $J^A$, $J^B$, $J^C$, R, R', $R^1$, $R^s$, p, and k are each and independently as described above in any one of the first through fifteenth sets of values of the variables of Structural Formula (I).

$R^a$ is independently: i) a $C_1$-$C_6$ alkyl group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), —O($C_1$-$C_4$ alkyl), optionally substituted $C_3$-$C_8$ carbocyclic group, optionally substituted 4-8 membered heterocyclic group, optionally substituted 5-6 membered heteroaryl, and optionally substituted phenyl group; ii) an optionally substituted $C_3$-$C_8$ carbocyclic group; iii) optionally substituted 4-8 membered heterocyclic group; iv) an optionally substituted 5-6 membered heteroaryl group; v) or optionally substituted phenyl group;

$R^b$ and $R^c$ are each independently $R^a$ or H; or optionally, $R^b$ and $R^c$, together with the nitrogen atom(s) to which they are attached, each independently form an optionally substituted, 4-8 membered heterocyclic group; and R and R' are each and independently —H or $C_{1-4}$ alkyl, or optionally R and R', together with the nitrogen to which they are attached, form an optionally substituted 4-8 membered heterocyclic group, or optionally R', together with $R^1$ and the nitrogen to which they are attached, form an optionally substituted 4-8 membered heterocyclic group.

The remaining variables of Structural Formula (I) are each and independently as described above in the first set of values of the variables of Structural Formula (I).

The seventeenth set of values of the variables of Structural Formula (I) is as follows:

Values of Ring T, $Q^1$, $Y^1$, $R^1$, $R^2$, $R^3$, $J^A$, $J^B$, $J^C$, R, R', $R^a$, $R^b$, $R^c$, $R^t$, $R^s$, p, and k are each and independently as described above in any one of the first through sixteenth sets of values of the variables of Structural Formula (I).

X is —Cl, —F, —CN, or —$CF_3$.

The remaining variables of Structural Formula (I) are each and independently as described above in the first set of values of the variables of Structural Formula (I).

The eighteenth set of values of the variables of Structural Formula (I) is as follows:

Values of Ring T, $Q^1$, $Y^1$, $R^1$, $R^2$, $R^3$, $J^A$, $J^B$, $J^C$, R, R', $R^a$, $R^b$, $R^c$, $R^t$, $R^s$, p, and k are each and independently as described above in any one of the first through seventeenth sets of values of the variables of Structural Formula (I).

X is —Cl or —F.

The remaining variables of Structural Formula (I) are each and independently as described above in the first set of values of the variables of Structural Formula (I).

The nineteenth set of values of the variables of Structural Formula (I) is as follows:

Values of X, $Q^1$, $Y^1$, $R^1$, $R^2$, $R^3$, $J^A$, $J^B$, $J^C$, R, R', $R^a$, $R^b$, $R^c$, $R^t$, $R^s$, p, and k are each and independently as described above in any one of the first through eighteenth sets of values of the variables of Structural Formula (I).

Ring T is an optionally substituted, bridged, $C_5$-$C_{10}$ carbocyclic group.

The remaining variables of Structural Formula (I) are each and independently as described above in the first set of values of the variables of Structural Formula (I).

The twenty first set of values of the variables of Structural Formula (I) is as follows:

Values of X, $Q^1$, $Y^1$, $R^1$, $R^2$, $R^3$, $J^A$, $J^B$, $J^C$, R, R', $R^a$, $R^b$, $R^c$, $R^t$, $R^s$, p, and k are each and independently as described above in any one of the first through eighteenth sets of values of the variables of Structural Formula (I).

Ring T is an optionally substituted, monocyclic, $C_5$-$C_8$ carbocyclic group.

The remaining variables of Structural Formula (I) are each and independently as described above in the first set of values of the variables of Structural Formula (I).

The twenty second set of values of the variables of Structural Formula (I) is as follows:

Values of X, $Q^1$, $Y^1$, $R^1$, $R^2$, $R^3$, $J^A$, $J^B$, $J^C$, R, R', $R^a$, $R^b$, $R^c$, $R^t$, $R^s$, p, and k are each and independently as described above in any one of the first through eighteenth sets of values of the variables of Structural Formula (I).

Ring T is:

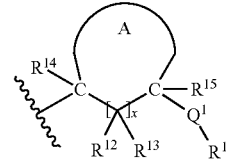

and wherein:

Ring A is a 5-10 membered carbocyclic group or 5-10 membered heterocyclic group, each of which is optionally further substituted with one or more instances of $J^T$; or optionally Ring A and $R^{15}$, Ring A and $R^{14}$, or Ring A and $R^{13}$ independently and optionally form a 4-10 membered, bridged ring optionally further substituted with one or more instances of $J^T$; and each of $R^{12}$, $R^{13}$, and $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —CO$_2$H, or —CO$_2$($C_1$-$C_6$ alkyl), wherein each said $C_1$-$C_6$ alkyl is optionally and independently substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl);

each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl); and x is 0, 1 or 2.

The remaining variables of Structural Formula (I) are each and independently as described above in the first set of values of the variables of Structural Formula (I).

The twenty third set of values of the variables of Structural Formula (I) is as follows:

Values of Ring T, X, $Q^1$, $Y^1$, $R^1$, $R^2$, $R^3$, $R^{12}$, $R^{13}$, $R^{14}$, $R^{15}$, R, R', $R^a$, $R^b$, $R^c$, $R^t$, $R^s$, p, k, and x are each and independently as described above in any one of the first through twenty second sets of values of the variables of Structural Formula (I).

$J^A$, $J^B$, $J^C$, and $J^T$ are each independently selected from the group consisting of halogen, cyano, $R^a$, —$OR^b$, —$NHR^c$, —C(O)$R^b$, —C(O)O$R^b$, —OC(O)$R^b$, —NHC(O)$R^b$, —C(O)NH$R^c$, —NHC(O)NH$R^c$, —NHC(O)O$R^b$, —OCONH$R^c$, —N(CH$_3$)$R^c$, —N(CH$_3$)C(O)$R^b$, —C(O)N(CH$_3$)$R^c$, —N(CH$_3$)C(O)NH$R^c$, —N(CH$_3$)C(O)O$R^b$, —NHSO$_2$$R^b$, —SO$_2$NH$R^b$, —SO$_2$N(CH$_3$)$R^b$, and —N(CH$_3$)SO$_2$$R^b$; or optionally, two $J^T$, two $J^A$, two $J^B$, and two $J^C$, respectively, together with the atom(s) to which they are attached, independently form a 4-10-membered ring that is optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl).

The remaining variables of Structural Formula (I) are each and independently as described above in the first set of values of the variables of Structural Formula (I).

The twenty fourth set of values of the variables of Structural Formula (I) is as follows:

Values of Ring T, $J^A$, $J^B$, $J^C$, $J^T$, X, $Q^1$, $Y^1$, $R^1$, $R^2$, $R^3$, $R^{12}$, $R^{13}$, $R^{14}$, $R^{15}$, R, R', $R^t$, $R^s$, p, k, and x are each and independently as described above in any one of the first through twenty third sets of values of the variables of Structural Formula (I).

$R^a$ is independently: i) a $C_1$-$C_6$ alkyl group optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), —O($C_1$-$C_4$ alkyl), $C_3$-$C_8$ carbocycle, 4-8 membered heterocycle, 5-6 membered heteroaryl, and phenyl; ii) a $C_3$-$C_8$ carbocyclic group or 4-8 membered heterocyclic group, each of which is independently and optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl); or iii) a 5-6 membered heteroaryl group or phenyl group, each of which is independently and optionally substituted with one or more substituents selected from the group consisting of halogen, cyano, hydroxy, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl); and $R^b$ and $R^c$ are each independently $R^a$ or —H; or optionally, $R^b$ and $R^c$, together with the nitrogen atom(s) to which they are attached, each independently form a 4-8 membered heterocyclic group optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl).

The remaining variables of Structural Formula (I) are each and independently as described above in the first set of values of the variables of Structural Formula (I).

The twenty fifth set of values of the variables of Structural Formula (I) is as follows:

Values of Ring T, $J^A$, $J^B$, $J^C$, $J^T$, X, $R^1$, $R^2$, $R^3$, $R^{12}$, $R^{13}$, $R^{14}$, $R^{15}$, $R^a$, $R^b$, $R^c$, R, R', p, k, and x are each and independently as described above in any one of the first through twenty third sets of values of the variables of Structural Formula (I).

$Q^1$ is —C(O)—, —CO$_2$, —OC(O)—, —O(C$R^t$$R^s$)$_k$—C(O)O—, —C(O)NR'—, —C(O)NRC(O)O—, —NRC(O)—, —NRC(O)NR'—, —NRCO$_2$—, —OC(O)NR'—, or —(C$R^t$$R^s$)$_p$—$Y^1$—.

$Y^1$ is —C(O)—, —CO$_2$—, —OC(O)—, —O(C$R^t$$R^s$)$_k$—C(O)O—, —C(O)NR'—, —C(O)NRC(O)O—, —NRC(O)—, —NRC(O)NR'—, —NRCO$_2$—, or —OC(O)NR'—.

The remaining variables of Structural Formula (I) are each and independently as described above in the first set of values of the variables of Structural Formula (I).

The twenty sixth set of values of the variables of Structural Formula (I) is as follows:

Ring T is as described above in the twenty second set of values of the variables of Structural Formula (I).

$R^{12}$, $R^{13}$, and $R^{14}$ are each and independently —H, halogen, cyano, hydroxy, —O($C_1$-$C_6$ alkyl), or optionally substituted $C_1$-$C_6$ alkyl.

$R^{15}$ is —H or optionally substituted $C_1$-$C_6$ alkyl.

$R^t$ and $R^s$ are each independently —H, halogen, $C_1$-$C_6$ alkyl, or $C_1$-$C_6$ haloalkyl.

Values of $Q^1$, $Y^1$, $J^A$, $J^B$, $J^C$, $J^T$, X, $R^1$, $R^2$, $R^3$, $R^{12}$, $R^{13}$, $R^{14}$, $R^{15}$, $R^a$, $R^b$, $R^c$, R, R', p, and k are each and independently as described above in any one of the first through twenty fifth sets of values of the variables of Structural Formula (I).

The remaining variables of Structural Formula (I) are each and independently as described above in the first set of values of the variables of Structural Formula (I).

The twenty seventh set of values of the variables of Structural Formula (I) is as follows:

Ring T is as described above in the twenty second set of values of the variables of Structural Formula (I).

Values of Ring X, $Q^1$, $Y^1$, $R^1$, $R^2$, $R^3$, $R^a$, $R^b$, $R^c$, R, R', $J^A$, $J^B$, $J^C$, or $J^T$, p, and k are each and independently as described above in any one of the first through twenty fifth sets of values of the variables of Structural Formula (I).

$R^{12}$ and $R^{13}$ are each independently —H, halogen, hydroxy, $C_1$-$C_6$ alkyl, $C_1$-$C_6$ haloalkyl, or —O($C_1$-$C_6$ alkyl).

$R^{14}$ and $R^{15}$ are each independently —H, $C_1$-$C_6$ alkyl, or $C_1$-$C_6$ haloalkyl.

$R^t$ and $R^s$ are each independently —H or $C_1$-$C_6$ alkyl.

The remaining variables of Structural Formula (I) are each and independently as described above in the first set of values of the variables of Structural Formula (I).

The twenty eighth set of values of the variables of Structural Formula (I) is as follows:

Values of Ring T, X, $Q^1$, $Y^1$, $R^2$, $R^3$, $R^{12}$, $R^{13}$, $R^{14}$, $R^{15}$, $R^s$, $R^t$, $R^a$, $R^b$, $R^c$, R, R', $J^A$, $J^B$, $J^C$, or $J^T$, p, k and x are each and independently as described above in any one of the first through twenty seventh sets of values of the variables of Structural Formula (I).

$R^1$ is independently: i) —H; ii) a $C_1$-$C_6$ aliphatic group optionally substituted with one or more substituents independently selected from the group consisting of halogen, cyano, hydroxy, oxo, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O) ($C_1$-$C_4$ alkyl), —C(O)O($C_1$-$C_4$ alkyl), —$CO_2H$, $C_3$-$C_8$ carbocyclic group, 4-8 membered heterocyclic group, phenyl, and 5-6 membered heteroaryl; iii) a $C_3$-$C_7$ carbocyclic group; iv) a 4-7 membered heterocyclic group; v) a phenyl group; or yl) a 5-6 membered heteroaryl group; or optionally $R^1$, together with R' and the nitrogen to which they are attached, form an optionally substituted, 4-8 membered heterocyclic group; and each of said carbocyclic, phenyl, heterocyclic, and heteroaryl groups represented by $R^1$ and for the substituents of the $C_1$-$C_6$-aliphatic group represented by $R^1$, and said heterocyclic group formed with $R^1$ and R' is independently and optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl).

The remaining variables of Structural Formula (I) are each and independently as described above in the first set of values of the variables of Structural Formula (I).

The twenty ninth set of values of the variables of Structural Formula (I) is as follows:

Ring T is as described above in the twenty second set of values of the variables of Structural Formula (I), wherein Ring A is a carbocyclic group or heterocyclic group, each of which is optionally and independently further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO ($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl); or Ring A and $R^{15}$, Ring A and $R^{14}$, or Ring A and $R^{13}$ independently and optionally form a bridged carbocyclic group or bridged heterocyclic group, each of which is optionally and independently substituted with one or more substituents selected from the group consisting of halogen, cyano, hydroxy, oxo, —$NH_2$, —NH ($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl).

Values of X, $Q^1$, $Y^1$, $R^1$, $R^2$, $R^3$, $R^{12}$, $R^{13}$, $R^{14}$, $R^{15}$, $R^s$, $R^t$, $R^a$, $R^b$, $R^c$, R, R', $J^A$, $J^B$, $J^C$, p, k, and x are each and independently as described above in any one of the first through twenty eighth sets of values of the variables of Structural Formula (I).

The remaining variables of Structural Formula (I) are each and independently as described above in the first set of values of the variables of Structural Formula (I).

The thirtieth set of values of the variables of Structural Formula (I) is as follows:

Values of X, $Q^1$, $Y^1$, $R^1$, $R^2$, $R^3$, $R^{12}$, $R^{13}$, $R^{14}$, $R^{15}$, $R^s$, $R^t$, $R^a$, $R^b$, $R^c$, R, R', $J^A$, $J^B$, $J^C$, p, k and x are each and independently as described above in any one of the first through twenty eighth sets of values of the variables of Structural Formula (I).

Ring T is as described above in the twenty second set of values of the variables of Structural Formula (I), wherein Ring A and $R^{15}$, Ring A and $R^{14}$, or Ring A and $R^{13}$ independently form an optionally substituted, 4-10 membered, bridged ring.

The remaining variables of Structural Formula (I) are each and independently as described above in the first set of values of the variables of Structural Formula (I).

The thirty first set of values of the variables of Structural Formula (I) is as follows:

Values of X, $Q^1$, $Y^1$, $R^1$, $R^2$, $R^3$, $R^s$, $R^t$, $R^a$, $R^b$, $R^c$, R, R', $J^A$, $J^B$, $J^C$, p, and k, are each and independently as described above in any one of the first through twenty eighth sets of values of the variables of Structural Formula (I).

Ring T is:

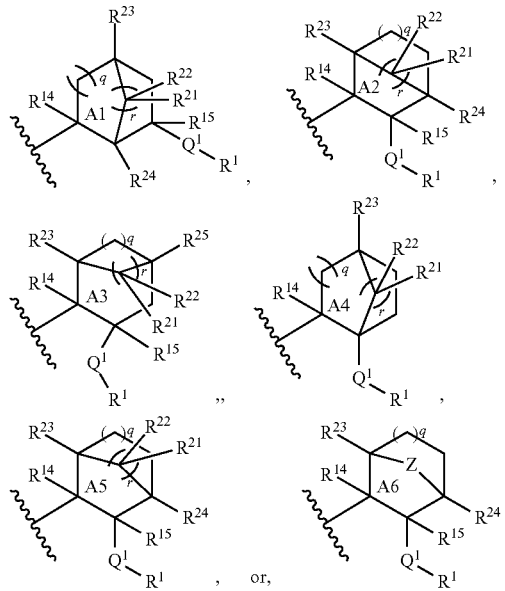

wherein:

each of Rings A1-A5 is independently a 5-10 membered, bridged carbocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl);

Ring A6 is a 5-10 membered, bridged heterocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl);

each $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —$CO_2H$, or —$CO_2$($C_1$-$C_6$ alkyl), wherein each said $C_1$-$C_6$ alkyl is optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl);

each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

R$^{21}$, R$^{22}$, R$^{23}$, R$^{24}$, and R$^{25}$ are each independently —H, halogen, —OH, C$_1$-C$_6$ alkoxy, or C$_1$-C$_6$ alkyl optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl);

Z is —O—, —S—, or —NR$^g$—;

R$^g$ is —H or C$_1$-C$_6$ alkyl optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

q is 0, 1 or 2; and r is 1 or 2.

The remaining variables of Structural Formula (I) are each and independently as described above in the first set of values of the variables of Structural Formula (I).

The thirty second set of values of the variables of Structural Formula (I) is as follows:

Values of Ring T are each and independently as described above in the thirty first set of values of the variables of Structural Formula (I), wherein R$^{14}$ and each R$^{15}$ are each independently —H, C$_1$-C$_6$ alkyl, or C$_1$-C$_6$ haloalkyl; and R$^{21}$, R$^{22}$, R$^{23}$, R$^{24}$, and R$^{25}$ are each independently —H, halogen, hydroxy, C$_1$-C$_6$ alkoxy, C$_1$-C$_6$ alkyl, or C$_1$-C$_6$ haloalkyl.

Values of X, Q$^1$, Y$^1$, R$^1$, R$^2$, R$^3$, R$^s$, R$^t$, R$^a$, R$^b$, R$^c$, R, R', J$^A$, J$^B$, J$^C$, p, and k are each and independently as described above in any one of the first through the twenty eighth sets of values of the variables of Structural Formula (I).

The remaining variables of Structural Formula (I) are each and independently as described above in the first set of values of the variables of Structural Formula (I).

The thirty third set of values of the variables of Structural Formula (I) is as follows:

Values of Ring T are each and independently as described above in the thirty first set of values of the variables of Structural Formula (I), wherein:

R$^{14}$, R$^{15}$, R$^{21}$, R$^{22}$, R$^{23}$, R$^{24}$, and R$^{25}$ are each independently as described above in the thirty first or thirty second set of values of the variables of Structural Formula (I);

Z is —O— or —NR$^g$—; and

R$^g$ is —H, C$_1$-C$_6$ alkyl, or C$_1$-C$_6$ haloalkyl.

Values of X, Q$^1$, Y$^1$, R$^1$, R$^2$, R$^3$, R$^s$, R$^t$, R$^a$, R$^b$, R$^c$, R, R', J$^A$, J$^B$, J$^C$, p, and k are each and independently as described above in any one of the first through twenty eighth sets of values of the variables of Structural Formula (I).

The remaining variables of Structural Formula (I) are each and independently as described above in the first set of values of the variables of Structural Formula (I).

The thirty fourth set of values of the variables of Structural Formula (I) is as follows:

Values of Ring T are each and independently as described above in the thirty first set of values of the variables of Structural Formula (I), wherein:

R$^{14}$, R$^{15}$, R$^{21}$, R$^{22}$, R$^{23}$, R$^{24}$, and R$^{25}$ are each independently as described above in the thirty first or thirty second set of values of the variables of Structural Formula (I);

Z is —O— or —NR$^g$—; and

R$^g$ is —H, C$_1$-C$_6$ alkyl, or C$_1$-C$_6$ haloalkyl.

Values of X, R$^1$, R$^2$, R$^3$, R$^s$, R$^t$, R$^a$, R$^b$, R$^c$, R, R', J$^A$, J$^B$, and J$^C$ are each and independently as described above in any one of the first through twenty eighth sets of values of the variables of Structural Formula (I).

Q$^1$ is independently —C(O)—, —C(O)O—, —NRC(O)—, —C(O)NR—, —NRC(O)NR'—, or —(CH$_2$)$_{1,2}$—Y$^1$—; and Y$^1$ is independently —C(O)—, —C(O)O—, —NRC(O)—, —C(O)NR—, or —NRC(O)NR'—.

The remaining variables of Structural Formula (I) are each and independently as described above in the first set of values of the variables of Structural Formula (I).

The thirty fifth set of values of the variables of Structural Formula (I) is as follows:

Values of Ring T are each and independently as described above in the thirty first set of values of the variables of Structural Formula (I), wherein:

R$^{14}$, R$^{15}$, R$^{21}$, R$^{22}$, R$^{23}$, R$^{24}$, and R$^{25}$ are each independently as described above in the thirty first or thirty second set of values of the variables of Structural Formula (I);

Z is —O— or —NR$^g$—; and

R$^g$ is —H, C$_1$-C$_6$ alkyl, or C$_1$-C$_6$ haloalkyl.

Values of X, R$^1$, R$^2$, R$^3$, R$^s$, R$^t$, R$^a$, R$^b$, R$^c$, R, R', J$^A$, J$^B$, and J$^C$ are each and independently as described above in any one of the first through twenty eighth sets of values of the variables of Structural Formula (I).

Q$^1$ is independently —C(O)O—, —NRC(O)—, —C(O)NR—, or —NRC(O)NR'—.

The remaining variables of Structural Formula (I) are each and independently as described above in the first set of values of the variables of Structural Formula (I).

The thirty sixth set of values of the variables of Structural Formula (I) is as follows:

Values of Ring T are each and independently as described above in the thirty first set of values of the variables of Structural Formula (I), wherein:

R$^{14}$, R$^{15}$, R$^{21}$, R$^{22}$, R$^{23}$, R$^{24}$, and R$^{25}$ are each independently as described above in the thirty first or thirty second set of values of the variables of Structural Formula (I);

Z is —O— or —NR$^g$—; and

R$^g$ is —H, C$_1$-C$_6$ alkyl, or C$_1$-C$_6$ haloalkyl.

Values of X, R$^1$, R$^2$, R$^3$, R$^s$, R$^t$, R$^a$, R$^b$, R$^c$, J$^A$, J$^B$, and J$^C$ are each and independently as described above i in any one of the first through twenty eighth sets of values of the variables of Structural Formula (I).

Q$^1$ is independently —C(O)O—, —NRC(O)—, —C(O)NR—, or —NRC(O)NR'—.

R and R' are each and independently —H or —CH$_3$.

The remaining variables of Structural Formula (I) are each and independently as described above in the first set of values of the variables of Structural Formula (I).

The thirty seventh set of values of the variables of Structural Formula (I) is as follows:

Values of Ring T are each and independently as described above in the thirty first set of values of the variables of Structural Formula (I), wherein:

R$^{14}$, R$^{15}$, R$^{21}$, R$^{22}$, R$^{23}$, R$^{24}$, and R$^{25}$ are each independently as described above in the thirty first or thirty second set of values of the variables of Structural Formula (I);

Z is —O— or —NR$^g$—; and

R$^g$ is —H, C$_1$-C$_6$ alkyl, or C$_1$-C$_6$ haloalkyl.

Values of X, R$^1$, R$^2$, R$^3$, R$^s$, R$^t$, R$^a$, R$^b$, R$^c$, J$^A$, J$^B$, and J$^C$ are each and independently as described above i in any one of the first through twenty eighth sets of values of the variables of Structural Formula (I).

Q$^1$ is independently —C(O)O—, —NHC(O)—, —C(O)NH—, or —NHC(O)NH—.

The remaining variables of Structural Formula (I) are each and independently as described above in the first set of values of the variables of Structural Formula (I).

The thirty eighth set of values of the variables of Structural Formula (I) is as follows:

Ring T is:

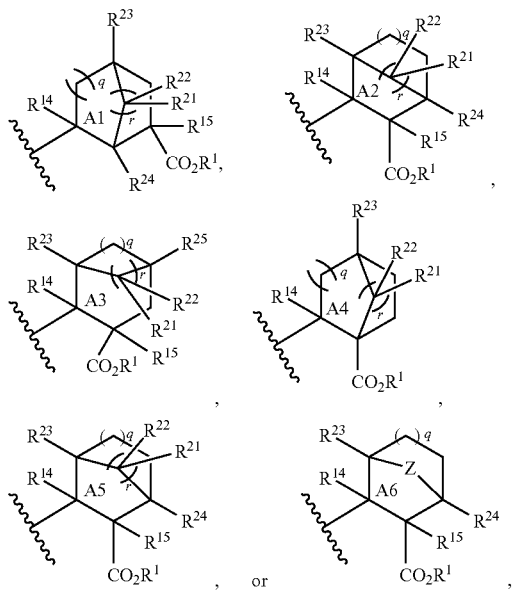

wherein each of Rings A1-A6 is independently and optionally further substituted with one or more substituents selected from the group consisting of halogen, cyano, hydroxy, $C_1$-$C_4$ alkyl, $C_1$-$C_4$ haloalkyl, and —O($C_1$-$C_4$ alkyl).

Values of $R^{14}$, $R^{15}$, $R^{21}$, $R^{22}$, $R^{23}$, $R^{24}$, and $R^{25}$ are each and independently as described above in the thirty first or thirty second set of values of the variables of Structural Formula (I).

Values of Z and $R^g$ are each and independently as described above in the thirty third set of values of the variables of Structural Formula (I).

Values of X, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth sets of values of the variables of Structural Formula (I).

The remaining variables of Structural Formula (I) are each and independently as described above in the first set of values of the variables of Structural Formula (I).

The thirty ninth set of values of the variables of Structural Formula (I) is as follows:

Values of Ring T, Z and $R^g$ are each and independently as described above in the thirty eighth set of values of the variables of Structural Formula (I).

$R^{14}$ and each $R^{15}$ are each independently —H or $C_{1-6}$ alkyl; and $R^{21}$, $R^{22}$, $R^{23}$, $R^{24}$, and $R^{25}$ are each independently —H or $C_{1-6}$ alkyl.

Values of X, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth sets of values of the variables of Structural Formula (I).

The remaining variables of Structural Formula (I) are each and independently as described above in the first set of values of the variables of Structural Formula (I).

The fortieth set of values of the variables of Structural Formula (I) is as follows:

Values of Ring T, Z and $R^g$ are each and independently as described above in the thirty eighth set of values of the variables of Structural Formula (I).

$R^{14}$, $R^{15}$, $R^{21}$, $R^{22}$, $R^{23}$, $R^{24}$, and $R^{25}$ are each independently —H.

Values of X, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth sets of the variables of Structural Formula (I).

The remaining variables of Structural Formula (I) are each and independently as described above in the first set of values of the variables of Structural Formula (I).

The fortieth first set of values of the variables of Structural Formula (I) is as follows:

Ring T is selected from:

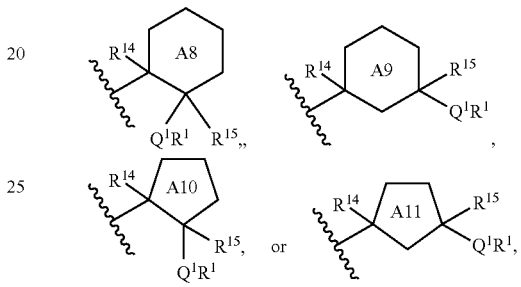

wherein:

each of Rings A8-A11 is independently and optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl).

Each $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —$CO_2H$, or —$CO_2$($C_1$-$C_6$ alkyl), wherein each said $C_1$-$C_6$ alkyl is optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl); and Each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl).

Values of X, $Q^1$, $Y^1$, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth sets of the variables of Structural Formula (I).

The remaining variables of Structural Formula (I) are each and independently as described above in the first set of values of the variables of Structural Formula (I).

The forty second set of values of the variables of Structural Formula (I) is as follows:

Ring T, $R^{14}$, $R^{15}$ are each and independently as described above in the forty first set of values of the variables of Structural Formula (I).

$Q^1$ is independently —C(O)—, —C(O)O—, —NRC(O)—, —C(O)NR—, —NRC(O)NR'—, or —(CH$_2$)$_{1,2}$—Y$^1$—.

$Y^1$ is independently —C(O)—, —C(O)O—, —NRC(O)—, —C(O)NR—, or —NRC(O)NR'—.

Values of X, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth sets of the variables of Structural Formula (I).

The remaining variables of Structural Formula (I) are each and independently as described above in the first set of values of the variables of Structural Formula (I).

The forty third set of values of the variables of Structural Formula (I) is as follows:

Ring T is as described above in the forty first set of values of the variables of Structural Formula (I), wherein each of Rings A8-A11 is independently and optionally substituted with one or more substituents selected from the group consisting of halogen, cyano, hydroxy, $C_1$-$C_4$ alkyl, $C_1$-$C_4$ haloalkyl, and —O($C_1$-$C_4$ alkyl).

$R^{14}$ and each $R^{15}$ are each independently —H or $C_{1-6}$ alkyl.

Values of X, $Q^1$, $Y^1$, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth, and forty second sets of the variables of Structural Formula (I).

The remaining variables of Structural Formula (I) are each and independently as described above in the first set of values of the variables of Structural Formula (I).

The forty third set of values of the variables of Structural Formula (I) is as follows:

Ring T, $R^{14}$, and $R^{15}$ are each and independently as described above in the forty first or forty third set of values of the variables of Structural Formula (I).

Values of X, $Q^1$, $Y^1$, $R^1$, $R^2$, $R^3$, $R^s$, $R^t$, $R^a$, $R^b$, $R^c$, R, R', $J^A$, $J^B$, and $J^C$ are each and independently as described above in any one of the first through the twenty eighth, and forty second sets of the variables of Structural Formula (I).

R and R' are each and independently —H or —CH$_3$.

The remaining variables of Structural Formula (I) are each and independently as described above in the first set of values of the variables of Structural Formula (I).

The forty fourth set of values of the variables of Structural Formula (I) is as follows:

Ring T, $R^{14}$, and $R^{15}$ are each and independently as described above in the forty first or forty third set of values of the variables of Structural Formula (I).

Values of X, $R^1$, $R^2$, $R^3$, $R^s$, $R^t$, $R^a$, $R^b$, $R^c$, $J^A$, $J^B$, and $J^C$ are each and independently as described above in any one of the first through the twenty eighth, and forty second sets of the variables of Structural Formula (I).

$Q^1$ is independently —NRC(O)—, —C(O)NR—, or —NRC(O)NR'—.

R and R' are each and independently —H or —CH$_3$.

The remaining variables of Structural Formula (I) are each and independently as described above in the first set of values of the variables of Structural Formula (I).

The forty fifth set of values of the variables of Structural Formula (I) is as follows:

Ring T, $R^{14}$, and $R^{15}$ are each and independently as described above in the forty first or forty third set of values of the variables of Structural Formula (I).

Values of X, $R^2$, $R^3$, $R^s$, $R^t$, $R^a$, $R^b$, $R^c$, $J^A$, $J^B$, and $J^C$ are each and independently as described above in any one of the first through the twenty eighth, and forty second sets of the variables of Structural Formula (I).

R and R' are each and independently —H or —CH$_3$; and $R^1$ is independently a 4-7 membered heterocyclic group, a phenyl group, or a 5-6 membered heteroaryl group, wherein each of said heterocyclic, phenyl and heteroaryl groups is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl); or optionally $R^1$ and R', together with the nitrogen atom to which they are attached, form a 4-7 membered heterocyclic group or a 5-6 membered heteroaryl group, each of which is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl).

The remaining variables of Structural Formula (I) are each and independently as described above in the first set of values of the variables of Structural Formula (I).

In another embodiment, the compounds of the invention are represented by Structural Formula (II) or a pharmaceutically acceptable salt thereof:

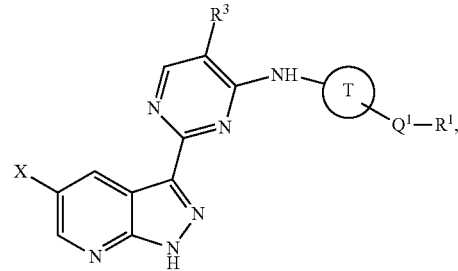

wherein values of the variables of Structural Formula (II) are each and independently as described above in any one of the first through forty fifth sets of values of the variables of Structural Formula (I).

The forty sixth set of values of the variables of Structural Formula (II) is as follows:

Ring T is an optionally substituted $C_5$-$C_{10}$ carbocyclic group or an optionally substituted 5-10 membered heterocarbocyclic group.

X is —Cl, —F, —Br, —CN, —CH$_3$, or —CF$_3$.

$R^2$ is —H, —O($C_1$-$C_4$ alkyl), $C_1$-$C_4$ allyl, or $C_1$-$C_4$ haloalkyl.

In one aspect, $R^3$ is —F, —Cl, —CN, —O($C_1$-$C_4$ alkyl), $C_1$-$C_4$ alkyl, or $C_1$-$C_4$ haloalkyl. In another aspect, $R^3$ is —F, —Cl, —CN, or $C_1$-$C_4$ haloalkyl.

p and k are each and independently 1 or 2.

$R^t$ and $R^s$ are each independently —H, halogen, or $C_1$-$C_4$ alkyl.

The remaining variables are each and independently as described above in the first set of values of the variables of Structural Formula (I).

The forty seventh set of values of the variables of Structural Formula (II) is as follows:

Values of Ring T, X, $R^2$, $R^3$, $R^t$, $R^s$, p, and k are each and independently as described above in the forty sixth set of values of the variables of Structural Formula (II).

$Q^1$ is —C(O)—, —CO$_2$—, —OC(O)—, —O(CR$^t$R$^s$)$_k$—C(O)O—, —C(O)NR'—, —C(O)N(R')—O—, —C(O)NRC(O)O—, —NRC(O)—, —NRC(O)NR'—, —NRCO$_2$—,

—OC(O)NR'—, —OSO$_2$NR'—, —S(O)—, —SO$_2$—, —SO$_2$NR'—, —NRSO$_2$—, —NRSO$_2$NR'—, or —(CR$^t$R$^s$)$_p$—Y$^1$—.

Y$^1$ is —C(O)—, —CO$_2$—, —OC(O)—, —O(CR$^t$R$^s$)$_k$—C(O)O—, —C(O)NR'—, —C(O)N(R')—O—, —C(O)NRC(O)O—, —NRC(O)—, —NRC(O)NR'—, —NRCO$_2$—, —OC(O)NR'—, —OSO$_2$NR'—, —S(O)—, —SO$_2$—, —SO$_2$NR'—, —NRSO$_2$—, or —NRSO$_2$NR'—.

The remaining variables are each and independently as described above in the first set of values of the variables of Structural Formula (I).

The forty eighth set of values of the variables of Structural Formula (II) is as follows:

Values of Ring T, X, R$^2$, R$^3$, R$^t$, R$^s$, p, and k are each and independently as described above in the forty sixth set of values of the variables of Structural Formula (II).

Q$^1$ is —CO$_2$—, —O(CR$^t$R$^s$)$_k$—C(O)O—, —P(O)(OR$^a$)O—, —OP(O)(OR$^a$)O—, —P(O)$_2$O—, —CO$_2$SO$_2$—, or —(CR$^t$R$^s$)$_p$—Y$^1$—.

Y$^1$ is —CO$_2$—, —O(CR$^t$R$^s$)$_k$—C(O)O—, —P(O)(OR$^a$)O—, —OP(O)(OR$^a$)O—, —P(O)$_2$O—, or —CO$_2$SO$_2$—.

The remaining variables are each and independently as described above in the first set of values of the variables of Structural Formula (I).

The forty ninth set of values of the variables of Structural Formula (II) is as follows:

Values of Ring T, X, R$^2$, R$^3$, R$^t$, R$^s$, p, and k are each and independently as described above in the forty sixth set of values of the variables of Structural Formula (II).

Values of Q$^1$ and Y$^1$ are each and independently as described above in the forty seventh or forty eighth set of values of the variables of Structural Formula (II).

R$^1$ is independently i) —H; ii) a C$_1$-C$_6$-aliphatic group optionally substituted with one or more instances of J$^A$; iii) a C$_3$-C$_8$ carbocyclic group or 4-8 membered heterocyclic group, each of which is optionally and independently substituted with one or more instances of J$^B$; iv) a phenyl group or 5-6 membered heteroaryl group, each of which is optionally and independently substituted with one or more instances of J$^T$; or optionally R$^1$, together with R' and the nitrogen to which they are attached, form a 4-8 membered heterocyclic group optionally substituted with one or more instances of J$^2$; and J$^A$, J$^B$, and J$^T$ are each independently oxo or J$^C$; and J$^C$ is selected from the group consisting of halogen, cyano, R$^a$, —OR$^b$, —SR$^b$, —S(O)R$^a$, —SO$_2$R$^a$, —NHR$^c$, —C(O)R$^a$, —C(O)OR$^b$, —OC(O)R$^b$, —NHC(O)R$^b$, —C(O)NHR$^c$, —NHC(O)NHR$^c$, —NHC(O)OR$^b$, —OCONHR$^c$, —NHC(O)NHC(O)OR$^b$, —N(CH$_3$)R$^c$, —N(CH$_3$)C(O)R$^b$, —C(O)N(CH$_3$)R$^c$, —N(CH$_3$)C(O)NHR$^c$, —N(CH$_3$)C(O)OR$^b$, —OCON(CH$_3$)R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N(CH$_3$)R$^b$, and —N(CH$_3$)SO$_2$R$^b$;

optionally, two J$^T$, two J$^A$, two J$^B$, and two J$^C$, respectively, together with the atom(s) to which they are attached, independently form an optionally substituted, 4-10-membered, non-aromatic ring.

The remaining variables are each and independently as described above in the first set of values of the variables of Structural Formula (I).

The fiftieth set of values of the variables of Structural Formula (II) is as follows:

Values of Ring T, X, R$^2$, R$^3$, R$^t$, R$^s$, p, and k are each and independently as described above in the forty sixth set of values of the variables of Structural Formula (II).

Values of Q$^1$ and Y$^1$ are each and independently as described above in the forty seventh or forty eighth set of values of the variables of Structural Formula (II).

Values of R$^1$, J$^A$, J$^B$, J$^C$, and J$^T$ are each and independently as described above in the forty seventh or forty eighth set of values of the variables of Structural Formula (II).

R$^a$ is independently: i) a C$_1$-C$_6$ alkyl group optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), optionally substituted C$_3$-C$_8$ carbocyclic group, optionally substituted 4-8 membered heterocyclic group, optionally substituted 5-6 membered heteroaryl, and optionally substituted phenyl group; ii) an optionally substituted C$_3$-C$_8$ carbocyclic group; iii) optionally substituted 4-8 membered heterocyclic group; iv) an optionally substituted 5-6 membered heteroaryl group; v) or optionally substituted phenyl group;

R$^b$ and R$^c$ are each independently R$^a$ or —H; or optionally, R$^b$ and R$^c$, together with the nitrogen atom(s) to which they are attached, each independently form an optionally substituted, 4-8 membered heterocyclic group; and R and R' are each and independently —H or C$_{1-4}$ alkyl, or optionally R and R', together with the nitrogen to which they are attached, form an optionally substituted 4-8 membered heterocyclic group, or optionally R', together with R$^1$ and the nitrogen to which they are attached, form an optionally substituted 4-8 membered heterocyclic group.

The remaining variables are each and independently as described above in the first set of values of the variables of Structural Formula (I).

In yet another embodiment, the compounds of the invention are represented by Structural Formula (IIIA) or (IIIB), or a pharmaceutically acceptable salt thereof:

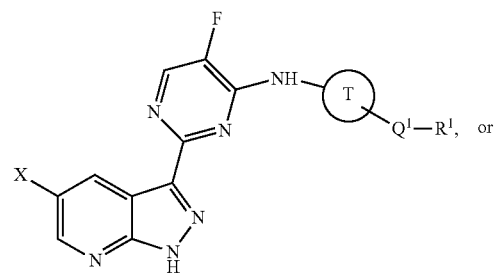

(IIIA)

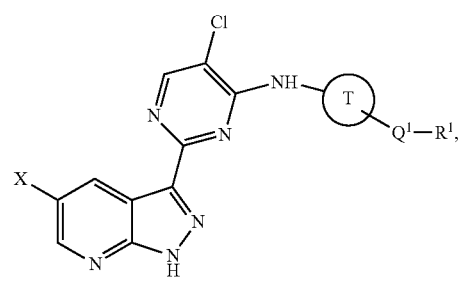

(IIIB)

wherein values of the variables of Structural Formula (II) are each and independently as described above in any one of the first through forty fifth sets of values of the variables of Structural Formula (I), or of the forty sixth through fiftieth sets of values of the variables of Structural Formula (II).

The fifty first set of values of the variables of Structural Formulae (IIIA) and (IIIB) is as follows:

Ring T is an optionally substituted $C_5$-$C_{10}$ carbocyclic group or an optionally substituted 5-10 membered heterocarbocyclic group.

$R^1$ is independently i) —H; ii) a $C_1$-$C_6$-aliphatic group optionally substituted with one or more instances of $J^A$; iii) a $C_3$-$C_8$ carbocyclic group or 4-8 membered heterocyclic group, each of which is optionally and independently substituted with one or more instances of $J^B$; iv) a phenyl group or 5-6 membered heteroaryl group, each of which is optionally and independently substituted with one or more instances of f; or optionally $R^1$, together with R' and the nitrogen to which they are attached, form a 4-8 membered heterocyclic group optionally substituted with one or more instances of $J^2$.

X is —Cl, —F, —Br, —CN, —$CH_3$, or —$CF_3$.

p and k are each and independently 1 or 2.

$R^t$ and $R^s$ are each independently —H, halogen, or $C_1$-$C_4$ alkyl.

$Q^1$ is —$CO_2$—, —$O(CR'R^s)_k$—C(O)O—, —P(O)(OR)O—, —OP(O)($OR^a$)O—, —$P(O)_2$O—, —$CO_2SO_2$—, or —$(CR'R^s)_p$—$Y^1$—.

$Y^1$ is —$CO_2$—, —$O(CR'R^s)_k$—C(O)O—, —P(O)(OR)O—, —OP(O)($OR^a$)O—, —$P(O)_2$O—, or —$CO_2SO_2$—.

$J^A$, $J^B$, and $J^T$ are each independently oxo or $J^C$; and $J^C$ is selected from the group consisting of halogen, cyano, $R^a$, —$OR^b$, —$SR^b$, —S(O)$R^a$, —$SO_2R^a$, —$NHR^c$, —C(O)$R^a$, —C(O)$OR^b$, —OC(O)$R^b$, —NHC(O)$R^b$, —C(O)$NHR^c$, —NHC(O)$NHR^c$, —NHC(O)$OR^b$, —$OCONHR^c$, —NHC(O)NHC(O)$OR^b$, —N($CH_3$)$R^c$, —N($CH_3$)C(O)$R^b$, —C(O)N($CH_3$)$R^c$, —N($CH_3$)C(O)$NHR^c$, —N($CH_3$)C(O)$OR^b$, —OCON($CH_3$)$R^c$, —C(O)$NHCO_2R^b$, —C(O)N($CH_3$)$CO_2R^b$, —N($CH_3$)C(O)NHC(O)$OR^b$, —$NHSO_2R^b$, —$SO_2NHR^b$, —$SO_2N(CH_3)R^b$, and —N($CH_3$)$SO_2R^b$; or optionally, two $J^T$, two $J^A$, two $J^B$, and two $J^C$, respectively, together with the atom(s) to which they are attached, independently form an optionally substituted, 4-10-membered, non-aromatic ring.

$R^a$ is independently: i) a $C_1$-$C_6$ alkyl group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), —O($C_1$-$C_4$ alkyl), optionally substituted $C_3$-$C_8$ carbocyclic group, optionally substituted 4-8 membered heterocyclic group, optionally substituted 5-6 membered heteroaryl, and optionally substituted phenyl group; ii) an optionally substituted $C_3$-$C_8$ carbocyclic group; iii) optionally substituted 4-8 membered heterocyclic group; iv) an optionally substituted 5-6 membered heteroaryl group; v) or optionally substituted phenyl group;

$R^b$ and $R^c$ are each independently $R^a$ or —H; or optionally, $R^b$ and $R^c$, together with the nitrogen atom(s) to which they are attached, each independently form an optionally substituted, 4-8 membered heterocyclic group; and R and R' are each and independently —H or $C_{1-4}$ alkyl, or optionally R and R', together with the nitrogen to which they are attached, form an optionally substituted 4-8 membered heterocyclic group, or optionally R', together with $R^1$ and the nitrogen to which they are attached, form an optionally substituted 4-8 membered heterocyclic group.

The remaining variables are each and independently as described above in the first set of values of the variables of Structural Formula (I).

The fifty second set of values of the variables of Structural Formulae (IIIA) and (IIIB) is as follows:

Values of Ring T, $R^1$, $R^t$, $R^s$, $R^a$, $R^b$, $R^c$, R, R', $Q^1$, $Y^1$, $J^A$, $J^B$, $J^C$, $J^T$, p, and k are each and independently as described above in the fifty first set of values of the variables of Structural Formulae (IIIA) and (IIIB).

In one aspect, X is —Cl, —F, —CN, or —$CF_3$. In another aspect, X is —Cl or —F.

The remaining variables of Structural Formula (I) are each and independently as described above in the first set of values of the variables of Structural Formula (I).

The fifty third set of values of the variables of Structural Formulae (IIIA) and (IIIB) is as follows:

In one aspect, Ring T is an optionally substituted, bridged, $C_5$-$C_{10}$ carbocyclic group. In another aspect, Ring T is an optionally substituted, monocyclic, $C_5$-$C_8$ carbocyclic group.

X is —Cl or —F.

Values of $R^1$, $R^t$, $R^s$, $R^a$, $R^b$, $R^c$, R, R', $Q^1$, $Y^1$, $J^A$, $J^B$, $J^C$, $J^T$, p, and k are each and independently as described above in the fifty first set of values of the variables of Structural Formulae (IIIA) and (IIIB).

The remaining variables are each and independently as described above in the first set of values of the variables of Structural Formula (I).

The fifty fourth set of values of the variables of Structural Formulae (IIIA) and (IIIB) is as follows:

Values of $R^1$, $R^t$, $R^s$, $R^a$, $R^b$, $R^c$, R, R', $Q^1$, $Y^1$, $J^A$, $J^B$, $J^C$, $J^T$, p, and k are each and independently as described above in the fifty first set of values of the variables of Structural Formulae (IIIA) and (IIIB).

X is —Cl or —F.

Ring T is:

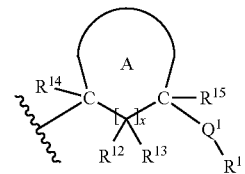

and wherein:

Ring A is a 5-10 membered carbocyclic group or 5-10 membered heterocyclic group, each of which is optionally further substituted with one or more instances of $J^T$; or optionally Ring A and $R^{15}$, Ring A and $R^{14}$, or Ring A and $R^{13}$ independently and optionally form a 4-10 membered, bridged ring optionally further substituted with one or more instances of $J^T$.

In one aspect: each of $R^{12}$, $R^{13}$, and $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —$CO_2H$, or —$CO_2$($C_1$-$C_6$ alkyl), wherein each said $C_1$-$C_6$ alkyl is optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl); each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl); and x is 0, 1 or 2.

In another aspect: $R^{12}$, $R^{13}$, and $R^{14}$ are each and independently —H, halogen, cyano, hydroxy, —O($C_1$-$C_6$ alkyl), or optionally substituted $C_1$-$C_6$ alkyl; $R^{15}$ is —H or optionally substituted $C_1$-$C_6$ alkyl; and x is 0, 1 or 2.

In yet another aspect: $R^{12}$ and $R^{13}$ are each independently —H, halogen, hydroxy, $C_1$-$C_6$ alkyl, $C_1$-$C_6$ haloalkyl, or —O($C_1$-$C_6$ alkyl); $R^{14}$ and $R^{15}$ are each independently —H, $C_1$-$C_6$ alkyl, or $C_1$-$C_6$ haloalkyl; and x is 0, 1 or 2.

The remaining variables are each and independently as described above in the first set of values of the variables of Structural Formula (I).

The fifty fifth set of values of the variables of Structural Formulae (IIIA) and (IIIB) is as follows:

Values of $R^1$, $R^t$, $R^s$, $R^a$, $R^b$, $R^c$, R, R', $Q^1$, $Y^1$, p, and k are each and independently as described above in the fifty first set of values of the variables of Structural Formulae (IIIA) and (IIIB).

Values of Ring T, $R^{12}$, $R^{13}$, $R^{14}$, $R^{15}$ and x are each and independently as described above in the fifty fourth set of values of the variables of Structural Formulae (IIIA) and (IIIB).

X is —Cl or —F.

$J^A$, $J^B$, $J^C$, and $J^T$ are each independently selected from the group consisting of halogen, cyano, $R^a$, —$OR^b$, —$NHR^c$, —C(O)$R^b$, —C(O)$OR^b$, —OC(O)$R^b$, —NHC(O)$R^b$, —C(O)$NHR^c$, —NHC(O)$NHR^c$, —NHC(O)$OR^b$, —OCONH$R^c$, —N(CH$_3$)$R^c$, —N(CH$_3$)C(O)$R^b$, —C(O)N(CH$_3$)$R^c$, —N(CH$_3$)C(O)NH$R^c$, —N(CH$_3$)C(O)$OR^b$, —NHSO$_2R^b$, —SO$_2$NH$R^b$, —SO$_2$N(CH$_3$)$R^b$, and —N(CH$_3$)SO$_2R^b$; or optionally, two $J^T$, two $J^A$, two $J^B$, and two $J^C$, respectively, together with the atom(s) to which they are attached, independently form a 4-10-membered ring that is optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl).

The remaining variables are each and independently as described above in the first set of values of the variables of Structural Formula (I).

The fifty sixth set of values of the variables of Structural Formulae (IIIA) and (IIIB) is as follows:

Values of $R^1$, $R^t$, $R^s$, R, R', $Q^1$, $Y^1$, p, and k are each and independently as described above in the fifty first set of values of the variables of Structural Formulae (IIIA) and (IIIB).

Values of Ring T, $R^{12}$, $R^{13}$, $R^{14}$, $R^{15}$ and x are each and independently as described above in the fifty fourth set of values of the variables of Structural Formulae (IIIA) and (IIIB).

Values of $J^A$, $J^B$, $J^C$, and $J^T$ are each and independently as described above in the fifty fifth set of the variables of Structural Formulae (IIIA) and (IIIB).

X is —Cl or —F.

$R^a$ is independently: i) a $C_1$-$C_6$ alkyl group optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), —O($C_1$-$C_4$ alkyl), $C_3$-$C_8$ carbocycle, 4-8 membered heterocycle, 5-6 membered heteroaryl, and phenyl; ii) a $C_3$-$C_8$ carbocyclic group or 4-8 membered heterocyclic group, each of which is independently and optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl); or iii) a 5-6 membered heteroaryl group or phenyl group, each of which is independently and optionally substituted with one or more substituents selected from the group consisting of halogen, cyano, hydroxy, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl); and $R^b$ and $R^c$ are each independently $R^a$ or —H; or optionally, $R^b$ and $R^c$, together with the nitrogen atom(s) to which they are attached, each independently form a 4-8 membered heterocyclic group optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl).

The remaining variables are each and independently as described above in the first set of values of the variables of Structural Formula (I).

The fifty seventh set of values of the variables of Structural Formulae (IIIA) and (IIIB) is as follows:

X is —Cl or —F.

Values of $R^1$, $R^t$, $R^s$, R, R', $Q^1$, $Y^1$, p, and k are each and independently as described above in the fifty first set of values of the variables of Structural Formulae (IIIA) and (IIIB).

Values of Ring T, $R^{12}$, $R^{13}$, $R^{14}$, $R^{15}$ and x are each and independently as described above in the fifty fourth set of values of the variables of Structural Formulae (IIIA) and (IIIB).

Values of $J^A$, $J^B$, $J^C$, and $J^T$ are each and independently as described above in the fifty fifth set of values of the variables of Structural Formulae (IIIA) and (IIIB).

Values of $R^a$, $R^b$, and $R^c$ are each and independently as described above in the fifty fifth set of values of the variables of Structural Formulae (IIIA) and (IIIB).

$Q^1$ is —C(O)—, —CO$_2$—, —OC(O)—, —O(CR$'R^s$)$_k$—C(O)O—, —C(O)NR'—, —C(O)NRC(O)O—, —NRC(O)—, —NRC(O)NR'—, —NRCO$_2$—, —OC(O)NR'—, or —(CR$^t$R$^s$)$_p$—Y$^1$—.

$Y^1$ is —C(O)—, —CO$_2$—, —OC(O)—, —O(CR$'R^s$)$_k$—C(O)O—, —C(O)NR'—, —C(O)NRC(O)O—, —NRC(O)—, —NRC(O)NR'—, —NRCO$_2$—, or —OC(O)NR'—.

The remaining variables are each and independently as described above in the first set of values of the variables of Structural Formula (I).

The fifty eighth set of values of the variables of Structural Formulae (IIIA) and (IIIB) is as follows:

X is —Cl or —F.

Values of $R^1$, $R^t$, $R^s$, R, R', $Q^1$, $Y^1$, p, and k are each and independently as described above in the fifty first set of values of the variables of Structural Formulae (IIIA) and (IIIB).

Values of Ring T, $R^{12}$, $R^{13}$, $R^{14}$, $R^{15}$ and x are each and independently as described above in the fifty fourth set of values of the variables of Structural Formulae (IIIA) and (IIIB).

Values of $J^A$, $J^B$, $J^C$, and $J^T$ are each and independently as described above in the fifty fifth set of values of the variables of Structural Formulae (IIIA) and (IIIB).

Values of $R^a$, $R^b$, and $R^c$ are each and independently as described above in the fifty fifth set of values of the variables of Structural Formulae (IIIA) and (IIIB).

Values of $Q^1$ and $Y^1$ are each and independently as described above in the fifty seventh set of values of the variables of Structural Formulae (IIIA) and (IIIB).

$R^1$ is independently: i) —H; ii) a $C_1$-$C_6$ aliphatic group optionally substituted with one or more substituents independently selected from the group consisting of halogen, cyano, hydroxy, oxo, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)

($C_1$-$C_4$ alkyl), —C(O)O($C_1$-$C_4$ alkyl), —$CO_2H$, $C_3$-$C_8$ carbocyclic group, 4-8 membered heterocyclic group, phenyl, and 5-6 membered heteroaryl; iii) a $C_3$-$C_7$ carbocyclic group; iv) a 4-7 membered heterocyclic group; v) a phenyl group; or vi) a 5-6 membered heteroaryl group; or optionally $R^1$, together with R' and the nitrogen to which they are attached, form an optionally substituted, 4-8 membered heterocyclic group; and each of said carbocyclic, phenyl, heterocyclic, and heteroaryl groups represented by $R^1$ and for the substituents of the $C_1$-$C_6$-aliphatic group represented by $R^1$, and said heterocyclic group formed with $R^1$ and R' is independently and optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl).

$R^r$ and $R^s$ are each independently —H, halogen, $C_1$-$C_6$ alkyl, or $C_1$-$C_6$ haloalkyl.

The remaining variables are each and independently as described above in the first set of values of the variables of Structural Formula (I).

The fifty ninth set of values of the variables of Structural Formulae (IIIA) and (IIIB) is as follows:

X is —Cl or —F.

Ring T is as described above, wherein $J^T$ is halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, or —O($C_1$-$C_4$ alkyl); $J^2$ is halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, or —O($C_1$-$C_4$ alkyl).

Values of R, R', p, and k are each and independently as described above in the fifty first set of values of the variables of Structural Formulae (IIIA) and (IIIB).

Values of $R^{12}$, $R^{13}$, $R^{14}$, $R^{15}$ and x are each and independently as described above in the fifty fourth set of values of the variables of Structural Formulae (IIIA) and (IIIB).

Values of $R^a$, $R^b$, and $R^c$ are each and independently as described above in the fifty fifth set of values of the variables of Structural Formulae (IIIA) and (IIIB).

Values of $Q^1$ and $Y^1$ are each and independently as described above in the fifty seventh set of values of the variables of Structural Formulae (IIIA) and (IIIB).

Values of $R^1$, $R^r$, and $R^s$ are each and independently as described above in the fifty eighth set of values of the variables of Structural Formulae (IIIA) and (IIIB).

The remaining variables of Structural Formula (I) are each and independently as described above in the first set of values of the variables of Structural Formula (I).

The sixtieth set of values of the variables of Structural Formulae (IIIA) and (IIIB) is as follows:

X is —Cl or —F.

Ring T is:

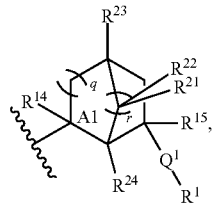

-continued

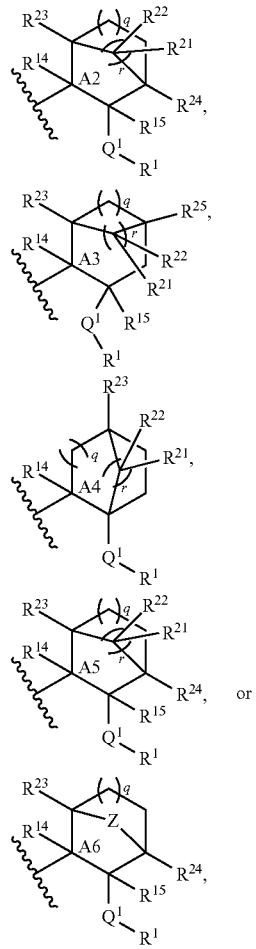

wherein:

each of Rings A1-A5 is independently a 5-10 membered, bridged carbocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl); and Ring A6 is a 5-10 membered, bridged heterocycle optionally further substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl).

Each $R^{14}$ is independently —H, halogen, cyano, hydroxy, $C_1$-$C_6$ alkyl, —O($C_1$-$C_6$ alkyl), —$NH_2$, —NH($C_1$-$C_6$ alkyl), —N($C_1$-$C_6$ alkyl)$_2$, —OCO($C_1$-$C_6$ alkyl), —CO($C_1$-$C_6$ alkyl), —$CO_2H$, or —$CO_2$($C_1$-$C_6$ alkyl), wherein each said $C_1$-$C_6$ alkyl is optionally and independently substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and —O($C_1$-$C_4$ alkyl).

Each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —$NH_2$, —NH($C_1$-$C_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl).

R$^{21}$, R$^{22}$, R$^{23}$, R$^{24}$, and R$^{25}$ are each independently —H, halogen, —OH, C$_1$-C$_6$ alkoxy, or C$_1$-C$_6$ alkyl optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

Z is —O—, —S—, or —NR$^g$—.

R$^g$ is —H or C$_1$-C$_6$ alkyl optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl).

q is 0, 1 or 2.

r is 1 or 2.

Values of R, R', p, and k are each and independently as described above in the fifty first set of values of the variables of Structural Formulae (IIIA) and (IIIB).

Values of Q$^1$ and Y$^1$ are each and independently as described above in the fifty seventh set of values of the variables of Structural Formulae (IIIA) and (IIIB).

Values of R', R$^t$, and R$^s$ are each and independently as described above in the fifty eighth set of values of the variables of Structural Formulae (IIIA) and (IIIB).

The remaining variables are each and independently as described above in the first set of values of the variables of Structural Formula (I).

The sixty first set of values of the variables of Structural Formulae (IIIA) and (IIIB) is as follows:

X is —Cl or —F.

Ring T is as described above in the sixtieth set of values of the variables of Structural Formulae (IIIA) and (IIIB), wherein R$^{14}$ and each R$^{15}$ are each independently —H, C$_1$-C$_6$ alkyl, or C$_1$-C$_6$ haloalkyl; and R$^{21}$, R$^{22}$, R$^{23}$, R$^{24}$, and R$^{25}$ are each independently —H, halogen, hydroxy, C$_1$-C$_6$ alkoxy, C$_1$-C$_6$ alkyl, or C$_1$-C$_6$ haloalkyl.

Values of R, R', p, and k are each and independently as described above in the fifty first set of values of the variables of Structural Formulae (IIIA) and (IIIB).

Values of Q$^1$ and Y$^1$ are each and independently as described above in the fifty seventh set of values of the variables of Structural Formulae (IIIA) and (IIIB).

Values of R$^1$, R$^t$, and R$^s$ are each and independently as described above in the fifty eighth set of values of the variables of Structural Formulae (IIIA) and (IIIB).

The remaining variables are each and independently as described above in the first set of values of the variables of Structural Formula (I).

The sixty second set of values of the variables of Structural Formulae (IIIA) and (IIIB) is as follows:

X is —Cl or —F.

In one aspect, Q$^1$ is independently —C(O)—, —C(O)O—, —NRC(O)—, —C(O)NR—, —NRC(O)NR'—, or —(CH$_2$)$_{1,2}$—Y$^1$—; and Y$^1$ is independently —C(O)—, —C(O)O—, —NRC(O)—, —C(O)NR—, or —NRC(O)NR'—. In another aspect, Q$^1$ is independently —C(O)O—, —NRC(O)—, —C(O)NR—, or —NRC(O)NR'—.

Ring T is as described above in the sixtieth set of values of the variables of Structural Formulae (IIIA) and (IIIB), wherein R$^{14}$ and each R$^{15}$ are each independently —H, C$_1$-C$_6$ alkyl, or C$_1$-C$_6$ haloalkyl; R$^{21}$, R$^{22}$, R$^{23}$, R$^{24}$, and R$^{25}$ are each independently —H, halogen, hydroxy, C$_1$-C$_6$ alkoxy, C$_1$-C$_6$ alkyl, or C$_1$-C$_6$ haloalkyl; Z is —O— or —NR$^g$—; and R$^g$ is —H, C$_1$-C$_6$ alkyl, or C$_1$-C$_6$ haloalkyl.

Values of R$^1$ are as described above in the fifty eighth set of values of the variables of Structural Formulae (IIIA) and (IIIB).

The remaining variables are each and independently as described above in the first set of values of the variables of Structural Formula (I).

The sixty third set of values of the variables of Structural Formulae (IIIA) and (IIIB) is as follows:

X is —Cl or —F.

Ring T is:

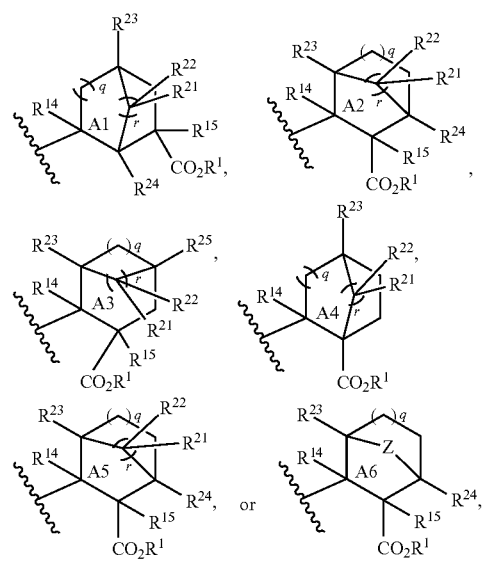

wherein each of Rings A1-A6 is independently and optionally further substituted with one or more substituents selected from the group consisting of halogen, cyano, hydroxy, C$_1$-C$_4$ alkyl, C$_1$-C$_4$ haloalkyl, and —O(C$_1$-C$_4$ alkyl); Z is —O— or —NR$^g$—; R$^g$ is —H, C$_1$-C$_6$ alkyl, or C$_1$-C$_6$ haloalkyl; and values of the other variables are each and independently as described above in the sixtieth set of values of Structural Formulae (IIIA) and (IIIB).

Q$^1$ is independently —C(O)O—, —NRC(O)—, —C(O)NR—, or —NRC(O)NR'—.

R$^1$ is independently: i) —H; ii) a C$_1$-C$_6$ aliphatic group optionally substituted with one or more substituents independently selected from the group consisting of halogen, cyano, hydroxy, oxo, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), —CO$_2$H, C$_3$-C$_8$ carbocyclic group, 4-8 membered heterocyclic group, phenyl, and 5-6 membered heteroaryl; iii) a C$_3$-C$_7$ carbocyclic group; iv) a 4-7 membered heterocyclic group; v) a phenyl group; or vi) a 5-6 membered heteroaryl group; or optionally R$^1$, together with R' and the nitrogen to which they are attached, form an optionally substituted, 4-8 membered heterocyclic group; and each of said carbocyclic, phenyl, heterocyclic, and heteroaryl groups represented by R$^1$ and for the substituents of the C$_1$-C$_6$-aliphatic group represented by R$^1$, and said heterocyclic group formed with R$^1$ and R' is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

In one aspect, R$^{14}$ and each R$^{15}$ are each independently —H, C$_1$-C$_6$ alkyl, or C$_1$-C$_6$ haloalkyl; and R$^{21}$, R$^{22}$, R$^{23}$, R$^{24}$, and R$^{25}$ are each independently —H, halogen, hydroxy, C$_1$-C$_6$ alkoxy, C$_1$-C$_6$ alkyl, or C$_1$-C$_6$ haloalkyl. In another aspect, R$^{14}$ and each R$^{15}$ are each independently —H or C$_{1-6}$ alkyl; and R$^{21}$, R$^{22}$, R$^{23}$, R$^{24}$, and R$^{25}$ are each independently —H or C$_{1-6}$ alkyl. In yet another aspect, R$^{14}$, R$^{15}$, R$^{21}$, R$^{22}$, R$^{23}$, R$^{24}$, and R$^{25}$ are each independently —H.

R and R' are each and independently —H or —CH$_3$.

q is 0, 1 or 2; and r is 1 or 2.

The remaining variables are each and independently as described above in the first set of values of the variables of Structural Formula (I).

The sixty fourth set of values of the variables of Structural Formulae (IIIA) and (IIIB) is as follows:

X is —Cl or —F.

Ring T is selected from:

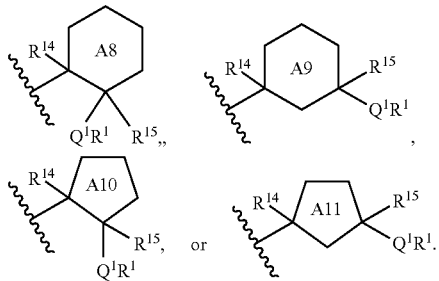

In one aspect: each of Rings A8-A11 is independently and optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl); each R$^{14}$ is independently —H, halogen, cyano, hydroxy, C$_1$-C$_6$ alkyl, —O(C$_1$-C$_6$ alkyl), —NH$_2$, —NH(C$_1$-C$_6$ alkyl), —N(C$_1$-C$_6$ alkyl)$_2$, —OCO(C$_1$-C$_6$ alkyl), —CO(C$_1$-C$_6$ alkyl), —CO$_2$H, or —CO$_2$(C$_1$-C$_6$ alkyl), wherein each said C$_1$-C$_6$ alkyl is optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl); and each R$^{15}$ is independently —H, halogen, cyano, hydroxy, or C$_1$-C$_6$ alkyl optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl).

In another aspect: Rings A8-A11 is independently and optionally substituted with one or more substituents selected from the group consisting of halogen, cyano, hydroxy, C$_1$-C$_4$ alkyl, C$_1$-C$_4$ haloalkyl, and —O(C$_1$-C$_4$ alkyl); and R$^{14}$ and each R$^{15}$ are each independently —H or C$_{1-6}$ alkyl.

R$^1$ is independently: i) —H; ii) a C$_1$-C$_6$ aliphatic group optionally substituted with one or more substituents independently selected from the group consisting of halogen, cyano, hydroxy, oxo, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), —CO$_2$H, C$_3$-C$_8$ carbocyclic group, 4-8 membered heterocyclic group, phenyl, and 5-6 membered heteroaryl; iii) a C$_3$-C$_7$ carbocyclic group; iv) a 4-7 membered heterocyclic group; v) a phenyl group; or vi) a 5-6 membered heteroaryl group; or optionally R$^1$, together with R' and the nitrogen to which they are attached, form an optionally substituted, 4-8 membered heterocyclic group; and each of said carbocyclic, phenyl, heterocyclic, and heteroaryl groups represented by R$^1$ and for the substituents of the C$_1$-C$_6$-aliphatic group represented by R$^1$, and said heterocyclic group formed with R$^1$ and R' is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

Q$^1$ is —CO$_2$—, —O(CR$^r$R$^s$)$_k$—C(O)O—, —P(O)(OR)O—, —OP(O)(OR$^a$)O—, —P(O)$_2$O—, —CO$_2$SO$_2$—, or —(CR$^r$R$^s$)$_p$—Y$^1$—.

Y$^1$ is —CO$_2$—, —O(CR$^r$R$^s$)$_k$—C(O)O—, —P(O)(OR)O—, —OP(O)(OR$^a$)O—, —P(O)$_2$O—, or —CO$_2$SO$_2$—.

p and k are each and independently 1 or 2.

R$^r$ and R$^s$ are each and independently —H, halogen, or C$_1$-C$_4$ alkyl.

R and R' are each and independently —H or C$_{1-4}$ alkyl, or optionally R and R', together with the nitrogen to which they are attached, form an optionally substituted 4-8 membered heterocyclic group, or optionally R', together with R$^1$ and the nitrogen to which they are attached, form an optionally substituted 4-8 membered heterocyclic group.

The remaining variables are each and independently as described above in the first set of values of the variables of Structural Formula (I).

The sixty fifth set of values of the variables of Structural Formulae (IIIA) and (IIIB) is as follows:

Values of X, Ring T, R', R, and R' are each and independently as described above in the sixty fourth set of variables of the variables of Structural Formulae (IIIA) and (IIIB).

Q$^1$ is —NRC(O)—, —C(O)NR—, or —NRC(O)NR'—.

The remaining variables are each and independently as described above in the first set of values of the variables of Structural Formula (I).

The sixty sixth set of values of the variables of Structural Formulae (IIIA) and (IIIB) is as follows:

Values of X and Ring T are each and independently as described above in the sixty fourth set of variables of the variables of Structural Formulae (IIIA) and (IIIB).

Q$^1$ is —NRC(O)—, —C(O)NR—, or —NRC(O)NR'—.

R and R' are each and independently —H or —CH$_3$; and

R$^1$ is independently a 4-7 membered heterocyclic group, a phenyl group, or a 5-6 membered heteroaryl group, wherein each of said heterocyclic, phenyl and heteroaryl groups is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl); or optionally R$^1$ and R', together with the nitrogen atom to which they are attached, form a 4-7 membered heterocyclic group or a 5-6 membered heteroaryl group, each of which is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

The remaining variables are each and independently as described above in the first set of values of the variables of Structural Formula (I).

In an additional embodiment, the compounds of the invention are presented by any one of Structural Formulae (I), (II), (IIIA), and (IIIB), or a pharmaceutically acceptable salt thereof, wherein values of the variables of Structural Formulae (I), (II), (IIIA), and (IIIB) are each and independently as described above in any one of the embodiments, provided that Q$^1$-R$^1$ is not at the same carbon atom is attached, to which —NH group that is attached to the pyrimidine ring of each structural formula.

Specific examples of the compounds represented by Structural Formula (I) include:

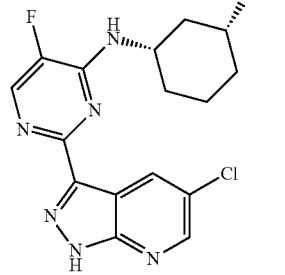

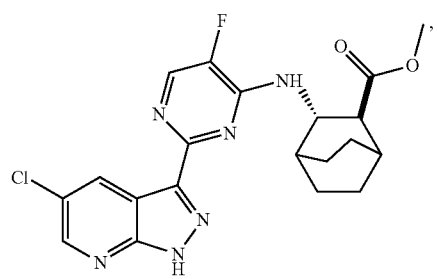

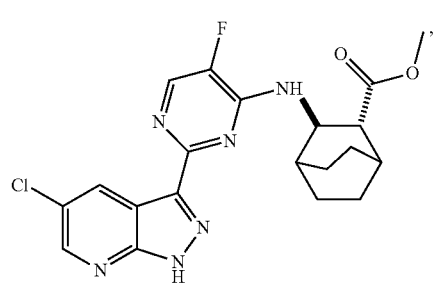

-continued

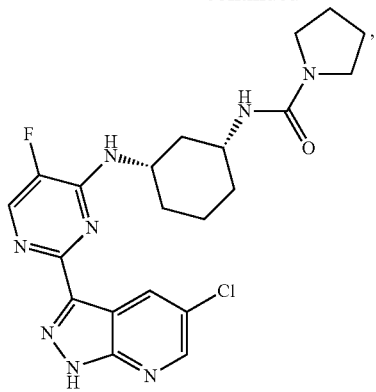

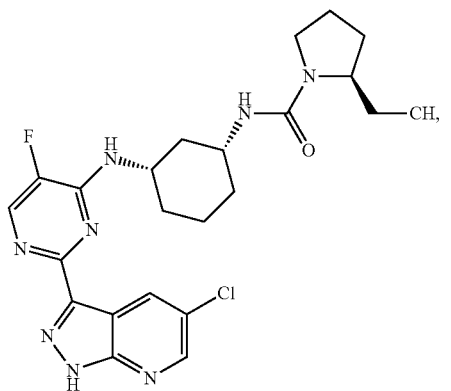

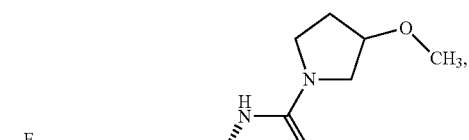

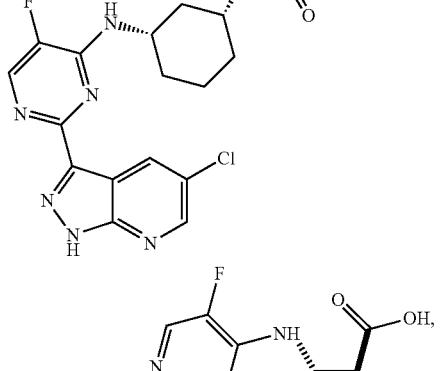

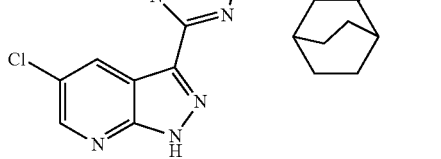

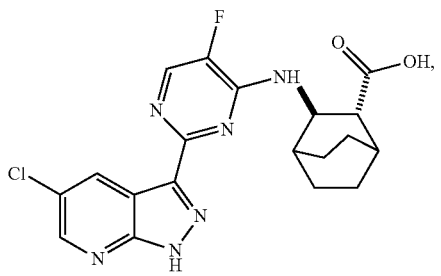

45
-continued
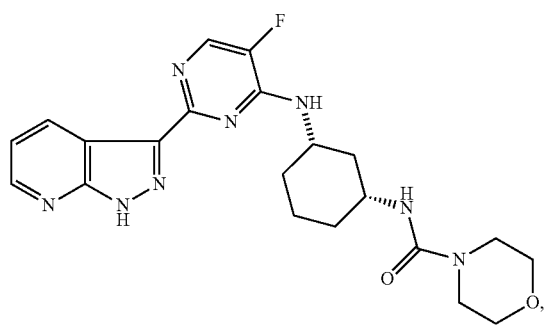
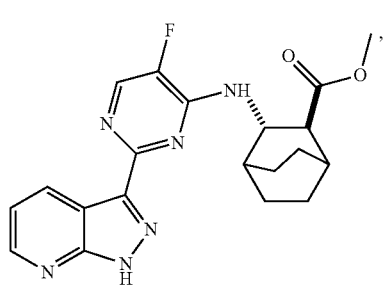
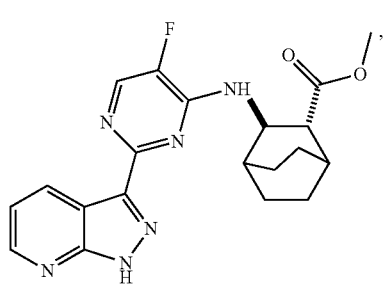
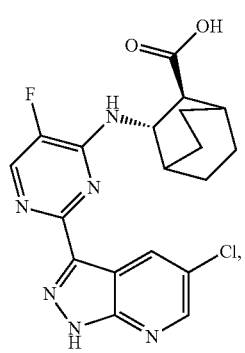
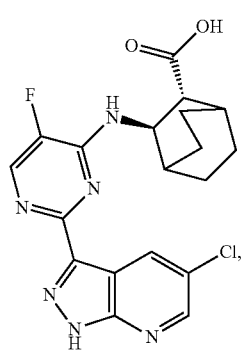
46
-continued
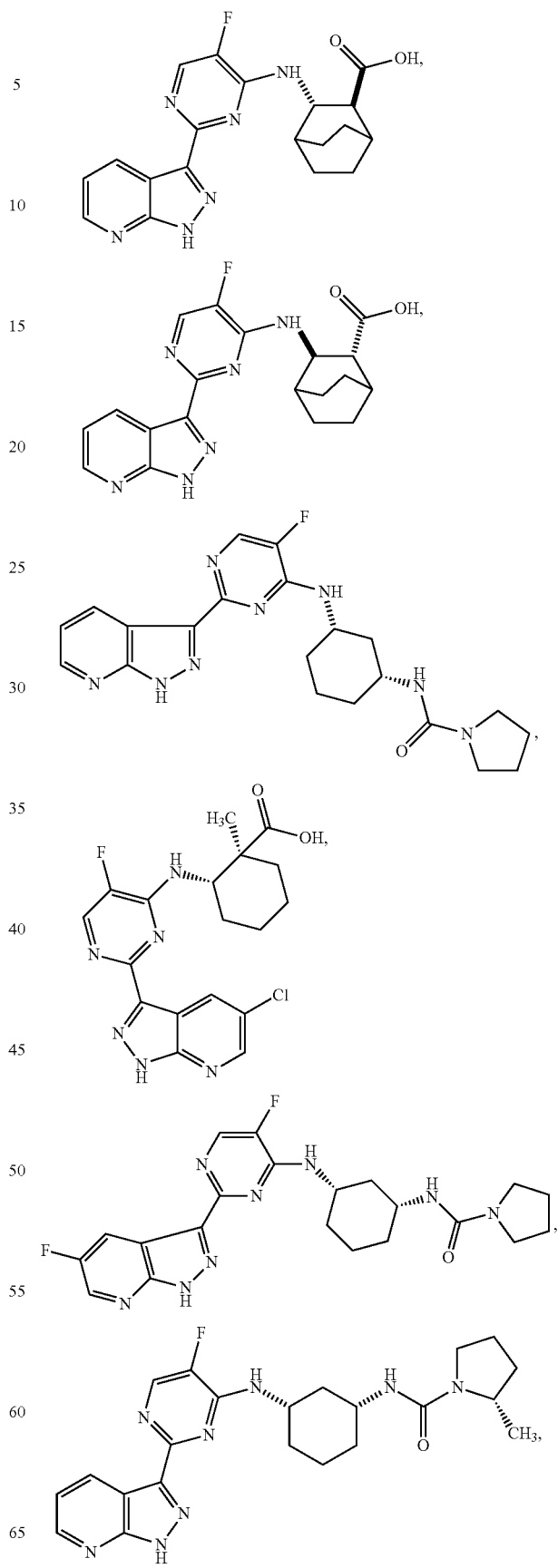

47
-continued
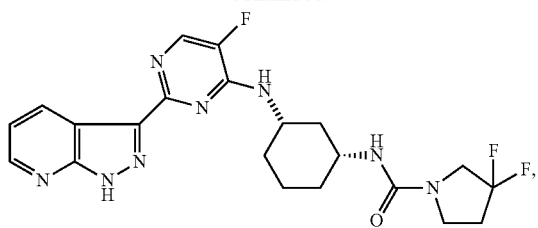
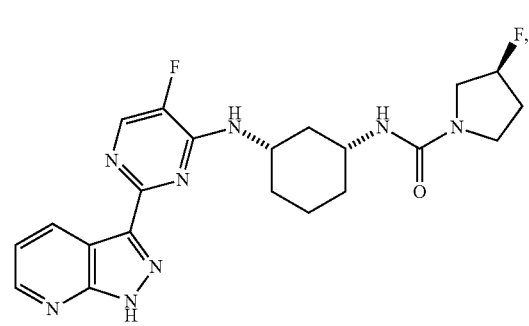
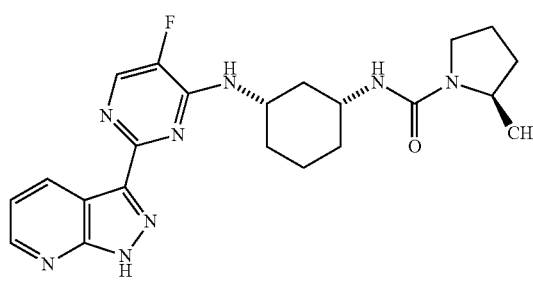
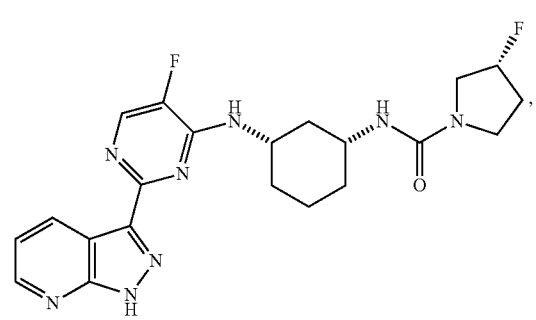
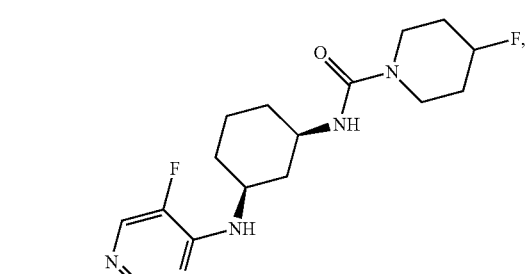
48
-continued
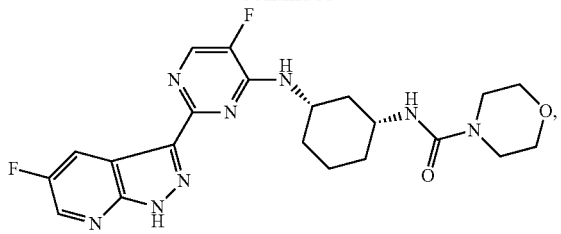
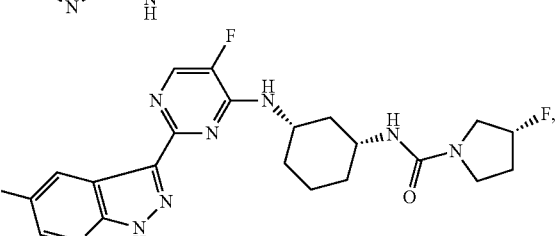
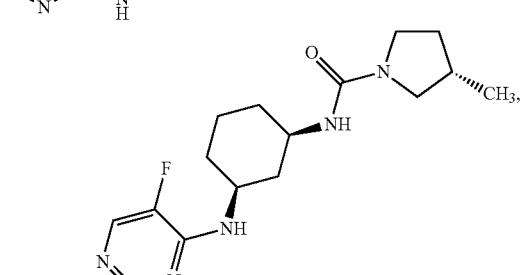

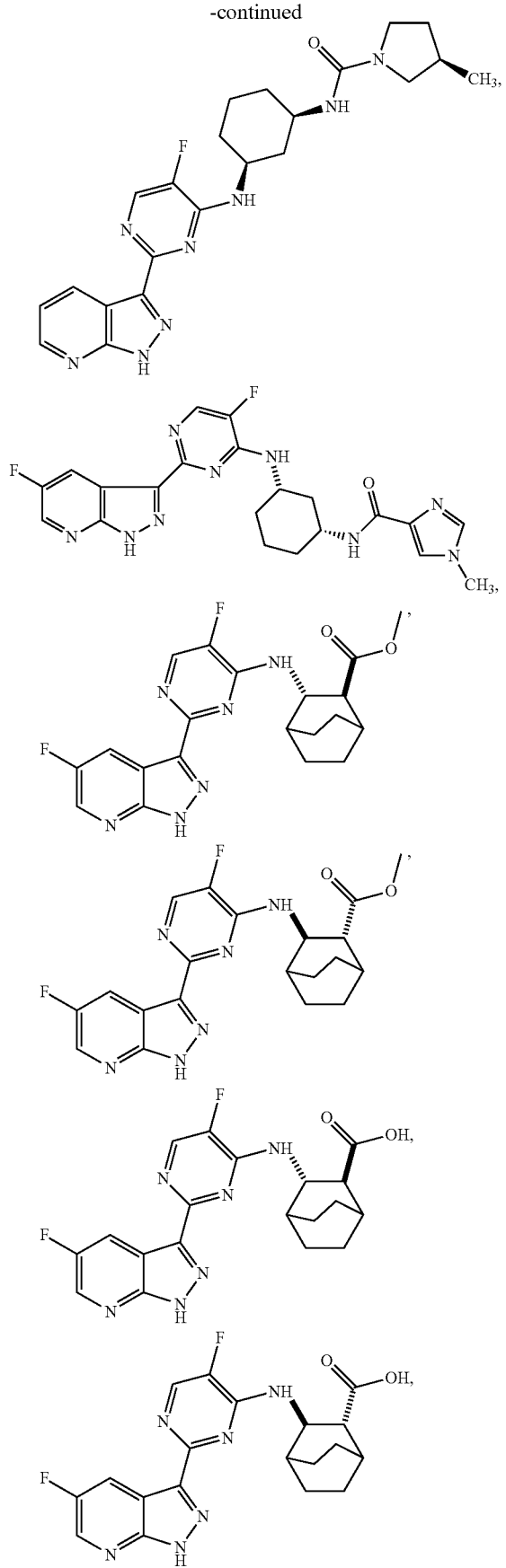
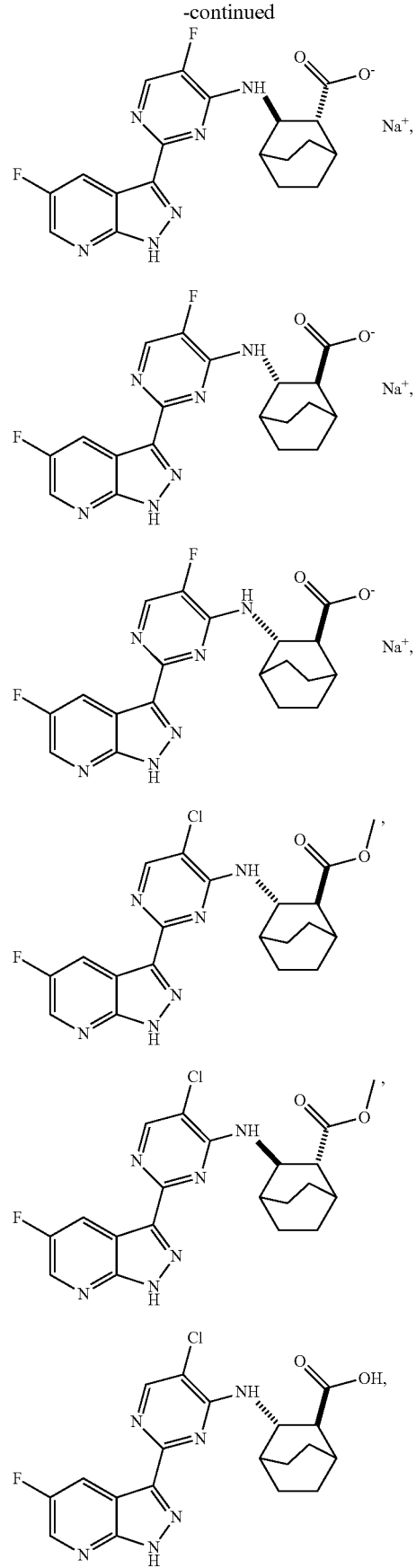

-continued
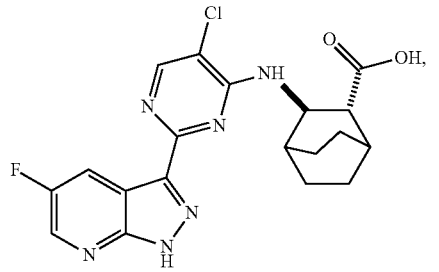
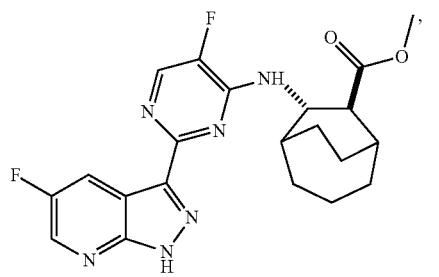
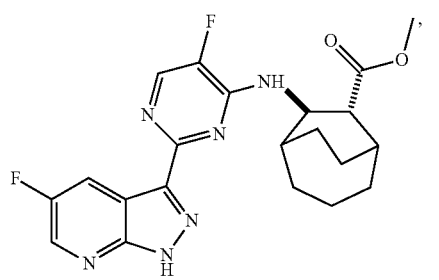
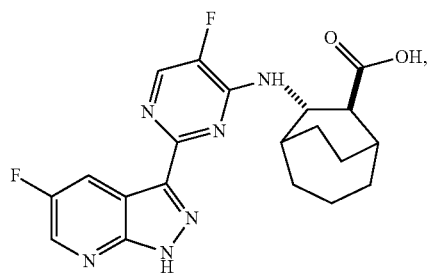
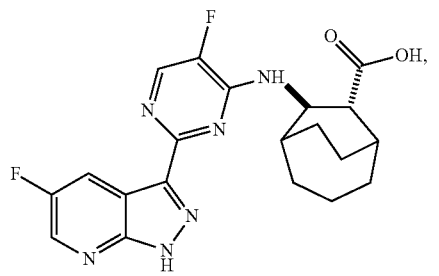
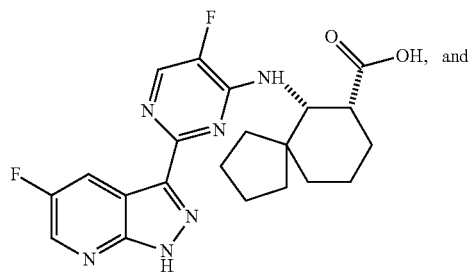
-continued
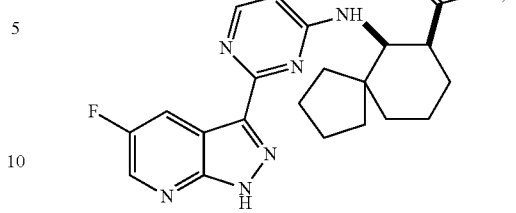
and
pharmaceutically acceptable salts thereof.
Additional specific examples of the compounds represented by Structural Formula (I) include:
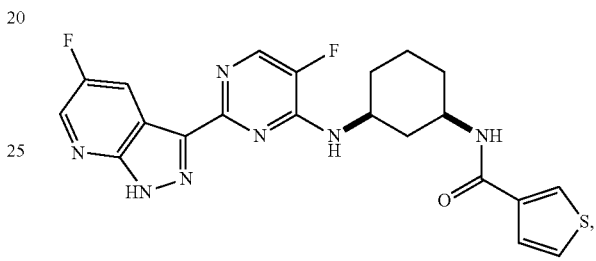
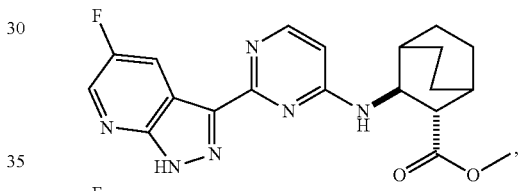
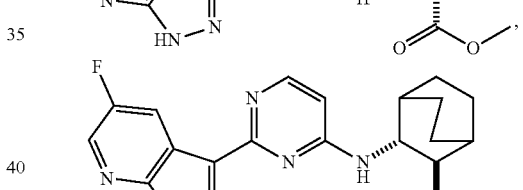
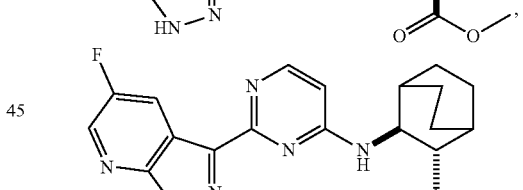
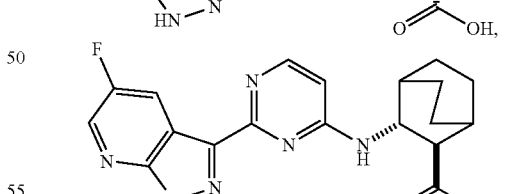
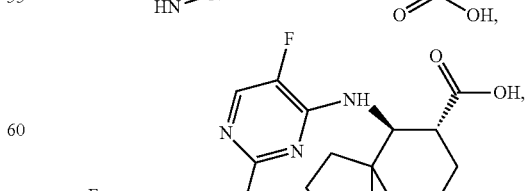

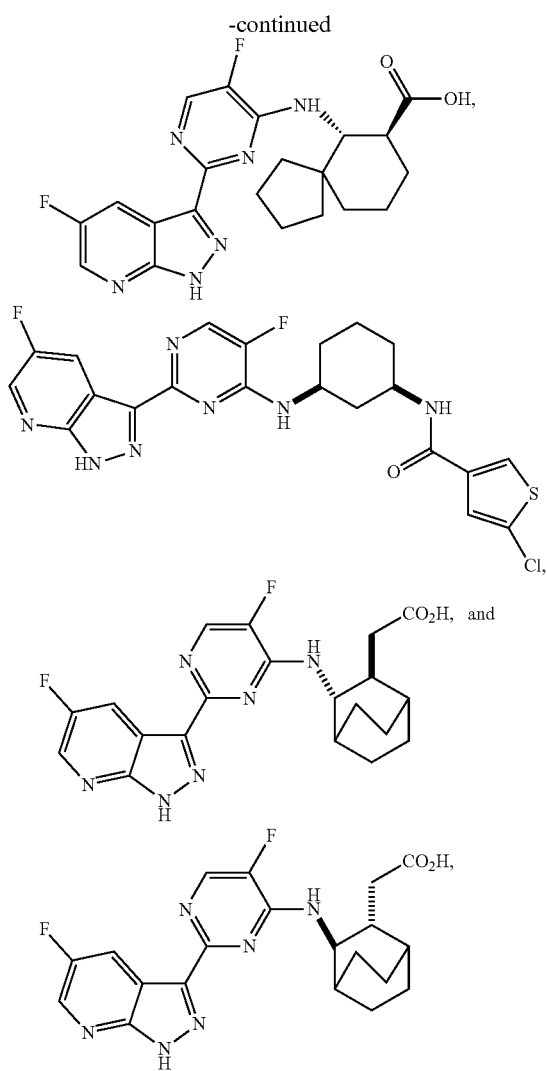

and pharmaceutically acceptable salts thereof.

In some embodiments, the compounds of the invention are selected from any one of the compounds depicted in Tables 1 and 2, or pharmaceutically acceptable salts thereof.

As used herein, a reference to compound(s) of the invention (for example, the compound(s) of Structural Formula (I), or compound(s) of claim 1) will include pharmaceutically acceptable salts thereof.

The compounds of the invention described herein can be prepared by any suitable method known in the art. For example, they can be prepared in accordance with procedures described in WO 2005/095400, WO 2007/084557, WO 2010/011768, WO 2010/011756, WO 2010/011772, WO 2009/073300, and PCT/US2010/038988 filed on Jun. 17, 2010. For example, the compounds shown in Tables 1 and 2, and the specific compounds depicted above can be prepared by any suitable method known in the art, for example, WO 2005/095400, WO 2007/084557, WO 2010/011768, WO 2010/011756, WP 2010/011772, WO 2009/073300, and PCT/US2010/038988, and by the exemplary syntheses described below under Exemplification.

The present invention provides methods of preparing a compound represented by Structural Formulae (I), (II), (IIIA) and (IIIB). In one embodiment, the compounds of the invention can be prepared as depicted in General Schemes 1-4. Any suitable condition(s) known in the art can be employed in the invention for each step depicted in the schemes.

In a specific embodiment, as shown in General Scheme 1, the methods comprise the step of reacting Compound (A) with Compound (B) under suitable conditions to form a compound of Structural Formula (XX), wherein each of $L^1$ and $L^2$ independently is a halogen (F, Cl, Br, or I), G is trityl and the remaining variables of Compounds (A), (B) and Structural Formula (XX) are each and independently as described herein. Typical examples for $L^1$ and $L^2$ are each and independently Cl or Br. The methods further comprise the step of deprotecting the G group under suitable conditions to form the compounds of Structural Formula (I). Any suitable condition(s) known in the art can be employed in the invention for each step depicted in the schemes. For example, any suitable condition described in WO 2005/095400 and WO 2007/084557 for the coupling of a dioxaboraolan with a chloropyrimidine can be employed for the reaction between Compounds (A) and (B). Specifically, the reaction between compounds (A) and (B) can be performed in the presence of $Pd(PPh_3)_4$ or $Pd_2(dba)_3$ (dba is dibenzylidene acetone). For example, the de-tritylation step can be performed under an acidic condition (e.g., trifluoroacetic acid (TFA)) in the presence of, for example, $Et_3SiH$ (Et is ethyl). Specific exemplary conditions are described in the Exemplification below Optionally, the method further comprises the step of preparing Compound (A) by reacting Compound (E) with Compound (D). Any suitable conditions know in the art can be employed in this step, and Compounds (E) and (D) can be prepared by any suitable method known in the art. Specific exemplary conditions are described in the Exemplification below.

General Scheme 1

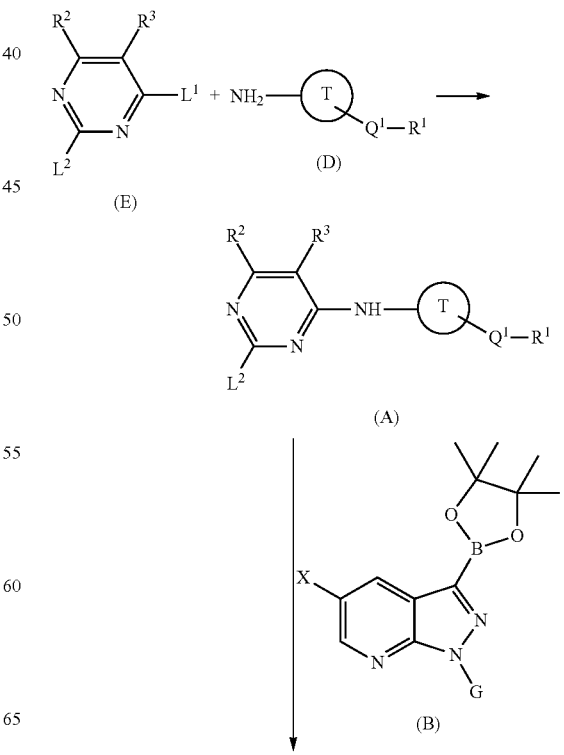

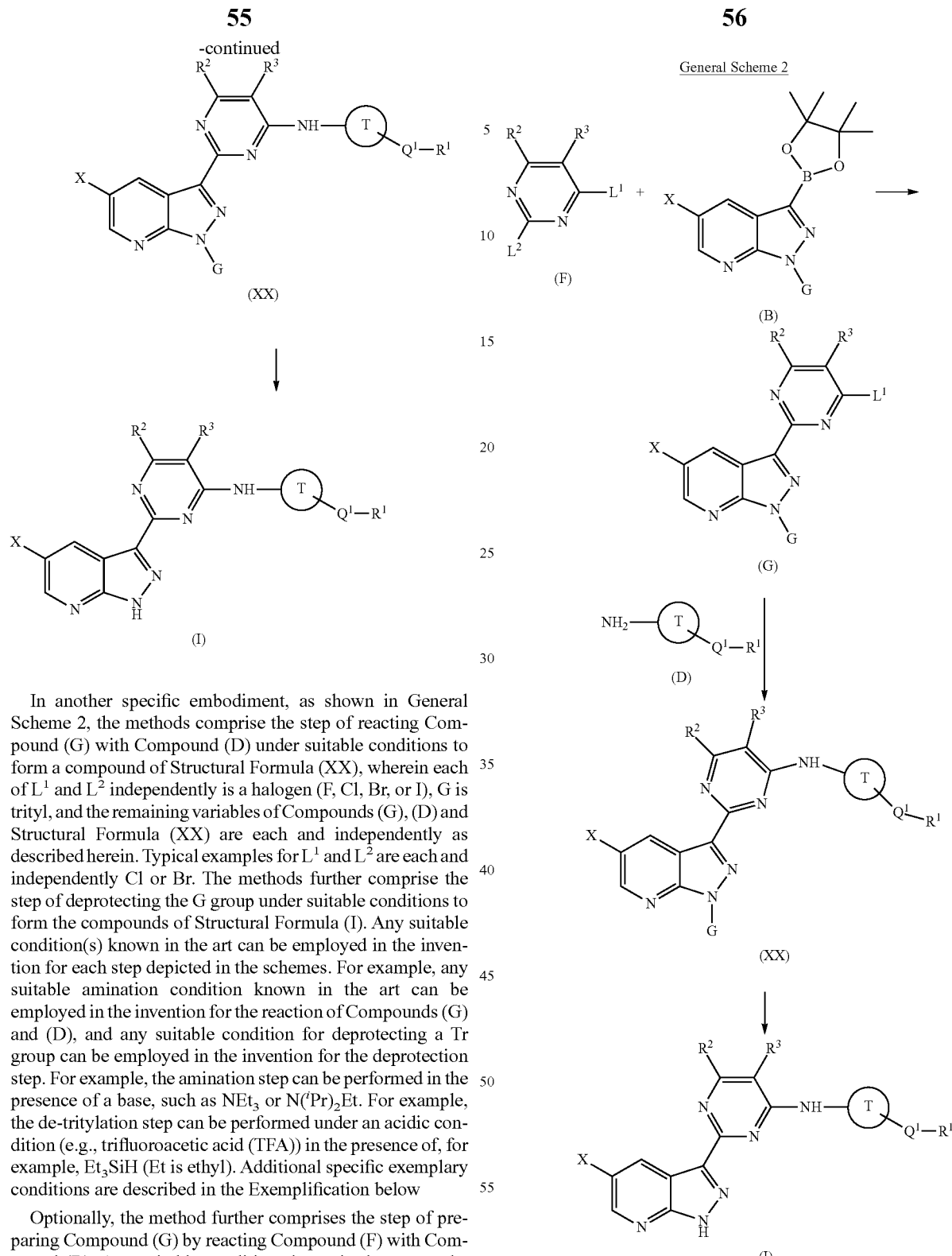

In another specific embodiment, as shown in General Scheme 2, the methods comprise the step of reacting Compound (G) with Compound (D) under suitable conditions to form a compound of Structural Formula (XX), wherein each of $L^1$ and $L^2$ independently is a halogen (F, Cl, Br, or I), G is trityl, and the remaining variables of Compounds (G), (D) and Structural Formula (XX) are each and independently as described herein. Typical examples for $L^1$ and $L^2$ are each and independently Cl or Br. The methods further comprise the step of deprotecting the G group under suitable conditions to form the compounds of Structural Formula (I). Any suitable condition(s) known in the art can be employed in the invention for each step depicted in the schemes. For example, any suitable amination condition known in the art can be employed in the invention for the reaction of Compounds (G) and (D), and any suitable condition for deprotecting a Tr group can be employed in the invention for the deprotection step. For example, the amination step can be performed in the presence of a base, such as $NEt_3$ or $N(^iPr)_2Et$. For example, the de-tritylation step can be performed under an acidic condition (e.g., trifluoroacetic acid (TFA)) in the presence of, for example, $Et_3SiH$ (Et is ethyl). Additional specific exemplary conditions are described in the Exemplification below Optionally, the method further comprises the step of preparing Compound (G) by reacting Compound (F) with Compound (B). Any suitable conditions know in the art can be employed in this step. For example, any suitable condition described in WO 2005/095400 and WO 2007/084557 for the coupling of a dioxaboralan with a chloro-pyrimidine can be employed for the reaction between Compounds (F) and (B). Specifically, the reaction between compounds (F) and (B) can be performed in the presence of $Pd(PPh_3)_4$ or $Pd_2(dba)_3$ (dba is dibenzylidene acetone). Specific exemplary conditions are described in the Exemplification below.

In yet another specific embodiment, as shown in General Scheme 3, the methods comprise the step of reacting Compound (K) with Compound (D) under suitable conditions to form a compound of Structural Formula (XX), wherein G is trityl and the remaining variables of Compounds (K), (D) and Structural Formula (XX) are each and independently as described herein. The methods further comprise the step of deprotecting the G group under suitable conditions to form the compounds of Structural Formula (I). Any suitable condition(s) known in the art can be employed in the invention for each step depicted in the schemes. For example, any suitable reaction condition known in the art, for example, in WO 2005/095400 and WO 2007/084557 for the coupling of an amine with a sulfinyl group can be employed for the reaction of Compounds (K) with Compound (D). For example, Compounds (D) and (K) can be reacted in the presence of a base, such as NEt$_3$ or N($^i$Pr)$_2$(Et). For example, the de-tritylation step can be performed under an acidic condition (e.g., trifluoroacetic acid (TFA)) in the presence of, for example, Et$_3$SiH (Et is ethyl). Additional specific exemplary conditions are described in the Exemplification below Optionally, the method further comprises the step of preparing Compound (K) by oxidizing Compound (J), for example, by treatment with meta-chloroperbenzoic acid.

Optionally, the method further comprises the step of preparing Compound (J) by reacting Compound (H) with Compound (B). Any suitable conditions know in the art can be employed in this step. For example, any suitable condition described in WO 2005/095400 and WO 2007/084557 for the coupling of a dioxaboraolan with a chloro-pyrimidine can be employed for the reaction between Compounds (H) and (B). Specifically, the reaction between compounds (H) and (B) can be performed in the presence of Pd(PPh$_3$)$_4$ or Pd$_2$(dba)$_3$ (dba is dibenzylidene acetone) Specific exemplary conditions are described in the Exemplification below.

General Scheme 3

In yet another specific embodiment, as shown in General Scheme 4, the methods comprise the step of reacting Compound (L) with Compound (D) under suitable conditions to form a compound of Structural Formula (XX), wherein G is trityl and the remaining variables of Compounds (L), (D) and Structural Formula (XX) are each and independently as described herein. The methods further comprise the step of Optionally, the method further comprises the step of preparing Compound (L) by oxidizing Compound (J), for example, by treatment with meta-chloroperbenzoic acid.

Optionally, the method further comprises the step of preparing Compound (J) by reacting Compound (H) with Compound (B). Reaction conditions are as described above for General Scheme 3.

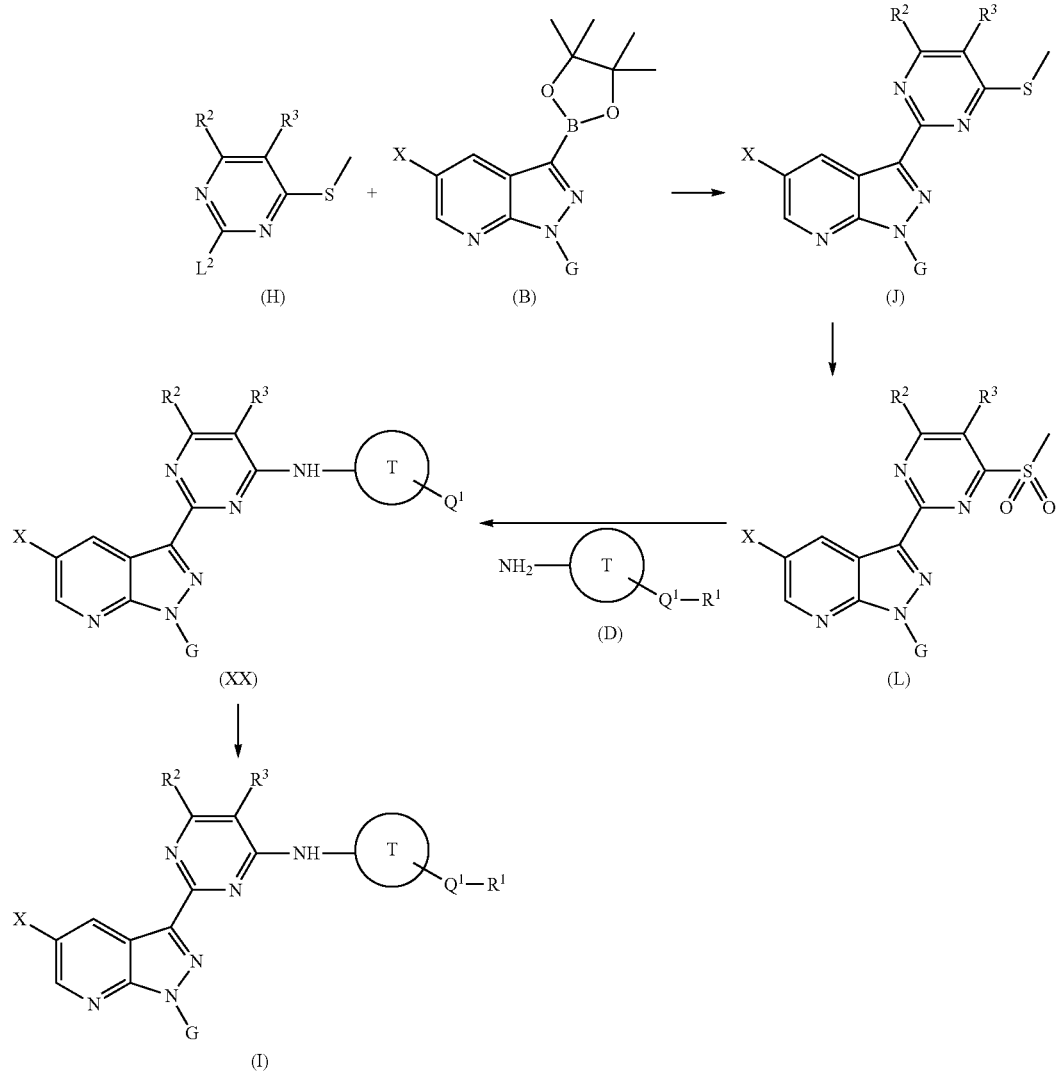

deprotecting the G group under suitable conditions to form the compounds of Structural Formula (I). Any suitable condition(s) known in the art can be employed in the invention for each step depicted in the schemes. For example, any suitable reaction condition known in the art, for example, in WO 2005/095400 and WO 2007/084557 for the coupling of an amine with a sulfonyl group can be employed for the reaction of Compounds (L) with Compound (D). For example, Compounds (D) and (L) can be reacted in the presence of a base, such as $NEt_3$ or $N(^iPr)_2(Et)$. For example, the de-tritylation step can be performed under an acidic condition (e.g., trifluoroacetic acid (TFA)) in the presence of, for example, $Et_3SiH$ (Et is ethyl). Additional specific exemplary conditions are described in the Exemplification below Compounds (A)-(K) can be prepared by any suitable method known in the art. Specific exemplary synthetic methods of these compounds are described below in the Exemplification. In one embodiment, Compounds (A), (G), (J), (K) and (L) can be prepared as described in General Schemes 1-4.

In some embodiments, the present invention is directed to a compound represented by Structural Formula (XX), wherein the variables of Structural Formula (XX) are each and independently as described herein, and G is trityl. Specific examples of the compounds represented by Structural formula (XX) include:

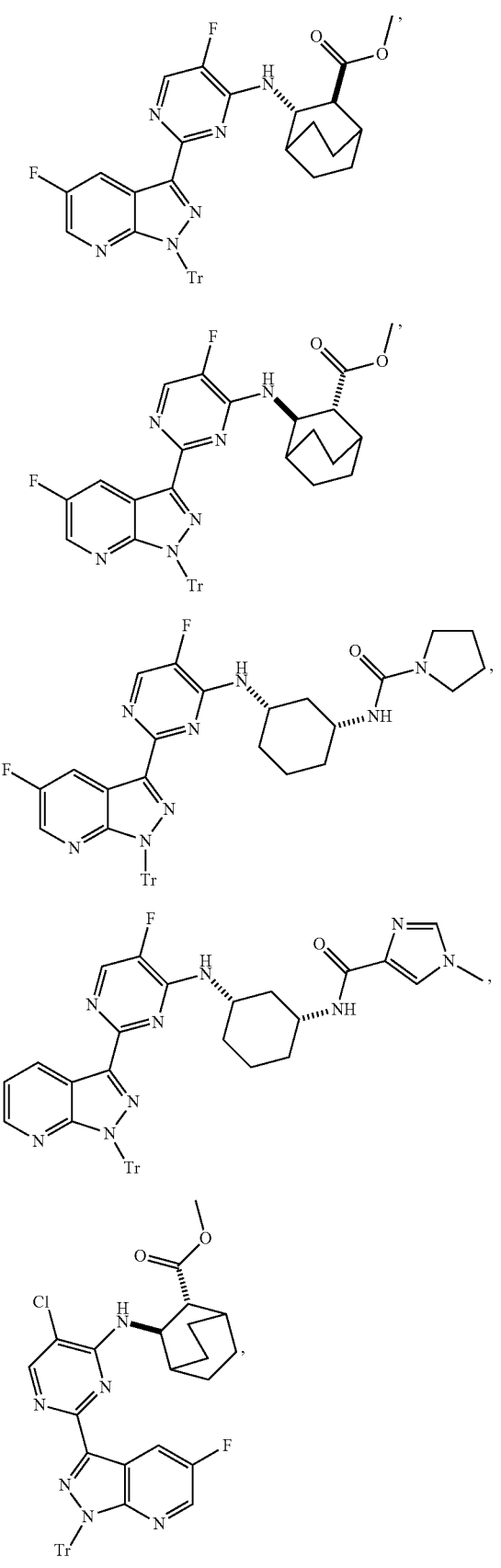
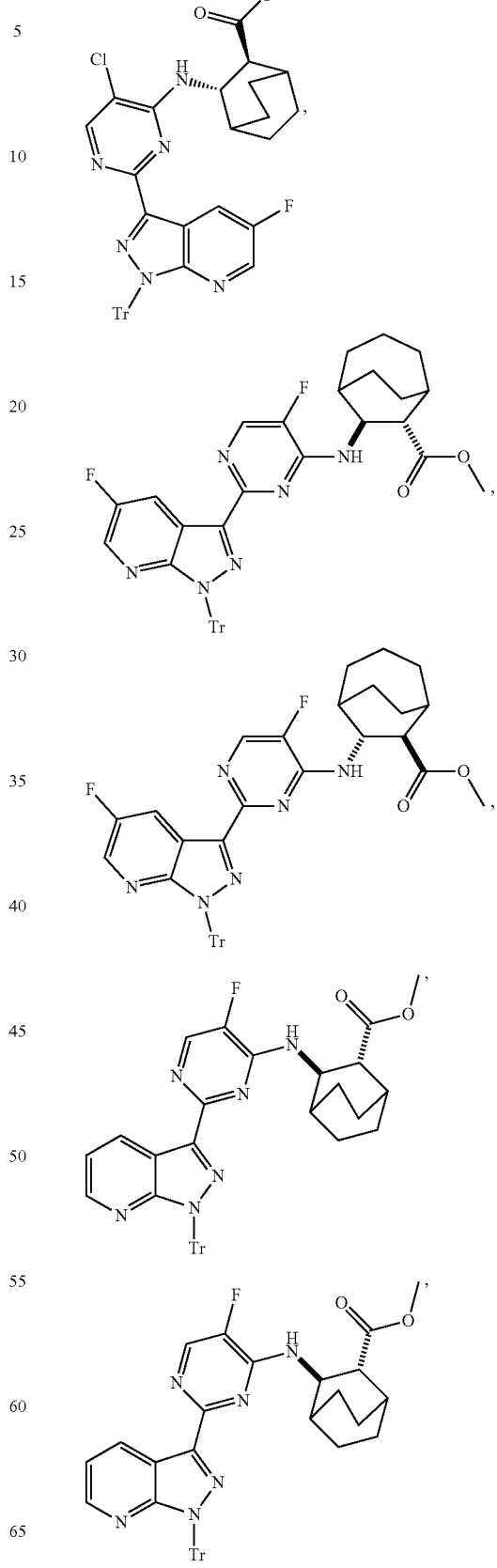

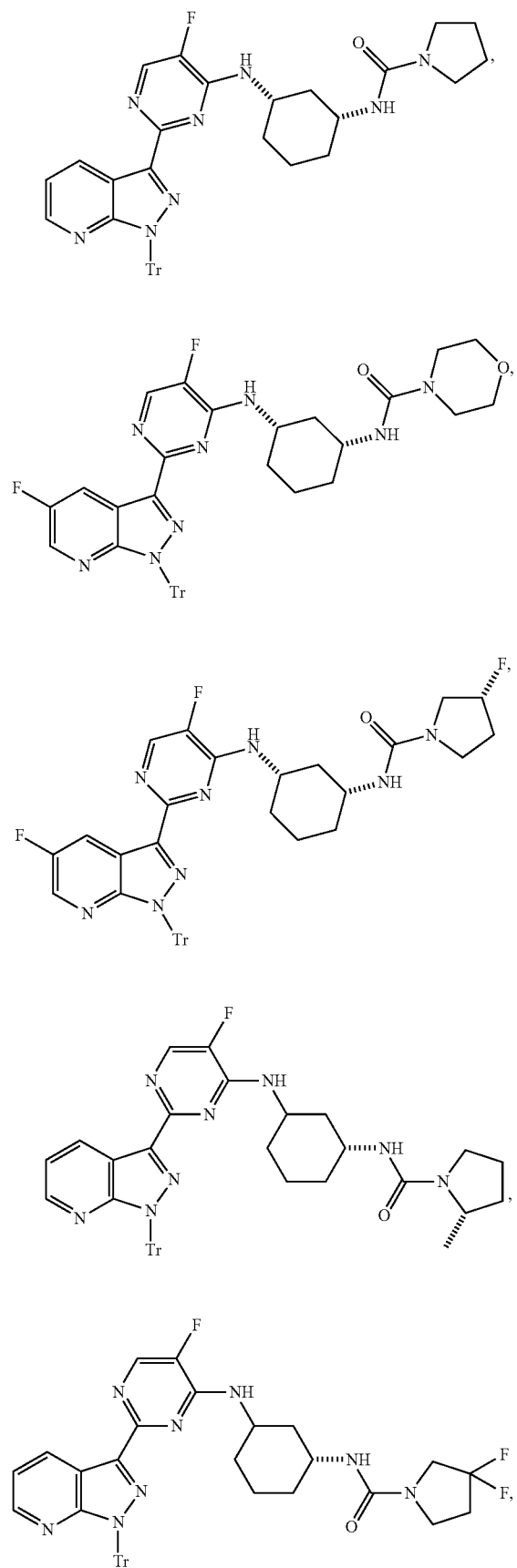
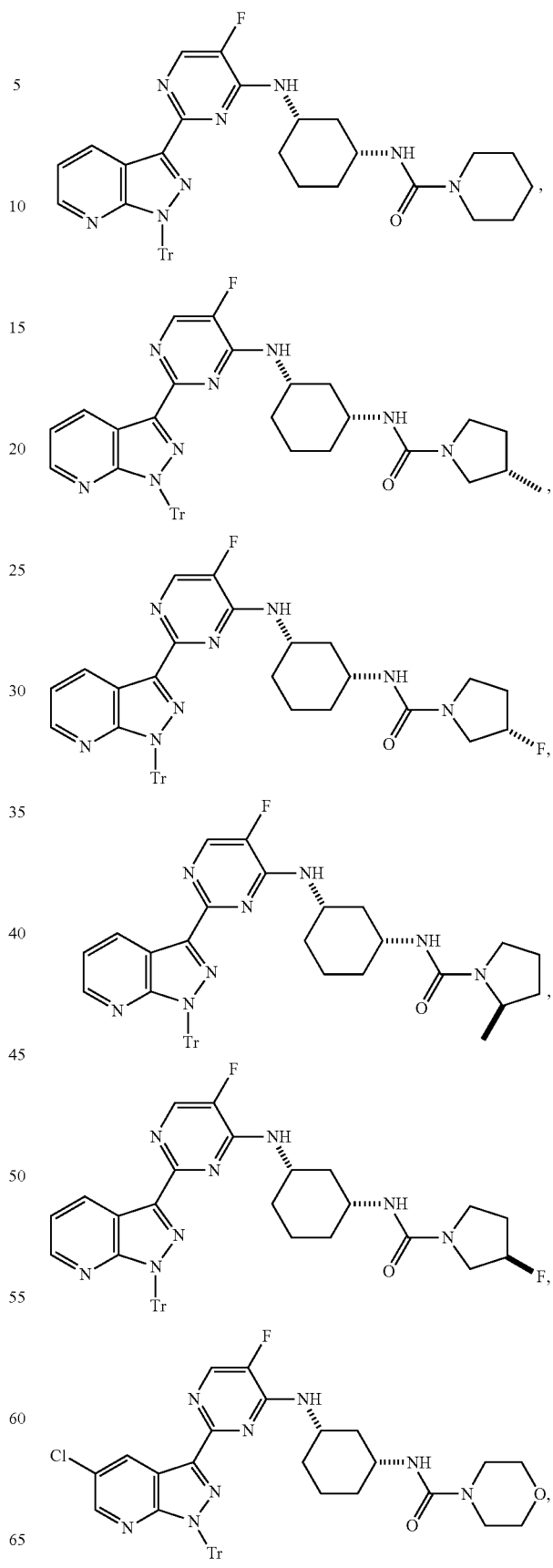

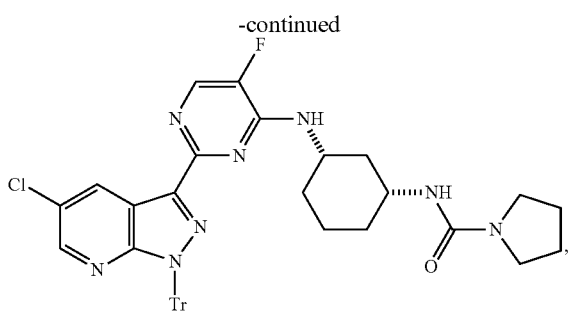
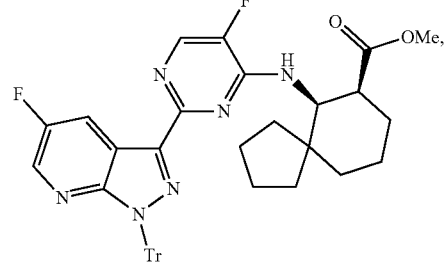
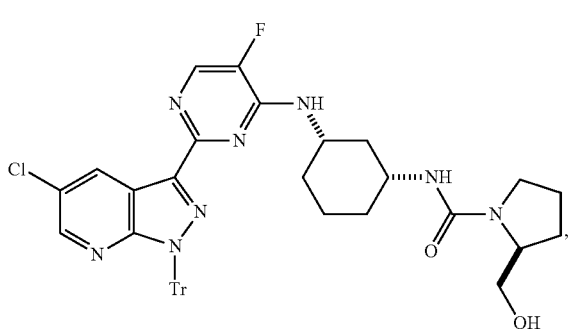
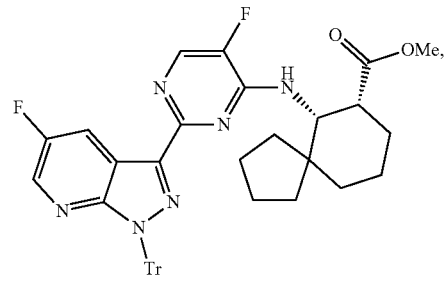
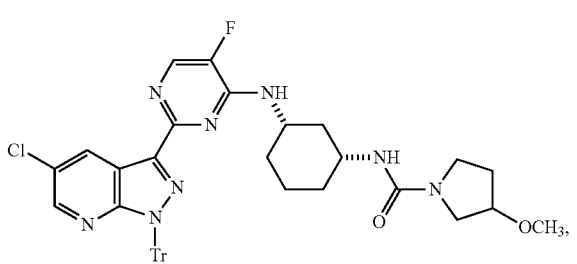
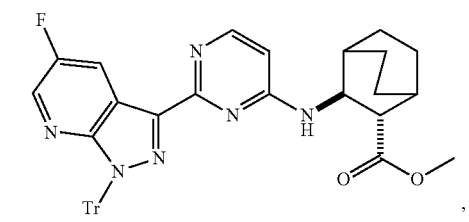
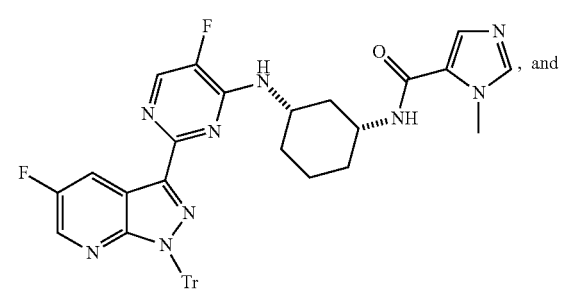
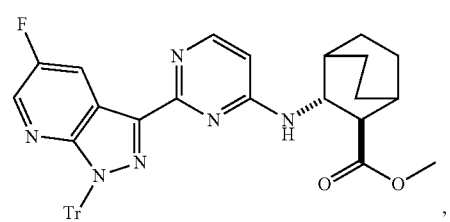
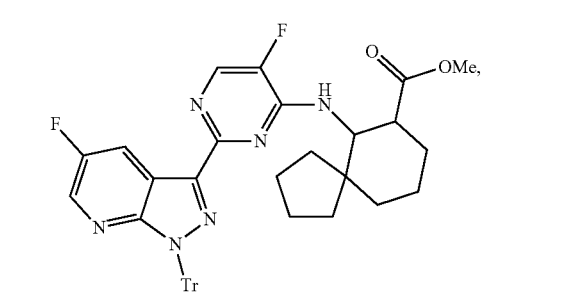
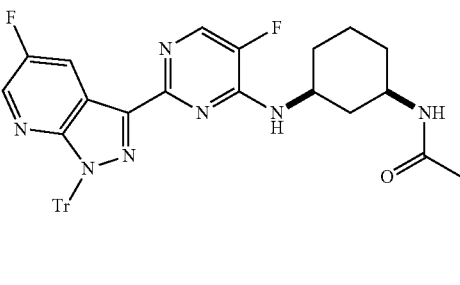
and pharmaceutically acceptable salts thereof, wherein Tr is trityl. Additional specific examples include:

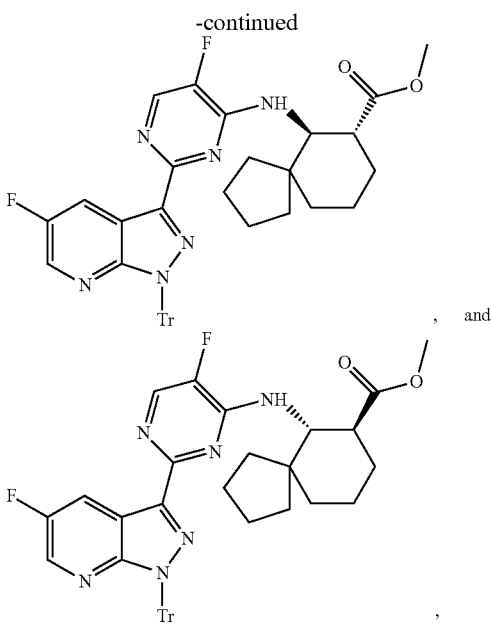

and pharmaceutically acceptable salts thereof.

DEFINITIONS AND GENERAL TERMINOLOGY

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as illustrated generally below, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$-$C_3$alkyl or phenyl; X may be either optionally substituted $C_1$-$C_3$ alkyl or optionally substituted phenyl. Likewise, if the term "optionally substituted" follows a list, said term also refers to all of the substitutable groups in the prior list unless otherwise indicated. For example: if X is $C_1$-$C_3$alkyl or phenyl wherein X is optionally and independently substituted by $J^X$, then both $C_1$-$C_3$alkyl and phenyl may be optionally substituted by $J^X$.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to carbocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0³,⁷]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl) carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic or heteroaliphatic group, or a non-aromatic heterocyclic ring may contain one or more substituents. Suitable substituents on the saturated carbon of an aliphatic or heteroaliphatic group, or of a heterocyclic ring are selected from those listed above. Other suitable substitutents include those listed as suitable for the unsaturated carbon of a carbocyclic aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, O($C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$ aliphatic groups of R* is unsubstituted.

In some embodiments, optional substituents on the nitrogen of a heterocyclic ring include those used above. Other suitable substituents include —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^+)_2$, —$C(=NH)—N(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of $R^+$, on the same substituent or different substituents, taken together with the atom(s) to which each $R^+$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, O($C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of a carbocyclic aryl or heteroaryl group are selected from those listed above. Other suitable substituents include: halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1-2}$(Ph), optionally substituted with $R^\circ$; —CH=CH (Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2R^\circ$; —$NR^\circ NR^\circ C(O)R^\circ$; —$NR^\circ NR^\circ C(O)N(R^\circ)_2$; —$NR^\circ NR^\circ CO_2R^\circ$; —C(O)C(O)$R^\circ$; —$C(O)CH_2C(O)R^\circ$; —$CO_2R^\circ$; —$C(O)R^\circ$; —$C(S)R^\circ$; —$C(O)N(R^\circ)_2$; —$C(S)N(R^\circ)_2$; —$OC(O)N(R^\circ)_2$; —OC(O)$R^\circ$; —$C(O)N(OR^\circ)R^\circ$; —$C(NOR^\circ)R^\circ$; —$S(O)_2R^\circ$; —$S(O)_3R^\circ$; —$SO_2N(R^\circ)_2$; —$S(O)R^\circ$; —$NR^\circ SO_2N(R^\circ)_2$; —$NR^\circ SO_2R^\circ$; —$N(OR^\circ)R^\circ$; —C(=NH)—$N(R^\circ)_2$; or —$(CH_2)_{0-2}NHC(O)R^\circ$; wherein each independent occurrence of $R^\circ$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, two independent occurrences of $R^\circ$, on the same substituent or different substituents, taken together with the atom(s) to which each $R^\circ$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of $R^\circ$ are selected from $NH_2$, $NH(C_{1-4}$aliphatic), $N(C_{1-4}$aliphatic)$_2$, halogen, $C_{1-4}$aliphatic, OH, O($C_{1-4}$aliphatic), $NO_2$, CN, $CO_2H$, $CO_2(C_{1-4}$aliphatic), O(halo$C_{1-4}$ aliphatic), or halo$C_{1-4}$aliphatic, CHO, N(CO)($C_{1-4}$ aliphatic), C(O)N($C_{1-4}$ aliphatic), wherein each of the foregoing $C_{1-4}$aliphatic groups of $R^\circ$ is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation.

As detailed above, in some embodiments, two independent occurrences of $R^\circ$ (or $R^+$, or any other variable similarly defined herein), may be taken together with the atom(s) to which each variable is bound to form a 5-8-membered heterocyclyl, carbocyclic aryl, or heteroaryl ring or a 3-8-membered cycloalkyl ring. Exemplary rings that are formed when two independent occurrences of $R^\circ$ (or $R^+$, or any other variable similarly defined herein) are taken together with the atom(s) to which each variable is bound include, but are not limited to the following: a) two independent occurrences of $R^\circ$ (or $R^+$, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

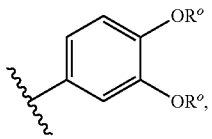

these two occurrences of R° are taken together with the oxygen atoms to which they are bound to form a fused 6-membered oxygen containing ring:

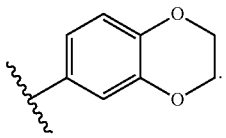

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

The term "hydroxyl" or "hydroxy" or "alcohol moiety" refers to —OH.

As used herein, an "alkoxycarbonyl," which is encompassed by the term carboxy, used alone or in connection with another group refers to a group such as (alkyl-O)—C(O)—.

As used herein, a "carbonyl" refers to —C(O)—.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O-alkyl) or sulfur ("alkylthio" e.g., —S-alkyl) atom.

As used herein, the terms "halogen", "halo", and "hal" mean F, Cl, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF₃ and —CF₂CF₃.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (NC)-alkyl-.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above. In some embodiments, the aminoaliphatic is a C1-C6 aliphatic group substituted with one or more —NH₂ groups. In some embodiments, the aminoalkyl refers to the structure (R^X R^Y)N-alkyl-, wherein each of R^X and R^Y independently is as defined above. In some specific embodiments, the aminoalkyl is C1-C6 alkyl substituted with one or more —NH₂ groups. In some specific embodiments, the aminoalkenyl is C1-C6 alkenyl substituted with one or more —NH₂ groups. In some embodiments, the aminoalkoxy is —O(C1-C6 alkyl) wherein the alkyl group is substituted with one or more —NH₂ groups.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)-alkyl-, wherein alkyl is as defined above.

The term "carboxyalkyl" means alkyl substituted with one or more carboxy groups, wherein alkyl and carboxy are as defined above.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

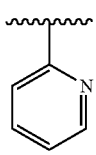

also represents

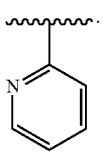

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters. Pharmaceutically acceptable prodrugs of the compounds described herein include, without limitation, esters, amino acid esters, phosphate esters, metal salts and sulfonate esters.

Uses of Disclosed Compounds

One aspect of the present invention is generally related to the use of the compounds described herein or pharmaceutically acceptable salts, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

In one embodiment, the present invention is generally related to the use of compounds represented by Structural Formulae (I), (II), (IIIA) or (IIIB), or pharmaceutically acceptable salts thereof for any of the uses specified above:

In yet another embodiment, the present invention is directed to the use of any compound selected from the compounds depicted in Tables 1 and 2, or a pharmaceutically acceptable salt thereof, for any of the uses described above.

In some embodiments, the compounds are represented by any one of Structural Formulae (I), (II), (IIIA) or (IIIB), and the variables are each independently as depicted in the compounds of Tables 1 and 2.

In yet another embodiment, the compounds described herein or pharmaceutically acceptable salts thereof can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenzavirus A, Influenzavirus B, Influenzavirus C, Isavirus and Thogotovirus. Influenzavirus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Influenzavirus B genus has one species, influenza B virus. Influenza B almost exclusively infects humans and is less common than influenza A. Influenzavirus C genus has one species, Influenzavirus C virus, which infects humans and pigs and can cause severe illness and local epidemics. However, Influenzavirus C is less common than the other types and usually seems to cause mild disease in children.

In some embodiments of the invention, influenza or influenza viruses are associated with Influenzavirus A or B. In some embodiments of the invention, influenza or influenza viruses are associated with Influenzavirus A. In some specific embodiments of the invention, Influenzavirus A is H1N1, H2N2, H3N2 or H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically $1/10$ to $1/1000$), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, . . . , $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc). It also includes the use among populations who require protection from the influenza but who either do not get protection after vaccination (e.g. due to weak immunse system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc).

According to the US CDC, an influenza "outbreak" is defined as a sudden increase of acute febrile respiratory illness (AFR1) occurring within a 48 to 72 hour period, in a group of people who are in close proximity to each other (e.g. in the same area of an assisted living facility, in the same household, etc) over the normal background rate or when any subject in the population being analyzed tests positive for influenza. One case of confirmed influenza by any testing method is considered an outbreak.

A "cluster" is defined as a group of three or more cases of AFR1 occurring within a 48 to 72 hour period, in a group of people who are in close proximity to each other (e.g. in the same area of an assisted living facility, in the same household, etc).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In one embodiment, the methods of the invention are a preventative or "pre-emptive" measure to a patient, specifically a human, having a predisposition to complications resulting from infection by an influenza virus. The term "pre-emptive" as used herein as for example in pre-emptive use, "pre-emptively", etc, is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), tree times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Various types of administration methods can be employed in the invention, and are described in detail below under the section entitled "Administration Methods."

Combination Therapy

An effective amount can be achieved in the method or pharmaceutical composition of the invention employing a compound of the invention (including a pharmaceutically acceptable salt or solvate (e.g., hydrate)) alone or in combination with an additional suitable therapeutic agent, for example, an antiviral agent or a vaccine. When "combination therapy" is employed, an effective amount can be achieved using a first amount of a compound of the invention and a second amount of an additional suitable therapeutic agent (e.g. an antiviral agent or vaccine).

In another embodiment of this invention, a compound of the invention and the additional therapeutic agent, are each administered in an effective amount (i.e., each in an amount which would be therapeutically effective if administered alone). In another embodiment, a compound of the invention and the additional therapeutic agent, are each administered in an amount which alone does not provide a therapeutic effect (a sub-therapeutic dose). In yet another embodiment, a compound of the invention can be administered in an effective amount, while the additional therapeutic agent is administered in a sub-therapeutic dose. In still another embodiment, a compound of the invention can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In one embodiment, the present invention is directed to methods of combination therapy for inhibiting Flu viruses replication in biological samples or patients, or for treating or preventing Influenza virus infections in patients using the compounds or pharmaceutical compositions of the invention. Accordingly, pharmaceutical compositions of the invention also include those comprising an inhibitor of Flu virus replication of this invention in combination with an anti-viral compound exhibiting anti-Influenza virus activity.

Methods of use of the compounds and compositions of the invention also include combination of chemotherapy with a compound or composition of the invention, or with a combination of a compound or composition of this invention with another anti-viral agent and vaccination with a Flu vaccine.

When co-administration involves the separate administration of the first amount of a compound of the invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of the invention and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of the invention and a second amount of an additional therapeutic agent can result in an enhanced or synergistic therapeutic effect, wherein the combined effect is greater than the additive effect that would result from separate administration of the first amount of a compound of the invention and the second amount of an additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using the compounds of the present invention is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See alsoRuruta et al., Antiviral Reasearch, 82: 95-102 (2009), "T-705 (flavipiravir) and related compounds: Novel broad-spectrum inhibitors of RNA viral infections.") In some embodiments, the compounds described herein can be co-administered with a traditional influenza vaccine.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

EXEMPLIFICATION

Synthesis of Compounds of the Invention

The compounds disclosed herein can be prepared by any suitble method known in the art, for example, WO 2005/095400, WO 2007/084557, WO 2010/011768, WO 2010/011756, WP 2010/011772, WO 2009/073300, and PCT/US2010/038988 filed on Jun. 17, 2010. For example, the compounds shown in Tables 1 and 2 can be prepared by any suitble method known in the art, for example, WO 2005/095400, WO 2007/084557, WO 2010/011768, WO 2010/011756, WP 2010/011772, WO 2009/073300, and PCT/US2010/038988, and by the exemplary syntheses described below. Generally, the compounds of the invention can be prepared as shown in those syntheses optionally with any desired appropriate modification.

Methodology for Synthesis and Characterization of Compounds

Syntheses of certain exemplary compounds of the invention are described below. NMR and Mass Spectroscopy data of certain specific compounds are summarized in Tables 1 and 2. As used herein the term RT (min) refers to the LCMS retention time, in minutes, associated with the compound.

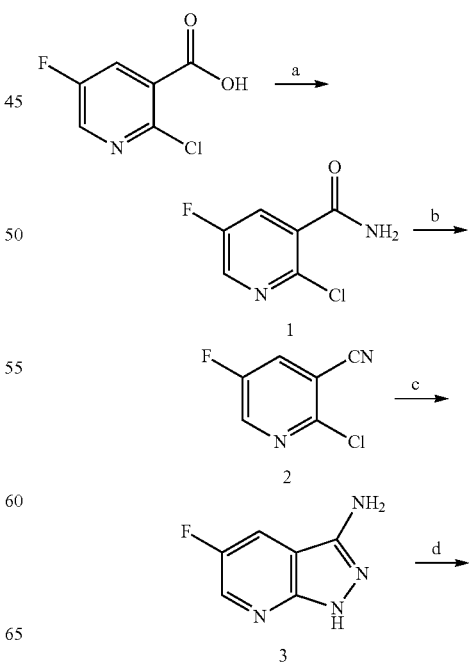

Synthetic Scheme 1

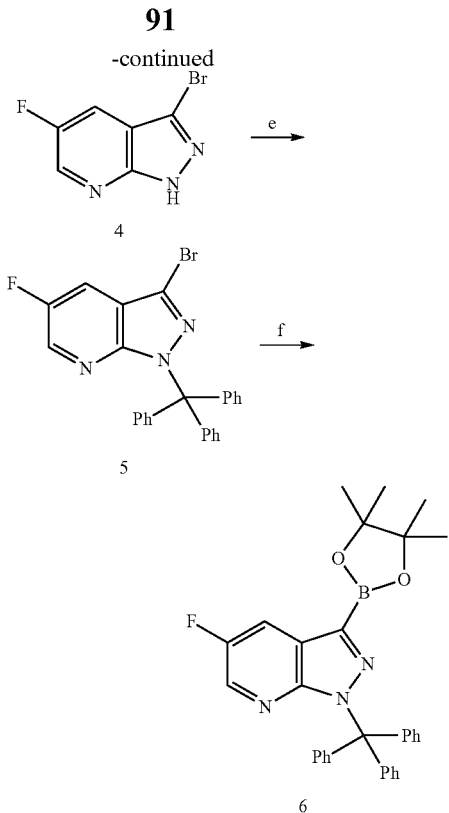

(a) (CO)₂Cl₂, DMF/CH₂Cl₂, NH₄OH; (b) Et₃N, TFAA, CH₂Cl₂ (c) N₂H₄·H₂O, nBuOH, reflux; (d) tBuNO₂, Br₃CH, 60-90° C.; (e) Ph₃CCl, K₂CO₃, DMF (f) KOAc, 4,4,5,5-tetramethyl-2-(4,4,5,5-tetramethyl-1,3,2-dioxaborolan-2-yl)-1,3,2-dioxaborolane, Pd(dppf)₂Cl₂, DMF Formation of
2-chloro-5-fluoropyridine-3-carboxamide (1)

To the suspension of 2-chloro-5-fluoropyridine-3-carboxylic acid (37.0 g, 210.8 mmol) in dichloromethane (555 mL) was added oxalyl chloride (56.2 g, 442.7 mmol) under nitrogen. DMF (1.54 g, 21.08 mmol) was added slowly to the reaction mixture. The mixture was stirred at room temperature for 2 hr and dichloromethane was removed under reduced pressure. The residue was dissolved in THF (300 mL) and cooled down to 0° C. by ice bath. Ammonium hydroxide (28-30%, 113.0 mL, 1.8 mmol) was added in one portion. The mixture was stirred for another 15 min. The mixture was diluted into ethyl acetate (300 mL) and water (300 mL) and the phases were separated. The organic layer was washed with brine and dried over Na₂SO₄, filtered, and concentrated in vacuo to afford 29.8 g desired product as white solid: $^1$H NMR (300 MHz, DMSO) δ 8.53 (d, J=3.0 Hz, 1H), 8.11 (s, 1H), 8.00 (dd, J=8.0, 3.0 Hz, 1H), 7.89 (s, 1H); LC/MS Gradient 10-90%, 0.1% formic 5 min, C18/ACN, RT=1.11 min, (M+H) 175.02.

Formation of
2-chloro-5-fluoropyridine-3-carbonitrile (2)

To the suspension of 2-chloro-5-fluoropyridine-3-carboxamide, 1, (29.8 g, 170.4 mmol) in dichloromethane (327 mL) was added triethylamine (52.3 mL, 374.9 mmol). This mixture was cooled down to 0° C. Trifluoroacetic anhydride (26.1 mL, 187.4 mmol) was added slowly over period of 15 min. The mixture was stirred at 0° C. for 90 min. The mixture was diluted into dichloromethane (300 mL) and the resulting organic phase was washed with aqueous saturated NaHCO₃ solution (300 mL) and brine (300 mL). The organic layer was dried over Na₂SO₄, filtered, concentrated in vacuo. The product was purified by silica gel chromatography (40% to 60% ethyl acetate/hexanes) giving 24.7 g of product as a white solid: $^1$H NMR (300 MHz, CDCl₃) δ 8.50 (d, J=3.0 Hz, 1H), 7.77 (dd, J=6.8, 3.0 Hz, 1H); LC/MS Gradient 10-90%, 0.1% formic 5 min, C18/ACN, Retention Time=2.50 min, (M+H) 157.06.

Formation of
5-fluoro-1H-pyrazolo[3,4-b]pyridin-3-Amine (3)

To the mixture of 2-chloro-5-fluoropyridine-3-carbonitrile, 2, (29.6 g, 157.1 mmol) in n-butanol (492 mL) was added hydrazine hydrate (76.4 mL, 1.6 mol). This mixture was heated to reflux for 4.5 h and cooled down. n-Butanol was removed under reduced pressure and water (300 mL) was added resulting in a yellow precipitate. The suspension was filtered and washed with water twice, followed by a MTBE wash. The yellow solid was dried in a vacuum oven to give 18 g of the desired product: $^1$H NMR (300 MHz, d6-DMSO) δ 12.08 (s, 1H), 8.38 (dd, J=2.7, 1.9 Hz, 1H), 7.97 (dd, J=8.8, 2.7 Hz, 1H), 5.56 (s, 2H); LC/MS Gradient 10-90%, 0.1% formic 5 min, C18/ACN, Retention Time=1.25 min, (M+H) 152.95.

Formation of
3-bromo-5-fluoro-1H-pyrazolo[3,4-b]pyridine (4)

To the miture of 5-fluoro-1H-pyrazolo[3,4-b]pyridin-3-amine, 3, (0.88 g, 5.79 mmol) in bromoform (8.8 mL) was added tert-butyl nitrite (1.38 mL, 11.57 mmol). This mixture was heated to 61° C. for 1 h and then heated to 90° C. for an additional hour. The mixture was cooled to room temperature and bromoform was removed under reduced pressure. The resulting crude residue was purified by silica gel chromatography (5-50% ethyl acetate/hexanes) to afford 970 mg of the desired product as a white solid: $^1$H NMR (300 MHz, DMSO) δ 14.22 (s, 1H), 8.67 (dd, J=2.7, 1.9 Hz, 1H), 8.07 (dd, J=8.2, 2.7 Hz, 1H); LC/MS Gradient 10-90%, 0.1% formic 5 min, C18/ACN, Retention Time=2.42 min, (M+H) 216.11.

Formation of 3-bromo-5-fluoro-1-trityl-1H-pyrazolo [3,4-b]pyridine (5)

A mixture of 3-bromo-5-fluoro-1H-pyrazolo[3,4-b]pyridine, 4, (0.97 g, 4.49 mmol) and K₂CO₃ (1.86 g, 13.47 mmol) in DMF (9.7 mL) was cooled to 0° C. Chlorodiphenylmethylbenzene (1.38 g, 4.94 mmol) was added. The mixture was stirred at room temperature overnight. The mixture was diluted with 40 mL of ethyl acetate and washed with 30 mL of water. The organic layer was washed with brine, dried over Na₂SO₄, filtered and concentrated in vacuo. The product was purified by silica gel chromatography (40% ethyl acetate/hexanes) to afford 1.68 g of the desired product as a white solid: $^1$H NMR (300 MHz, d6-DMSO) δ 8.45-8.38 (m, 1H), 8.04 (dd, J=8.0, 2.7 Hz, 1H), 7.35-7.16 (m, 15H); LC/MS Gradient 10-90%, 0.1% formic 5 min, C18/ACN, Retention Time=3.03 min, (M+H) 459.46.

Formation of 5-fluoro-3-(4,4,5,5-tetramethyl-1,3,2-dioxaborolan-2-yl)-1-trityl-1H-pyrazolo[3,4-b]pyridine (6)

Degassed a solution of 3-bromo-5-fluoro-1-trityl-pyrazolo [3,4-b]pyridine, 5, (3.43 g, 7.48 mmol), KOAc (2.20 g, 22.45 mmol) and 4,4,5,5-tetramethyl-2-(4,4,5,5-tetramethyl-1,3,2-dioxaborolan-2-yl)-1,3,2-dioxaborolane (2.85 g, 11.23 mmol) in DMF (50 ml) for 40 min. To the mixture was added 1,1'-Bis(diphenylphosphino)ferrocene-palladium(II)dichloride dichloromethane (0.610 g, 0.748 mmol) The reaction mixture was heated at 100° C. for 90 minutes. The reaction mixture was filtered through a pad of celite. To the resulting filtrate was added ether and brine. The organic phase was dried over MgSO$_4$, filtered and concentrated in vacuo to afford 4.0 g crude product that was used in the next step without further purification (note, the product decomposes if purification is attempted via silica gel chromatography).

Synthetic Scheme 2

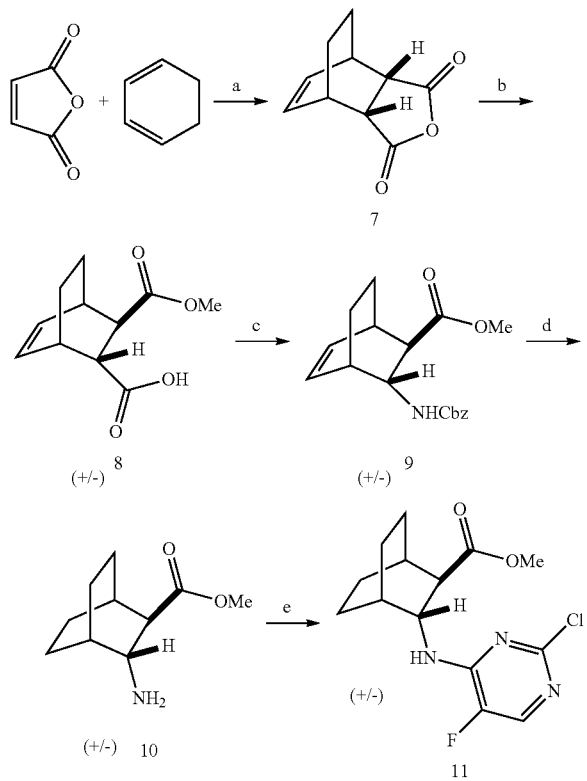

(a) CHCl$_3$; (b) NaOMe, MeOH; (c) DPPA, Et$_3$N, BnOH; (d) H$_2$, Pd/C; (e) 2,4-dichloro-5-fluoropyrimidine, N,N-diisopropylethylamine, DMF Formation of endo-tetrahydro-4,7-ethanoisobenzofuran-1,3-dione (7)

To a cold (0° C.) solution of maleic anhydride (210.0 g, 2142.0 mmol) in CHCl$_3$ (2.3 L) was added cyclohexa-1,3-diene (224.5 mL, 2356.0 mmol) slowly over 50 minutes. The reaction was warmed to room temperature and stirred overnight in the dark. After removing the solvent under reduced pressure, 2.1 L of MeOH was added to the mixture and the mixture was heated to 50° C. for 10 min and then cooled down to 0° C. The resulting precipitate was filtered and dried in an oven at 45° C. overnight to afford 283 g of a white solid. The resulting endo (meso) Diels-Alder cycloaddition product was used without further purification.

Formation of (+/−)-trans-3-(methoxycarbonyl)bicyclo[2.2.2]oct-5-ene-2-carboxylic acid (8)

To a solution of endo-(+/−)-tetrahydro-4,7-ethanoisobenzofuran-1,3-dione, 7, (74.5 g, 418.1 mmol) was stirred in NaOMe (764.9 mL of 25% w/w solution in MeOH, 3.3 mol). The reaction mixture was stirred at room temperature for 4 days yielding a white suspension. The reaction mixture was concentrated in vacuo to remove approximately 300 mL of MeOH. In another flask, HCl (315.9 mL of 36.5% w/w, 3763.0 mmol) in 300 mL of water was cooled to 0° C. The reaction mixture was added into this HCl solution slowly and a white solid precipitated. The remaining methanol was removed under reduced pressure. The mixture was cooled to 0° C. and stirred for 30 minutes. The precipitate was filtered, and washed with water 3 times, giving an off-white solid. The remaining water was removed under reduced pressure to afford 82 g of a white solid.

Formation of (+/−)-trans-methyl 3-(((benzyloxy)carbonyl)amino)bicyclo[2.2.2]oct-5-ene-2-carboxylate (9)

To a solution of racemic-trans-3-methoxycarbonylbicyclo[2.2.2]oct-5-ene-2-carboxylic acid, 8, (100.0 g, 475.7 mmol) in toluene (1.0 L) was added diphenylphosphoryl azide (112.8 mL, 523.3 mmol) and triethylamine (72.9 mL, 523.3 mmol). The reaction mixture was heated to 90° C. for 2 hours. Then, benzyl alcohol (49.2 mL, 475.7 mmol) was added and the mixture and heated to 90° C. over 3 days. The mixture was cooled to room temperature and diluted with EtOAc (500 mL) and aqueous sat. NaHCO$_3$ solution. The organic phase was washed with brine, dried (MgSO$_4$), filtered and concentrated in vacuo. The resulting crude material was purified by silica gel chromatography (100% dichloromethane) to afford 115 g oil. $^1$H NMR show it contains BnOH (about 0.05 equiv). The product was used without further purification: $^1$H NMR (300 MHz, CDCl$_3$) δ 7.40-7.24 (m, 5H), 6.41 (t, J=7.4 Hz, 1H), 6.21-6.04 (m, 1H), 5.15-4.94 (m, 2H), 4.63-4.45 (m, 1H), 4.30-4.18 (m, 1H), 3.70 (s, 2H), 3.49 (s, 1H), 2.81 (br s, 1H), 2.68 (br s, 1H), 2.08 (s, 1H), 1.76-1.56 (m, 1H), 1.52-1.35 (m, 1H), 1.33-1.14 (m, 1H), 1.12-0.87 (m, 1H).

Formation of (+/−)-trans-methyl 3-aminobicyclo[2.2.2]octane-2-carboxylate (10)

To a solution of racemic trans-methyl 3-(((benzyloxy)carbonyl)amino)-bicyclo[2.2.2]oct-5-ene-2-carboxylate, 9, (115.0 g, 364.7 mmol) in THF (253 mL) and MeOH (253 mL) was added Pd/C and the mixture was placed under 40 psi of hydrogen atmosphere overnight. Some exotherm was observed. $^1$H NMR shows the reaction is complete and there is BnOH present. The reaction mixture was filtered through celite and washed with MeOH. Concentrated filtrate in vacuo to afford 69 g oil: $^1$H NMR (400 MHz, CDCl$_3$) δ 3.63 (d, J=5.6 Hz, 3H), 3.30 (d, J=6.7 Hz, 1H), 2.11 (d, J=6.6 Hz, 1H), 1.91 (t, J=7.3 Hz, 1H), 1.80-1.64 (m, 1H), 1.63-1.38 (m, 6H), 1.36-1.23 (m, 2H).

Formation of (+/−)-trans-methyl 3-((2-chloro-5-fluoropyrimidin-4-yl)amino)bicycle[2.2.2]octane-2-carboxylate (11)

To a solution of racemic-trans-methyl 3-aminobicyclo[2.2.2]octane-2-carboxylate, 10, (1.30 g, 7.09 mmol) and 2,4-dichloro-5-fluoro-pyrimidine (1.77 g, 10.64 mmol) in DMF (20 mL) was added N,N-diisopropylethylamine (4.94 mL, 28.38 mmol). The reaction mixture was stirred at room temperature for 100 min. The mixture was diluted into aqueous saturated NH₄Cl solution and extracted twice with EtOAc. The combined organic phases were washed three times with brine, dried (MgSO₄), filtered and concentrated in vacuo. The crude residue was purified via silica gel chromatography (0-10% MeOH/CH₂Cl₂ gradient) to afford 1.41 g of the desired product: LC/MS Gradient 10-90%, 0.1% formic 5 min, C18/ACN RT=1.14 min (M+H) 314.11.

The following compound was made by methods similar to those described above:

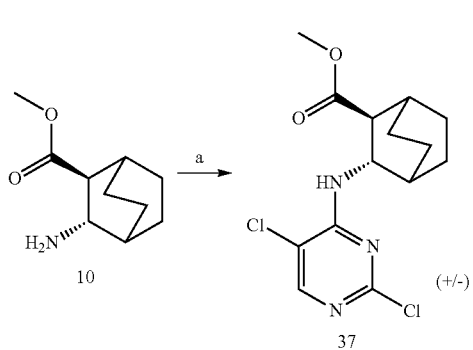 [SMILES: COC(=O)[C@H]1C2CCC(CC2)[C@@H]1N ; COC(=O)[C@H]1C2CCC(CC2)[C@@H]1Nc1nc(Cl)ncc1Cl]

Formation of (+/−)-trans-(2,3)-methyl 3-((2,5-dichloropyrimidin-4-yl)amino)bicyclo-[2.2.2]octane-2-carboxylate (37)

To a solution of racemic-trans-(2,3)-methyl 3-aminobicyclo[2.2.2]octane-2-carboxylate, 10, (2.0 g, 10.9 mmol) in THF (15.6 mL) at room temperature was added 2,4,5-trichloropyrimidine (2.2 g, 1.4 mL, 12.0 mmol) followed by N,N-diisopropylethylamine (2.3 mL, 13.1 mmol). The vessel was sealed and heated to 60° C. After 2.5 hr., the solution was diluted with EtOAc, washed twice with half saturated brine, dried over Na₂SO₄, filtered through a small plug of silica and concentrated in vacuo. Flash chromatography (SiO₂, 0-30% EtOAc-hexanes, gradient elution) provided the desired product (3.09 g, 85% yield): ¹H NMR (400 MHz, MeOD) δ 8.04 (s, 1H), 4.53 (d, J=6.5 Hz, 1H), 3.71 (s, 3H), 2.77 (d, J=6.6 Hz, 1H), 1.99 (d, J=2.1 Hz, 1H), 1.84 (d, J=2.1 Hz, 1H), 1.81-1.69 (m, 3H), 1.69-1.54 (m, 3H), 1.54-1.38 (m, 2H).

Synthetic Scheme 3: Preparation of Compound I-31

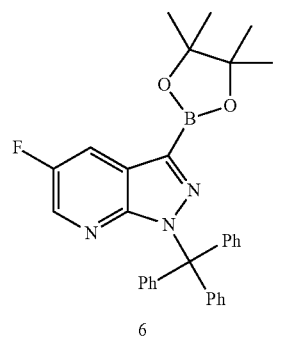

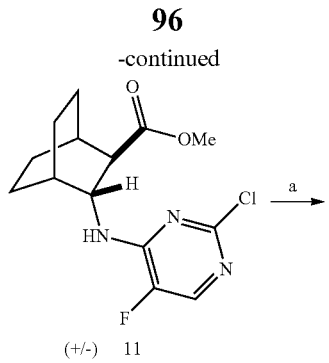

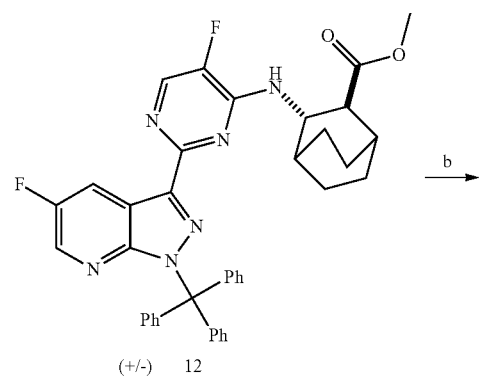

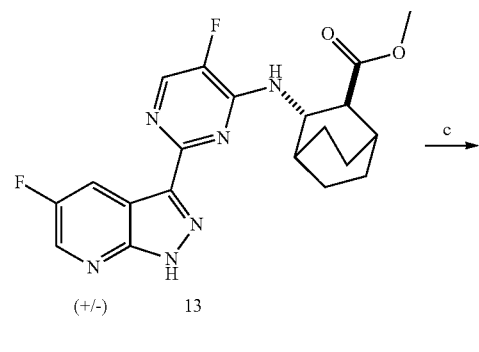

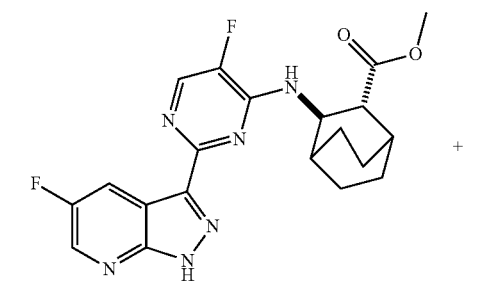

-continued

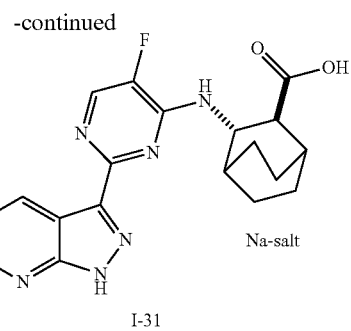

I-31

(a) X-phos, Pd$_2$(dba)$_3$, K$_3$PO$_4$, 2-MeTHF, 120° C.; (b) Et$_3$SiH, TFA, CH$_2$Cl$_2$ (c) SFC chromatographic resolution (d) LiOH•H$_2$O, THF, H$_2$O Formation of (+/−) trans-methyl 3-(5-fluoro-2-(5-fluoro-1-trityl-1H-pyrazolo[3,4-b]pyridin-3-yl)pyrimidin-4-ylamino)bicyclo[2.2.2]octane-2-carboxylate (12)

A solution of racemic-trans-methyl-3-[(2-chloro-5-fluoropyrimidin-4-yl)amino]bicyclo[2.2.2]octane-2-carboxylate, 11, (0.94 g, 3.00 mmol) and 5-fluoro-3-(4,4,5,5-tetramethyl-1,3,2-dioxaborolan-2-yl)-1-trityl-pyrazolo[3,4-b]pyridine, 6, (1.67 g, 3.30 mmol) and K$_3$PO$_4$ (2.54 g, 12.00 mmol) in 2-methyl THF (30 mL) and H$_2$O (6 mL) was degassed under a stream of nitrogen for 1 h. To the mixture was added dicyclohexyl-[2-(2,4,6-triisopropylphenyl)phenyl]phosphane (0.17 g, 0.36 mmol) and 1,5-diphenylpenta-1,4-dien-3-one; palladium (0.07 g, 0.08 mmol). The reaction mixture was heated at 120° C. in a pressure bottle for 2 hr. The reaction mixture was filtered through Florisil and celite, then washed with brine and dried over MgSO$_4$, the solvent was concentrated in vacuo. The crude residue was purified by silica gel chromatography (30% EtOAc/hexanes): $^1$H NMR (300 MHz, CDCl$_3$) δ 8.50 (dd, J=8.4, 2.9 Hz, 1H), 8.11 (dd, J=20.6, 17.2 Hz, 2H), 7.35-7.16 (m, 16H), 5.07 (d, J=6.1 Hz, 1H), 4.81 (t, J=7.2 Hz, 1H), 3.60 (s, 3H), 2.38 (d, J=6.6 Hz, 1H), 2.07 (d, J=10.6 Hz, 1H), 1.85-1.35 (m, 10H); LC/MS Gradient 10-90%, 0.1% formic 5 min, C18/ACN, Retention Time=3.42 min, (M+H) 657.28.

Formation of (+/−) trans-methyl 3-(5-fluoro-2-(5-fluoro-1H-pyrazolo[3,4-b]pyridin-3-yl)pyrimidin-4-ylamino)bicyclo[2.2.2]octane-2-carboxylate (13)

To a solution of racemic methyl 3-[[5-fluoro-2-(5-fluoro-1-trityl-pyrazolo[3,4-b]pyridin-3-yl)pyrimidin-4-yl]amino]bicyclo[2.2.2]octane-2-carboxylate, 12, (2.40 g, 3.66 mmol) in CH$_2$Cl$_2$ (52 mL) was added Et$_3$SiH (5.84 mL, 36.55 mmol) followed by trifluoroacetic acid (5.63 mL, 73.10 mmol). The reaction mixture was stirred at room temperature for 1 h. To the reaction mixture was added CH$_2$Cl$_2$ and aqueous saturated NaHCO$_3$ solution. The organic phase was washed with brine, dried over MgSO$_4$, filtered and the solvent was removed under reduced pressure. The crude residue was purified by silica gel chromatography with CH$_2$Cl$_2$ and MeOH to afford 780 mg of azaindazole 13 as a racemic mixture: $^1$H NMR (300 MHz, CDCl$_3$) δ 12.96 (s, 1H), 8.69-8.47 (m, 2H), 8.26 (d, J=3.0 Hz, 1H), 4.91 (t, J=6.3 Hz, 1H), 3.70 (s, 3H), 2.46 (dd, J=22.4, 6.6 Hz, 1H), 2.14 (dd, J=15.9, 13.2 Hz, 3H), 1.93 (d, J=13.8 Hz, 1H), 1.83-1.64 (m, 5H), 1.52 (dd, J=24.2, 9.5 Hz, 2H); LC/MS Gradient 10-90%, 0.1% formic 5 min, C18/ACN, Retention Time=2.93 min, (M+H) 414.89. The racemic mixture was resolved by SFC chromatography on a chiral support to afford the individual enantiomers 14 and 15. The (S,S)-enantiomer (15) was taken onto the next step.

Formation of (2S,3S)-3-(5-fluoro-2-(5-fluoro-1H-pyrazolo[3,4-b]pyridin-3-yl)pyrimidin-4-ylamino)bicyclo[2.2.2]octane-2-carboxylic acid sodium salt (I-31)

To a solution of racemic-methyl 3-(5-fluoro-2-(5-fluoro-1H-pyrazolo[3,4-b]pyridin-3-yl)pyrimidin-4-ylamino)bicyclo[2.2.2]octane-2-carboxylate, 15, (0.130 g, 0.296 mmol) in THF (10 mL) was added a 3 ml H$_2$O solution of lithium hydroxide hydrate (0.037 g, 0.889 mmol). The reaction mixture was heated at 60° C. for 5 hr. The solvents were removed under reduced pressure. The residue was dissolved in CH$_2$Cl$_2$ and MeOH and then purified by silica gel chromatography with CH$_2$Cl$_2$ and 76% chloroform, 20% MeOH and 4% NH$_4$OH. The product was eluted with 76% chloroform, 20% MeOH and 4% NH$_4$OH to afford 50 mg of the desired product as an ammonium salt. To the 50 mg of ammonium salt in MeOH suspension was added 119.9 uL 1N NaOH. The suspension became clear and the solution was stirred at room temperature for 1 h. The solvent was removed under reduced pressure to afford 50 mg of the desired product as a sodium salt: $^1$H NMR (300.0 MHz, MeOD) δ 8.71 (d, J=6.1 Hz, H), 8.50 (s, 1H), 8.05 (d, J=4.0 Hz, 1H), 4.98 (d, J=6.7 Hz, 1H), 4.89 (s, 1H), 3.31 (m, 1H), 2.53 (d, J=6.8 Hz, 1H), 2.12-1.99 (m, 3H), 1.87-1.81 (m, 3H), 1.76-1.58 (m, 2H) and 1.46 (dd, J=21.8 Hz, 2H); LC/MS Gradient 10-90%, 0.1% formic 5 min, C18/ACN RT=2.26 min (M+H) 401.3.

The following compounds can be prepared in the same fashion using the procedures above:

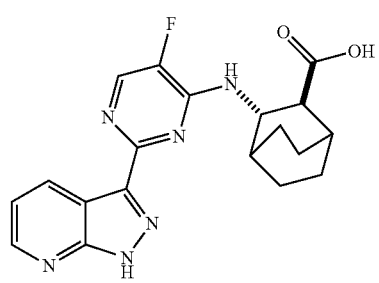

(I-11)

(+/−)-trans-3-((5-fluoro-2-(1H-pyrazolo[3,4-b]pyridin-3-yl)pyrimidin-4-yl)amino)bicyclo-[2.2.2]octane-2-carboxylic acid $^1$H NMR (300 MHz, DMSO) δ 13.97 (s, 1H), 12.35 (s, 1H), 8.81 (d, J=8.1 Hz, 1H), 8.56 (s, 1H), 8.29 (d, J=3.6 Hz, 1H), 7.77 (s, 1H), 7.32 (s, 1H), 4.74 (s, 1H), 2.89 (d, J=6.3 Hz, 1H), 2.08 (s, 1H), 1.98 (d, J=24.8 Hz, 2H), 1.83-1.32 (m, 6H); LCMS Gradient 10-90%, formic 5 min, C18/AcN, RT=2.40 min (M+H) 383.06.

Synthetic Scheme 4

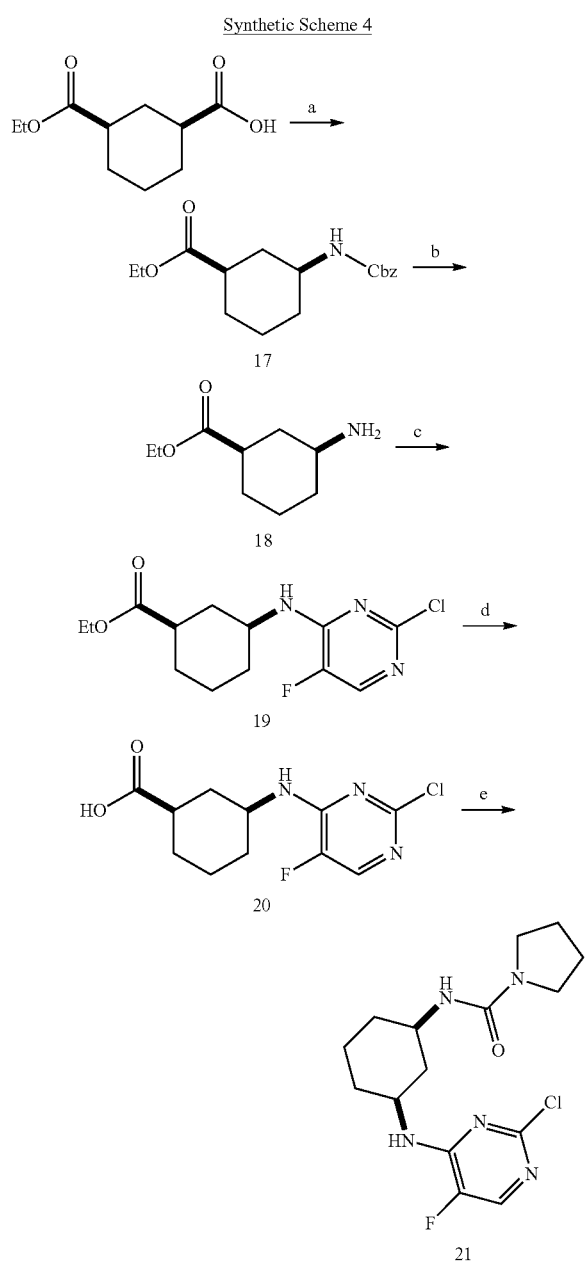

(a) DPPA, Et₃N, toluene, 110° C.; ii BnOH, 85° C. (b) Pd/C (wet, Degussa), hydrogen, EtOH (c) 2,4-dichloro-5-fluoropyrimidine, $^i$Pr₂NEt, THF, reflux (d) LiOH, THF/water, 50° C. (e) DPPA, Et₃N, THF, then pyrrolidine, 85° C.

Formation of (1S,3R)-3-(ethoxycarbonyl)cyclohexanecarboxylic acid (1S,3R)-3-(ethoxycarbonyl)cyclohexanecarboxylic acid starting material can be prepared following the literature procedures described in: Barnett, C. J., Gu, R. L., Kobierski, M. E., WO-2002024705, Stereoselective process for preparing cyclohexyl amine derivatives.

Formation of ethyl (1R,3S)-3-benzyloxycarbony-laminocyclohexanecarboxylate (17)

(1S,3R)-3-(Ethoxycarbonyl)cyclohexanecarboxylic acid, 16, (10.0 g, 49.9 mmol) was dissolved in toluene (100 mL) and treated with triethylamine (7.6 mL, 54.9 mmol) and DPPA (12.2 mL, 54.9 mmol). The resulting solution was heated to 110° C. and stirred for 1 hour. After cooling to 70° C., benzyl alcohol (7.7 mL, 74.9 mmol) was added, and the mixture was heated to 85° C. overnight. The resulting solution was cooled to room temperature, poured into EtOAc (150 mL) and water (150 mL) and the layers were separated. The aqueous layer was extracted with EtOAc (2×75 mL) and the combined organic extracts were washed with water (100 mL) and brine (100 mL), dried over Na₂SO₄ and concentrated in vacuo. The crude material was purified by silica gel chromatography (0%-50% EtOAc/hexanes) to provide 17 (15.3 g, containing 25% benzyl alcohol), which was used for the next step without further purification.

Formation (1R,3S)-ethyl 3-aminocyclohexanecarboxylate (18)

To a solution of (1R,3S)-ethyl 3-(benzyloxycarbony-lamino)cyclohexane-carboxylate, 17, (14.0 g, 45.9 mmol) in ethanol (3 mL) was added Pd/C (wet, Degussa (2.4 g, 2.3 mmol). The mixture was evacuated and then stirred under atmosphere of nitrogen at room temperature overnight. The reaction mixture was filtered through a pad of celite and the resulting filtrate concentrated in vacuo to provide an oil that was used without further purification.

Formation (1R,3S)-ethyl 3-(2-chloro-5-fluoropyrimidin-4-ylamino)cyclohexane-carboxylate (19)

To a solution of (1R,3S)-ethyl 3-aminocyclohexanecarboxylate, 18, (5.1 g, 24.1 mmol) and 2,4-dichloro-5-fluoropyrimidine (6.0 g, 36.0 mmol) in THF (60 mL) was added diisopropylethylamine (9.6 mL, 55.4 mmol). The mixture was heated to reflux overnight. The reaction was cooled to room temperature and concentrated in vacuo. The residue was diluted with water and extracted twice with ethyl acetate. The combined organic phases were dried (MgSO₄), filtered and concentrated in vacuo. The residue was purified by silica gel chromatography (0-40% EtOAc/hexanes gradient) to provide 6.7 g of (1R,3S)-ethyl 3-(2-chloro-5-fluoropyrimidin-4-ylamino)cyclohexane-carboxylate as a white solid: LCMS RT=3.1 (M+H) 302.2.

Formation (1R,3S)-3-(2-chloro-5-fluoropyrimidin-4-ylamino)cyclohexanecarboxylic acid (20)

To a solution of (1R,3S)-ethyl 3-(2-chloro-5-fluoropyrimidin-4-ylamino)cyclohexane-carboxylate, 19, (20.0 g, 66.3 mmol) in THF (150 mL) was added added a solution of LiOH hydrate (8.3 g, 198.8 mmol) in 100 ml water. The reaction mixture was stirred at 50° C. overnight, To the reaction mixture was added HCl (16.6 mL of 12 M solution, 198.8 mmol) and EtOAc. The organic phase was washed with brine and dried over MgSO₄ and the solvent was removed under reduced pressure to afford 17.5 g of product that was used without further purification: $^1$H NMR (300 MHz, CDCl₃) δ 7.91 (d, J=2.7 Hz, 2H), 5.24 (d, J=7.3 Hz, 2H), 4.19-4.03 (m, 3H), 3.84-3.68 (m, 3H), 2.59 (ddd, J=11.5, 8.2, 3.6 Hz, 2H), 2.38 (d, J=12.4 Hz, 2H), 2.08 (d, J=9.6 Hz, 6H), 1.99-1.76 (m, 5H), 1.63-1.34 (m, 6H), 1.32-1.15 (m, 4H).

Formation N-((1R,3S)-3-(2-chloro-5-fluoropyrimidin-4-ylamino)cyclohexyl)-pyrrolidine-1-carboxamide (21)

A solution of (1R,3S)-3-(2-chloro-5-fluoropyrimidin-4-ylamino)cyclohexane-carboxylic acid, 20, (8.2 g, 30.0 mmol), (azido(phenoxy)phosphoryl)oxybenzene (9.7 mL, 45.0 mmol) and triethylamine (5.8 mL, 42.0 mmol) in THF (200 mL) was degassed under nitrogen for 15 minutes. The reaction mixture was heated at 85° C. for 30 minutes. To the reaction mixture was added pyrrolidine (7.5 mL, 90.0 mmol) and the reaction was heated at 85° C. for an additional 15 min. The mixture was diluted into brine and extracted with EtOAc. The organic phase was separated, dried over MgSO$_4$. The product was isolated (6.25 g) by filtration after partial removal of solvent in vacuo: $^1$H NMR (300 MHz, CDCl$_3$) δ 7.87 (d, J=2.8 Hz, 2H), 5.04 (d, J=8.1 Hz, 2H), 4.09 (ddd, J=26.9, 13.4, 5.6 Hz, 4H), 3.91-3.71 (m, 2H), 3.32 (t, J=6.5 Hz, 7H), 2.45 (d, J=11.5 Hz, 2H), 2.08 (dd, J=22.1, 12.0 Hz, 4H), 1.96-1.82 (m, 9H), 1.54 (dd, J=18.6, 8.5 Hz, 2H), 1.22-1.01 (m, 6H).

Synthetic Scheme 5: Preparation of Compound I-14

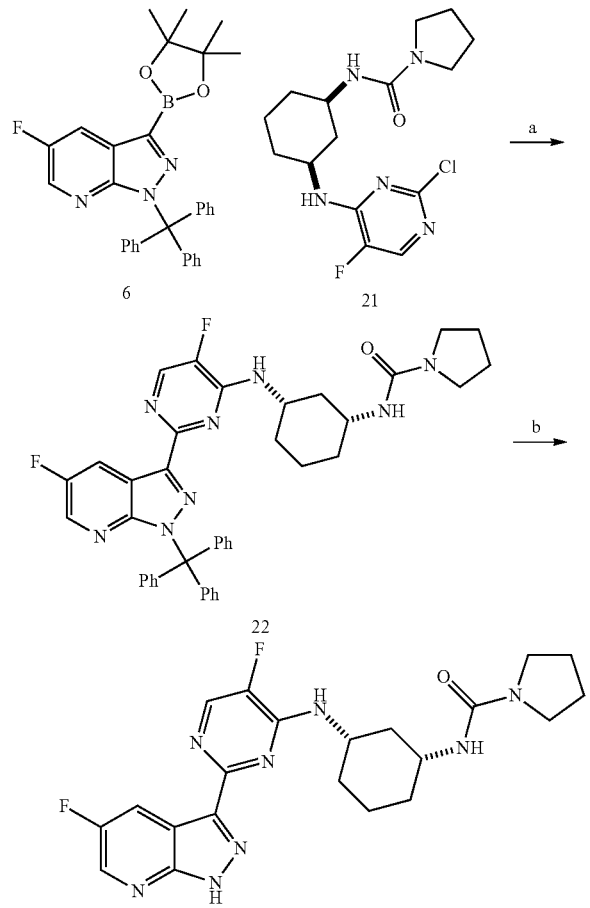

(a) X-Phos, Pd$_2$(dba)$_3$, K$_3$PO$_4$, 2-MeTHF, 120° C.; (b) Et$_3$SiH, TFA, CH$_2$Cl$_2$ Formation of N-((1R,3S)-3-(5-fluoro-2-(5-fluoro-1-trityl-1H-pyrazolo[3,4-b]pyridin-3-yl)pyrimidin-4-ylamino)cyclohexyl)cyclopentanecarboxamide (22)

A solution of 5-fluoro-3-(4,4,5,5-tetramethyl-1,3,2-dioxaborolan-2-yl)-1-trityl-pyrazolo[3,4-b]pyridine, 6, (0.178 g, 0.352 mmol) and N-[(1R,3S)-3-[(2-chloro-5-fluoro-pyrimidin-4-yl)amino]cyclohexyl]pyrrolidine-1-carboxamide, 21, (0.100 g, 0.293 mmol) in 2-methyl THF (8 mL) and H$_2$O (0.8 mL) was degassed under a stream of nitrogen for 30 min. To the mixture was added 1,5-diphenylpenta-1,4-dien-3-one; palladium (0.007 g, 0.007 mmol), dicyclohexyl-[2-(2,4,6-triisopropylphenyl)phenyl]phosphane (0.017 g, 0.035 mmol) and K$_3$PO$_4$ (0.249 g, 1.174 mmol) and the mixture was degassed for an additional 15 min. The reaction mixture was heated at 115° C. in a sealable tube for 1 h. The aqueous phase was removed and the organic phase was filtered through a pad of celite. The mixture was purifed by silica gel chromatography (0-100% EtOAc/hexanes gradient) to afford 100 mg of the desired product: $^1$H NMR (300 MHz, CDCl$_3$) δ 8.45 (dd, J=8.4, 2.9 Hz, 1H), 8.14 (dd, J=3.7, 1.7 Hz, 2H), 7.36-7.25 (m, 15H), 4.95 (d, J=5.8 Hz, 1H), 4.20 (d, J=10.9 Hz, 1H), 4.05 (d, J=7.4 Hz, 1H), 3.86 (dd, J=11.4, 4.2 Hz, 1H), 3.33 (t, J=6.6 Hz, 4H), 2.46 (d, J=11.4 Hz, 1H), 2.32-2.10 (m, 2H), 1.90 (dt, J=13.8, 5.1 Hz, 5H), 1.55 (dd, J=26.4, 12.8 Hz, 1H), 1.14 (dd, J=24.5, 12.2 Hz, 3H); LC/MS Gradient 10-90%, 0.1% formic 5 min, C18/ACN, RT=1.59 min, (M+H) 685.37.

Formation of N-((1R,3S)-3-(5-fluoro-2-(5-fluoro-1H-pyrazolo[3,4-b]pyridin-3-yl)pyrimidin-4-ylamino)cyclohexyl)cyclopentanecarboxamide (I-14)

To a solution of N-[(1R,3S)-3-[[5-fluoro-2-(5-fluoro-1-trityl-pyrazolo[3,4-b]pyridin-3-yl)pyrimidin-4-yl]amino]cyclohexyl]pyrrolidine-1-carboxamide, 22, (0.100 g, 0.146 mmol) in dichloromethane (5 mL) was added triethylsilane (0.350 mL, 2.190 mmol) followed by trifluoroacetic acid (0.337 mL, 4.380 mmol). The reaction mixture was stirred at room temperature for 1 h. The reaction mixture was diluted into 30 ml CH$_2$Cl$_2$ and aqueous saturated NaHCO$_3$ solution. The organic phase was washed with brine, dried over MgSO$_4$ and the solvent was removed under reduced pressure. The crude residue was purified by silica gel chromatography (12% MeOH and 88% CH$_2$Cl$_2$) to afford 64 mg of the desired product: $^1$H NMR (300 MHz, CDCl$_3$) δ 8.42 (dd, J=2.7, 1.4 Hz, 1H), 7.90 (d, J=3.2 Hz, 1H), 7.51 (dd, J=8.6, 2.7 Hz, 1H), 5.15 (d, J=5.5 Hz, 1H), 4.26 (d, J=7.9 Hz, 1H), 3.99-3.79 (m, 1H), 3.38 (d, J=3.2 Hz, 4H), 3.09 (d, J=6.6 Hz, 1H), 2.82 (d, J=11.3 Hz, 1H), 2.16-2.05 (m, 1H), 2.01-1.85 (m, 5H), 1.78 (d, J=13.2 Hz, 1H), 1.32-1.04 (m, 4H), 0.92 (dd, J=21.7, 11.8 Hz, 1H); LC/MS Gradient 10-90%, 0.1% formic 5 min, C18/ACN, RT=2.31 min, (M+H) 443.34.

Preparation of Compounds I-1, I-3, I-4, I-5, I-12, I-15, I-16, I-17, I-18, I=19, I-21, I-22, I-23, and I-25

The following compounds were prepared in the a similar manner as described above for Compound I-14.

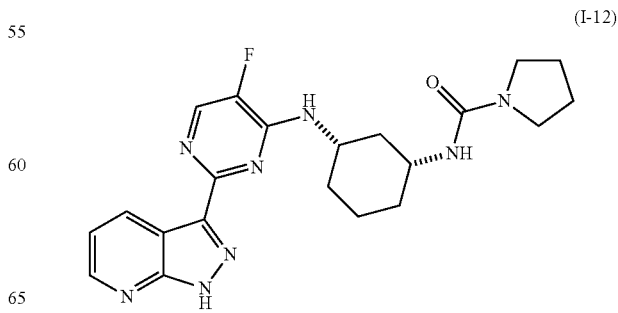

(I-12)

N-((1R,3S)-3-((5-fluoro-2-(1H-pyrazolo[3,4-b]pyridin-3-yl)pyrimidin-4-yl)amino)cyclohexyl)pyrrolidine-1-carboxamide ¹H NMR (300 MHz, CDCl₃) δ 13.85 (s, 1H), 8.56 (dd, J=4.5, 1.6 Hz, 1H), 8.36 (dd, J=8.1, 1.4 Hz, 1H), 8.06 (d, J=3.1 Hz, 1H), 7.00 (dd, J=8.1, 4.6 Hz, 1H), 5.07 (t, J=15.4 Hz, 1H), 4.17 (d, J=7.9 Hz, 1H), 3.89-3.69 (m, 1H), 3.35 (t, J=6.4 Hz, 4H), 2.77 (d, J=11.4 Hz, 1H), 2.11 (dd, J=29.5, 11.4 Hz, 2H), 1.93-1.79 (m, 5H), 1.44 (dd, J=26.4, 13.3 Hz, 1H), 1.28-0.91 (m, 3H); LC/MS Gradient 10-90%, 0.1% formic 5 min, C18/ACN, RT=2.12 min (M+H) 425.67.

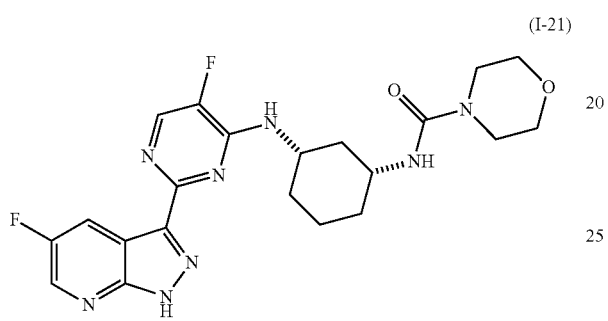

(I-21)

N-((1R,3S)-3-((5-fluoro-2-(5-fluoro-1H-pyrazolo[3,4-b]pyridin-3-yl)pyrimidin-4-yl)amino)cyclohexyl)morpholine-4-carboxamide ¹H NMR (300 MHz, MeOD) δ 8.46 (s, 1H), 8.30 (dd, J=8.5, 2.7 Hz, 1H), 8.04 (d, J=3.8 Hz, 1H), 4.13 (t, J=11.6 Hz, 1H), 3.81 (td, J=8.5, 4.2 Hz, 1H), 3.67-3.57 (m, 3H), 3.40-3.33 (m, 3H), 3.31 (dd, J=3.3, 1.6 Hz, 1H), 2.32 (t, J=14.1 Hz, 1H), 2.16 (d, J=11.9 Hz, 1H), 2.04-1.84 (m, 2H), 1.66-1.36 (m, 2H), 1.35-1.11 (m, 2H); LC/MS Gradient 10-90%, 0.1% formic 5 min, C18/ACN, RT=1.76 min (M+H) 459.17.

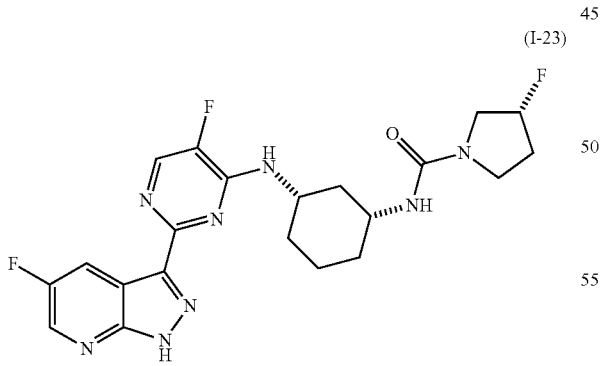

(I-23)

(R)-3-fluoro-N-((1R,3S)-3-((5-fluoro-2-(5-fluoro-1H-pyrazolo[3,4-b]pyridin-3-yl)pyrimidin-4-yl)amino)cyclohexyl)pyrrolidine-1-carboxamide ¹H NMR (300 MHz, MeOD) δ 8.47 (s, 4H), 8.34 (dd, J=8.5, 2.8 Hz, 4H), 8.06 (t, J=3.2 Hz, 4H), 5.37-5.11 (m, 4H), 4.16 (dd, J=15.4, 7.6 Hz, 4H), 3.82 (td, J=8.6, 4.4 Hz, 4H), 3.65 (t, J=12.9 Hz, 3H), 3.60-3.34 (m, 15H), 3.31 (dt, J=3.2, 1.6 Hz, 6H), 2.33 (t, J=10.7 Hz, 4H), 2.26-2.07 (m, 9H), 1.95 (ddd, J=15.0, 13.6, 9.2 Hz, 10H), 1.67-1.38 (m, 8H), 1.37-1.15 (m, 8H); LC/MS Gradient 10-90%, 0.1% formic 5 min, C18/ACN, RT=1.87 min (M+H) 461.68.

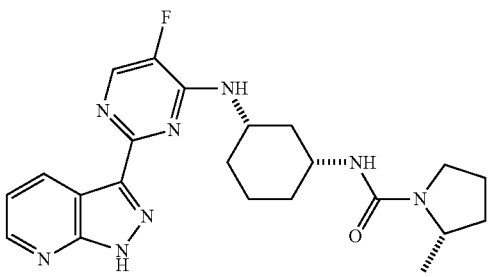

(I-15)

(S)—N-((1R,3S)-3-((5-fluoro-2-(1H-pyrazolo[3,4-b]pyridin-3-yl)pyrimidin-4-yl)-amino)cyclohexyl)-2-methylpyrrolidine-1-carboxamide ¹H NMR (300 MHz, d6-DMSO) δ 9.02 (s, 1H), 8.69 (dd, J=4.8, 3.3 Hz, 2H), 8.48 (d, J=5.0 Hz, 1H), 7.52 (dd, J=7.9, 4.8 Hz, 3H), 5.87 (d, J=8.2 Hz, 1H), 4.23 (s, 1H), 3.90-3.70 (m, 2H), 3.31-3.21 (m, 1H), 3.19-3.01 (m, 1H), 2.76 (s, 1H), 2.20 (d, J=11.4 Hz, 1H), 2.01-1.67 (m, 5H), 1.55-1.20 (m, 5H), 1.05 (d, J=6.2 Hz, 2H).

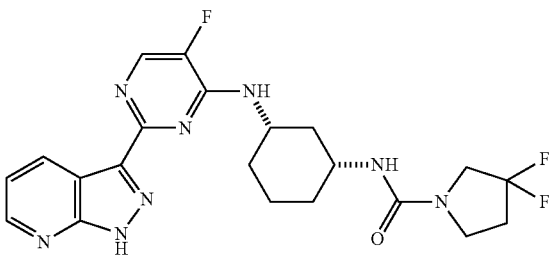

(I-16)

3,3-difluoro-N-((1R,3S)-3-((5-fluoro-2-(1H-pyrazolo[3,4-b]pyridin-3-yl)pyrimidin-4-yl)amino)cyclohexyl)pyrrolidine-1-carboxamide ¹H NMR (300 MHz, d6-DMSO) δ 8.99 (s, 1H), 8.75 (d, J=8.4 Hz, 1H), 7.54 (s, 1H), 7.35 (s, 1H), 6.26 (d, J=7.9 Hz, 2H), 4.22 (s, 1H), 3.74 (s, 1H), 3.62 (t, J=13.4 Hz, 2H), 3.43 (t, J=7.3 Hz, 2H), 2.35 (dd, J=22.3, 14.9 Hz, 2H), 2.24 (d, J=22.1 Hz, 2H), 2.09-1.16 (m, 7H).

(I-22)

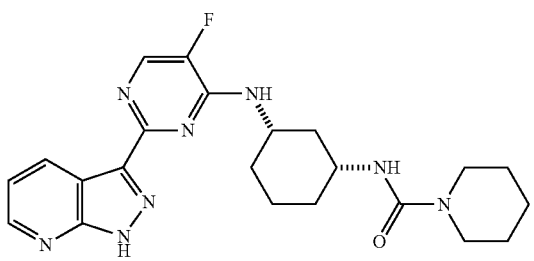

N-((1R,3S)-3-((5-fluoro-2-(1H-pyrazolo[3,4-b]pyridin-3-yl)pyrimidin-4-yl)amino)-cyclohexyl)piperidine-1-carboxamide ¹H NMR (300 MHz, d6-DMSO) δ 13.93 (s, 1H), 8.80-8.64 (m, 1H), 8.56 (s, 1H), 8.27 (d, J=3.8 Hz, 1H), 7.70 (d, J=7.4 Hz, 1H), 6.23 (d, J=7.9 Hz, 1H), 3.68 (s, 1H), 3.28-3.19 (m, 3H), 3.17 (d, J=5.2 Hz, 3H), 2.16 (d, J=11.5 Hz, 1H), 1.94 (d, J=13.4 Hz, 1H), 1.82 (s, 1H), 1.58-1.09 (m, 11H).

(I-25)

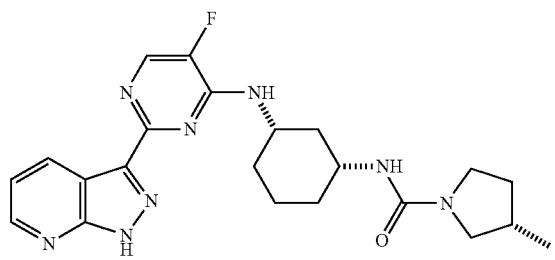

(S)—N-((1R,3S)-3-((5-fluoro-2-(1H-pyrazolo[3,4-b]pyridin-3-yl)pyrimidin-4-yl)-amino)cyclohexyl)-3-methylpyrrolidine-1-carboxamide ¹H NMR (300 MHz, d6-DMSO) δ 13.86 (s, 1H), 8.83-8.69 (m, 1H), 8.58 (d, J=3.7 Hz, 1H), 8.29 (t, J=3.6 Hz, 1H), 7.73 (d, J=6.2 Hz, 1H), 7.38 (dd, J=8.0, 3.9 Hz, 1H), 4.15 (s, 1H), 3.68 (d, J=7.6 Hz, 1H), 3.16 (d, J=8.4 Hz, 1H), 2.73 (t, J=7.3 Hz, 1H), 2.52 (s, 1H), 2.18 (d, J=9.0 Hz, 2H), 2.06-1.72 (m, 5H), 1.54-1.12 (m, 6H), 0.98 (dd, J=6.4, 3.5 Hz, 3H).

(I-17)

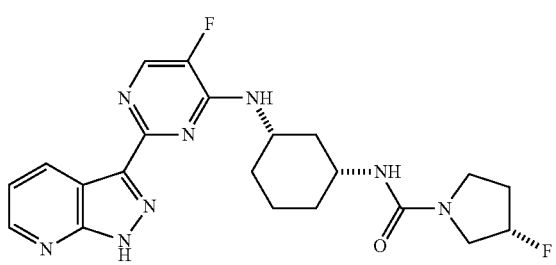

(S)-3-fluoro-N-((1R,3S)-3-((5-fluoro-2-(1H-pyrazolo[3,4-b]pyridin-3-yl)pyrimidin-4-yl)amino)cyclohexyl)pyrrolidine-1-carboxamide LC/MS Gradient 10-90%, 0.1% formic 5 min, C18/ACN, RT=1.69 min (M+H) 443.53 [10-90%, formic acid, 5 min, C18/AcN]

(I-18)

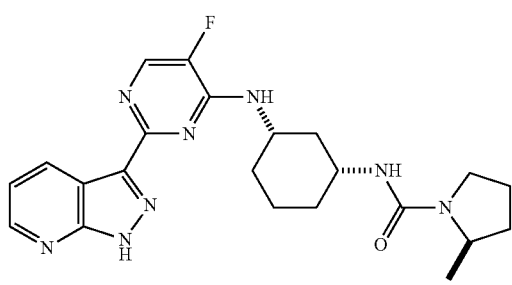

(R)—N-((1R,3S)-3-((5-fluoro-2-(1H-pyrazolo[3,4-b]pyridin-3-yl)pyrimidin-4-yl)amino)cyclohexyl)-2-methylpyrrolidine-1-carboxamide LC/MS Gradient 10-90%, 0.1% formic 5 min, C18/ACN, RT=1.87 min (M+H) 439.56 [10-90%, formic acid, 5 min, C18/AcN]

(I-19)

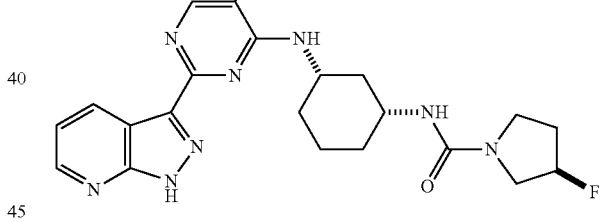

(R)-3-fluoro-N-((1R,3S)-3-((5-fluoro-2-(1H-pyrazolo[3,4-b]pyridin-3-yl)pyrimidin-4-yl)amino)cyclohexyl)pyrrolidine-1-carboxamide LC/MS Gradient 10-90%, 0.1% formic 5 min, C18/ACN, RT=1.68 min (M+H) 443.53 [10-90%, formic acid, 5 min, C18/AcN]

(I-1)

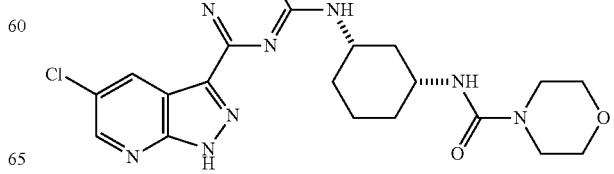

N-((1R,3S)-3-((2-(5-chloro-1H-pyrazolo[3,4-b]pyridin-3-yl)-5-fluoropyrimidin-4-yl)amino)cyclohexyl)morpholine-4-carboxamide ¹H NMR (300 MHz, MeOD) δ 8.73 (s, 1H), 8.64 (s, 1H), 8.29 (d, J=4.8 Hz, 1H), 4.43 (m, 1H), 3.83 (m, 1H), 3.65-3.62 (m, 4H), 3.35 (burried m, 4H), 2.38 (d, J=12.1 Hz, 1H), 2.23 (d, J=9.5 Hz, 1H), 2.03 (br m, 2H) and 1.70-1.29 (complex m, 4H) ppm; LC/MS Gradient 10-90%, 0.1% formic 5 min, C18/ACN, RT=2.3 min, (M+H) 475.56.14.

(I-3)

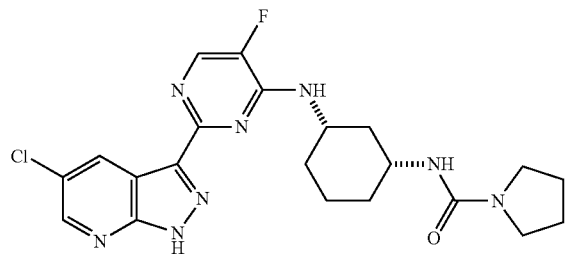

N-((1R,3S)-3-((2-(5-chloro-1H-pyrazolo[3,4-b]pyridin-3-yl)-5-fluoropyrimidin-4-yl)amino)cyclohexyl)pyrrolidine-1-carboxamide LC/MS Gradient 10-90%, 0.1% formic 5 min, C18/ACN, RT=2.52 min, (M+H) 459.61.

(I-4)

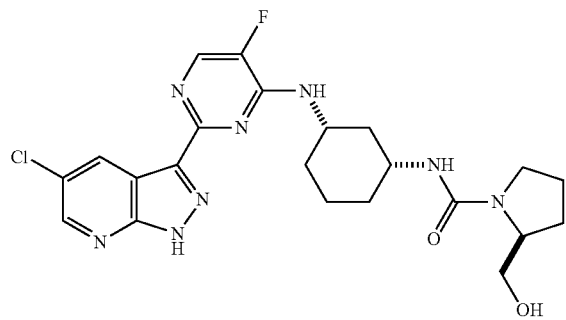

(S)—N-((1R,3S)-3-((2-(5-chloro-1H-pyrazolo[3,4-b]pyridin-3-yl)-5-fluoropyrimidin-4-yl)amino)cyclohexyl)-2-(hydroxymethyl)pyrrolidine-1-carboxamide LC/MS Gradient 10-90%, 0.1% formic 5 min, C18/ACN, RT=2.33 min, (M+H) 489.65.

(I-5)

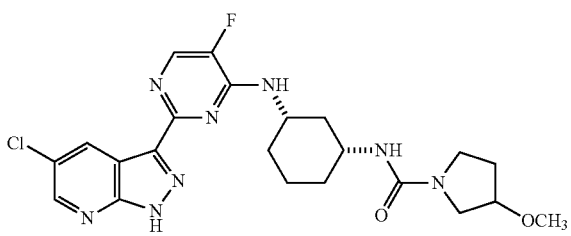

N-((1R,3S)-3-((2-(5-chloro-1H-pyrazolo[3,4-b]pyridin-3-yl)-5-fluoropyrimidin-4-yl)amino)cyclohexyl)-3-methoxypyrrolidine-1-carboxamide LC/MS Gradient 10-90%, 0.1% formic 5 min, C18/ACN, RT=2.38 min, (M+H) 489.6.

Synthetic Scheme 6: Preparation of Compound I-24

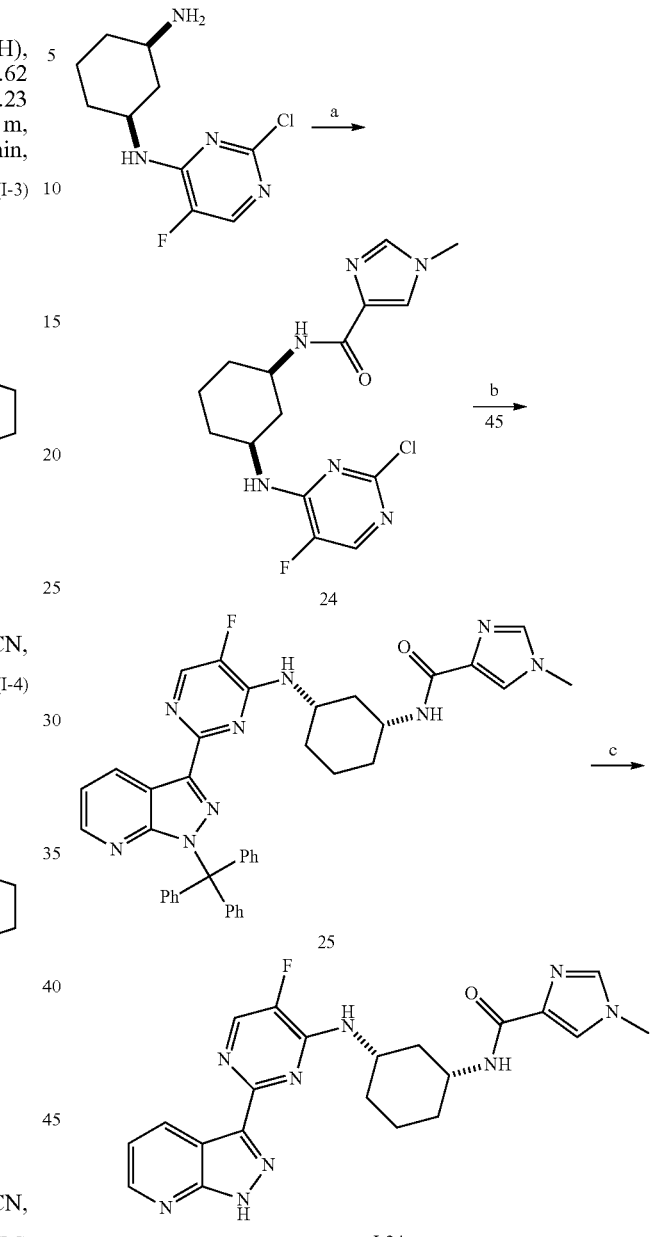

(a) 1-methylimidazole-4-carboxylic acid, HATU, ⁱPr₂NEt, THF (b) 3-(4,4,5,5-tetramethyl-1,3,2-dioxaborolan-2-yl)-1-trityl-pyrazolo[5,4-b]pyridine (45), X-phos, Pd₂(dba)₃, K₃PO₄, 2-MeTHF, 120° C.; (c) Et₃SiH, TFA, CH₂Cl₂

Formation of N-((1R,3S)-3-((2-chloro-5-fluoropyrimidin-4-yl)amino)cyclohexyl)-1-methyl-1H-imidazole-4-carboxamide (24)

To a solution of 1-methylimidazole-4-carboxylic acid (0.113 g, 0.899 mmol) and HATU (0.342 g, 0.899 mmol) in THF (0.009 mL) at room temperature was added (1S,3R)—N-1-(2-chloro-5-fluoro-pyrimidin-4-yl)cyclohexane-1,3-diamine (0.200 g, 0.817 mmol) followed by N,N-diisopropylethylamine (0.214 mL, 1.226 mmol). The reaction was stirred for 4 hours at room temperature. The mixture was diluted with water (20 mL) and extracted with ethyl acetate. The organic phase was washed with brine (20 mL), dried over sodium sulfate, filtered and concentrated in vacuo. The crude residue was purified by silica gel chromatography (50-100% ethyl acetate in hexanes) to afford the desired product: LC/MS Gradient 10-90%, 0.1% formic 5 min, C18/ACN, RT=1.67 min (M+H)=353.44.

Formation of N-((1R,3S)-3-((5-fluoro-2-(1-trityl-1H-pyrazolo[3,4-b]pyridin-3-yl)pyrimidin-4-yl)amino)cyclohexyl)-1-methyl-1H-imidazole-4-carboxamide (25)

To a solution of 3-(4,4,5,5-tetramethyl-1,3,2-dioxaborolan-2-yl)-1-trityl-pyrazolo[5,4-b]pyridine, 45, (0.259 g, 0.532 mmol) and N-[(1R,3S)-3-[(2-chloro-5-fluoro-pyrimidin-4-yl)amino]cyclohexyl]-1-methyl-imidazole-4-carboxamide, 24, (0.150 g, 0.425 mmol) in 2-Me-THF (7.1 mL) and water (1.4 mL) was added $K_3PO_4$ (0.316 g, 1.488 mmol). The solution was degassed for 10 minutes under flow of nitrogen. $Pd_2(dba)_3$ (0.027 g, 0.030 mmol) and dicyclohexyl-[2-(2,4,6-triisopropylphenyl)-phenyl]phosphane (0.030 g, 0.064 mmol) were added and solution was again degassed under flow of nitrogen. The reaction tube was sealed and heated to 80° C. for 2 hours. The mixture was cooled to room temperature and diluted with water (10 mL). The organic phase was extracted with ethyl acetate, washed with brine (10 mL). The crude was dried over sodium sulfate, filtered and concentrated in vacuo. The crude residue was purified by silica gel chromatography (0-7% MeOH [2N $NH_3$] in ethyl acetate) to give the desired compound: LC/MS Gradient 10-90%, 0.1% formic 5 min, C18/ACN, RT=2.78 min (M+H)=678.73.

Formation of N-((1R,3S)-3-((5-fluoro-2-(1H-pyrazolo[3,4-b]pyridin-3-yl)pyrimidin-4-yl)amino)cyclohexyl)-1-methyl-1H-imidazole-4-carboxamide (I-24)

To a solution of N-[(1R,3S)-3-[[5-fluoro-2-(1-tritylpyrazolo[3,4-b]pyridin-3-yl)pyrimidin-4-yl]amino]cyclohexyl]-1-methyl-imidazole-4-carboxamide, 25, (0.235 g, 0.347 mmol) in dichloromethane (6.90 mL) at room temperature was added $Et_3SiH$ (1.661 mL, 10.40 mmol) followed by TFA (0.401 mL, 5.200 mmol). The reaction mixture was stirred for 1 hour. The mixture was diluted with dichloromethane and quenched with aqueous saturated $Na_2CO_3$ solution. The organic phase was extracted with ethyl acetate, washed with brine (10 mL), dried over sodium sulfate and concentrated in vacuo. The crude residue was purified by silica chromatography (0-7% MeOH [2N $NH_3$] in ethyl acetate) to give the desired product: LC/MS Gradient 10-90%, 0.1% formic 5 min, C18/ACN, RT=1.46 min (M+H)=436.62.

Preparation of Compounds I-27

The following compounds were prepared in a similar manner as described above for Compound I-24.

(I-27)

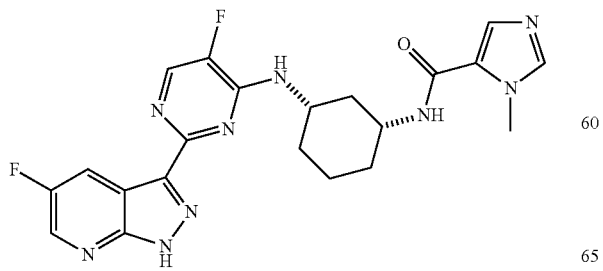

N-((1R,3S)-3-((5-fluoro-2-(5-fluoro-1H-pyrazolo[3,4-b]pyridin-3-yl)pyrimidin-4-yl)amino)cyclohexyl)-1-methyl-tH-imidazole-5-carboxamide LC/MS Gradient 10-90%, 0.1% formic 5 min, C18/ACN, RT=1.61 min (M+H) 454.34.

Synthetic Scheme 7

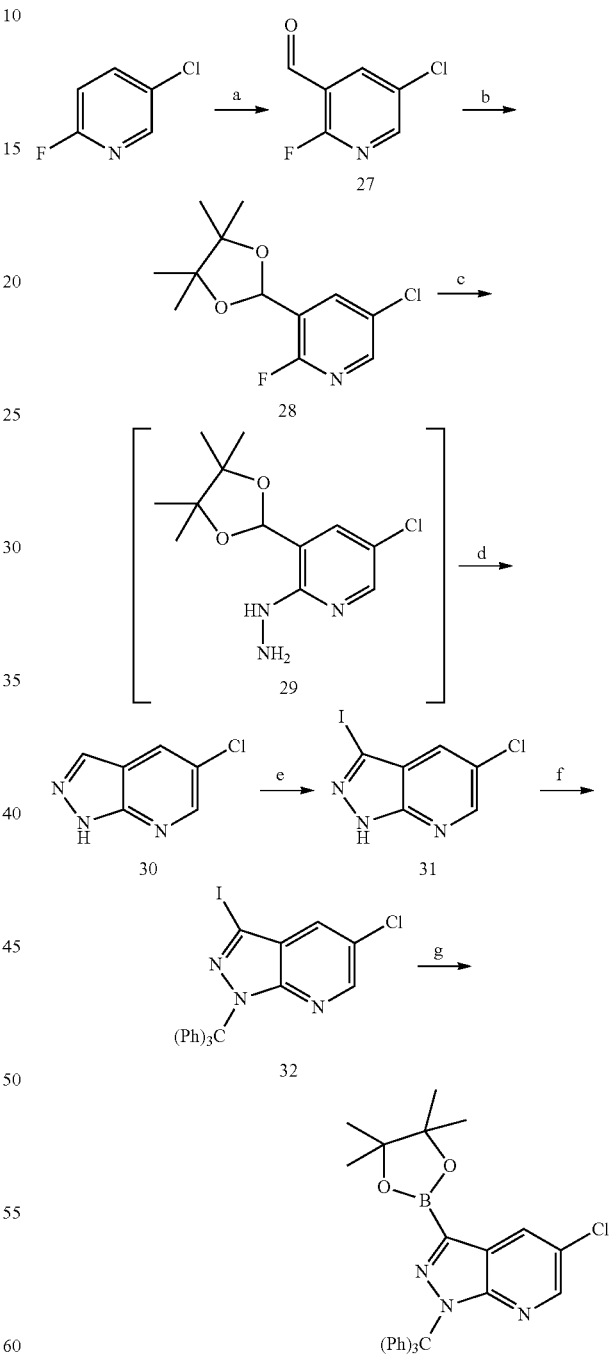

(a) i: Diisopropylamine, n-butyllithium, THF, -78° C., then ii: morpholine-4-carbaldehyde; (b) pinacol, pTsOH, toluene, reflux; (c) hydrazine, $^i$PrNEt, iPrOH, 60° C.; (d) 6N HCl, EtOH, 45° C.; (e) NIS, DCE, 60° C.; (f) trityl-Cl, $Na_2CO_3$, DMF; (g) bis(pinacolatoborane), Pd(dppf)$_2$Cl$_2$, KOAc, DMF Formation of 5-chloro-2-fluoronicotinaldehyde (27)

To a cold (0° C.) solution of diisopropylamine (12.8 mL, 91.2 mmol) in THF (100 mL) was added butyllithium (31.9 mL of 2.5 M, 79.8 mmol) over 5 min. After 5 min, the reaction was cooled to −78° C. for 15 min. Then 5-chloro-2-fluoropyridine (10.0 g, 76.0 mmol) was slowly added over 5 min. The reaction was kept at −78° C. for an additional 1.5 hr. Then, morpholine-4-carbaldehyde (17.5 g, 152.1 mmol) was added rapidly. The mixture was stirred for a further 2 min and quenched with 10% citric acid and the mixture was allowed to warm to room temperature. The pH was adjusted to 5-6 with additional citric acid solution. The mixture was extracted with dichloromethane (3×200 mL) and the combined organic layers were dried over $Na_2SO_4$, filtered and concentrated. Flash chromatography ($SiO_2$, 0-25% EtOAc-Hexanes, gradient elution) provided the desired product as an off-white crystalline solid (8.95 g, 74% yield). LC-MS shows the mass for the desired product and the corresponding hydrate: $^1$H NMR (300 MHz, $CDCl_3$) δ 10.28 (d, J=8.4 Hz, 1H), 8.41 (t, J=1.4 Hz, 1H) and 8.25 (dd, J=2.7, 7.8 Hz, 1H) ppm; LC/MS Gradient 10-90%, 0.1% formic 5 min, C18/ACN, RT=2.45 min, (M+H) 159.91.

Formation of 5-chloro-2-fluoro-3-(4,4,5,5-tetramethyl-1,3-dioxolan-2-yl)pyridine (28)

A flask fitted with a Dean-Stark trap was charged with a solution of 5-chloro-2-fluoronicotinaldehyde, 27, (8.95 g, 56.10 mmol) and 2,3-dimethylbutane-2,3-diol (8.00 g, 67.70 mmol) and p-toluene sulfonic acid mono hydrate (0.54 g, 2.81 mmol) in toluene (250 mL) and heated to vigorous reflux for 3 hr. The mixture was cooled, diluted with EtOAc, washed with $NaHCO_3$ (2×) and brine (1×). The organic phase was dried over $Na_2SO_4$, filtered through a silica plug and concentrated in vacuo. A crystalline solid formed on standing (14.47 g): $^1$H NMR (300.0 MHz, $CDCl_3$) δ 8.12 (s, 1H), 7.97 (dd, J=2.7, 7.8 Hz, 1H), 6.08 (s, 1H), 1.33 (s, 3H) and 1.26 (s, 3H) ppm.

Formation of 5-chloro-1H-pyrazolo[3,4-b]pyridine (30)

To a solution of 5-chloro-2-fluoro-3-(4,4,5,5-tetramethyl-1,3-dioxolan-2-yl)pyridine, 28, (14.5 g, 55.8 mmol) and N,N-diisopropylethylamine (19.5 mL, 112.0 mmol) in isopropanol (200 mL) was added hydrazine (12.0 mL, 382.3 mmol). The mixture was heated to 65° C. overnight. LC-MS indicates desired hydrazine compound formed and the mixture was concentrated in vacuo. The crude residue was taken up in 300 mL of water and 120 mL of EtOH followed by 50 mL of 6N HCl. The resulting mixture was warmed to 45° C. overnight. Once LC-MS indicated completion of the reaction, the mixture was neutralized with 6N NaOH and the pH adjusted to 8. The mixture was concentrated in vacuo to remove volatile EtOH and extracted with EtOAc (3×). The combined organic layer was dried over $Na_2SO_4$, filtered through a plug of silica and concentrated in vacuo. Trituration with 10% aqueous acetonitrile provided the desired product (6.15 g, 72% yield, 90% purity by NMR): $^1$H NMR (300.0 MHz, $CDCl_3$) δ 11.43 (s, 1H), 8.55 (d, J=2.2 Hz, 1H), 8.10 (d, J=2.2 Hz, 1H) and 8.08 (s, 1H) ppm; LC/MS Gradient 10-90%, 0.1% formic 5 min, C18/ACN, RT=2.05 min (M+H) 153.91.

Formation of 5-chloro-3-iodo-1H-pyrazolo[3,4-b]pyridine (31)

A mixture of 5-chloro-1H-pyrazolo[3,4-b]pyridine, 30, (6.15 g, 40.10 mmol) and N-iodosuccinimide (9.46 g, 42.1 mmol) in DCE was heated to 50° C. overnight. After 16H, the reaction was cooled to room temperature and stirred overnight for 48 hr. An additional 0.20 equivalent of N-iodosuccinimide (1.80 g, 8.01 mmol) was added and the mixture was heated overnight. Then, the mixture was cooled, diluted with $Et_2O$, washed with aq. $NaHCO_3$, sodium thiosulfate solution, water and brine. The aqueous initial wash was back extracted with EtOAc. The combined organic layers were washed with brine, dried over $Na_2SO_4$, filtered through silica and concentrated in vacuo. Trituration of the resulting solid with minimal amounts of dichloromethane and $Et_2O$ provided the desired product as an off white solid. (2.02 g, 96% yield) in sufficient purity for use in the next reaction: $^1$H NMR (300 MHz, $CDCl_3$) δ 11.28 (s, 1H), 8.55 (d, J=2.2 Hz, 1H) and 7.86 (d, J=2.2 Hz, 1H) ppm; LC/MS Gradient 10-90%, 0.1% formic 5 min, C18/ACN, RT=2.76 min, (M+H) 280.06.

Formation of 5-chloro-3-iodo-1-trityl-1H-pyrazolo[3,4-b]pyridine (32)

To a stirred mixture of 5-chloro-3-iodo-1H-pyrazolo[3,4-b]pyridine, 31, (11.6 g, 38.5 mmol), and $Na_2CO_3$ (12.2 g, 115 mmol) in N,N-dimethylformamide (200 mL) was added trityl chloride (11.8 g, 42.4 mmol). The mixture was stirred at room temperature overnight. After 16 hr, additional trityl chloride (1.61 g, 5.78 mmol) was added. And the mixture was heated to 60° C. for 45 min. The mixture was cooled, diluted with $Et_2O$, washed with water (2×), brine (2×), dried over $Na_2SO_4$, filtered and concentrated in vacuo. Flash chromatography ($SiO_2$, 0-40% EtOAc-Hexanes, gradient elution) provided the desired product as a colorless material which was further purified by flash chromatography ($SiO_2$, 100% DCM, isocratic elution): $^1$H NMR (300 MHz, $CDCl_3$) δ 8.15 (d, J=2.3 Hz, 1H), 7.70 (d, J=2.3 Hz, 1H) and 7.23-7.18 (m, 15H) ppm.

Formation of 5-chloro-3-(4,4,5,5-tetramethyl-1,3,2-dioxaborolan-2-yl)-1-trityl-1H-pyrazolo[3,4-b]pyridine (33)

A dry flask was charged with 5-chloro-3-iodo-1-trityl-1H-pyrazolo[3,4-b]pyridine, 32, (3.00 g, 5.75 mmol), 4,4,5,5-tetramethyl-2-(4,4,5,5-tetramethyl-1,3,2-dioxaborolan-2-yl)-1,3,2-dioxaborolane (1.90 g, 7.48 mmol) and potassium acetate (2.26 g, 23.0 mmol) and DMF (50 mL) was added. The mixture was degassed for 30 min with a stream of nitrogen. Then, $Pd(dppf)_2Cl_2$ (0.14 g, 0.17 mmol) was added and the vessel was sealed and heated to 90° C. for 16 hr. The mixture was cooled and diluted with 450 mL $Et_2O$. The organic layer was washed with water (3×) and brine (2×), dried over $Na_2SO_4$, and filtered through a thin bed of neutral alumina under mild vacuum. The resulting clear yellow solution was concentrated in vacuo to obtain the crude desired product in sufficient purity (technical grade) for use in the subsequent coupling reactions: LCMS RT=2.76 min (M+H) 440.43.

Synthetic Scheme 8: Preparation of Compound I-9 and I-10

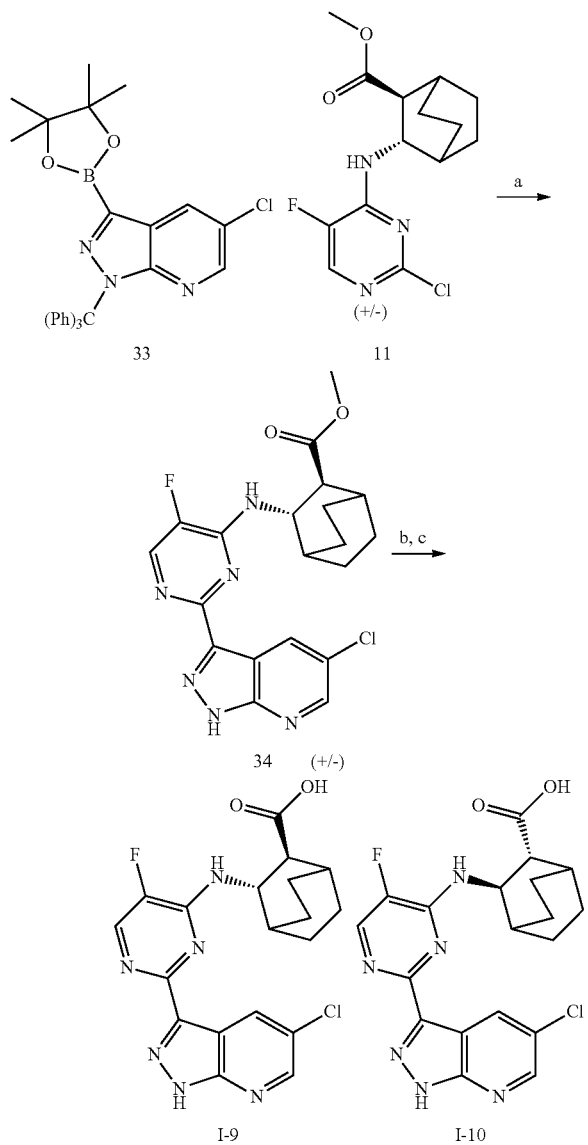

(a) i. Pd$_2$(dba)$_3$, X-Phos, K$_3$PO$_4$, MeTHF—H$_2$O, 125° C., ii. Et$_3$SiH, TFA, DCM, 0° C.; (b) NaOH, THF—MeOH—H$_2$O; (c) chiral SFC separation.

Formation of (+/−)-trans-(2,3)-methyl 3-((2-(5-chloro-1H-pyrazolo[3,4-b]pyridin-3-yl)-5-fluoropyrimidin-4-yl)amino)bicyclo[2.2.2]octane-2-carboxylate (34)

A mixture of racemic methyl trans-(7,8)-7-[(2-chloro-5-fluoro-pyrimidin-4-yl)amino]bicyclo[2.2.2]octane-8-carboxylate, 11, (0.30 g, 0.96 mmol) and 5-chloro-3-(4,4,5,5-tetramethyl-1,3,2-dioxaborolan-2-yl)-1-trityl-pyrazolo[3,4-b]pyridine, 33, (0.75 g, 1.43 mmol) and K$_3$PO$_4$ (0.64 g, 3.00 mmol) in water (1.5 mL) and 2-Me-THF (8.5 mL) was degassed with a stream of nitrogen for 5-10 min. Then, X-Phos (0.05 g, 0.10 mmol) and Pd$_2$(dba)$_3$ (0.02 g, 0.02 mmol) was added and the vessel was sealed and heated to 120° C. via microwave irradiation for 25 min. After cooling to room temperature, the organic layer was separated and concentrated in vacuo. Flash chromatography (SiO$_2$, 0-100% EtOAc-hexanes, gradient elution) provided the desired product contaminated with the starting chloropyrimidine, 11, (280 mg combine weight). This material was taken forward into the deprotection step without further purification: LC/MS Gradient 10-90%, 0.1% formic 5 min, C18/ACN, RT=3.84 min, (M+H) 673.55.

To a solution of the crude product (280 mg) in CH$_2$Cl$_2$ (5 mL) was added Et$_3$SiH (2.0 mL, 12.5 mmol) and TFA (2.0 mL, 26.0 mmol) at room temperature. After 1 hour, the solution was diluted with EtOAc, and concentrated in vacuo. Careful flash chromatography (SiO$_2$, 0-20% MeOH—CH$_2$Cl$_2$, gradient elution) provided 77 mg of the desired product: $^1$H NMR (300 MHz, MeOD) δ 8.98 (d, J=2.3 Hz, 1H), 8.53 (d, J=2.3 Hz, 1H), 8.12 (d, J=3.8 Hz, 1H), 4.99 (d, J=6.8 Hz, 1H), 3.67 (s, 3H), 2.85 (d, J=7.1 Hz, 1H), 2.08 (s, 1H), 1.93-1.42 (m, 8H), 1.20 (d, J=4.7 Hz, 1H); LC/MS Gradient 10-90%, 0.1% formic 5 min, C18/ACN, RT=2.52 min, (M+H) 431.69.

Formation of (+/−) trans-(2S,3S)-3-((2-(5-chloro-1H-pyrazolo[3,4-b]pyridin-3-yl)-5-fluoropyrimidin-4-yl)amino)bicyclo[2.2.2]octane-2-carboxylic acid To a solution of (+/−)-trans-(2,3)-methyl 3-((2-(5-chloro-1H-pyrazolo[3,4-b]pyridin-3-yl)-5-fluoropyrimidin-4-yl)amino)bicyclo[2.2.2]octane-2-carboxylate, 34, (0.06 g, 0.13 mmol) in THF (0.75 mL) and MeOH (0.25 mL) was added NaOH (0.25 mL of 2 M, 0.50 mmol). The mixture was stirred at room temperature for 16 hours. The mixture was diluted with MeOH (2 mL), neutralized with 2N HCl (0.251 mL) and concentrated in vacuo. The white solid, which formed during the acidification, was repeatedly triturated with a minimal amount of water to provide 52 mg of the desired product (racemic mixture) as an amorphous white solid: $^1$H NMR (300 MHz, MeOD) δ 8.96 (d, J=2.4 Hz, 1H), 8.58 (d, J=2.4 Hz, 1H), 8.19 (d, J=4.4 Hz, 1H), 5.06 (d, J=6.9 Hz, 1H), 2.85 (d, J=7.0 Hz, 1H), 2.20-2.12 (m, 1H), 2.09-1.97 (m, 2H), 1.91-1.47 (m, 8H); LC/MS Gradient 10-90%, 0.1% formic 5 min, C18/ACN, RT=2.23 min, (M+H) 417.28.

Separation of the racemic mixture using chiral SFC: 30% MeOH, 70% CO$_2$ (DEA modifier) on Chiralpak IC provided the individual enantiomers, I-9 and I-10.

(2R,3R)-3-((2-(5-chloro-1H-pyrazolo[3,4-b]pyridin-3-yl)-5-fluoropyrimidin-4-yl)-amino)bicyclo[2.2.2]octane-2-carboxylic acid (I-10)

Fast eluting enantiomer: 30% MeOH, 70% CO$_2$ (5 mL/min, DEA modifier) on Chiralpak IC (4.6×250), R$_t$=3.93 min.

$^1$H NMR (300 MHz, MeOD) δ 8.96 (s, 1H), 8.57 (d, J=2.0 Hz, 1H), 8.18 (d, J=3.8 Hz, 1H), 5.04 (d, J=6.9 Hz, 1H), 2.85 (d, J=6.9 Hz, 1H), 2.15 (s, 1H), 2.04 (s, 2H), 1.96-1.45 (m, 7H); LC/MS Gradient 10-90%, 0.1% formic 5 min, C18/ACN, RT=2.24 min (M+H) 417.08.

(2S,3S)-3-((2-(5-chloro-1H-pyrazolo[3,4-b]pyridin-3-yl)-5-fluoropyrimidin-4-yl)-amino)bicyclo[2.2.2]octane-2-carboxylic acid (I-9)

Slow eluting enantiomer: 30% MeOH 70% CO$_2$ (5 mL/min, DEA modifier) on Chiralpak IC (4.6×250), RT=4.53 min.

$^1$H NMR (300 MHz, MeOD) δ 8.96 (s, 1H), 8.57 (d, J=2.0 Hz, 1H), 8.18 (d, J=3.8 Hz, 1H), 5.04 (d, J=6.9 Hz, 1H), 2.85 (d, J=6.9 Hz, 1H), 2.15 (s, 1H), 2.04 (s, 2H), 1.96-1.45 (m, 7H); LC/MS Gradient 10-90%, 0.1% formic 5 min, C18/ACN, RT=2.24 min (M+H) 417.33.

Synthetic Scheme 9: Preparation of Compound I-32, I-34 and I-35

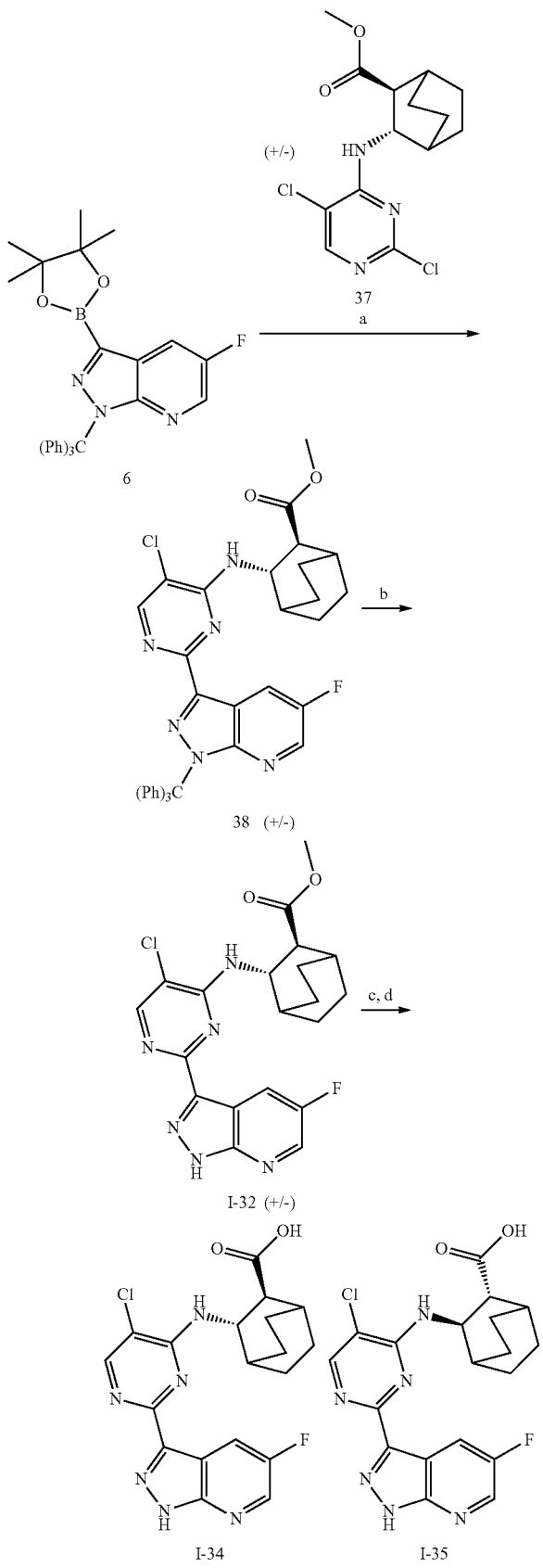

-continued
(a) Pd(PPh₃)₄, K₃PO₄, THF—H₂O, 90° C.; (b) Et₃SiH, TFA, DCM, 0° C; (c) NaOH, THF—MeOH—H₂O; (d) chiral SFC separation.

Formation of (+/−)-trans-(2,3)-methyl 3-((5-chloro-2-(5-fluoro-1-trityl-1H-pyrazolo-[3,4-b]pyridin-3-yl)pyrimidin-4-yl)amino)bicyclo[2.2.2]octane-2-carboxylate (38)

A solution of (+/−)-trans-(2,3)-methyl 3-((2,5-dichloropyrimidin-4-yl)amino)-bicyclo-[2.2.2]octane-2-carboxylate, 37, (0.50 g, 1.51 mmol) and K₃PO₄ (0.96 g, 4.54 mmol) in water (2.5 mL) and THF (10.00 mL) was degassed for 15 min with a stream of nitrogen. Then, 5-fluoro-3-(4,4,5,5-tetramethyl-1,3,2-dioxaborolan-2-yl)-1-trityl-pyrazolo[3,4-b]pyridine, 6, (0.84 g, 1.67 mmol) was added and the mixture was degassed for an additional 15 min. Then, Pd(PPh₃)₄ (0.09 g, 0.08 mmol) was added to the mixture. The vessel was sealed and heated to 90° C. After 2.5 hr., an additional 0.1 equivalent of boronate, 6, was added and the mixture was heated for an additional 30 min. The cooled solution was diluted with EtOAc, washed with water, dried over Na₂SO₄, filtered and concentrated in vacuo. Flash chromatography (SiO₂, 0-35% EtOAc in DCM) gave the desired product (0.85 g, 83% yield) which was sufficiently pure for use in the next reaction: LC/MS Gradient 10-90%, 0.1% formic 5 min, C18/ACN, RT=3.85 min, (M+H) 673.27.

Formation of (+/−)-trans-(2,3)-methyl 3-((5-chloro-2-(5-fluoro-1H-pyrazolo[3,4-b]pyridin-3-yl)pyrimidin-4-yl)amino)bicyclo[2.2.2]octane-2-carboxylate (I-32)

To a solution of (+/−)-trans-(2,3)-methyl 3-((5-chloro-2-(5-fluoro-1-trityl-1H-pyrazolo[3,4-b]pyridin-3-yl)pyrimidin-4-yl)amino)bicyclo[2.2.2]octane-2-carboxylate, 38, (0.85 g, 1.26 mmol) in CH₂Cl₂ (42.5 mL) at room temperature was added Et₃SiH (1.00 mL, 6.32 mmol) followed by trifluoroacetic acid (0.97 mL, 12.60 mmol). The reaction was stirred at room temperature. After the reaction was complete, as judged by LC-MS, the solution was concentrated in vacuo. Careful flash chromatography (SiO₂, 0-7% MeOH—CH₂Cl₂, gradient elution) provided the desired product (373 mg, 66% yield)L ¹H NMR (400 MHz, MeOD) δ 8.66 (dd, J=8.3, 2.5 Hz, 1H), 8.53 (s, 1H), 8.28 (s, 1H), 5.05 (d, J=6.5 Hz, 1H), 3.69 (s, 3H), 2.95 (d, J=6.8 Hz, 1H), 2.09 (s, 1H), 1.98 (s, 1H), 1.96-1.79 (m, 3H), 1.77-1.61 (m, 3H), 1.61-1.45 (m, 2H); LC/MS Gradient 10-90%, 0.1% formic 5 min, C18/ACN, RT=2.55 min, (M+H) 431.14.

Formation of (+/−)-trans-(2,3)-3-((5-chloro-2-(5-fluoro-1H-pyrazolo[3,4-b]pyridin-3-yl)pyrimidin-4-yl)amino)bicyclo[2.2.2]octane-2-carboxylic acid A solution of racemic-trans-(2,3)-methyl 3-((5-chloro-2-(5-fluoro-1H-pyrazolo[3,4-b]pyridin-3-yl)pyrimidin-4-yl)amino)bicyclo[2.2.2]octane-2-carboxylate, I-32, (0.31 g, 0.72 mmol) in THF (5.4 mL) and MeOH (1.8 mL) was treated with NaOH (1.80 mL of 2 M, 3.60 mmol) at room temperature for 16 hr. The reaction was diluted with 5-7 mL of water, concentrated to remove organic solvents and extracted with MBTE (2×) to remove neutral organics. The mixture was acidified with 6N HCl to pH 6 and extracted with EtOAc several times. The milky organic layer was diluted with acetonitrile and CH₂Cl₂ and then concentrated in vacuo. The resulting solid was suspended in acetonitrile and concentrated in vacuo twice to provide the desired product (280 mg, 90% yield) as an off-white amorphous solid: $^1$H NMR (400 MHz, MeOD) δ 8.67 (dd, J=8.4, 2.5 Hz, 1H), 8.53 (s, 1H), 8.27 (s, 1H), 5.05 (d, J=6.7 Hz, 1H), 2.92 (d, J=6.6 Hz, 1H), 2.15 (s, 1H), 2.03-1.79 (m, 4H), 1.79-1.62 (m, 3H), 1.62-1.45 (m, 2H); LC/MS Gradient 10-90%, 0.1% formic 5 min, C18/ACN, RT=2.28 min, (M+H) 417.09.

Separation of the racemic mixture using chiral SFC chromatographic resolution: 20% MeOH, 80% CO$_2$ (10 mL/min) on Chiralpak IC (10×250) provided the individual enantiomers.

(2S,3S)-3-((5-chloro-2-(5-fluoro-1H-pyrazolo[3,4-b]pyridin-3-yl)pyrimidin-4-yl)amino)bicyclo[2.2.2]octane-2-carboxylic acid (I-34)

Fast eluting enantiomer: 20% MeOH, 80% CO$_2$ (10 mL/min) on Chiralpak IC (10×250), RT=8.18 min.
$^1$H NMR (300 MHz, MeOD) δ 8.67 (d, J=6.6 Hz, 1H), 8.53 (s, 1H), 8.27 (s, 1H), 5.13-4.98 (m, 1H), 2.98-2.87 (m, 1H), 2.11 (broad s, 1H), 2.05-1.82 (m, J=36.5 Hz, 3H), 1.82-1.44 (m, 4H); LC/MS Gradient 10-90%, 0.1% formic 5 min, C18/ACN, RT=2.27 min (M+H) 417.09.

(2R,3R)-3-((5-chloro-2-(5-fluoro-1H-pyrazolo[3,4-b]pyridin-3-yl)pyrimidin-4-yl)amino)bicyclo[2.2.2]octane-2-carboxylic acid (I-35)

Slow eluting enantiomer: 20% MeOH, 80% CO$_2$ (10 mL/min) on Chiralpak IC (10×250), RT=9.56 min.
$^1$H NMR (300 MHz, MeOD) δ 8.69 (s, 1H), 8.52 (s, 1H), 8.27 (s, 1H), 5.18-4.99 (m, 1H), 3.00-2.86 (m, 1H), 2.15 (s, 1H), 2.07-1.82 (m, 3H), 1.81-1.45 (m, 4H); LC/MS Gradient 10-90%, 0.1% formic 5 min, C18/ACN, RT=2.27 min (M+H) 417.09.

Synthetic Scheme 10

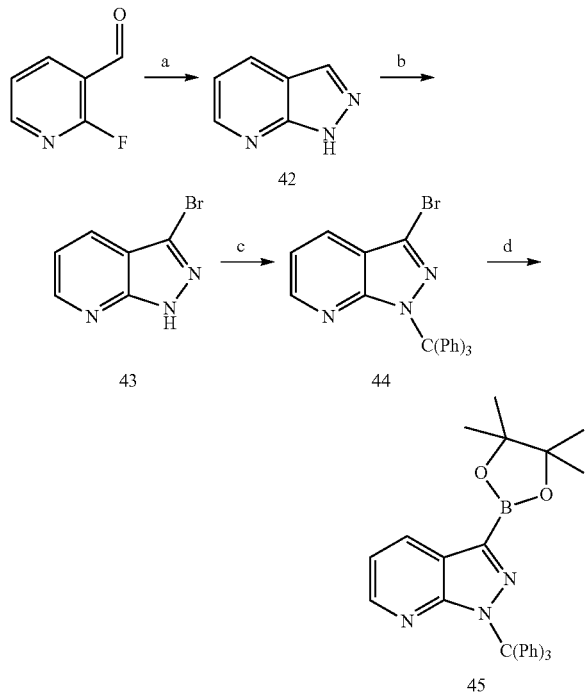

(a) hydrazine hydrate, ethanol 80° C.; (b) NBS, DMF; (c) trityl-Cl, NaH, DMF, 0° C.; (d) bis(pinacolatoborane), Pd(dppf)$_2$Cl$_2$, KOAc, DMF Formation of 1H-pyrazolo[3,4-b]pyridine (42)

Hydrazine hydrate (64%, 0.29 L, 5.99 mol hydrazine, 3 eq) was added dropwise to a solution of 2-fluoropyridine-3-carboxylaldehyde (0.25 kg, 1.99 mol) in EtOH (600 mL) over 1 hr. During the addition, a thick suspension formed, which turned into a clear red solution towards the end of the addition. The reaction mixture was heated to 80° C. overnight. The reaction mixture was cooled to room temperature, quenched with H$_2$O/aqueous saturated NaHCO$_3$ (1/1 mixture, 600 mL) and extracted with EtOAc (2×800 mL, 1×500 mL). The combined organic layers were washed with brine (400 mL), dried over Na$_2$SO$_4$ and concentrated in vacuo. The resulting solid was washed with heptanes (3×800 mL), dried under reduced pressure and stripped twice with heptanes. The product (214 g, 90% yield) was obtained as a light-yellow solid: $^1$H NMR (CDCl$_3$, 300 MHz) δ 8.65-8.64 (m, 1H); 8.14-8.10 (m, 2H); 7.17-7.12 (m, 1H) ppm.

Formation of 3-bromo-1H-pyrazolo[3,4-b]pyridine (43)

To a solution of 1H-pyrazolo[3,4-b]pyridine, 42, (0.21 kg, 1.79 mol) in DMF (2 L) was added NBS (0.34 kg, 1.07 eq) portionwise over 1 hour. The temperature reached 44° C. during addition. The reaction mixture was stirred for 40 minutes. Ice water (3 L total volume) was added and the resulting precipitate was collected by filtration. The product was washed with H$_2$O (3×2 L) and left on the filter over 3 days. The product was washed with heptanes (1×) and dissolved in EtOAc (4 L). The aqueous phase was separated and the remaining organic layer was washed with brine and concentrated to dryness to afford the product (229 g, 65% yield) as a light-yellow solid: $^1$H NMR (CDCl$_3$, 300 MHz) δ 8.71-8.64 (m, 1H); 8.08-8.02 (m, 1H); 7.30-7.24 m, 1H) ppm.

Formation of 3-bromo-1-trityl-1H-pyrazolo[3,4-b]pyridine (44)

To a solution of 3-bromo-1H-pyrazolo[3,4-b]pyridine, 43, (0.23 kg, 1.16 mmol) in DMF (2.2 L) was added trityl chloride (0.34 kg, 1.21 mol, 1.05 eq). The reaction mixture was cooled to <0° C. with an ice-salt bath and 60% NaH (0.05 kg of 60% suspension, 1.35 mol, 1.17 eq) was added portionwise over 1 hour. During the addition the temperature did not exceed 5° C. After the addition was complete the reaction mixture was allowed to reach room temperature overnight. Ice (2 L) and H$_2$O (1 L) were added and the reaction mixture was stirred vigorously for 30 minutes. The precipitated product was collected by filtration and washed with H$_2$O (3×1.5 L) and heptanes (2×). The product was dissolved in CH$_2$Cl$_2$ (2.5 L) and diluted with heptanes (1.5 L). The solution was filtered through silica gel (1.5 kg) and eluted with 50% CH$_2$Cl$_2$/heptanes. Product-containing fractions were pooled and concentrated in vacuo to a small volume. The suspension was cooled and the product was collected by filtration and washed with heptanes (3×) and TBME (1×). After drying under reduced pressure the product (369 g, 72% yield) was isolated as a yellow solid: $^1$H NMR (CDCl$_3$, 300 MHz) δ 8.30-8.26 (m, 1H); 7.91-7.88 (m, 1H); 7.34-7.18 (m, 15H); 7.10-7.04 (m, 1H) ppm.

Formation of 3-bromo-1-trityl-1H-pyrazolo[3,4-b]pyridine (45)

A solution of 3-bromo-5-fluoro-1-trityl-pyrazolo[3,4-b]pyridine, 44, (16.86 g, 36.79 mmol), KOAc (10.83 g, 110.4 mmol) and 4,4,5,5-tetramethyl-2-(4,4,5,5-tetramethyl-1,3,2-dioxaborolan-2-yl)-1,3,2-dioxaborolane (14.01 g, 55.18 mmol) in DMF (250 mL) was degassed under a nitrogen stream for 40 min. To the mixture was added Pd(dppf)$_2$Cl$_2$ (3.00 g, 3.68 mmol). The reaction mixture was heated at 100° C. for 90 minutes. The reaction mixture was filtered through a pad of florisil and celite. The filtrate was diluted with ether and brine. The organic phase was dried over MgSO$_4$, filtered and concentrated in vacuo. The product was dried on high vacuum pump 3 days. To the product was added 200 mL Et$_2$O and the mixture was stirred and filtered. The filtrate was concentrated in vacuo. The crude residue was diluted with 150 mL hexanes and the suspension was stirred for 3 hours, filtered and concentrated in vacuo to afford 12.6 g of desired product.

Synthetic Scheme 11: Preparation of Compound I-13

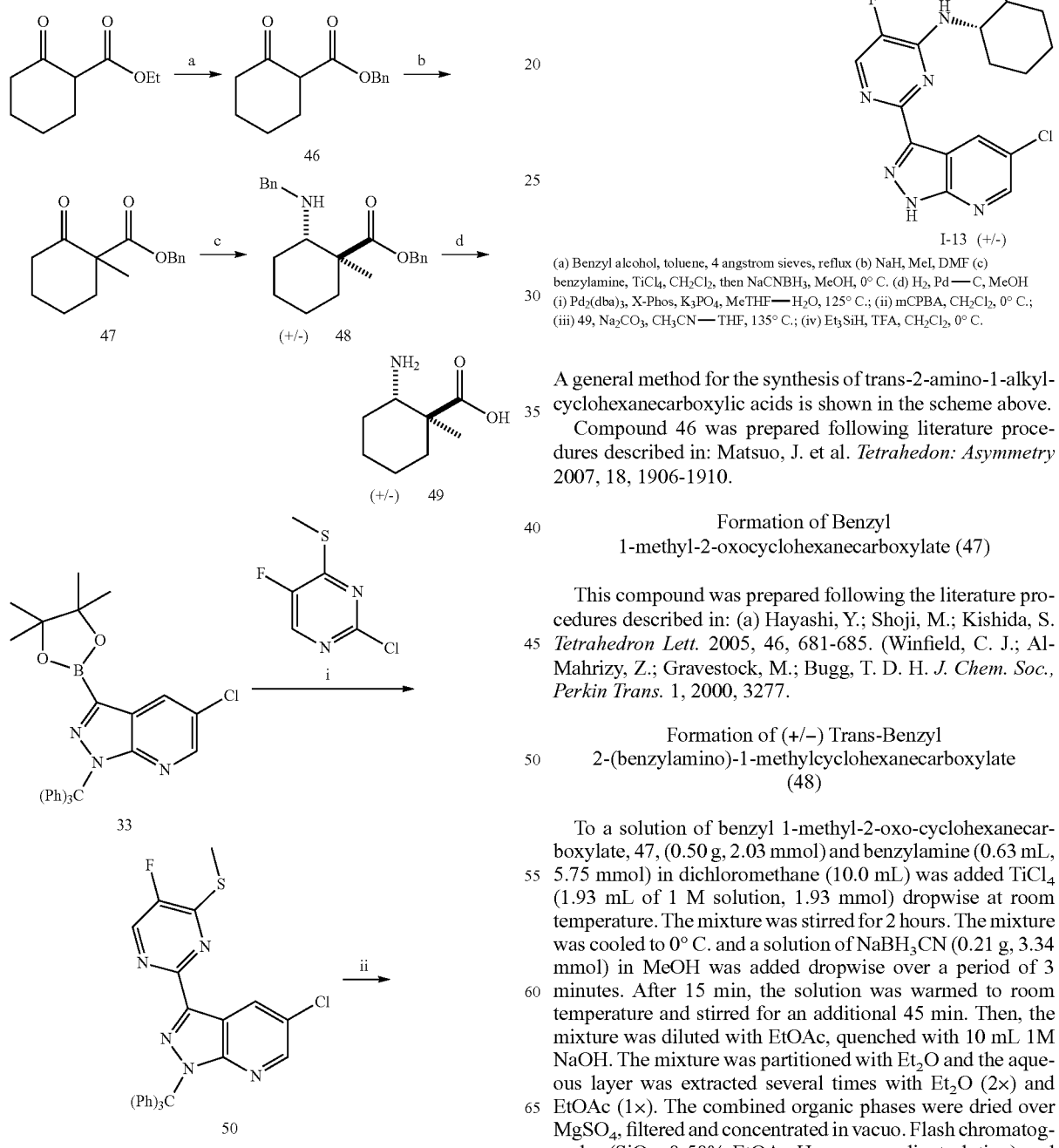

(a) Benzyl alcohol, toluene, 4 angstrom sieves, reflux (b) NaH, MeI, DMF (c) benzylamine, TiCl$_4$, CH$_2$Cl$_2$, then NaCNBH$_3$, MeOH, 0° C. (d) H$_2$, Pd—C, MeOH
(i) Pd$_2$(dba)$_3$, X-Phos, K$_3$PO$_4$, MeTHF—H$_2$O, 125° C.; (ii) mCPBA, CH$_2$Cl$_2$, 0° C.;
(iii) 49, Na$_2$CO$_3$, CH$_3$CN—THF, 135° C.; (iv) Et$_3$SiH, TFA, CH$_2$Cl$_2$, 0° C.

A general method for the synthesis of trans-2-amino-1-alkyl-cyclohexanecarboxylic acids is shown in the scheme above.

Compound 46 was prepared following literature procedures described in: Matsuo, J. et al. *Tetrahedon: Asymmetry* 2007, 18, 1906-1910.

Formation of Benzyl 1-methyl-2-oxocyclohexanecarboxylate (47)

This compound was prepared following the literature procedures described in: (a) Hayashi, Y.; Shoji, M.; Kishida, S. *Tetrahedron Lett.* 2005, 46, 681-685. (Winfield, C. J.; Al-Mahrizy, Z.; Gravestock, M.; Bugg, T. D. H. *J. Chem. Soc., Perkin Trans.* 1, 2000, 3277.

Formation of (+/−) Trans-Benzyl 2-(benzylamino)-1-methylcyclohexanecarboxylate (48)

To a solution of benzyl 1-methyl-2-oxo-cyclohexanecarboxylate, 47, (0.50 g, 2.03 mmol) and benzylamine (0.63 mL, 5.75 mmol) in dichloromethane (10.0 mL) was added TiCl$_4$ (1.93 mL of 1 M solution, 1.93 mmol) dropwise at room temperature. The mixture was stirred for 2 hours. The mixture was cooled to 0° C. and a solution of NaBH$_3$CN (0.21 g, 3.34 mmol) in MeOH was added dropwise over a period of 3 minutes. After 15 min, the solution was warmed to room temperature and stirred for an additional 45 min. Then, the mixture was diluted with EtOAc, quenched with 10 mL 1M NaOH. The mixture was partitioned with Et$_2$O and the aqueous layer was extracted several times with Et$_2$O (2×) and EtOAc (1×). The combined organic phases were dried over MgSO$_4$, filtered and concentrated in vacuo. Flash chromatography (SiO$_2$, 0-50% EtOAc-Hexanes gradient elution) and isolation of the major component provided the desired product (320 mg) as a single racemic trans isomer: ¹H NMR (300 MHz, MeOD) δ 7.34-7.16 (m, 10H), 5.07 (dd, J=12.4, 31.2 Hz, 2H), 3.78 (d, J=13.0 Hz, 1H), 3.57 (d, J=13.0 Hz, 1H), 2.96 (m, 1H), 1.86 (m, 1H), 1.74-1.57 (m, 3H), 1.52-1.25 (m, 4H) and 1.20 (s, 3H) ppm.

Formation of (+/−)-Trans-2-Amino-1-methylcyclohexanecarboxylic acid (49)

To a solution of racemic trans-benzyl (1S,2S)-2-(benzylamino)-1-ethyl-cyclohexanecarboxylate, 48, (0.32 g, 0.91 mmol) in MeOH (12.8 mL), was added Pd (5% Pd on carbon, 0.07 g). The solution was degassed and placed under 50 PSI H₂ atmosphere (Parr shaker) overnight. The mixture was filtered through celite and the filtrate was rinsed with MeOH. Concentration of the mother liquor followed by acetonitrile azeotrope (2×) to remove residual MeOH provided the desired product (162 mg): ¹H NMR (300 MHz, MeOD) δ 3.22 (m, 1H), 1.93 (m, 1H), 1.77 (m, 2H), 1.57-1.23 (m, 5H) and 1.17 (s, 3H) ppm.

Formation of 5-chloro-3-(5-fluoro-4-(methylthio)pyrimidin-2-yl)-1-trityl-1H-pyrazolo[3,4-b]pyridine (50)

A mixture of 2-chloro-5-fluoro-4-methylsulfanyl-pyrimidine (0.26 g, 1.44 mmol) and 5-chloro-3-(4,4,5,5-tetramethyl-1,3,2-dioxaborolan-2-yl)-1-trityl-pyrazolo[3,4-b]pyridine, 33, (0.75 g, 1.44 mmol) and K₃PO₄ (0.96 g, 4.53 mmol) in water (1.5 mL) and 2-Me-THF (7.5 mL) was degassed with nitrogen bubbling for 15 min. Then, X-Phos (0.07 g, 0.14 mmol) and Pd₂(dba)₃ (0.03 g, 0.04 mmol) was added and the vessel was sealed and heated to 125° C. with microwave irradiation for 30 min. After cooling to room temperature, water was added and the mixture was extracted and with ether and 2-Me-THF. The combined organic phases were dried over Na₂SO₄, filtered and concentrated in vacuo. Flash chromatography (SiO₂, 0-100% EtOAc-hexanes, gradient elution) provided 230 mg of the desired product which was used without further purification: LC/MS Gradient 10-90%, 0.1% formic 5 min, C18/ACN, RT=3.46 min (M+H) 538.01.

Formation of 5-chloro-3-(5-fluoro-4-(methylsulfinyl)pyrimidin-2-yl)-1-trityl-1H-pyrazolo[3,4-b]pyridine (51)

To a stirred solution of 5-chloro-3-(5-fluoro-4-(methylthio)pyrimidin-2-yl)-1-trityl-1H-pyrazolo[3,4-b]pyridine, 50, (0.078 g, 0.150 mmol) in CH₂Cl₂ at 0° C. was added mCPBA (0.036 g, 0.160 mmol). The mixture was kept at 0° C. for 2 hr. Then, the mixture was diluted with CH₂Cl₂, washed with K₂CO₃ (2×), dried over Na₂SO₄, filtered and concentrated in vacuo to provide 78 mg of the desired crude which was carried forward without further purification: LC/MS Gradient 10-90%, 0.1% formic 5 min, C18/ACN, RT=1.62 min (M+H) 554.47.

Formation of (+/−)-2-((2-(5-chloro-1H-pyrazolo[3,4-b]pyridin-3-yl)-5-fluoropyrimidin-4-yl)amino)-1-methylcyclohexanecarboxylic acid (I-13)

A mixture of crude 5-chloro-3-(5-fluoro-4-(methylsulfinyl)pyrimidin-2-yl)-1-trityl-1H-pyrazolo[3,4-b]pyridine, 51, (0.078 g, 0.140 mmol) and (1S,2S)-2-amino-1-methylcyclohexanecarboxylic acid, 49, (0.044 g, 0.280 mmol) with Na₂CO₃ (0.059 g, 0.560 mmol) in dry CH₃CN and THF was heated in a sealed vial at 135° C. (30 min, microwave irradiation). The reaction mixture was neutralized with a slight excess of 2N HCl and water and the mixture was extracted with CH₂Cl₂ (3×). The combined organic layers were dried over Na₂SO₄, filtered and concentrated in vacuo to afford 68 mg of trityl protected product: LC/MS Gradient 10-90%, 0.1% formic 5 min, C18/ACN, RT=3.43 min (M+H) 647.67.

The above crude product was dissolved in CH₂Cl₂ (3 mL) at 0° C. and treated with triethylsilane (0.75 mL, 4.70 mmol) followed by 2,2,2-trifluoroacetic acid (0.75 mL, 9.70 mmol) for 30 min. The solution was concentrated in vacuo. Preparative HPLC provided 16 mg of the desired product: ¹H NMR (300 MHz, d6-DMSO) δ 8.96 (s, 1H), 8.64 (s, 1H), 8.36 (br, 1H), 7.58 (br s, 1H), 5.08-4.88 (m, 1H), 2.04-1.85 (m, 1H), 1.85-1.61 (m, 4H), 1.61-1.32 (m, 3H), 1.21 (s, 3H) ppm; LC/MS Gradient 10-90%, 0.1% formic 5 min, C18/ACN, RT=2.17 min (M+H) 405.01.

Synthetic Scheme 12: Preparation of Compound I-36 and I-37

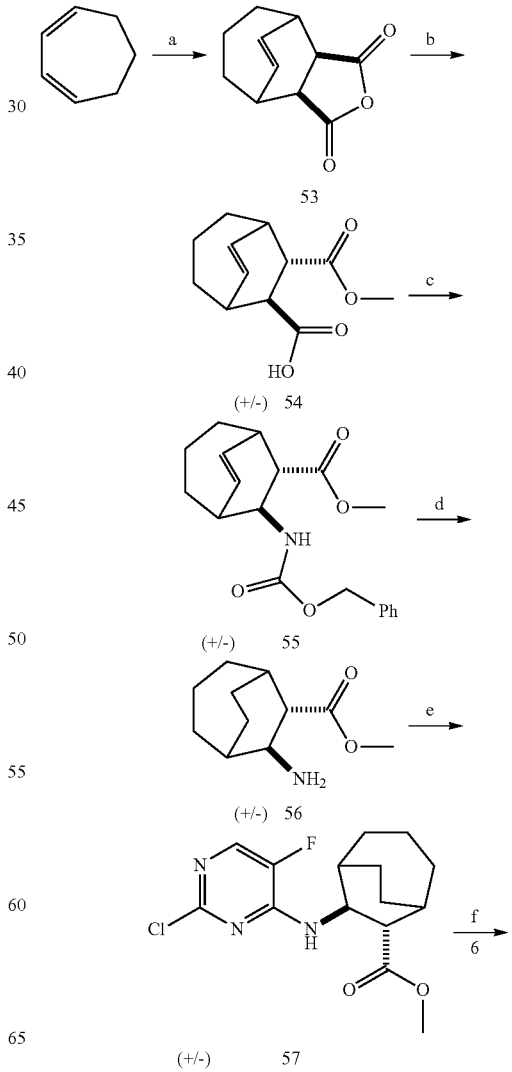

-continued

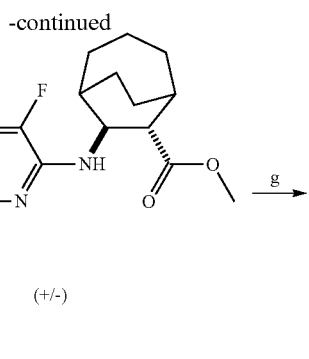

58

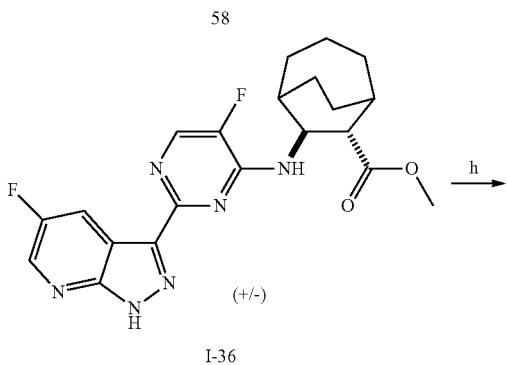

I-36

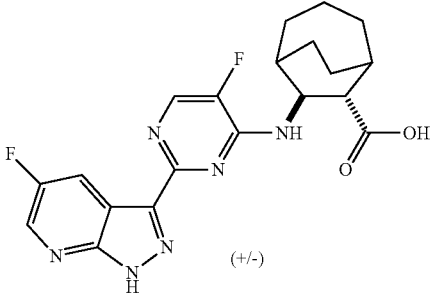

I-37

(a) maleic anhydride, benzene, 150° C.; (b) sodium methoxide, MeOH; (c) ethylchloroformate, Et₃N, THF, 0° C., 1 hr, then sodium azide, H₂O, 0° C., 2 hr, then benzyl alcohol, Et₃N, CH₂Cl₂; (d) hydrogen, Pd/C, EtOAc; (e) 2,4-dichloro-5-fluoropyrimidine, THF, MeOH, reflux; (f) 5-fluoro-3-(4,4,5,5-tetramethyl-1,3,2-dioxaborolan-2-yl)-1-trityl-1H-pyrrolo[2,3-b]pyridine (6), Pd₂(dba)₃, XPhos, water/2-methyl-THF, 120° C.; (g) triethylsilane, TFA, CH₂Cl₂; (h) LiOH, H₂O/THF, 85° C.

Formation of (di-exo)-4,5,6,7,8,8a-hexahydro-1H-4,8-ethenocyclohepta[c]furan-1,3(3aH)-dione (53)

Solid maleic anhydride (4.73 g, 48.23 mmol) was added to a stirred solution of cyclohepta-1,3-diene (5.00 g, 53.10 mmol) in benzene (10 mL) in a sealed tube (Q-tube). The suspension was heated at 150° C. for 18 hr to give a clear yellow solution. The reaction mixture was cooled to room temperature and concentrated in vacuo to give 9.3 g of the desired product as an off white solid: $^1$H NMR (400 MHz, d6-DMSO) δ 6.16 (dt, J=9.1, 4.5 Hz, 2H), 3.50 (s, 2H), 2.82 (s, 2H), 1.77-1.55 (m, 4H), 1.52-1.38 (m, 2H).

Formation of (+/−)-(exo)-trans-7-(methoxycarbonyl)bicyclo[3.2.2]non-8-ene-6-carboxylic acid (54)

A solution of sodium methoxide (40.5 mL 25% W/W solution in methanol, 176.9 mmol) was added to a finely powdered (di-exo)-4,5,6,7,8,8a-hexahydro-1H-4,8-ethenocyclohepta[c]furan-1,3(3aH)-dione, 53, (8.5 g, 44.2 mmol) and the suspension was diluted with methanol (10 mL). The resulting suspension was stirred at room temperature vigorously for 24 hr to give a thick white suspension. The suspension was cooled to 0° C. The cold suspension was added dropwise to a cold solution (0° C.) of concentrated HCl (22.0 mL, 265.3 mmol) in water (22 mL) with cooling on ice. The dropping funnel was washed with methanol (25 mL) and the solution was added dropwise to the HCl solution. The suspension was diluted with water (500 mL) and the aqueous phase was extracted with EtOAc (3×100 mL). The organic layers were dried over Na₂SO₄, filtered and concentrated under reduced pressure. The crude residue was purified by silica gel chromatography (0-50% EtOAC/hexanes) to give 7.5 g of the desired product as a white solid: $^1$H NMR (400 MHz, CDCl₃) δ 6.23 (t, J=8.2 Hz, 1H), 6.15-6.03 (m, 1H), 3.76 (s, 3H), 3.52 (d, J=6.9 Hz, 1H), 3.20 (dd, J=6.7, 4.7 Hz, 1H), 3.06-2.85 (m, 2H), 1.79-1.37 (m, 6H).

Formation of (+/−)-(exo)-trans-methyl 9-(((benzyloxy)carbonyl)amino)bicyclo[3.2.2]-non-6-ene-8-carboxylate (55)

Ethyl chloroformate (3.36 mL, 35.11 mmol) was added dropwise to a stirred solution of racemic-(exo)-trans-7-(methoxycarbonyl)bicyclo[3.2.2]non-8-ene-6-carboxylic acid, 54, (7.50 g, 33.44 mmol) and Et₃N (6.39 mL, 45.81 mmol) in THF (100 mL) at 0° C. with vigorous stirring. A white precipitate was formed and THF (50 mL) was added. The suspension was stirred at 0° C. for 1 hr. A solution of sodium azide (7.39 g, 113.70 mmol) in water (30 mL) was added dropwise at 0° C. The reaction mixture was stirred at room temperature for 2 hr. The mixture was concentrated in vacuo and water (200 mL) was added. The aqueous phase was extracted with EtOAc (3×100 mL). The combined organic phases were dried (MgSO₄), filtered and concentrated in vacuo to give 7.7 g of azide as a clear oil. The crude azide was dissolved in benzene (80 mL) and refluxed for 2 hr. The solution was cooled to room temperature and concentrated in vacuo to give an intermediate isocyanate as a thick oil. The oil was dissolved in dichloromethane (25 mL) and a solution of benzyl alcohol (3.90 mL, 37.69 mmol) and Et₃N (18.65 mL, 133.80 mmol) was added. The clear solution was stirred at room temperature for 18 hr and concentrated in vacuo. The crude product was purified by silica gel chromatography (0-30% EtOAc/hexanes) to give 10.8 g of desired product as a clear oil: $^1$H NMR (400 MHz, CDCl₃) δ 7.24 (m, 5H), 6.16 (t, J=8.1 Hz, 1H), 5.98 (t, J=7.8 Hz, 1H), 5.00 (s, 2H), 4.58 (m, 1H), 3.67 (s, 3H), 2.75 (brs, 1H), 2.36-2.44 (m, 2H), 1.66-1.29 (m, 6H); LC/MS Gradient 10-90%, 0.1% formic 5 min, C18/ACN, RT=3.4 minutes (M+H) 330.17.

Formation of (+/−)-(exo)-methyl 7-aminobicyclo[3.2.2]nonane-6-carboxylate (56)

Pd/C (1.65 g, 1.55 mmol, 10% Degussa type, wet) was added to a nitrogen purged solution of racemic-(exo)-methyl 9-(((benzyloxy)carbonyl)amino)bicyclo[3.2.2]-non-6-ene-8-carboxylate, 55 (10.0 g) in EtOAc (50 mL). The solution was kept under hydrogen atmosphere (1 atm) at room temperature for 18 hr. The resulting solid suspension was diluted with dichloromethane (100 mL) and stirred at room temperature for 1 hr. The solution was filtered through a celite pad and the pad was washed thoroughly with dichloromethane (3×50 mL). The filtrate was concentrated in vacuo to afford 5.7 g of desired product: $^1$H NMR (400 MHz, CDCl3) δ 3.77-3.59 (m, 3H), 3.47 (d, J=7.4 Hz, 1H), 2.27 (m, 1H), 2.09 (dd, J=7.4, 3.3 Hz, 1H), 1.85-1.33 (m, 11H).

Formation of (+/−)-methyl 7-(2-chloro-5-fluoropyrimidin-4-ylamino)bicyclo-[3.2.2]nonane-6-carboxylate (57)

A solution of racemic-trans-methyl 7-aminobicyclo[3.2.2]nonane-6-carboxylate, 56, (1.00 g, 5.07 mmol), 2,4-dichloro-5-fluoro-pyrimidine (0.85 g, 5.07 mmol) and N,N-diisopropylethylamine (1.94 mL, 11.15 mmol) in THF (20 mL) and MeOH (5 mL) was heated at 85° C. for 2 hr. The solvent was evaporated. The crude product was purified by silica gel chromatography (0%-30% EtOAc/hexanes gradient) to afford 1.2 g of the desired product as an oil which solidified upon standing: $^1$H NMR (400 MHz, CDCl$_3$) δ 7.78 (d, J=2.8 Hz, 1H), 5.16 (m, 1H), 4.63 (m, 1H), 3.67 (s, 3H), 2.34 (m, 2H), 1.97 (m, 1H), 1.88 (m, 1H), 1.77-1.38 (m, 8H); LC/MS Gradient 10-90%, 0.1% formic 5 min, C18/ACN, RT=3.43 minutes (M+H) 328.43.

Formation of (+/−)-trans-methyl 7-(5-fluoro-2-(5-fluoro-1-trityl-1H-pyrazolo[3,4-b]pyridin-3-yl)pyrimidin-4-ylamino)bicyclo[3.2.2]nonane-6-carboxylate (58)

A solution of racemic methyl 7-(2-chloro-5-fluoropyrimidin-4-ylamino)bicycle[3.2.2]nonane-6-carboxylate, 57, (0.20 g, 0.61 mmol), 5-fluoro-3-(4,4,5,5-tetramethyl-1,3,2-dioxaborolan-2-yl)-1-trityl-pyrazolo[3,4-b]pyridine, 6, (0.370 g, 0.732 mmol) and K$_3$PO$_4$ (0.39 g mg, 1.83 mmol) in 2-MeTHF (4.0 mL) and H$_2$O (0.40 mL) was purged with nitrogen for 30 min. X-phos (0.035 g, 0.073 mmol) and Pd$_2$(dba)$_3$ (0.014 g, 0.015 mmol) were added. The reaction mixture was heated at 135° C. in a sealed tube for 3 hr. The reaction mixture was cooled to room temperature and concentrated in vacuo. The crude product was purified by silica gel chromatography (0-30% EtOAc/hexanes gradient) to afford 365 mg of the desired product as a white foamy solid: $^1$H NMR (400 MHz, CDCl$_3$) δ 8.57 (dd, J=8.3, 2.8 Hz, 1H), 8.14 (s, 1H), 8.11 (s, 1H), 7.41-7.02 (m, 15H), 5.10 (m, 1H), 3.66 (s, 3H), 2.52 (m, 2H), 2.17 (d, J=25.1 Hz, 1H), 1.95-1.50 (m, 10H); LC/MS Gradient 10-90%, 0.1% formic 5 min, C18/ACN, RT=3.09 minutes (M+H) 671.19.

Formation of (+/−)-methyl 7-(5-fluoro-2-(5-fluoro-1H-pyrazolo[3,4-b]pyridin-3-yl)pyrimidin-4-ylamino)bicyclo[3.2.2]nonane-6-carboxylate (I-36)

Triethylsilane (0.434 mL, 2.721 mmol) was added to a stirred solution of racemic methyl 7-(5-fluoro-2-(5-fluoro-1-trityl-1H-pyrazolo[3,4-b]pyridin-3-yl)pyrimidin-4-ylamino) bicyclo[3.2.2]nonane-6-carboxylate, 58, (0.365 g, 0.544 mmol) and trifluoroacetic acid (0.419 mL, 5.440 mmol) in dichloromethane (20 mL). The resulting yellow solution was stirred at room temperature for 2 hr and concentrated in vacuo. Water (10 mL) and aqueous saturated NaHCO$_3$ (5 mL) were added and the aqueous layer was extracted with EtOAc (3×10 mL). The combined organic phases were dried (MgSO$_4$), filtered and the solvent was removed under reduced pressure. The crude product was purified by silica gel chromatography (10-90% MeOH/CH$_2$Cl$_2$ gradient) to afford 178 mg of the desired product as a white foamy solid: $^1$H NMR (400 MHz, CDCl$_3$) δ 8.63 (s, 1H), 8.55 (s, 1H), 8.31 (s, 1H), 5.20 (s, 1H), 3.71 (s, 3H), 2.62 (m, 1H), 2.53 (m, 1H), 2.24 (m, 1H), 2.06 (m, 1H), 1.98-1.58 (m, 9H); LC/MS Gradient 10-90%, 0.1% formic 5 min, C18/ACN, RT=2.74 minutes (M+H) 329.86.

Formation of (+/−)-7-(5-fluoro-2-(5-fluoro-1H-pyrazolo[3,4-b]pyridin-3-yl)pyrimidin-4-ylamino)bicyclo[3.2.2]nonane-6-carboxylic acid (I-37)

A solution of lithium hydroxide (2.10 mL of 2N solution, 4.15 mmol) was added to a stirred solution of racemic methyl 7-(5-fluoro-2-(5-fluoro-1H-pyrazolo[3,4-b]pyridin-3-yl)pyrimidin-4-ylamino)bicyclo[3.2.2]nonane-6-carboxylate, I-36, (0.18 g, 0.42 mmol) in THF (7 mL). The solution was heated at 85° C. for 6 hr and cooled to room temperature. The solution was concentrated in vacuo and water (5 mL) was added. The solution was slowly neutralized with 1N HCl to produce a white precipitate. The precipitate was filtered and washed with water (10 mL). The wet solid was lyophilized for 2 days to 112 mg of the desired product as a white powder: $^1$H NMR (400 MHz, CD$_3$OD) δ 8.77 (s, 1H), 8.52 (s, 1H), 8.10 (s, 1H), 5.29 (m, 1H), 2.82 (m, 1H), 2.53 (m, 1H), 2.11-1.54 (brm, 10H), 1.29 (m, 1H); LC/MS Gradient 10-90%, 0.1% formic 5 min, C18/ACN, RT=2.33 minutes (M+H) 415.44.

Synthetic Scheme 13: Preparation of Compound I-38 (I-39 and I-40)

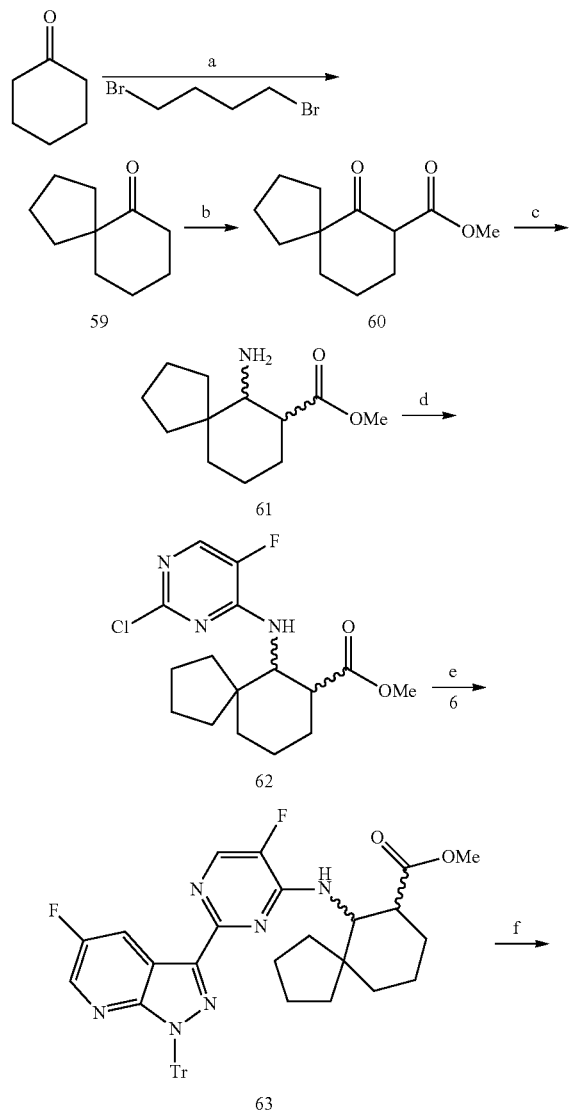

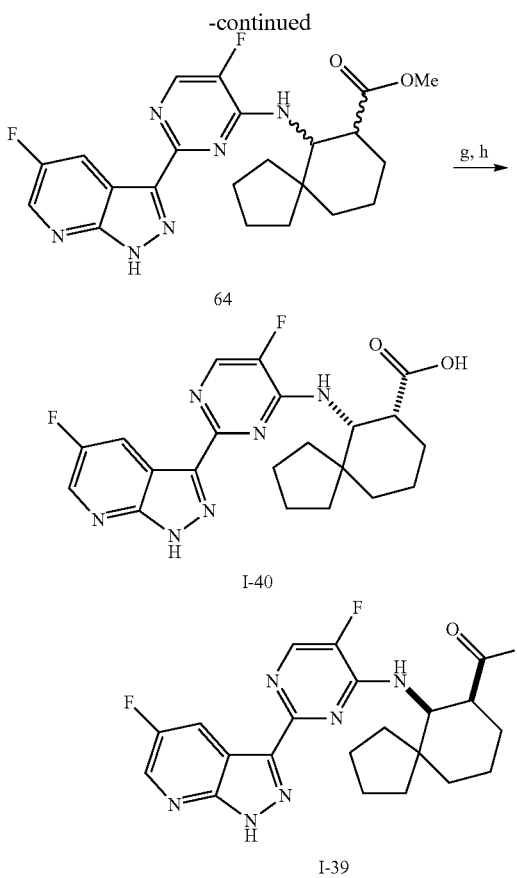

(a) KO'Bu, 'BuOH, benzene, 120° C.; (b) NaH, dimethylcarbonate, THF, 80° C; (c) NH₄OAc, NaCNBH₃, MeOH; (d) 2,4-dichloro-5-fluoropyrimidine, 'Pr₂NEt, THF, 80° C.; (e) 5-fluoro-3-(4,4,5,5-tetramethyl-1,3,2-dioxaborolan-2-yl)-1-trityl-1H-pyrrolo[2,3-b]pyridine (6), K₃PO₄, Pd₂(dba)₃, XPhos, water/2-methyl-THF, 100° C.; (f) Et₃SiH, TFA, CH₂Cl₂; (g) HCl, THF, 80° C.; (h) chiral SFC separation.

Formation of spiro[4.5]decan-6-one (59)

In a flask containing potassium tert-butoxide (45.7 g, 407.6 mmol) in t-BuOH (200 mL) and Benzene (150 mL) was added cyclohexanone (20.0 g, 203.8 mmol) and 1,4-dibromobutane (44.0 g, 203.8 mmol). The solution was heated at 120° C. for 6 hrs. The mixture was cooled to room temperature and neutralized with HCl (1N). The solution was extracted with ether, dried over Na₂SO₄, filtered and concentrated in vacuo. The resulting crude residue was purified by silica gel chromatography (1% EtOAc/hexanes) to afford the title compound: GCMS ES+=153.1.

Formation of methyl 6-oxospiro[4.5]decane-7-carboxylate (60)

In a flask containing NaH (4.73 g, 118.20 mmol) in THF (30 mL) was added dimethylcarbonate (8.30 mL, 98.52 mmol). The mixture was heated at 80° C. To the mixture was added a solution of spiro[4.5]decan-10-one, 59, (6.00 g, 39.41 mmol) in THF dropwise (25 mL). The reaction was heated for 6 hrs at 80° C. The mixture was cooled to room temperature and hydrolyzed with AcOH. The solvent was evaporated and the crude residue was diluted with water and extracted with EtOAc. The organic layer was washed with aqueous saturated NaHCO₃ and brine, dried over Na₂SO₄, filtered and concentrated in vacuo.

The resulting crude material was purified by silica gel chromatography (0-15% ether/hexanes) to afford the title compound as a racemic mixture: GCMS ES+=211.1.

Formation of methyl 6-aminospiro[4.5]decane-7-carboxylate (61)

In a flask containing methyl 6-oxospiro[4.5]decane-7-carboxylate, 60, (4.10 g, 19.50 mmol) in MeOH (35 mL) was added ammonium acetate (10.52 g, 136.50 mmol) and NaCNBH₃ (1.47 g, 23.40 mmol). The mixture was stirred at room temperature for 24 hrs. GCMS showed conversion to product SM (Rt=12.3 min, E+=211), product (Rt=12.6 min, ES+=212 [major] and Rt=12.45 min, ES+=212 [minor]). The solvent was evaporated, HCl (1N) was added and the aqueous phase was extracted with EtOAc. The organic phase was neutralized with NaOH (6N) to pH ~10. The aqueous phase was extracted three times with EtOAc and twice with dichloromethane, dried over Na₂SO₄ to yield 1.6 g of product.

Formation of methyl 6-((2-chloro-5-fluoropyrimidin-4-yl)amino)spiro[4.5]decane-7-carboxylate (62)

In a flask containing methyl 6-aminospiro[4.5]decane-7-carboxylate, 61, (3.60 g, 10.22 mmol) in THF (18.44 mL) was added N,N-diisopropylethylamine (4.10 mL, 23.51 mmol). To the mixture was added a solution of 2,4-dichloro-5-fluoropyrimidine (2.39 g, 14.31 mmol) in THF. The mixture was stirred at 80° C. for 12 hrs. The reaction was diluted into EtOAc and washed with water, then brine. The organic phase was dried over Na₂SO₄, filtered and concentrated in vacuo. The resulting crude residue was purified by silica gel chromatography (0-40% EtOAc/hexanes gradient) to afford 2.0 g of a yellow oil that solidified upon standing: LC/MS Gradient 10-90%, 0.1% formic 5 min, C18/ACN, RT=3.6 minutes (M+H) 343.2.

Formation of 63

To a solution of 5-fluoro-3-(4,4,5,5-tetramethyl-1,3,2-dioxaborolan-2-yl)-1-trityl-pyrazolo[3,4-b]pyridine, 6, (0.886 g, 1.756 mmol) and methyl 6-((2-chloro-5-fluoropyrimidin-4-yl)amino)spiro[4.5]decane-7-carboxylate, 62, (0.500 g, 1.463 mmol) in 2-MeTHF (17 mL) followed by K₃PO₄ (0.777 g, 3.658 mmol) and H₂O (2.83 mL). The mixture was degassed for 5 minutes under flow of nitrogen. Pd₂(dba)₃ (0.094 g, 0.102 mmol) and X-Phos (0.105 g, 0.220 mmol) were then added and the solution was again degassed under flow of nitrogen. The reaction mixture was sealed and heated to 100° C. for 3 hours. The solution was diluted with water and EtOAc and the aqueous layer was extracted with EtOAc, washed with brine, dried over Na₂SO₄, filtered and concentrated in vacuo. The crude residue was purified by silica gel chromatography (50-100% EtOAc/hexanes) to afford the title compound.

Formation of methyl 6-((5-fluoro-2-(5-fluoro-1H-pyrazolo[3,4-b]pyridin-3-yl)pyrimidin-4-yl)amino)spiro[4.5]decane-7-carboxylate (64)

To a solution of 63 (0.100 g, 0.146 mmol) in dichloromethane was added triethylsilane (0.233 mL, 1.460 mmol) followed by trifluoroacetic acid (0.337 mL, 4.380 mmol). The reaction mixture was stirred at room temperature for 1 hr. The solvent was removed under reduced pressure and the product was purified by silica gel chromatography (50-100% EtOAc/

Formation of (6R,7R)-6-((5-fluoro-2-(5-fluoro-1H-pyrazolo[3,4-b]pyridin-3-yl)-pyrimidin-4-yl)amino)spiro[4.5]decane-7-carboxylic acid (I-40) and (6S,7S)-6-((5-fluoro-2-(5-fluoro-1H-pyrazolo[3,4-b]pyridin-3-yl)pyrimidin-4-yl)amino)spiro[4.5]decane-7-carboxylic acid (I-39)

To a solution of methyl 6-((5-fluoro-2-(5-fluoro-1H-pyrazolo[3,4-b]pyridin-3-yl)pyrimidin-4-yl)amino)spiro[4.5]decane-7-carboxylate, 64, (0.500 g, 1.130 mmol) in THF was added HCl (18.83 mL of 6N solution, 113.0 mmol). The reaction mixture was stirred at 80° C. for 1 hr. The solvent was removed under reduced pressure and the product was purified by Prep HPLC, followed by SFC chiral separation to afford the racemic mixture of cis-isomers.

Spectral data for I-40: $^1$H NMR (MeOH-d4) δ 8.6 (m, 2H), 8.3 (d, 1H), 5.2 (s, 1H), 3.0 (m, 1H), 1.3-2.0 (m, 14H); LC/MS Gradient 10-90%, 0.1% formic 5 min, C18/ACN, RT=2.79 minutes (M+H) 429.4.

Spectral data for I-39: same as the spectral data for I-40: $^1$H NMR (MeOH-d4) δ 8.6 (m, 2H), 8.3 (d, 1H), 5.2 (s, 1H), 3.0 (m, 1H), 1.3-2.0 (m, 14H); LC/MS Gradient 10-90%, 0.1% formic 5 min, C18/ACN, RT=2.75 minutes (M+H) 429.3.

Preparation of Compounds I-41, I-47, I-42 and I-43

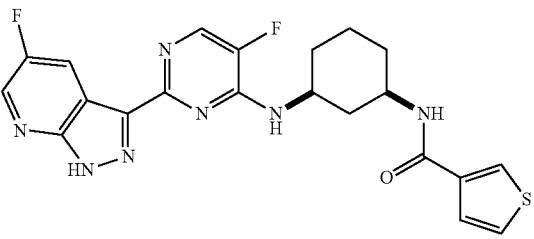

Formation of N-((1R,3S)-3-((5-fluoro-2-(5-fluoro-1H-pyrazolo[3,4-b]pyridin-3-yl)pyrimidin-4-yl)amino)cyclohexyl)thiophene-3-carboxamide (I-41)

The compound was prepared in a similar fashion as described for Compound I-24.

LCMS Gradient 10-90%, 0.1% formic acid, 5 min, C18/ACN, RT=2.07 min, (M+H) 457.0.

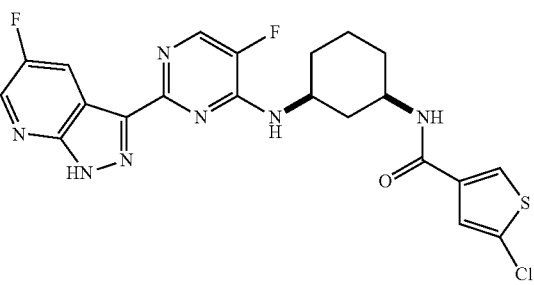

Formation of 5-chloro-N-((1R,3S)-3-((5-fluoro-2-(5-fluoro-1H-pyrazolo[3,4-b]pyridin-3-yl)pyrimidin-4-yl)amino)cyclohexyl)thiophene-3-carboxamide (I-47)

The compound was prepared in a similar fashion as described for Compound I-24.

LCMS Gradient 10-90%, 0.1% formic acid, 5 min, C18/ACN, RT=2.46 min, (M+H) 490.3.

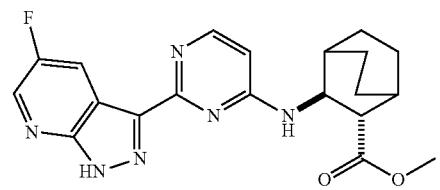

Formation of (+/−)-trans-methyl-3-((2-(5-fluoro-1H-pyrazolo[3,4-b]pyridin-3-yl)pyrimidin-4-yl)amino)bicyclo[2.2.2]octane-2-carboxylate (I-42)

The compound was prepared in a similar fashion as described for Compound I-32.

$^1$H NMR (300 MHz, MeOD) δ 8.71 (s, 1H), 8.62-8.45 (m, 1H), 8.11 (s, 1H), 6.44 (d, J=6.1 Hz, 1H), 3.65 (s, 3H), 2.61 (s, 1H), 2.03 (s, 1H), 2.01-1.39 (m, 8H); LCMS Gradient 10-90%, 0.1% formic acid, 5 min, C18/ACN, RT=2.33, (M+H) 397.06.

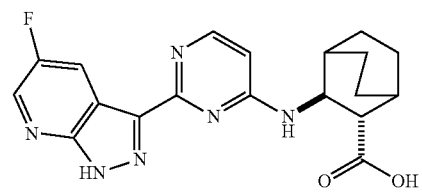

Formation of (+/−)-trans-3-((2-(5-fluoro-1H-pyrazolo[3,4-b]pyridin-3-yl)pyrimidin-4-yl)amino)bicyclo[2.2.2]octane-2-carboxylic acid (I-43)

The compound was prepared in a similar fashion as described for Compound I-31.

$^1$H NMR (300 MHz, d6-DMSO) δ 14.19 (s, 1H), 12.43 (s, 1H), 9.08-8.49 (m, 2H), 8.49-8.08 (m, 1H), 7.74 (s, 1H), 6.50 (d, J=5.4 Hz, 1H), 4.71 (s, 1H), 2.21-1.90 (m, 1H), 1.67 (d, J=50.0 Hz, 6H); LCMS Gradient 10-90%, 0.1% formic acid, 5 min, C18/ACN, RT=2.13, (M+H) 383.05.

Synthetic Scheme 14: Preparation of Compounds I-48 and I-49

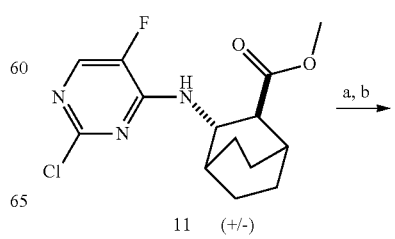

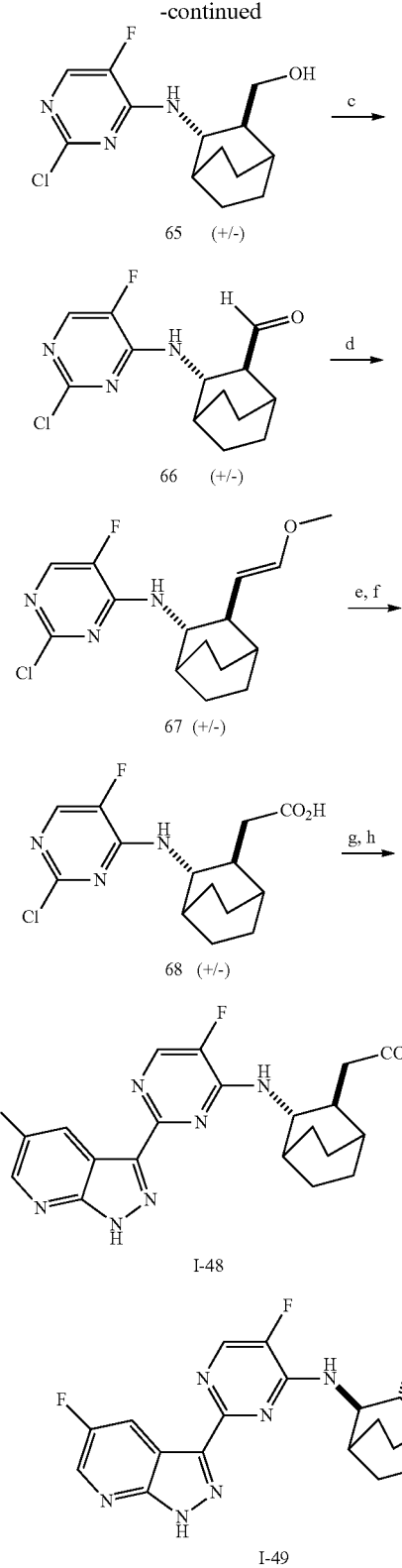

Formation of (+/−)-trans-3-((2-chloro-5-fluoropyrimidin-4-yl)amino)bicycle[2.2.2]-octan-2-yl)methanol (65)

To a solution of racemic methyl 3-[(2-chloro-5-fluoro-pyrimidin-4-yl)amino]bicyclo[2.2.2]octane-2-carboxylate, 11, (3.00 g, 9.56 mmol) in THF (50 mL) was added LiOH (10 mL of 1N solution, 10.00 mmol. The reaction mixture was heated to reflux and stirred overnight. The mixture was concentrated under reduced pressure and the residue was dissolved THF (50 mL). To the mixture was added borane-DMS (3 mL of 10 mmol solution). The reaction mixture was stirred for 2 hours at room temperature. The mixture was carefully quenched with methanol. The mixture was concentrated in vacuo and redissolved in methanol. To the mixture was added citric acid (2.0 g) and the mixture was allowed to stir overnight at room temperature. The mixture was concentrated in vacuo and the resulting residue was purified via silica gel chromatography (EtOAc) to afford 1.5 g of desired product.

Formation of (+/−)-trans 3-((2-chloro-5-fluoropyrimidin-4-yl)amino)bicyclo[2.2.2]-octane-2-carbaldehyde (66)

To a solution of racemic trans-3-((2-chloro-5-fluoropyrimidin-4-yl)amino)bicycle[2.2.2]-octan-2-yl)methanol, 65, (0.200 g, 0.700 mmol) in THF (10 mL) was added Dess-Martin periodinane (0.300 g, 0.700 mmol). The reaction in vacuo mixture was stirred overnight at room temperature. The mixture was concentrated and the resulting residue was purified via silica gel chromatography (50% EtOAc/CH2Cl2) to afford 120 mg of the desired product.

Formation of (+/−)-trans 2-chloro-5-fluoro-N-3-((E)-2-methoxyvinyl)bicyclo[2.2.2]-octan-2-yl)pyrimidin-4-amine (67)

To a cold (0° C.) suspension of methoxymethyl(triphenyl)phosphonium chloride (1.657 g, 4.833 mmol) in THF (20 mL) was added [bis(trimethylsilyl)amino]lithium (3.947 mL of 1 M solution, 3.947 mmol). After stirring the mixture for 10 minutes, racemic-trans-3-[(2-chloro-5-fluoro-pyrimidin-4-yl)amino]bicyclo[2.2.2]octane-2-carbaldehyde, 66, (0.700 g, 2.467 mmol) was added and the reaction mixture was stirred for an additional 30 minutes. After concentrating in vacuo, the resulting residue was purified via silica gel chromatography (100% EtOAc) to afford 365 mg of desired product.

Formation of (+/−)-trans-3-((2-chloro-5-fluoropyrimidin-4-yl)amino)bicyclo-[2.2.2]octan-2-yl)acetic acid (68)

To a solution of racemic-trans 2-chloro-5-fluoro-N-3-((E)-2-methoxyvinyl)-bicyclo[2.2.2]-octan-2-yl)pyrimidin-4-amine, 67, (0.37 g, 1.17 mmol) in THF (5 mL) was added aqueous HCl (1.00 mL of 1N solution, 1.00 mmol). The reaction mixture was stirred overnight at room temperature. After the mixture was concentrated in vacuo and redissolved in 10 mL of dichloromethane, 2 methyl butane (0.10 mL) was added, followed by a a solution of NaClO$_2$ (0.10 g) in water (1.00 mL). The mixture was stirred for 1 hour at room temperature. The mixture was concentrated in vacuo and the (a) 1N LiOH, THF, reflux; (b) BH$_3$-DMS, THF; (c) Dess-Martin periodinane; (d) MeOCH$_2$P$^+$Ph$_3$, LiHMDS, THF, 0° C.; (e) 1N HCl, THF; (f) NaClO$_2$, H$_2$O, CH$_2$Cl$_2$; (g) 5-fluoro-3-(4,4,5,5-tetramethyl-1,3,2-dioxaborolan-2-yl)-1-trityl-1H-pyrrolo[2,3-b]pyridine (6), K$_3$PO$_4$, Pd$_2$(dba)$_3$, XPhos, water/2-methyl-THF, 100° C.; (h) chiral SFC separation.

resulting residue was purified by silica gel chromatography (EtOAc) to afford the desired product.

Formation of 2-((2S,3S)-3-((5-fluoro-2-(5-fluoro-1H-pyrazolo[3,4-b]pyridin-3-yl)pyrimidin-4-yl)amino)bicyclo[2.2.2]octan-2-yl)acetic acid (I-48) and 2-((2R,3R)-3-((5-fluoro-2-(5-fluoro-1H-pyrazolo[3,4-b]pyridin-3-yl)pyrimidin-4-yl)amino)bicyclo[2.2.2]octan-2-yl)acetic acid (I-49)

To a solution of racemic-trans-3-((2-chloro-5-fluoropyrimidin-4-yl)amino)bicyclo-[2.2.2]octan-2-yl)acetic acid, 68, (0.300 g, 0.956 mmol), 5-fluoro-3-(4,4,5,5-tetramethyl-1,3,2-dioxaborolan-2-yl)-1-trityl-pyrazolo[3,4-b], 6, (0.720 g, 1.430 mmol), Pd(dppf) (0.080 g, 0.096 mmol) and NaHCO$_3$ (0.080 g, 0.956 mmol) in THF (10 mL) and water (1 mL). The reaction mixture was stirred at 135° C. for 15 minutes under microwave irradiation. The mixture was concentrated in vacuo and the resulting residue was purified via silica gel chromatography (EtOAc/CH$_2$Cl$_2$ gradient) to afford the Suzuki product. The intermediate was treated with 1N LiOH and heated to 65° C. for 3 hours. After cooling to room temperature, the mixture was concentrated in vacuo and the resulting residue was purified via SFC chiral separation to afford the individual enantiomers, I48 and I-49. Compound I-48: H NMR (300.0 MHz, DMSO) d 8.62 (dd, J=1.6, 2.8 Hz, H), 8.50 (s, H), 8.43 (dd, J=2.8, 8.8 Hz, H), 8.25 (d, J=3.8 Hz, H), 7.79 (d, J=6.3 Hz, H), 3.57 (d, J=7.0 Hz, H), 3.44 (q, J=7.0 Hz, H), 3.36-3.24 (m, H), 2.93 (s, H), 2.73 (d, J=2.0 Hz, H), 2.60-2.49 (m, H), 2.33-2.18 (m, H), 1.85 (d, J=12.7 Hz, H), 1.65 (d, J=7.9 Hz, H), 1.48-1.39 (m, H), 1.35-1.22 (m, H) and 1.08-0.92 (m, H) ppm. LC/MS: 2.28 min (m201)/415.37 (M+H). Compound I-49: LC/MS: 2.28 min (m201)/414.37 (M+H).

Influenza Antiviral Assay

Antiviral assays were performed using two cell-based methods:

A 384-well microtiter plate modification of the standard cytopathic effect (CPE) assay method was developed, similar to that of Noah, et al. (Antiviral Res. 73:50-60, 2006). Briefly, MDCK cells were incubated with test compounds and influenza A virus (A/PR/8/34), at a low multiplicity of infection (approximate MOI=0.005), for 72 hours at 37° C., and cell viability was measured using ATP detection (CellTiter Glo, Promega Inc.). Control wells containing cells and virus show cell death while wells containing cells, virus, and active antiviral compounds show cell survival (cell protection). Different concentrations of test compounds were evaluated, in quadruplicate, for example, over a range from approximately 20 µM to 1 nM. Dose-response curves were prepared using standard 4-parameter curve fitting methods, and the concentration of test compound resulting in 50% cell protection, or cell survival equivalent to 50% of the uninfected wells, was reported as the IC$_{50}$.

A second cell-based antiviral assay was developed that depends on the multiplication of virus-specific RNA molecules in the infected cells, with RNA levels being directly measured using the branched-chain DNA (bDNA), hybridization method (Wagaman et al, J. Virol Meth, 105:105-114, 2002). In this assay, cells are initially infected in wells of a 96-well microtiter plate, the virus is allowed to replicate in the infected cells and spread to additional rounds of cells, then the cells are lysed and viral RNA content is measured. This assay is stopped earlier that the CPE assay, usually after 18-36 hours, while all the target cells are still viable. Viral RNA is quantitated by hybridization of well lysates to specific oligonucleotide probes fixed to wells of an assay plate, then amplification of the signal by hybridization with additional probes linked to a reporter enzyme, according to the kit manufacturer's instructions (Quantigene 1.0, Panomics, Inc.). Minus-strand viral RNA is measured using probes designed for the consensus type A hemagglutination gene. Control wells containing cells and virus were used to define the 100% viral replication level, and dose-response curves for antiviral test compounds were analyzed using 4-parameter curve fitting methods. The concentration of test compound resulting in viral RNA levels equal to that of 50% of the control wells were reported as EC$_{50}$.

Virus and Cell culture methods: Madin-Darby Canine Kidney cells (CCL-34 American Type Culture Collection) were maintained in Dulbecco's Modfied Eagle Medium (DMEM) supplemented with 2 mM L-glutamine, 1,000 U/ml penicillin, 1,000 ug/ml streptomycin, 10 mM HEPES, and 10% fetal bovine medium. For the CPE assay, the day before the assay, cells were suspended by trypsinization and 10,000 cells per well were distributed to wells of a 384 well plate in 50 µl. On the day of the assay, adherent cells were washed with three changes of DMEM containing 1 ug/ml TPCK-treated trypsin, without fetal bovine serum. Assays were initiated with the addition of 30 TCID$_{50}$ of virus and test compound, in medium containing 1 µg/ml TPCK-treated trypsin, in a final volume of 50 µl. Plates were incubated for 72 hours at 37° C. in a humidified, 5% CO$_2$ atmosphere. Alternatively, cells were grown in DMEM+fetal bovine serum as above, but on the day of the assay they were trypsinized, washed 2 times and suspended in serum-free EX-Cell MDCK cell medium (SAFC Biosciences, Lenexa, Kans.) and plated into wells at 20,000 cells per well. These wells were then used for assay after 5 hours of incubation, without the need for washing.

Influenza virus, strain A/PR/8/34 (tissue culture adapted) was obtained from ATCC (VR-1469). Low-passage virus stocks were prepared in MDCK cells using standard methods (WHO Manual on Animal Influenza Diagnosis and Surveillance, 2002), and TCID$_{50}$ measurements were performed by testing serial dilutions on MDCK cells in the 384-well CPE assay format, above, and calculating results using the Karber method.

Mean IC$_{50}$ values (mean all) for certain specific compounds are summarized in Tables 1 and 2:

A: IC$_{50}$<3.3 µM;

B: IC$_{50}$≥3.3 µM.

Mean EC$_{50}$ values (mean all) for certain compounds are also summarized in Tables 1 and 2:

A: EC$_{50}$<3.3 µM;

B: EC$_{50}$≥3.3 µM.

For example, IC$_{50}$ and EC$_{50}$ values of Compound I-14 are both 0.001 µM.

TABLE 1

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-1 | A | A | 475.46 | 2.3 | 1H NMR (300 MHz, MeOD) δ 8.73 (s, 1H), 8.64 (s, 1H), 8.29 (d, J = 4.8 Hz, 1H), 4.43 (m, 1H), 3.83 (m, 1H), 3.65-3.62 (m, 4H), 3.35 (burried m, 4H), 2.38 (d, J = 12.1 Hz, 1H), 2.23 (d, J = 9.5 Hz, 1H), 2.03 (br m, 2H) and 1.70-1.29 (complex m, 4H) ppm |
| I-2 | A | A | 431.44 | 2.52 | 1H NMR (300 MHz, DMSO-d6) δ 14.24 (s, 1H), 8.83 (d, J = 2.3 Hz, 1H), 8.61 (d, J = 2.3 Hz, 1H), 8.30 (d, J = 3.7 Hz, 1H), 7.84 (d, J = 7.2 Hz, 1H), 4.79 (d, J = 6.8 Hz, 1H), 3.59 (d, J = 14.8 Hz, 3H), 3.00 (d, J = 6.8 Hz, 1H), 1.97 (d, J = 16.6 Hz, 2H), 1.87-1.32 (m, 9H). [1], 1H NMR (300 MHz, MeOD) d 8.98 (d, J = 2.3 Hz, 1H), 8.53 (d, J = 2.3 Hz, 1H), 8.12 (d, J = 3.8 Hz, 1H), 4.99 (d, J = 6.8 Hz, 1H), 3.67 (s, 3H), 2.85 (d, J = 7.1 Hz, 1H), 2.08 (s, 1H), 1.93-1.42 (m, 8H), 1.20 (d, J = 4.7 Hz, 1H). |
| I-3 | A | A | 459.61 | 2.52 | |

TABLE 1-continued

IC50, EC50, NMR and LCMS Data of Compounds of Invention.

| Molecule | Flu, MDCK IC50 (uM) | bDNA EC50 (uM) | M + 1 | RT | NMR |
|---|---|---|---|---|---|
| I-4 | A | A | 489.65 | 2.33 | |
| I-5 | A | A | 489.6 | 2.38 | |
| I-6 | A | A | 417.28 | 2.23 | 1H NMR (300 MHz, MeOD) δ 8.96 (d, J = 2.4 Hz, 1H), 8.58 (d, J = 2.4 Hz, 1H), 8.19 (d, J = 4.4 Hz, 1H), 5.06 (d, J = 6.9 Hz, 1H), 2.85 (d, J = 7.0 Hz, 1H), 2.20-2.12 (m, 1H), 2.09-1.97 (m, 2H), 1.91-1.47 (m, 8H). [1] |
| I-7 | A | A | 441.43 | 2 | 1H NMR (300.0 MHz, MeOD) δ 8.82-8.79 (m, 1H), 8.54 (d, J = 3.5 Hz, 1H), 8.09 (s, 1H), 7.35 (dd, J = 4.5, 8.0 Hz, 1H), 4.28-4.21 (m, 1H), 3.90-3.81 (m, 1H), 3.64-3.61 (m, 4H), 3.37-3.31 (m, 5H), 2.40 (d, J = 11.6 Hz, 1H), 2.12 (d, J = 12.0 Hz, 1H), 1.96-1.90 (m, 2H), 1.65-1.52 (m, 1H), 1.47-1.21 (m, 3H) and −0.00 (TMS) ppm |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-8 | A | A | 397.39 | 2.72 | 1H NMR (300 MHz, CDCl3) δ 8.97 (dd, J = 1.5, 8.1 Hz, 1H), 8.68 (dd, J = 1.5, 4.6 Hz, 1H), 8.26 (d, J = 3.2 Hz, 1H), 7.33 (dd, J = 4.6, 8.1 Hz, 1H), 7.28 (s, 1H), 5.31-5.26 (m, 1H), 4.93 (t, J = 6.6 Hz, 1H), 3.51 (s, 3H), 2.49 (d, J = 6.1 Hz, 1H), 2.11 (s, 2H), 1.91 (d, J = 11.9 Hz, 3H) and 1.78-1.53 (m, 7H) ppm |
| I-9 | A | A | 417.33 | 2.24 | 1H NMR (300 MHz, MeOD) δ 8.98 (d, J = 2.4 Hz, 1H), 8.55 (d, J = 2.3 Hz, 1H), 8.15 (d, J = 4.1 Hz, 1H), 5.02 (d, J = 7.1 Hz, 1H), 2.83 (d, J = 6.9 Hz, 1H), 2.14 (s, 1H), 2.03 (s, 2H), 1.91-1.45 (m, 7H). |
| I-10 | A | A | 417.08 | 2.24 | 1H NMR (300 MHz, MeOD) δ 8.96 (s, 1H), 8.57 (d, J = 2.0 Hz, 1H), 8.18 (d, J = 3.8 Hz, 1H), 5.04 (d, J = 6.9 Hz, 1H), 2.85 (d, J = 6.9 Hz, 1H), 2.15 (s, 1H), 2.04 (s, 2H), 1.96-1.45 (m, 7H). |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-11 | A | A | 383.06 | 2.4 | 1H NMR (300 MHz, DMSO-d6) δ 13.97 (s, 1H), 12.35 (s, 1H), 8.81 (d, J = 8.1 Hz, 1H), 8.56 (s, 1H), 8.29 (d, J = 3.6 Hz, 1H), 7.77 (s, 1H), 7.32 (s, 1H), 4.74 (s, 1H), 2.89 (d, J = 6.3 Hz, 1H), 2.08 (s, 1H), 1.96 (d, J = 24.8 Hz, 2H), 1.83-1.32 (m, 6H). |
| I-12 | A | A | 425.67 | 2.12 | 1H NMR (300 MHz, CDCl3) δ 13.85 (s, 1H), 8.56 (dd, J = 1.5, 4.5 Hz, 1H), 8.36 (dd, J = 1.4, 8.1 Hz, 1H), 8.06 (d, J = 3.2 Hz, 1H), 7.28 (s, H), 7.28 (s, H) (CDCl3), 7.00 (dd, J = 4.5, 8.1 Hz, 1H), 5.10 (d, J = 6.0 Hz, 1H), 4.17 (d, J = 7.9 Hz, 1H), 3.98 (s, 1H), 3.98 (td, J = 11.3, 6.5 Hz, 1H), 3.79 (q, J = 3.7 Hz, 1H), 3.76 (s, 1H), 3.35 (t, J = 6.3 Hz, 3H), 2.77 (d, J = 11.5 Hz, 1H), 2.16 (d, J = 11.4 Hz, 1H), 2.08-2.02 (m, 1H), 1.95-1.82 (m, 4H), 1.48 (d, J = 13.0 Hz, H) and 1.25-1.02 (m, 5H) ppm |
| I-13 | A | A | 405.01 [1] | 2.17 [1] | 1H NMR (300 MHz, DMSO-d6) δ 8.96 (s, 1H), 8.64 (s, 1H), 8.36 (br, 1H), 7.58 (br s, 1H), 5.08-4.88 (m, 1H), 2.04-1.85 (m, 1H), 1.85-1.61 (m, 4H), 1.61-1.32 (m, 3H), 1.21 (s, 3H). |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-14 | A | A | 443.34 | 2.31 | 1H NMR (300 MHz, CDCl3) δ 8.42 (q, J = 1.4 Hz, 1H), 7.90 (d, J = 3.1 Hz, 1H), 7.51 (dd, J = 2.7, 8.6 Hz, 1H), 7.28 (s, H), 5.15 (d, J = 5.5 Hz, 1H), 4.26 (d, J = 7.9 Hz, 1H), 3.89 (t, J = 3.9 Hz, 1H), 3.38 (d, J = 3.2 Hz, 4H), 3.10-3.08 (m, 1H), 2.82 (d, J = 11.3 Hz, 1H), 2.11-2.05 (m, 1H), 1.93 (t, J = 6.4 Hz, 4H), 1.76 (s, 1H), 1.32-1.09 (m, 4H) and 1.01-0.86 (m, 1H) ppm |
| I-15 | A | A | 439.56 | 1.85 | 1H NMR (300 MHz, DMSO-d6) δ 9.02 (s, 1H), 8.69 (dd, J = 4.8, 3.3 Hz, 2H), 8.48 (d, J = 5.0 Hz, 1H), 7.52 (dd, J = 7.9, 4.8 Hz, 3H), 5.87 (d, J = 8.2 Hz, 1H), 4.23 (s, 1H), 3.90-3.70 (m, 2H), 3.31-3.21 (m, 1H), 3.19-3.01 (m, 1H), 2.76 (s, 1H), 2.20 (d, J = 11.4 Hz, 1H), 2.01-1.67 (m, 5H), 1.55-1.20 (m, 5H), 1.05 (d, J = 6.2 Hz, 2H). |
| I-16 | A | A | 461.57 | 1.85 | 1H NMR (300 MHz, DMSO-d6) δ 8.99 (s, 1H), 8.75 (d, J = 8.4 Hz, 1H), 7.54 (s, 1H), 7.35 (s, 1H), 6.26 (d, J = 7.9 Hz, 2H), 4.22 (s, 1H), 3.74 (s, 1H), 3.62 (t, J = 13.4 Hz, 2H), 3.43 (t, J = 7.3 Hz, 2H), 2.35 (dd, J = 22.3, 14.9 Hz, 2H), 2.24 (d, J = 22.1 Hz, 2H), 2.09-1.16 (m, 7H). [1] |
| I-17 | A | A | 443.53 | 1.69 | |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-18 | A | A | 439.56 | 1.87 | |
| I-19 | A | A | 443.53 | 1.68 | |
| I-20 | A | A | 457.6 | 1.8 | 1H NMR (300 MHz, DMSO-d6) δ 8.75 (dd, J = 8.1, 1.5 Hz, 1H), 8.57 (dd, J = 4.4, 1.5 Hz, 1H), 8.27 (d, J = 3.8 Hz, 1H), 7.71 (d, J = 7.3 Hz, 1H), 6.41 (d, J = 7.8 Hz, 1H), 4.86 (d, J = 3.6 Hz, 1H), 4.69 (d, J = 3.6 Hz, 1H), 4.21-4.06 (m, 1H), 3.66 (s, 1H), 3.47 (s, 2H), 3.29-3.11 (m, 3H), 2.16 (d, J = 11.2 Hz, 1H), 2.02-1.86 (m, 2H), 1.64-1.08 (m, 8H), 0.82 (d, J = 6.7 Hz, 1H). |
| I-21 | A | A | 459.17 | 1.76 | 1H NMR (300 MHz, MeOD) δ 8.46 (s, H), 8.30 (dd, J = 2.7, 8.5 Hz, 1H), 8.04 (d, J = 3.8 Hz, 1H), 4.13 (t, J = 11.6 Hz, 1H), 4.11 (s, 1H), 3.87-3.78 (m, 1H), 3.65-3.62 (m, 4H), 3.38-3.30 (m, 6H), 2.34 (d, J = 11.6 Hz, 1H), 2.16 (d, J = 11.9 Hz, 1H), 1.98-1.88 (m, 2H), 1.54-1.21 (m, 4H) and −0.00 (TMS) ppm |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-22 | A | A | 439.69 | 1.87 | 1H NMR (300 MHz, DMSO-d6) δ 13.93 (s, 1H), 8.80-8.64 (m, 1H), 8.56 (s, 1H), 8.27 (d, J = 3.8 Hz, 1H), 7.70 (d, J = 7.4 Hz, 1H), 6.23 (d, J = 7.9 Hz, 1H), 3.68 (s, 1H), 3.28-3.19 (m, 3H), 3.17 (d, J = 5.2 Hz, 3H), 2.16 (d, J = 11.5 Hz, 1H), 1.94 (d, J = 13.4 Hz, 1H), 1.82 (s, 1H), 1.58-1.09 (m, 11H), 0.82 (d, J = 6.7 Hz, 0H). |
| I-23 | A | A | 461.68 | 1.87 | 1H NMR (300.0 MHz, MeOD) δ 8.46 (s, H), 8.34 (dd, J = 2.8, 8.5 Hz, 1H), 8.07-8.04 (m, 1H), 5.49 (s, H), 5.34-5.16 (m, 1H), 4.17 (t, J = 11.6 Hz, H), 4.14 (s, H), 3.86-3.78 (m, 1H), 3.65-3.52 (m, 2H), 3.46-3.40 (m, 2H), 3.36-3.30 (m, 2H), 2.34 (d, J = 11.9 Hz, 1H), 2.24-2.13 (m, 2H), 2.04-1.89 (m, 2H), 1.61-1.24 (m, 4H) and −0.00 (s, H) ppm |
| I-24 | A | A | 436.62 | 1.46 | |

TABLE 1-continued

IC₅₀, EC₅₀, NMR and LCMS Data of Compounds of Invention.

| Molecule | | Flu, MDCK IC50 (uM) | bDNA EC50 (uM) | M + 1 | RT | NMR |
|---|---|---|---|---|---|---|
| I-25 | | A | A | 439.56 | 1.87 | 1H NMR (300 MHz, DMSO-d6) δ 13.86 (s, 1H), 8.83-8.69 (m, 1H), 8.58 (d, J = 3.7 Hz, 1H), 8.29 (t, J = 3.6 Hz, 1H), 7.73 (d, J = 6.2 Hz, 1H), 7.38 (dd, J = 8.0, 3.9 Hz, 1H), 4.15 (s, 1H), 3.68 (d, J = 7.6 Hz, 1H), 3.16 (d, J = 8.4 Hz, 1H), 2.73 (t, J = 7.3 Hz, 1H), 2.52 (s, 1H), 2.18 (d, J = 9.0 Hz, 2H), 2.06-1.72 (m, 5H), 1.54-1.12 (m, 6H), 0.98 (dd, J = 6.4, 3.5 Hz, 3H). |
| I-26 | | | | 439.62 | 1.9 | |
| I-27 | | A | A | 454.34 | 1.61 | |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-28 | A | A | 414.89 | 2.93 | 1H NMR (300 MHz, CDCl) δ 12.96 (s, 1H), 8.69-8.47 (m, 2H), 8.26 (d, J = 3.0 Hz, 1H), 4.91 (t, J = 6.3 Hz, 1H), 3.70 (s, 3H), 2.46 (dd, J = 22.4, 6.6 Hz, 1H), 2.14 (dd, J = 15.9, 13.2 Hz, 3H), 1.93 (d, J = 13.8 Hz, 1H), 1.83-1.64 (m, 5H), 1.52 (dd, J = 24.2, 9.5 Hz, 2H). |
| I-29 | A | A | 401.64 | 2.6 | 1H NMR (400 MHz, DMSO-d6) δ 14.17 (s, 1H), 12.37 (s, 1H), 8.64 (s, 1H), 8.51 (d, J = 7.4 Hz, 1H), 8.29 (d, J = 3.6 Hz, 1H), 7.82 (d, J = 5.7 Hz, 1H), 4.75 (s, 1H), 2.89 (d, J = 6.4 Hz, 1H), 2.03 (s, 1H), 1.94 (s, 1H), 1.76 (d, J = 7.8 Hz, 3H), 1.63 (d, J = 6.1 Hz, 1H), 1.57-1.42 (m, 3H), 1.39 (d, J = 10.3 Hz, 1H). |
| I-30 | A | A | 400.87 | 2.2 | 1H NMR (400 MHz, DMSO-d6) δ 8.51 (d, J = 12.0 Hz, 2H), 8.16 (d, J = 3.8 Hz, 1H), 7.38 (d, J = 6.3 Hz, 1H), 4.82 (s, 1H), 2.50 (s, H), 2.34 (d, J = 5.9 Hz, 1H), 1.99 (s, 1H), 1.90 (s, 1H), 1.74-1.66 (m, 5H), 1.55 (d, J = 10.7 Hz, 1H), 1.43 (d, J = 10.6 Hz, 1H), 1.28 (s, 2H) and 0.00 (s, H) ppm |

TABLE 1-continued

IC50, EC50, NMR and LCMS Data of Compounds of Invention.

| Molecule | Flu, MDCK IC50 (uM) | bDNA EC50 (uM) | M + 1 | RT | NMR |
|---|---|---|---|---|---|
| I-31 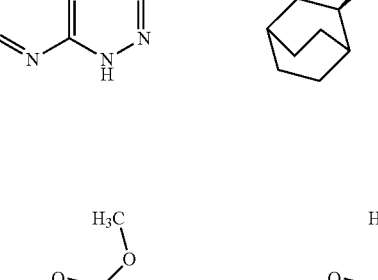 | A | A | 401.3 | 2.26 | 1H NMR (300 MHz, MeOD) δ 8.71 (d, J = 6.1 Hz, H), 8.50 (s, 1H), 8.05 (d, J = 4.0 Hz, 1H), 4.98 (d, J = 6.7 Hz, 1H), 4.89 (s, 1H), 3.31 (qn, J = 1.6 Hz, H), 2.53 (d, J = 6.8 Hz, 1H), 2.12-1.99 (m, 3H), 1.87-1.81 (m, 3H), 1.76-1.58 (m, 2H), 1.46 (dd, J = 10.5, 21.8 Hz, 2H) and −0.00 (s, H) ppm |
| I-32 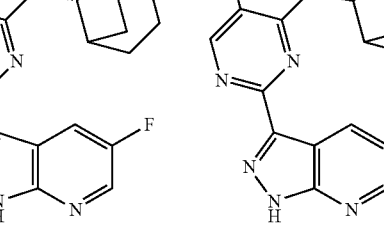 | A | A | 431.14 | 2.55 | 1H NMR (400 MHz, MeOD) δ 8.66 (dd, J = 8.3, 2.5 Hz, 1H), 8.53 (s, 1H), 8.28 (s, 1H), 5.05 (d, J = 6.5 Hz, 1H), 3.69 (s, 3H), 2.95 (d, J = 6.8 Hz, 1H), 2.09 (s, 1H), 1.98 (s, 1H), 1.96-1.79 (m, 3H), 1.77-1.61 (m, 3H), 1.61-1.45 (m, 2H). |
| I-33 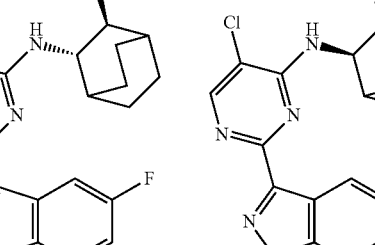 | A | A | 417.09 | 2.28 | 1H NMR (400 MHz, MeOD) δ 8.67 (dd, J = 8.4, 2.5 Hz, 1H), 8.53 (s, 1H), 8.27 (s, 1H), 5.05 (d, J = 6.7 Hz, 1H), 2.92 (d, J = 6.6 Hz, 1H), 2.15 (s, 1H), 2.03-1.79 (m, 4H), 1.79-1.62 (m, 3H), 1.62-1.45 (m, 2H). |
| I-34 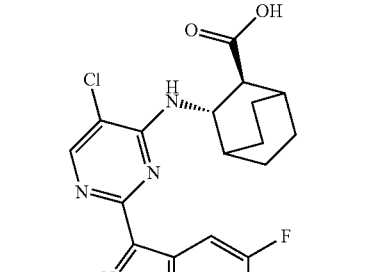 | A | A | 417.09 [1] | 2.27 [1] | 1H NMR (300 MHz, MeOD) δ 8.67 (d, J = 6.6 Hz, 1H), 8.53 (s, 1H), 8.27 (s, 1H), 5.13-4.98 (m, 1H), 2.98-2.87 (m, 1H), 2.11 (burried s, 1H), 2.05-1.82 (m, J = 36.5 Hz, 3H), 1.82-1.44 (m, 4H). [1] |

TABLE 1-continued

IC$_{50}$, EC$_{50}$, NMR and LCMS Data of Compounds of Invention.

| Molecule | Flu, MDCK IC50 (uM) | bDNA EC50 (uM) | M + 1 | RT | NMR |
|---|---|---|---|---|---|
| I-35 | A | A | 417.09 | 2.27 | 1H NMR (300 MHz, MeOD) δ 8.69 (s, 1H), 8.52 (s, 1H), 8.27 (s, 1H), 5.18-4.99 (m, 1H), 3.00-2.86 (m, 1H), 2.15 (s, 1H), 2.07-1.82 (m, 3H), 1.81-1.45 (m, 4H). |
| I-36 | A | A | 429.47 | 2.74 | 1H NMR (400 MHz, CDCl3) δ 8.62 (d, J = 6.7 Hz, 1H), 8.55 (s, 1H), 8.31 (s, 1H), 5.20 (m, 1H), 3.71 (s, 3H), 2.62 (m, 1H), 2.52 (m, 1H), 2.24 (m, 1H), 2.06 (m, 1H), 1.96-1.48 (m, 10H). |
| I-37 | A | A | 415 [1] | 2.32 | 1H NMR (400 MHz, MeOD) δ 8.77 (m, 1H), 8.77 (s, 1H), 8.52 (s, 1H), 8.10 (s, 1H), 5.29 (m, 1H), 2.82 (m, 1H), 2.53 (m, 1H), 2.11-1.54 (brm, 10H), 1.29 (m, 1H). |

TABLE 1-continued

IC₅₀, EC₅₀, NMR and LCMS Data of Compounds of Invention.

| Molecule | Flu, MDCK IC50 (uM) | bDNA EC50 (uM) | M + 1 | RT | NMR |
|---|---|---|---|---|---|
| I-38 | A | A | 429.4 | 2.79 | 1H NMR (MeOH-d4) d 8.6 (m, 2H), 8.3 (d, 1H), 5.2 (s, 1H), 3.0 (m, 1H), 1.3-2.0 (m, 14H). |
| | | | | | |

TABLE 2

IC₅₀, EC₅₀, NMR and LCMS Data of Compounds of Invention.

| Molecule | Flu MDCK IC50 (uM) | bDNA EC50 (uM) | LCMS RT | M + 1 | NMR |
|---|---|---|---|---|---|
| I-39 | A | A | 2.75 | 429.3 | NMR 1H (MeOH-d4): 8.6 (d, 1S), 8.5 (s, 1H), 8.2 (s, 1H), 5.2 (s, 1H), 3.0 (m, 1H), 1.1-1.8 (m, 14H). |
| I-40 | A | A | 2.79 | 429.4 | NMR 1H (MeOH-d4): 8.6 (d, 1S), 8.5 (s, 1H), 8.2 (s, 1H), 5.2 (s, 1H), 3.0 (m, 1H), 1.1-1.8 (m, 14H). |

TABLE 2-continued

IC$_{50}$, EC$_{50}$, NMR and LCMS Data of Compounds of Invention.

| Molecule | Flu MDCK IC50 (uM) | bDNA EC50 (uM) | LCMS RT | M + 1 | NMR |
|---|---|---|---|---|---|
| I-41 | A | A | 2.07 | 457 | |
| I-42 | A | A | 2.33 | 397.06 | 1H NMR (300 MHz, MeOD) δ 8.71 (s, 1H), 8.62-8.45 (m, 1H), 8.11 (s, 1H), 6.44 (d, J = 6.1 Hz, 1H), 3.65 (s, 3H), 2.61 (s, 1H), 2.03 (s, 1H), 2.01-1.39 (m, 8H). |
| I-43 | A | A | 2.13 | 383.05 | 1H NMR (300 MHz, DMSO) δ 14.19 (s, 1H), 12.43 (s, 1H), 9.08-8.49 (m, 2H), 8.49-8.08 (m, 1H), 7.74 (s, 1H), 6.50 (d, J = 5.4 Hz, 1H), 4.71 (s, 1H), 2.21-1.90 (m, 1H), 1.67 (d, J = 50.0 Hz, 6H). |
| I-44 | A | A | 2.24 | 401.23 [1], 401.17 | 1H NMR (300 MHz, DMSO) δ 14.17 (s, 1H), 12.37 (s, 1H), 8.64 (s, 1H), 8.52 (d, J = 8.0 Hz, 1H), 8.29 (d, J = 3.8 Hz, 1H), 7.82 (d, J = 7.1 Hz, 1H), 4.74 (d, J = 6.6 Hz, 1H), 2.89 (d, J = 6.8 Hz, 1H), 2.03 (s, 1H), 1.94 (s, 1H), 1.77 (d, J = 8.2 Hz, 3H), 1.66-1.23 (m, 5H). |
| I-45 | A | A | 2.58 | 429.3 | NMR 1H (MeOH-d4): 8.6 (m, 2H), 8.3 (d, 1H), 5.2 (s, 1H), 3.0 (m, 1H), 1.3-2.0 (m, 14H). |

US 8,871,774 B2

TABLE 2-continued

IC$_{50}$, EC$_{50}$, NMR and LCMS Data of Compounds of Invention.

| Molecule | Flu MDCK IC50 (uM) | bDNA EC50 (uM) | LCMS RT | M + 1 | NMR |
|---|---|---|---|---|---|
| I-46 | A | B | 2.58 | 429.3 | NMR 1H (MeOH-d4): 8.6 (m, 2H), 8.3 (d, 1H), 5.2 (s, 1H), 3.0 (m, 1H), 1.3-2.0 (m, 14H). |
| I-47 | A | A | 2.46 | 490.3 | |
| I-48 | A | A | 2.28 | 415.37 | H NMR (300.0 MHz, DMSO) d 8.62 (dd, J = 1.6, 2.8 Hz, H), 8.50 (s, H), 8.43 (dd, J = 2.8, 8.8 Hz, H), 8.25 (d, J = 3.8 Hz, H), 7.79 (d, J = 6.3 Hz, H), 3.57 (d, J = 7.0 Hz, H), 3.44 (q, J = 7.0 Hz, H), 3.36-3.24 (m, H), 2.93 (s, H), 2.73 (d, J = 2.0 Hz, H), 2.60-2.49 (m, H), 2.33-2.18 (m, H), 1.85 (d, J = 12.7 Hz, H), 1.65 (d, J = 7.9 Hz, H), 1.48-1.39 (m, H), 1.35-1.22 (m, H) and 1.08-0.92 (m, H) ppm |
| I-49 | | | 2.28 | 414.37 | |

IN VIVO ASSAY

For efficacy studies, Balb/c mice (4-5 weeks of age) were challenged with 5×10$^3$ TCID$_{50}$ in a total volume of 50 µl by intranasal instillation (25 µl/nostril) under general anesthesia (Ketamine/Xylazine). Uninfected controls were challenged with tissue culture media (DMEM, 50 µl total volume). 48 hours post infection mice began treatment with Compound I-14 at 30 mg/kg bid for 10 days. Body weights and survival is scored daily for 21 days. In addition, Whole Body Plethysmography is conducted approximately every third day following challenge and is reported as enhanced pause (Penh). Total Survival, Percent Body Weight Loss on post challenge day 8 and Penh on study day 6/7 are reported.

TABLE 3

Influneza Therapeutic Mouse Model (Dosing @ 48 hours post infection with 30 mg/kg BID × 10 days)

| Compounds | Percent Survival | Percent Weight Loss (Day 8)[1] | WBP (Penh; Day 6)[2] |
|---|---|---|---|
| I-14 | 100 | 23.4 | 1.59 |

[1]Average weight loss for untreated controls on day 8 is 30-32%.
[2]Average Penh scores for untreated controls on study day 6 or 7 is 2.2-2.5, and for uninfected mice is ~0.35-0.45.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound represented by Structural Formula (I):

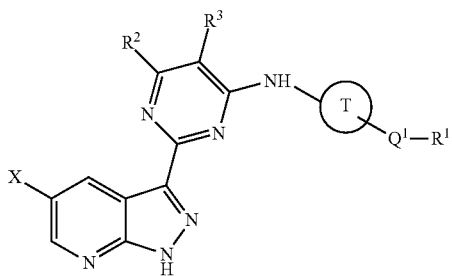

or a pharmaceutically acceptable salt thereof, wherein:

X is —H, —Cl, —Br, —F, —CN, or $C_1$-$C_6$ aliphatic optionally substituted with one or more instances of $J^1$;

Ring T is a $C_3$-$C_{10}$ non-aromatic carbocycle or 4-10 membered, non-aromatic, heterocycle optionally further substituted with one or more instances of $J^T$;

$Q^1$ is —C(O)—, —$CO_2$—, —OC(O)—, —O($CR^t R^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —P(O)(OR)O—, —OP(O)($OR^a$)O—, —P(O)$_2$O—, —$CO_2SO_2$—, —B(O)$_2$—, or —($CR^tR^s$)—$Y^1$—;

$Y^1$ is —C(O)—, —$CO_2$—, —OC(O)—, —O($CR^t R^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —P(O)(OR)O—, —OP(O)($OR^a$)O—, —P(O)$_2$O—, —B(O)$_2$—, or —$CO_2SO_2$—;

$R^1$ is: i) —H; ii) a $C_1$-$C_6$ aliphatic group optionally substituted with one or more instances of $J^4$; iii) a $C_3$-$C_{10}$ non-aromatic carbocyclic group or 4-10 membered, non-aromatic, heterocyclic group, each optionally and independently substituted with one or more instances of $J^B$; or iv) a 6-10 membered aryl group or 5-10 membered heteroaryl group, each optionally and independently substituted with one or more instances of $J^C$;

optionally $R^1$, together with R' and the nitrogen to which they are attached, forms a 4-8 membered, non-aromatic, heterocyclic group optionally substituted with one or more instances of $J^2$; or optionally -$Q^1$-$R^1$ forms, together with Ring T, a 4-10 membered, non-aromatic, spiro ring optionally substituted with one or more instances of $J^4$; and $R^2$ is —H, —OR, —$CO_2$R, —NRR', —CONRR', or $C_1$-$C_6$ aliphatic optionally substituted with one or more instances of $J^1$;

$R^3$ is —H, —F, —Cl, —CN, —$NO_2$, —OR, —$CO_2$R, —CONRR', or $C_1$-$C_6$ aliphatic optionally substituted with one or more instances of $J^1$;

$J^A$, $J^B$, and $J^T$ are each and independently oxo or $J^C$;

$J^C$ are each and independently selected from the group consisting of halogen, cyano, M, $R^a$, or $R^a$-M;

M is independently selected from the group consisting of —$OR^b$, —$SR^b$, —S(O)$R^a$, —$SO_2R^a$, —$NR^bR^c$, —C(O)$R^a$, —C(=NR)$R^c$, —C(=NR)$NR^bR^c$, —NRC(=NR)$NR^bR^c$, —C(O)$OR^b$, —OC(O)$R^b$, —NRC(O)$R^b$, —C(O)$NR^bR^c$, —NRC(O)$NR^bR^c$, —NRC(O)$OR^b$, —OCONR$^bR^c$, —C(O)$NRCO_2R^b$, —NRC(O)NRC(O)$OR^b$, —C(O)NR($OR^b$), —$OSO_2NR^bR^c$, —$SO_2NR^cR^b$, —$NRSO_2R^b$, —$NRSO_2NR^cR^b$, —P(O)($OR^b$)$_2$, —OP(O)($OR^b$)$_2$, —P(O)$_2OR^b$ and —$CO_2SO_2R^b$; or optionally, two $J^T$, two $J^A$, two $J^B$, and two $J^C$, respectively, together with the atom(s) to which they are attached, independently form a 4-10-membered ring that is optionally substituted with one or more instances of $J^4$; and $R^a$ is independently:

i) a $C_1$-$C_6$ aliphatic group optionally substituted with one or more substituents selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), —O($C_1$-$C_4$ alkyl), $C_3$-$C_8$ non-aromatic carbocyclic group optionally substituted with one or more instances of $J^2$, 4-8 membered, non-aromatic, heterocyclic group optionally substituted with one or more instances of $J^2$, 5-10 membered heteroaryl group optionally substituted with one or more instances of $J^3$, and 6-10 membered aryl group optionally substituted with one or more instances of $J^3$;

ii) a $C_3$-$C_8$ non-aromatic carbocyclic group, or 4-8 membered, non-aromatic, heterocyclic group, each of which is optionally and independently substituted with one or more instances of $J^2$; or iii) a 5-10 membered heteroaryl group, or 6-10 membered aryl group, each of which is optionally and independently substituted with one or more instances of $J^3$; and $R^b$ and $R^c$ are each independently $R^a$ or —H; or optionally, $R^b$ and $R^c$, together with the nitrogen atom(s) to which they are attached, each independently form a 4-8 membered, non-aromatic, heterocyclic group optionally substituted with one or more instances of $J^2$;

$R^t$ and $R^s$ are each independently —H, halogen, or $C_1$-$C_6$ alkyl optionally substituted with one or more instances of $J^1$, or optionally, $R^t$ and $R^s$, together with the carbon atom to which they are attached, form a cyclopropane ring optionally substituted with one or more instances of methyl;

R and R' are each independently —H or $C_1$-$C_6$ alkyl optionally and independently substituted with one or more instances of $J^1$, or optionally R and R', together with the nitrogen to which they are attached, form a 4-8 membered, non-aromatic, heterocyclic group optionally substituted with one or more instances of $J^2$;

each $J^1$ is independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), —O($C_1$-$C_4$ alkyl), and phenyl;

each $J^2$ is independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl);

each of $J^3$ and $J^4$ is independently selected from the group consisting of halogen, cyano, hydroxy, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkyl, $C_1$-$C_4$ haloalkyl, and —O($C_1$-$C_4$ alkyl);

p is 1, 2, 3 or 4; and k is 1, 2, 3 or 4.

2. The compound of claim 1, wherein:

X is —Cl, —Br, —F, —CN, or optionally substituted $C_1$-$C_6$ alkyl;

$R^2$ is —H, —O($C_1$-$C_4$ alkyl), —$NH_2$, —NH($C_1$-$C_4$ alkyl), —N($C_1$-$C_4$ alkyl)$_2$, —$CO_2H$, —$CO_2$($C_1$-$C_4$ alkyl), —C(O)$NH_2$, —C(O)NH($C_1$-$C_4$ alkyl), —C(O)N($C_1$-$C_4$ alkyl)$_2$, or optionally substituted $C_1$-$C_4$ alkyl;

—$R^3$ is —H, —F, —Cl, —CN, —$NO_2$, —O($C_1$-$C_4$ alkyl), —$CO_2H$, —$CO_2$($C_{1-4}$ alkyl), —C(O)$NH_2$, —C(O)NH($C_1$-$C_4$ alkyl), —C(O)N($C_1$-$C_4$ alkyl)$_2$, or optionally substituted $C_1$-$C_4$ alkyl;

p and k are each and independently 1 or 2; and $R^t$ and $R^s$ are each independently —H, halogen, or $C_1$-$C_4$ alkyl.

3. The compound of claim 2, wherein;

X is —Cl, —Br, —F, —CN, $C_1$-$C_4$ alkyl, or $C_1$-$C_4$ haloalkyl;

$R^2$ is —H, —O($C_1$-$C_4$ alkyl), $C_1$-$C_4$ alkyl, or $C_1$-$C_4$ haloalkyl; and $R^3$ is —H, —F, —Cl, —CN, —O($C_1$-$C_4$ alkyl), $C_1$-$C_4$ alkyl, or $C_1$-$C_4$ haloalkyl.

4. The compound of claim 3, wherein;

Ring T is an optionally substituted $C_5$-$C_{10}$ non-aromatic carbocyclic group or an optionally substituted 5-10 membered non-aromatic heterocyclic group; and $R^3$ is —F, —Cl, —CN, —O($C_1$-$C_4$ alkyl), $C_1$-$C_4$ alkyl, or $C_1$-$C_4$ haloalkyl.

5. The compound of claim 4, represented by Structural Formula (II):

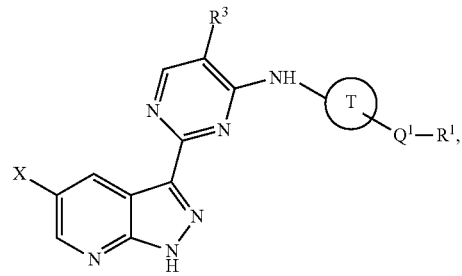

or a pharmaceutically acceptable salt thereof, wherein:

X is —Cl, —F, —Br, —CN, —$CH_3$, or —$CF_3$, $R^3$ is —F, —Cl, —CN, or $C_1$-$C_4$ haloalkyl;

$Q^1$ is —C(O)—, —$CO_2$—, —OC(O)—, —O(CR$^t$R$^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —$NRSO_2$NR'—, —B(O)$_2$—, or —(CR'R$^s$)$_p$—$Y^1$—;

$Y^1$ is —C(O)—, —$CO_2$—, —OC(O)—, —O(CR$^t$R$^s$)$_k$—C(O)O—, —C(O)NR'—, —C(O)N(R')—O—, —C(O)NRC(O)O—, —NRC(O)—, —NRC(O)NR'—, —$NRCO_2$—, —OC(O)NR'—, —$OSO_2$NR'—, —S(O)—, —$SO_2$—, —$SO_2$NR'—, —$NRSO_2$—, —B(O)$_2$—, or —$NRSO_2$NR'—;

$R^1$ is independently i) —H; ii) a $C_1$-$C_6$-aliphatic group optionally substituted with one or more instances of $J^A$; iii) a $C_3$-$C_8$ non-aromatic carbocyclic group or 4-8 membered, non-aromatic, heterocyclic group, each of which is optionally and independently substituted with one or more instances of $J^B$:

iv) a phenyl group or 5-6 membered heteroaryl group, each of which is optionally and independently substituted with one or more instances of $J^C$; or optionally $R^1$, together with R' and the nitrogen to which they are attached, form a 4-8 membered, non-aromatic, heterocyclic group optionally substituted with one or more instances of $J^2$; or optionally -$Q^1$-$R^1$ forms, together with Ring T, a 4-10 membered, non-aromatic, spiro rings optionally substituted with one or more instances of $J^4$; and $J^A$, $J^B$, and $J^T$ are each independently oxo or $J^C$; and $J^C$ is selected from the group consisting of halogen, cyano, $R^a$, —OR$^b$, —SR$^b$, —S(O)R$^a$, —$SO_2$R$^a$, —NHR$^c$, —C(O)R$^a$, —C(O)OR$^b$, —OC(O)R$^b$, —NHC(O)R$^b$, —C(O)NHR$^c$, —NHC(O)NHR$^c$, —NHC(O)OR$^b$, —OCONHR$^c$, —NHC(O)NHC(O)OR$^b$, —N(CH$_3$)R$^c$, —N(CH$_3$)C(O)R$^b$, —C(O)N(CH$_3$)R$^c$, —N(CH$_3$)C(O)NHR$^c$, —N(CH$_3$)C(O)OR$^b$, —OCON(CH$_3$)R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N(CH$_3$)R$^b$, and —N(CH$_3$)SO$_2$R$^b$;

optionally, two $J^A$, two $J^B$, two $J^C$, and two $J^T$, respectively, together with the atom(s) to which they are attached, independently form an optionally substituted. 4-10-membered, non-aromatic ring; and $R^a$ is independently: i) a $C_1$-$C_6$ alkyl group optionally substituted with one or more substituents selected from the group consisting of halogen, cyano, hydroxy, oxo, —NH, —NH($C_1$-$C_4$ alkyl), —N($C_1$-$C_4$ alkyl)$_2$, —OCO($C_1$-$C_4$ alkyl), —CO($C_{1-4}$ alkyl), —$CO_2H$, —$CO_2$($C_1$-$C_4$ alkyl), —O($C_1$-$C_4$ alkyl), optionally substituted, non-aromatic, $C_3$-$C_8$ carbocyclic group, optionally substituted, non-aromatic, 4-8 membered heterocyclic group, optionally substituted 5-6 membered heteroaryl, and optionally substituted phenyl group: ii) an optionally substituted, non-aromatic, $C_3$-$C_8$ carbocyclic group: iii) optionally substituted, non-aromatic, 4-8 membered heterocyclic group: iv) an optionally substituted 5-6 membered heteroaryl group: v) or optionally substituted phenyl group:

$R^b$ and $R^c$ are each independently $R^a$ or —H; or optionally, $R^b$ and $R^c$, together with the nitrogen atom(s) to which they are attached, each independently form an optionally substituted, non-aromatic, 4-8 membered heterocyclic group; and R and R' are each and independently —H or $C_{1-4}$ alkyl, or optionally R and R', together with the nitrogen to which they are attached, form an optionally substituted, non-aromatic, 4-8 membered heterocyclic group, or optionally R', together with $R^1$ and the nitrogen to which they are attached, form an optionally substituted, non-aromatic, 4-8 membered heterocyclic group.

6. The compound of claim 5, wherein:

$Q^1$ is —$CO_2$—, —$O(CR'R^s)_k$—$C(O)O$—, —$P(O)(OR)O$—, —$OP(O)(OR^a)O$—, —$P(O)_2O$—, —$CO_2SO_2$—, or —$(CR'R^s)_p$—$Y^1$—; and $Y^1$ is —$CO_2$—, —$O(CR'R^s)_k$—$C(O)O$—, —$P(O)(OR)O$—, —$OP(O)(OR^a)O$—, —$P(O)_2O$—, or —$CO_2SO_2$—.

7. The compound of claim 6 represented by Structural Formula (IIIA) or (IIIB):

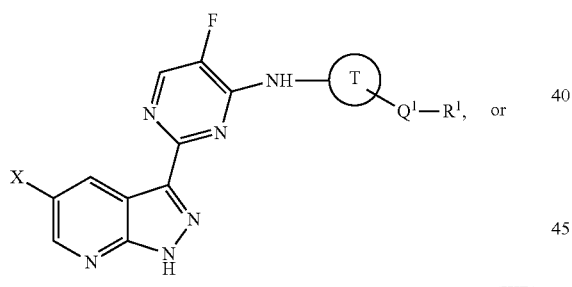

(IIIA)

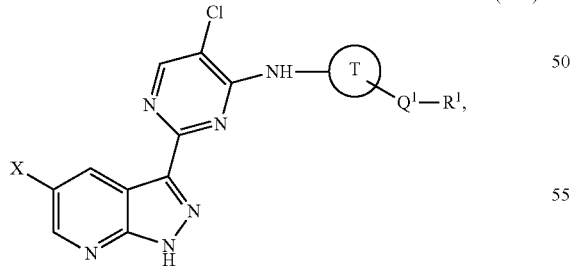

(IIIB)

or a pharmaceutically acceptable salt thereof, wherein X is —Cl, —F, —CN, or —$CF_3$.

8. The compound of claim 7, wherein:

X is —Cl or —F; and

Ring T is an optionally substituted, bridged, non-aromatic, $C_5$-$C_{10}$ carbocyclic group or an optionally substituted, non-aromatic, monocyclic, $C_5$-$C_8$ carbocyclic group.

9. The compound of claim 7, wherein Ring T is:

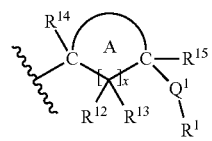

and wherein:

Ring A is a 5-10 membered, non-aromatic, carbocyclic group or 5-10 membered, non-aromatic, heterocyclic group, each of which is optionally further substituted with one or more substituents selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), $C_1$-$C_4$ alkyl, $C_1$-$C_4$ haloalkyl, and —$O(C_1$-$C_4$ alkyl); or Ring A and $R^{15}$, Ring A and $R^{14}$, or Ring A and $R^{13}$ independently and optionally form a bridged, non-aromatic, carbocyclic group or bridged, non-aromatic, heterocyclic group, each of which is optionally and independently substituted with one or more substituents selected from the group consisting of halogen, cyano, hydroxy, oxo, —$NH_2$, $C_4$ alkyl), $C_1$-$C_4$ alkyl, $C_1$-$C_4$ haloalkyl, and —$O(C_1$-$C_4$ alkyl)

$Q^1$ is —$C(O)$—, —$CO_2$—, —$OC(O)$—, —$O(CR^t R^s)_k$—$C(O)O$—, —$C(O)NR'$—, —$C(O)NRC(O)O$—, —$NRC(O)$—, —$NRC(O)NR'$—, —$NRCO_2$—, —$OC(O)NR'$—, or —$(CR'R^s)_p$—$Y^1$—; and $Y^1$ is —$C(O)$—, —$CO_2$—, —$OC(O)$—, —$O(CR^t R^s)_k$—$C(O)O$—, —$C(O)NR'$—, —$C(O)NRC(O)O$—, —$NRC(O)$—, —$NRC(O)NR'$—, —$NRCO_2$—, or —$OC(O)NR'$—, $R^1$ is independently: i) —H; ii) a $C_1$-$C_6$ aliphatic group optionally substituted with one or more substituents independently selected from the group consisting of halogen, cyano, hydroxy, oxo, —$O(C_1$-$C_4$ alkyl), —$NH_2$, —$NH(C_1$-$C_4$ alkyl), —$N(C_1$-$C_4$ alkyl)$_2$, —$C(O)(C_1$-$C_4$ alkyl), —$OC(O)(C_1$-$C_4$ alkyl), —$C(O)O(C_1$-$C_4$ alkyl), —$CO_2H$, $C_3$-$C_8$ non-aromatic carbocyclic group, 4-8 membered, non-aromatic, heterocyclic group, phenyl, and 5-6 membered heteroaryl; iii) a $C_3$-$C_7$ non-aromatic carbocyclic group; iv) a 4-7 membered, non-aromatic, heterocyclic group; v) a phenyl group; or vi) a 5-6 membered heteroaryl group; or optionally $R^1$, together with R' and the nitrogen to which they are attached, forms an optionally substituted, 4-8 membered, non-aromatic, heterocyclic group; and each of said carbocyclic, phenyl, heterocyclic, and heteroaryl groups represented by $R^1$ and for the substituents of the $C_1$-$C_6$-aliphatic group represented by $R^1$, and said heterocyclic group formed with $R^1$ and R' is independently and optionally substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), $C_1$-$C_4$ alkyl, $C_1$-$C_4$ haloalkyl, and —$O(C_1$-$C_4$ alkyl); and each of $R^{12}$, $R^{13}$, and $R^{14}$ is independently —H, halogen, cyano, hydroxy, $C_1$-$C_6$ alkyl, —$O(C_1$-$C_6$alkyl), —$NH_2$, —$NH(C_1$-$C_6$ alkyl), —$N(C_1$-$C_6$ alkyl)$_2$, —$OCO(C_1$-$C_6$ alkyl), —$CO(C_1$-$C_6$ alkyl), —$CO_2H$, or —$CO_2(C_1$-$C_6$ alkyl), wherein each said $C_1$-$C_6$ alkyl is optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

each R$^{15}$ is independently —H, halogen, cyano, hydroxy, or C$_1$-C$_6$ alkyl optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

x is 0, 1 or 2,

J$^A$, J$^B$, J$^C$, and J$^T$ are each independently selected from the group consisting of halogen, cyano, R$^a$, —OR$^b$, —NHR$^c$, —C(O)R$^b$, —C(O)OR$^b$, —OC(O)R$^b$, —NHC(O)R$^b$, —C(O)NHR$^c$, —NHC(O)NHR$^c$, —NHC(O)OR$^b$, —OCONHR$^c$, —N(CH$_3$)R$^c$, —N(CH$_3$)C(O)R$^b$, —C(O)N(CH$_3$)R$^c$, —N(CH$_3$)C(O)NHR$^c$, —N(CH$_3$)C(O)OR$^b$, —NHSO$_2$R$^b$, —SO—NHR$^b$, —SO$_2$N(CH$_3$)R$^b$, and —N(CH$_3$)SO$_2$R$^b$; or optionally, two J$^T$, two J$^A$, two J$^B$, and two J$^C$, respectively, together with the atom(s) to which they are attached, independently form a 4-10-membered, non-aromatic, ring that is optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl); and R$^a$ is independently: i) a C$_1$-C$_6$ alkyl group optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), —O(C$_1$-C$_4$ alkyl), C$_3$-C$_8$ non-aromatic carbocycle, 4-8 membered, non-aromatic, heterocycle, 5-6 membered, non-aromatic, heteroaryl, and phenyl; ii) a C$_3$-C$_8$ carbocyclic group or 4-8 membered heterocyclic group, each of which is independently and optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO(C$_1$-C$_4$ alkyl), C$_1$-C$_4$ alkyl, C$_1$-C$_4$ haloalkyl, and —O(C$_1$-C$_4$ alkyl); or iii) a 5-6 membered heteroaryl group or phenyl group, each of which is independently and optionally substituted with one or more substituents selected from the group consisting of halogen, cyano, hydroxy, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl and —O(C$_1$-C$_4$ alkyl); and R$^b$ and R$^c$ are each independently R$^a$ or —H; or optionally, R$^b$ and R$^c$, together with the nitrogen atom(s) to which they are attached, each independently form a 4-8 membered, non-aromatic, heterocyclic group optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

10. The compound of claim 9, wherein:
(a) R$^{12}$, R$^{13}$, and R$^{14}$ are each and independently —H, halogen, cyano, hydroxy, —O(C$_1$-C$_6$ alkyl), or optionally substituted C$_1$-C$_6$ alkyl;
R$^{15}$ is —H or optionally substituted C$_1$-C$_6$ alkyl; and
R$^t$ and R$^s$ are each independently —H, halogen, C$_1$-C$_6$ alkyl, or C$_1$-C$_6$ haloalkyl; or
(b) R$^{12}$ and R$^{13}$ are each independently —H, halogen, hydroxy, C$_1$-C$_6$ alkyl, C$_1$-C$_6$ haloalkyl, or —O(C$_1$-C$_6$ alkyl);
R$^{14}$ and R$^{15}$ are each independently —H, C$_1$-C$_6$ alkyl, or C$_1$-C$_6$ haloalkyl; and
R$^t$ and R$^s$ are each independently —H or C$_1$-C$_6$ alkyl.

11. The compound of claim 10, wherein
Ring A and R$^{15}$, Ring A and R$^{14}$, or Ring A and R$^{13}$ independently form an optionally substituted, 4-10 membered, non-aromatic, carbocyclic or heterocyclic, bridged ring.

12. The compound of claim 11, wherein Ring T is:

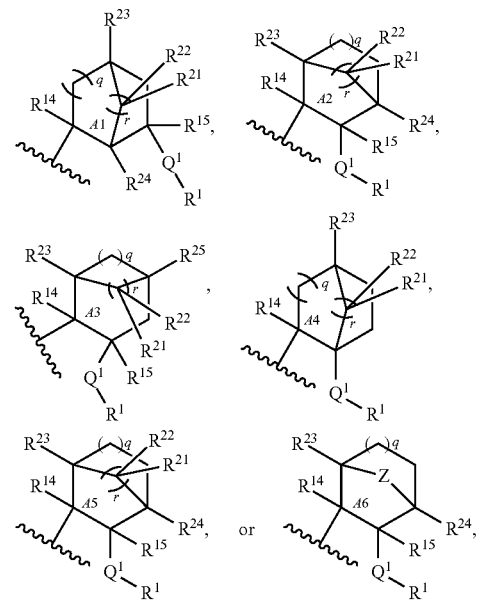

wherein:
each of Rings A1-A5 is independently a 5-10 membered, non-aromatic, bridged carbocycle optionally further substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl);
Ring A6 is a 5-10 membered, non-aromatic, bridged heterocycle optionally further substituted with one or more substituents selected from the group consisting of halogen, cyano, hydroxy, oxo, —NH$_2$, —NH(C$_1$-C$_4$ alkyl), —N(C$_1$-C$_4$ alkyl), —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl);
Q$^1$ is independently —C(O)—, —C(O)O—, —NRC(O)—, —C(O)NR—, —NRC(O)NR'—, or —(CH$_2$)$_{1,2}$—Y$^1$—:
Y$^1$ is independently —C(O)—, —C(O)O—, —NRC(O)—, —C(O)NR—, or —NRC(O)NR'—;

each $R^{14}$ is independently —H, halogen, cyano, hydroxy, $C_1$-$C_6$ alkyl, —O($C_1$-$C_6$ alkyl), —NH$_2$, —NH($C_1$-$C_6$ alkyl), —N($C_1$-$C_6$ alkyl), —OCO($C_1$-$C_6$ alkyl), —CO($C_1$-$C_6$ alkyl), —CO$_2$H, or —CO$_2$ ($C_1$-$C_6$ alkyl), wherein each said $C_1$-$C_6$ alkyl is optionally and independently substituted with one or more substituents selected from the group consisting of halogen, cyano, hydroxy, oxo, —NH$_2$, —NH($C_1$-$C_4$ alkyl), —N($C_1$-$C_4$ alkyl), —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl);

each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —NH$_2$, —NH($C_1$-$C_4$ alkyl), —N($C_1$-$C_4$ alkyl), —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl);

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl);

Z is —O—, —S—, or —NR$^g$—;

$R^g$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl);

q is 0, 1 or 2; and r is 1 or 2.

13. The compound of claim 12, wherein:

$Q^1$ is independently —C(O)O—, —NRC(O)—, —C(O)NR—, or —NRC(O)NR'—;

$R^{14}$ and each $R^{15}$ are each independently —H, $C_1$-$C_6$ alkyl, or $C_1$-$C_6$ haloalkyl; and $R^{21}$, $R^{22}$, $R^{23}$, $R^{24}$, and $R^{25}$ are each independently —H, halogen, hydroxy, $C_1$-$C_6$ alkoxy, $C_1$-$C_6$ alkyl, or $C_1$-$C_6$ haloalkyl;

Z is —O— or —NR$^g$—;

$R^g$ is —H, $C_1$-$C_6$ alkyl, or $C_1$-$C_6$ haloalkyl; and

R and R' are each and independently —H or —CH$_3$.

14. The compound of claim 13, wherein Ring T is:

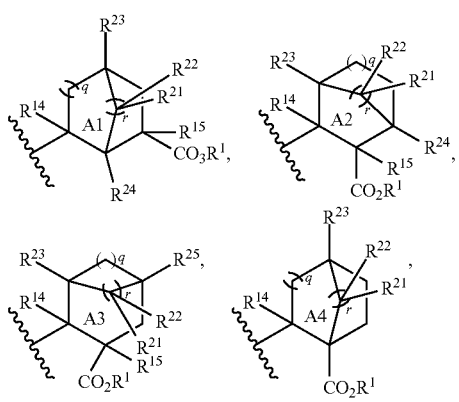

-continued

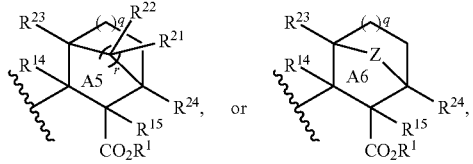

wherein each of Rings A1-A6 is independently and optionally further substituted with one or more substituents selected from the group consisting of halogen, cyano, hydroxy, $C_1$-$C_4$ alkyl, $C_1$-$C_4$ haloalkyl, and —O($C_1$-$C_4$ alkyl), $R^{14}$ and each $R^{15}$ are each independently —H or $C_{1-6}$ alkyl;

$R^{21}$, $R^{22}$, $R^{23}$, $R^{24}$, and $R^{25}$ are each independently —H or $C_{1-6}$ alkyl; and q is 1.

15. The compound of claim 14, wherein:

$R^{14}$, $R^{15}$, $R^{21}$, $R^{22}$, $R^{23}$, $R^{24}$, and $R^{25}$ are each independently —H.

16. The compound of claim 9, wherein Ring T is selected from:

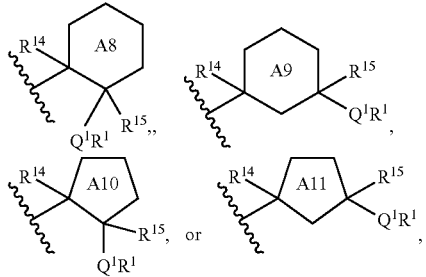

wherein:

$Q^1$ is independently —C(O)—, —C(O)O—, —NRC(O)—, —C(O)NR—, —NRC(O)NR'—, or —(CH$_2$)$_{1,2}$—Y—;

$Y^1$ is independently —C(O)—, —C(O)O—, —NRC(O)—, —C(O)NR—, or —NRC(O)NR'—;

each of Rings A8-A11 is independently and optionally substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkyl, $C_1$-$C_4$ haloalkyl, and —O($C_1$-$C_4$ alkyl);

each $R^{14}$ is independently —H, halogen, cyano, hydroxy, $C_1$-$C_6$ alkyl, —O($C_1$-$C_6$ alkyl), —NH$_2$, —NH($C_1$-$C_6$ alkyl)$_2$, —N($C_1$-$C_6$ alkyl), —OCO($C_1$-$C_6$ alkyl), —CO($C_1$-$C_6$ alkyl), —CO$_2$H, or —CO$_2$ ($C_1$-$C_6$ alkyl), wherein each said $C_1$-$C_6$ alkyl is optionally and independently substituted with one or more substituents selected from the group consisting of halogen, cyano, hydroxy, oxo, —NH$_2$, —NH($C_1$-$C_4$ alkyl)$_2$, —N($C_1$-$C_4$ alkyl), —OCO($C_1$-$C_4$ alkyl), —CO($C_1$-$C_4$ alkyl), —CO$_2$H, —CO$_2$($C_1$-$C_4$ alkyl), and —O($C_1$-$C_4$ alkyl);

each $R^{15}$ is independently —H, halogen, cyano, hydroxy, or $C_1$-$C_6$ alkyl optionally and independently substituted with one or more substituents selected from the group consisting of halogen, cyano, hydroxy, oxo, —NH$_2$, —NH($C_1$-$C_4$ alkyl), —N($C_1$-$C_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and —O(C$_1$-C$_4$ alkyl);

R and R' are each and independently —H or —CH$_3$; and

R$^1$ is independently a 4-7 membered, non-aromatic, heterocyclic group, a phenyl group, or a 5-6 membered heteroaryl group, wherein each of said heterocyclic, phenyl and heteroaryl groups is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl); or optionally R$^1$ and R', together with the nitrogen atom to which they are attached, form a 4-7 membered, non-aromatic, heterocyclic group or a 5-6 membered heteroaryl group, each of which is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkyl, C$_1$-C$_4$ haloalkyl, and —O(C$_1$-C$_4$ alkyl).

17. The compound of claim 16, wherein:

Q$^1$ is independently —NRC(O)—, —C(O)NR—, or —NRC(O)NR'—;

R$^{14}$ and each R$^{15}$ are each independently —H or C$_{1-6}$alkyl; and each of Rings A8-A11 is independently and optionally substituted with one or more substitutents selected from the group consisting of halogen, cyano, hydroxy, C$_1$-C$_4$ alkyl, C$_1$-C$_4$ haloalkyl, and —O(C$_1$-C$_4$ alkyl).

18. A compound selected from any of one of the structures depicted below:

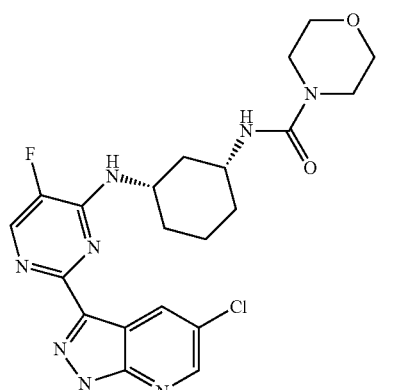

,

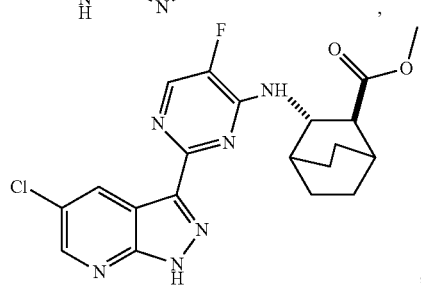

,

-continued

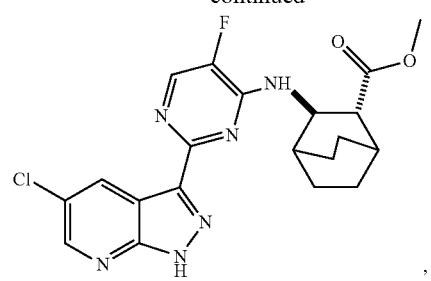

,

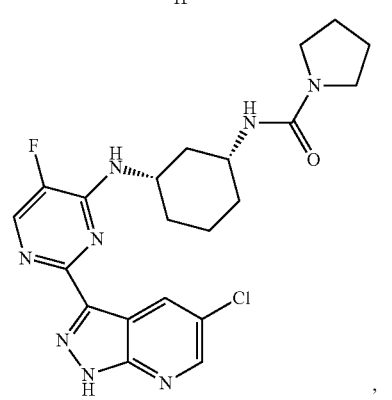

,

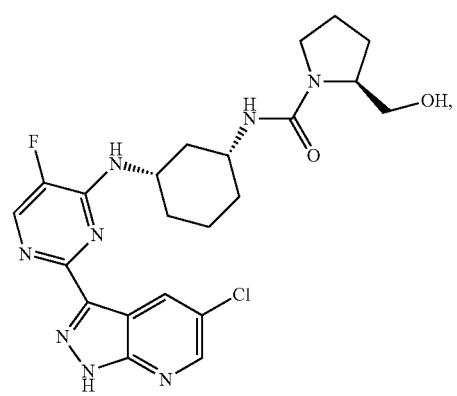

,

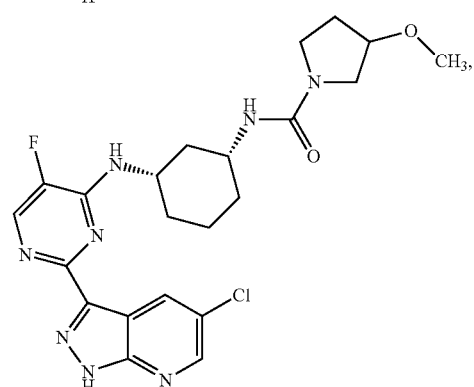

,

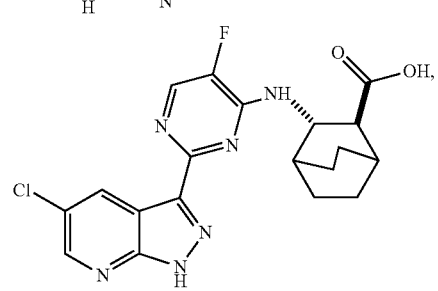

,

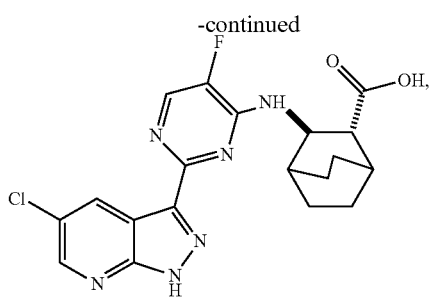
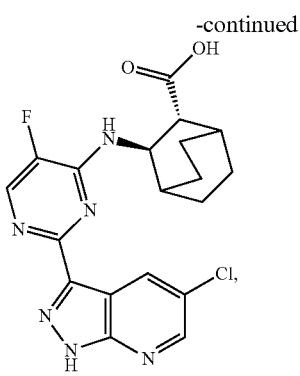
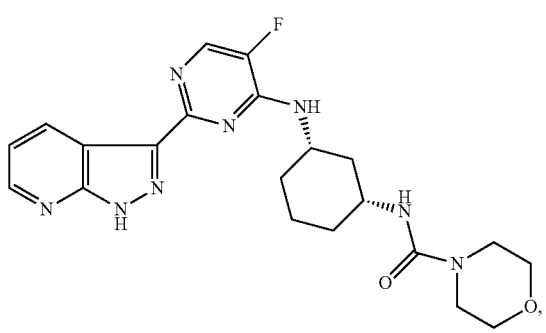 [SMILES: O=C(N[C@@H]1CCC[C@H](Nc2nc(-c3n[nH]c4ncccc34)ncc2F)C1)N1CCOCC1]
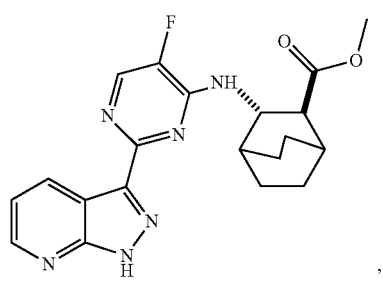
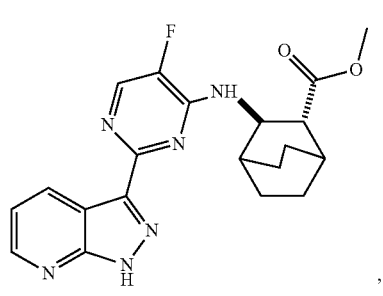
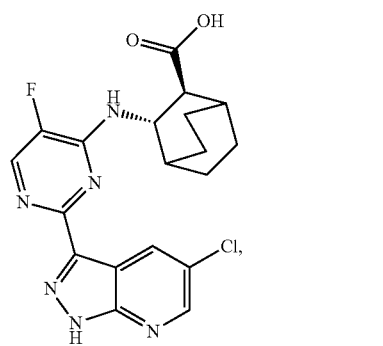

177
-continued
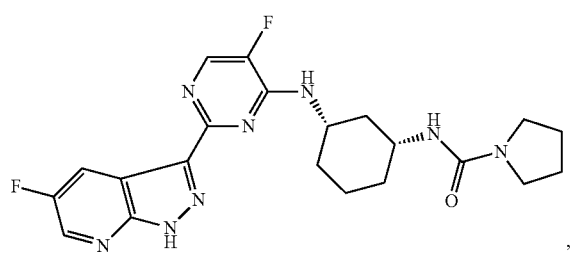
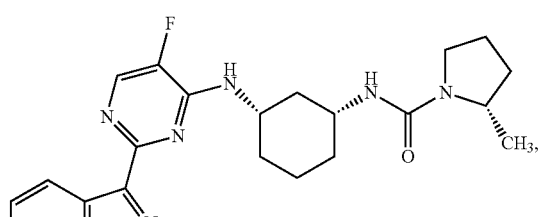
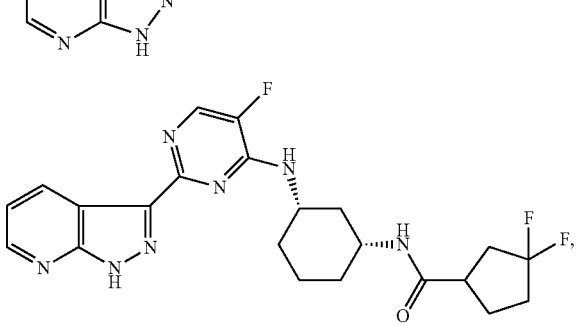
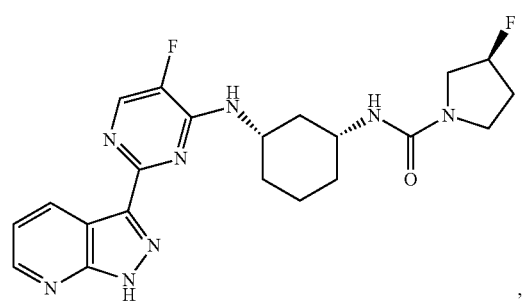
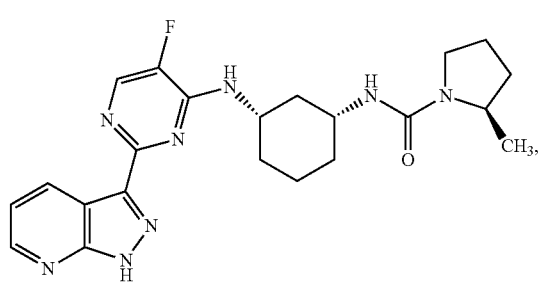
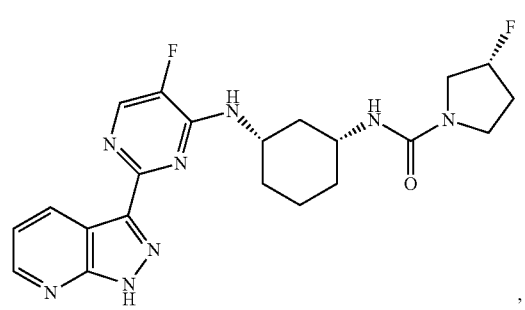
178
-continued
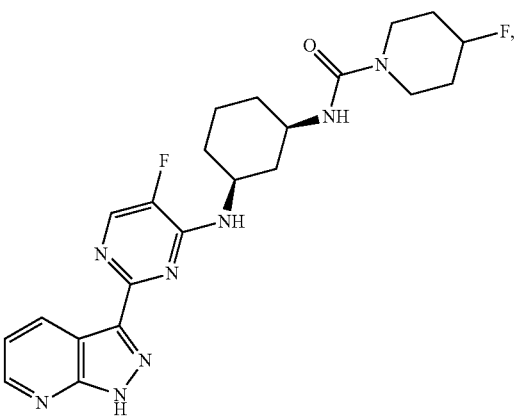 [SMILES: O=C(N[C@@H]1CCC[C@H](Nc2nc(-c3n[nH]c4ncccc34)ncc2F)C1)N1CCC(F)CC1]
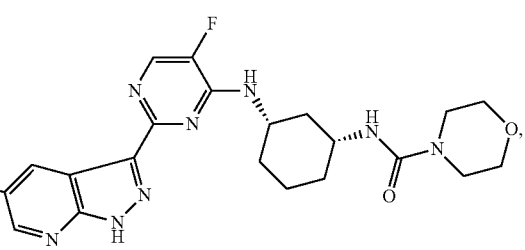
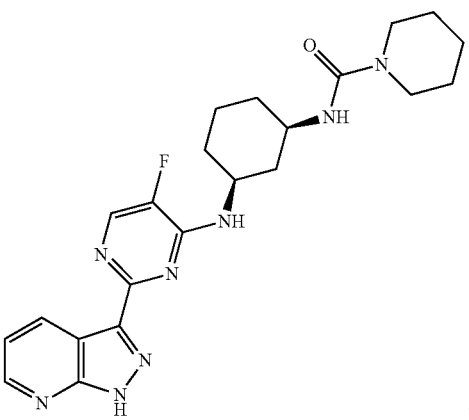 [SMILES: O=C(N[C@@H]1CCC[C@H](Nc2nc(-c3n[nH]c4ncccc34)ncc2F)C1)N1CCCCC1]
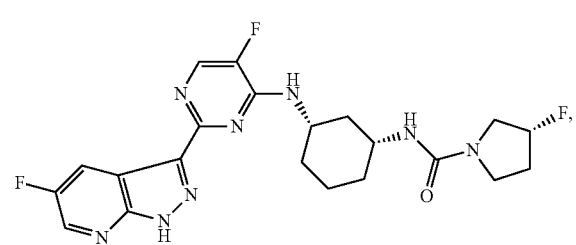

179
-continued
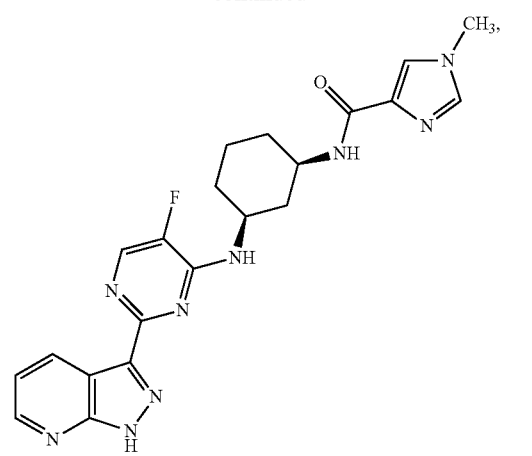 [SMILES: Cn1cnc(C(=O)N[C@@H]2CCC[C@H](Nc3nc(-c4n[nH]c5ncccc45)ncc3F)C2)c1]
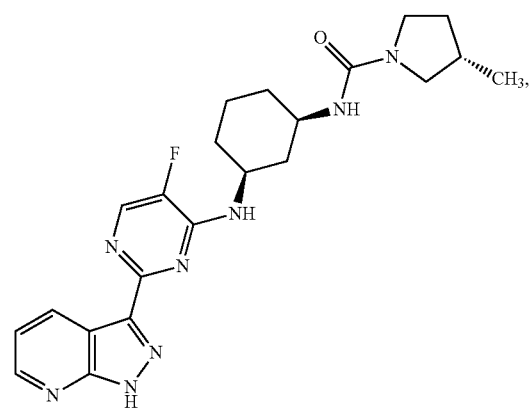 [SMILES: C[C@H]1CCN(C(=O)N[C@@H]2CCC[C@H](Nc3nc(-c4n[nH]c5ncccc45)ncc3F)C2)C1]
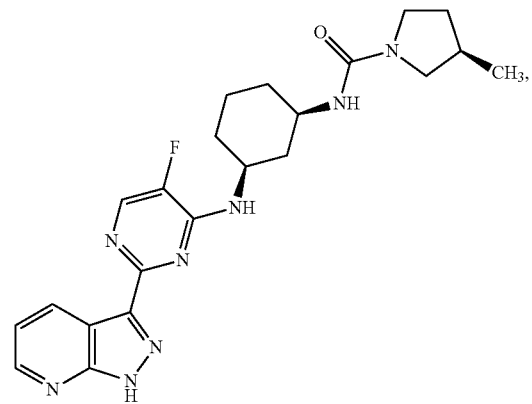 [SMILES: C[C@@H]1CCN(C(=O)N[C@@H]2CCC[C@H](Nc3nc(-c4n[nH]c5ncccc45)ncc3F)C2)C1]
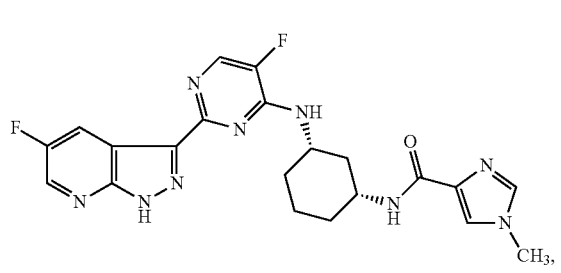
180
-continued
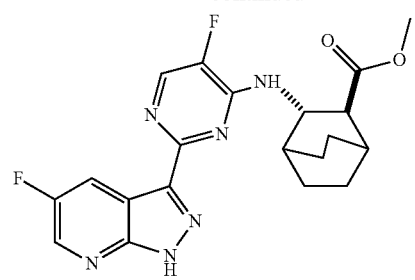
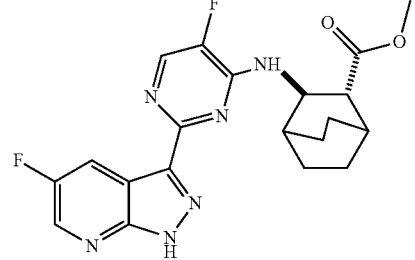
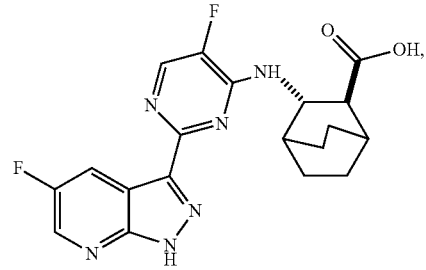
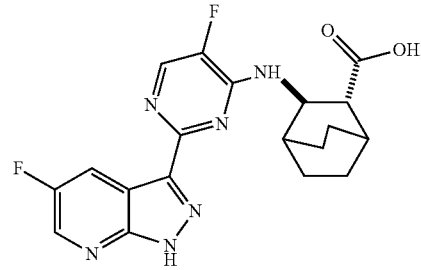
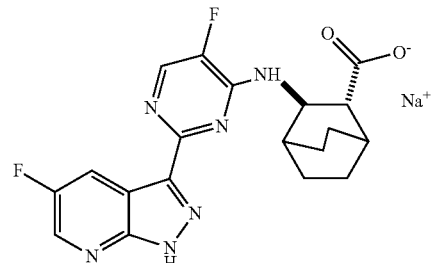
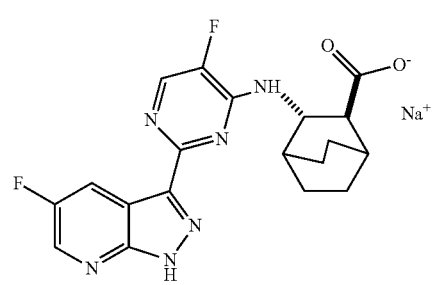

-continued
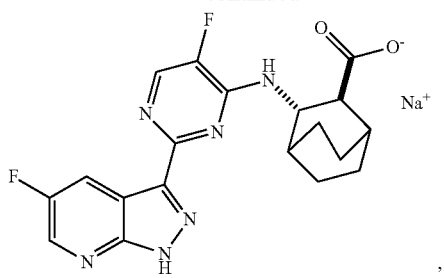
,
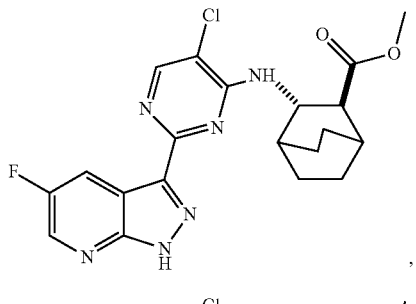
,
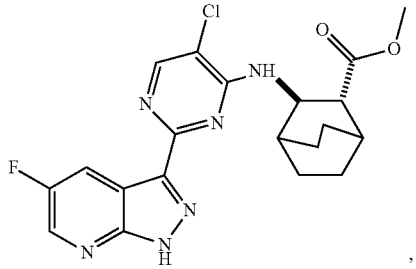
,
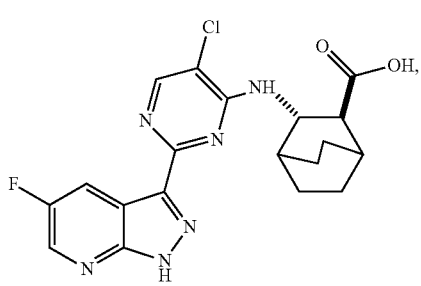
,
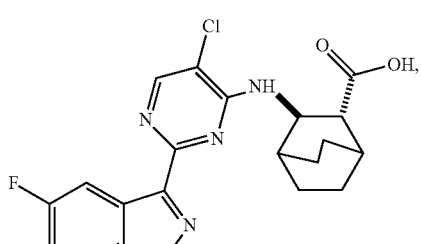
,
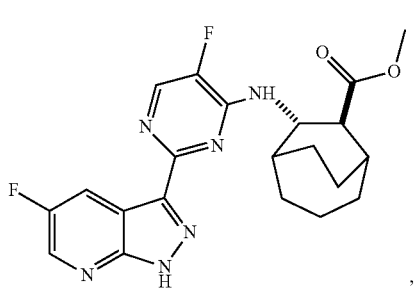
,
-continued
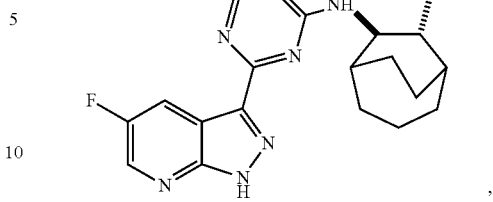
,
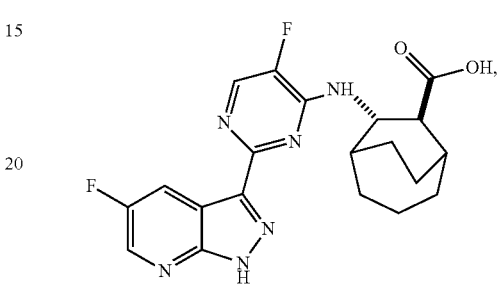
,
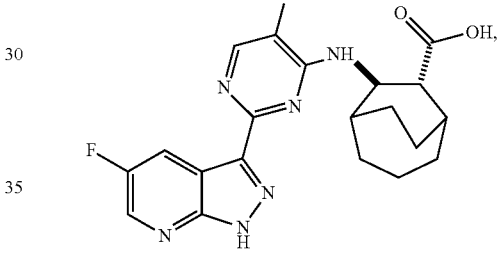
,
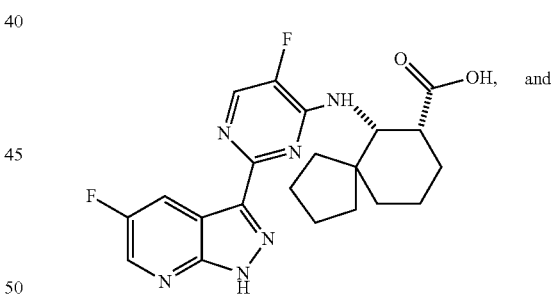
and
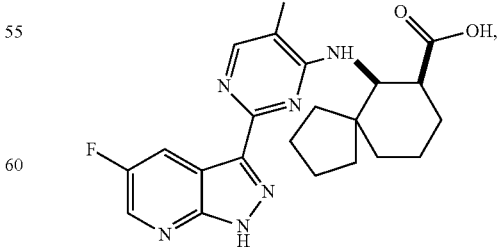
or pharmaceutically acceptable salt thereof.

19. A compound selected from any of one of the structures depicted below:

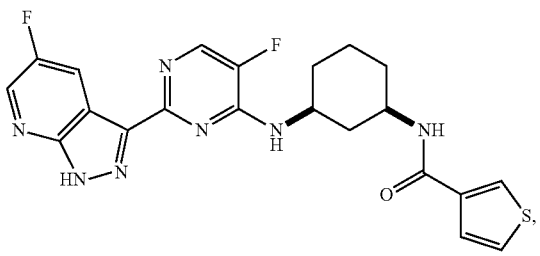
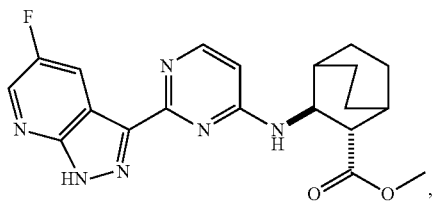
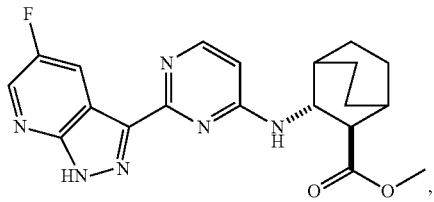
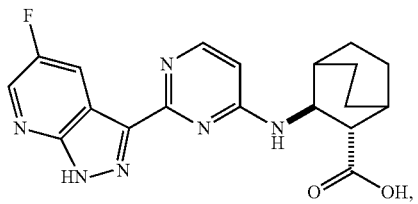
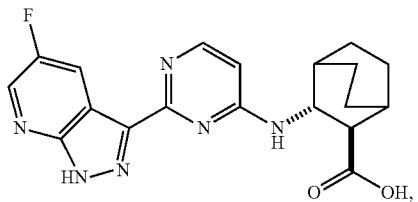
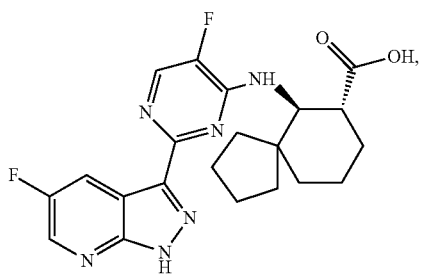
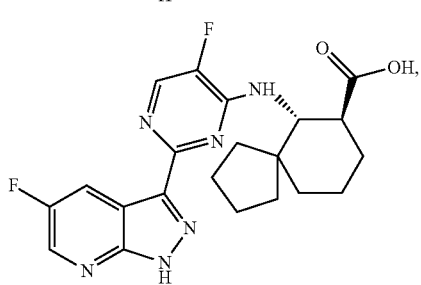

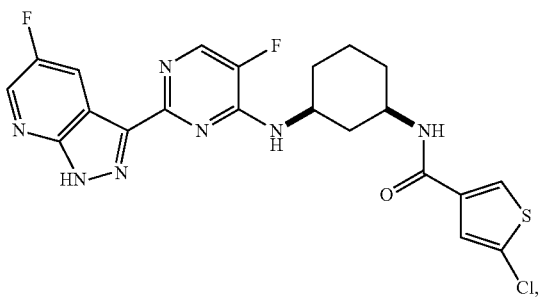

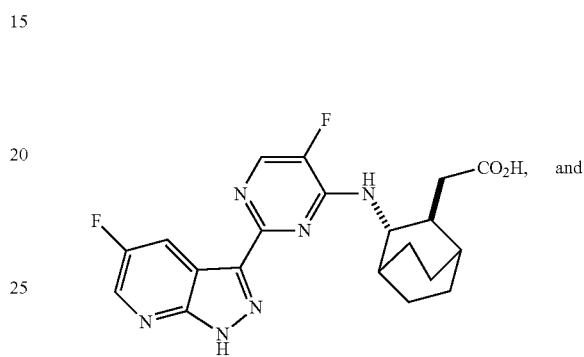

and

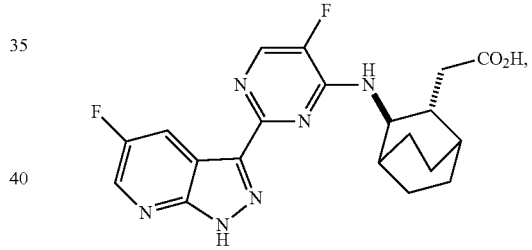

or a pharmaceutically acceptable salt thereof.

20. A pharmaceutical composition, comprising a compound according to any one of claims 1, 2, 3, 4, 5, 6, 7, 8, 9, 10, 11, 12, 13, 14, 15, 16, 17, 18, and 19, and a pharmaceutically acceptable carrier, adjuvant or vehicle.

21. A method of inhibiting the replication of influenza viruses in a biological sample or patient, comprising the step of administering to said biological sample or patient an effective amount of a compound as described in any one of claims 1, 2, 3, 4, 5, 6, 7, 8, 9, 10, 11, 12, 13, 14, 15, 16, 17, 18, and 19.

22. A method of reducing the amount of influenza viruses in a biological sample or in a patient, comprising administering to said biological sample or patient an effective amount of a compound as described in any one of claims 1, 2, 3, 4, 5, 6, 7, 8, 9, 10, 11, 12, 13, 14, 15, 16, 17, 18, and 19.

23. A method of treating influenza in a patient, comprising administering to said patient an effective amount of a compound described in any one of claims 1, 2, 3, 4, 5, 6, 7, 8, 9, 10, 11, 12, 13, 14, 15, 16, 17, 18, and 19.

24. A method preparing a compound represented by Structural Formula (I):

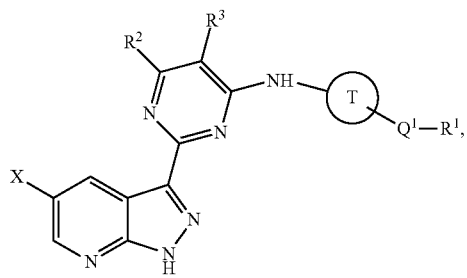

or a pharmaceutically acceptable salt thereof, comprising the steps of:

i) reacting compound A:

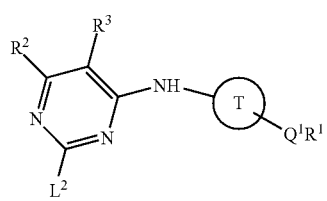

with compound B:

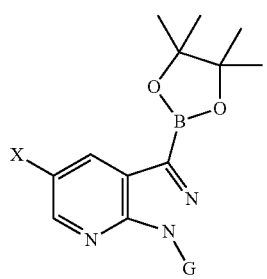

to form a compound represented by Structural Formula (XX):

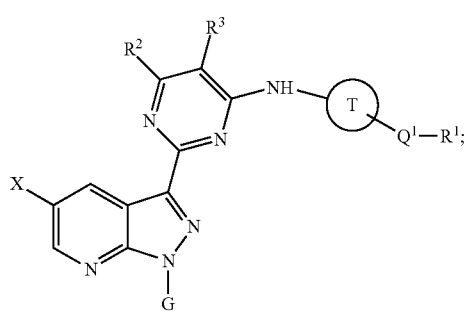

and ii) deprotecting the G group of the compound of Structural Formula (XX) under suitable conditions to form the compound of Structural Formula (I), wherein:

the variables of Structural Formulae (I) and (XX), and compounds (A) and (B) are independently as defined in any one of claims 1, 2, 3, 4, 5, 6, 7, 8, 9, 10, 11, 12, 13, 14, 15, 16, 17, 18, and 19; and $L^2$ is a halogen; and G is trityl.

25. A method preparing a compound represented by Structural Formula (I):

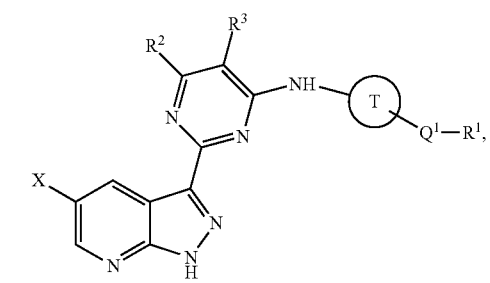

or a pharmaceutically acceptable salt thereof, comprising the steps of:

i) reacting compound K or L:

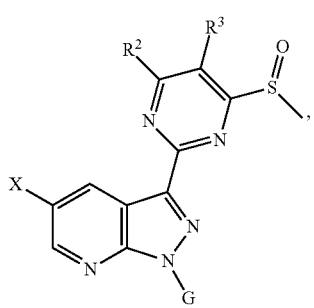

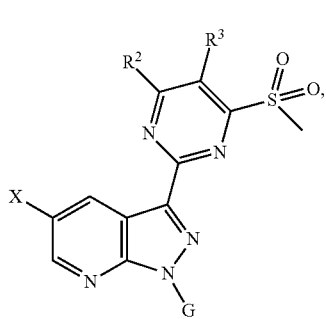

with compound D:

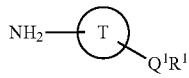

to form a compound represented by Structural Formula (XX):

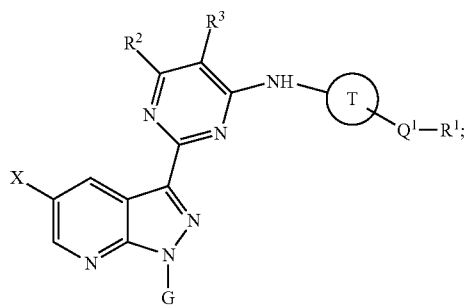
(XX)

and ii) deprotecting the G group of the compound of Structural Formula (XX) under suitable conditions to form the compound of Structural Formula (I), wherein:

the variables of Structural Formulae (I) and (XX), and compounds (L), (K), and (D) are each and independently as defined in any one of claims 1, 2, 3, 4, 5, 6, 7, 8, 9, 10, 11, 12, 13, 14, 15, 16, 17, 18, and 19; and G is trityl.

26. A method preparing a compound represented by Structural Formula (I):

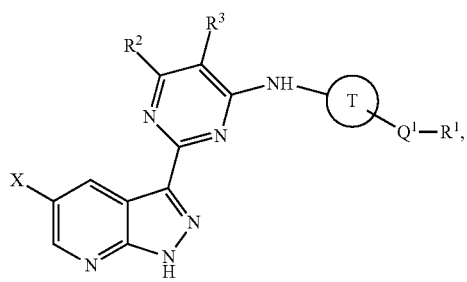

or a pharmaceutically acceptable salt thereof, comprising the steps of:

i) reacting Compound (G) with Compound (D):

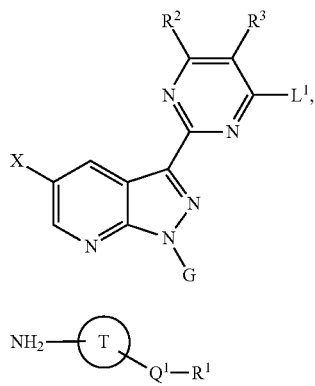
(G)

(D)

under suitable conditions to form a compound represented by Structural Formula (XX):

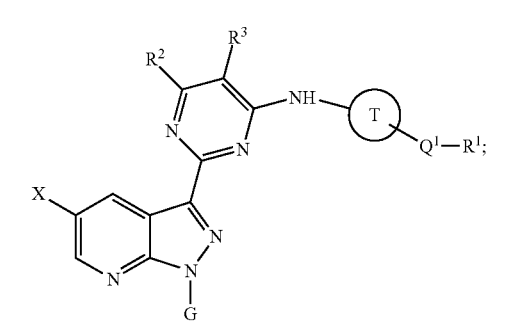
(XX)

and ii) deprotecting the G group of the compound of Structural Formula (XX) under suitable conditions to form the compound of Structural Formula (I), wherein:

the variables of Structural Formulae (I) and (XX), and Compounds (G) and (D) are each and independently as defined in any one of claims 1, 2, 3, 4, 5, 6, 7, 8, 9, 10, 11, 12, 13, 14, 15, 16, 17, 18, and 19;

$L^1$ is a halogen; and

G is trityl.

27. A compound represented by Structural Formula (XX):

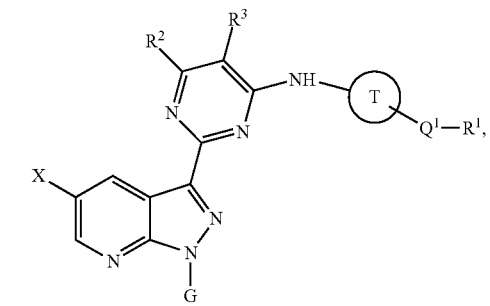

wherein the variables of Structural Formula (XX) are each and independently as defined in any one of claims 1, 2, 3, 4, 5, 6, 7, 8, 9, 10, 11, 12, 13, 14, 15, 16, 17, 18, and 19; and G is trityl.

28. The compound of claim 27, represented by any one of the following structural formulae:

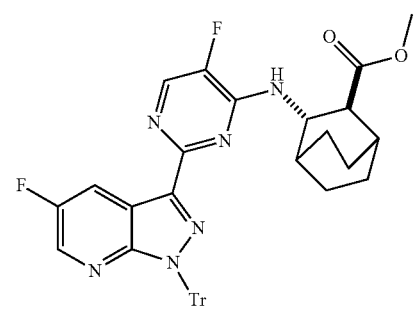

189
-continued
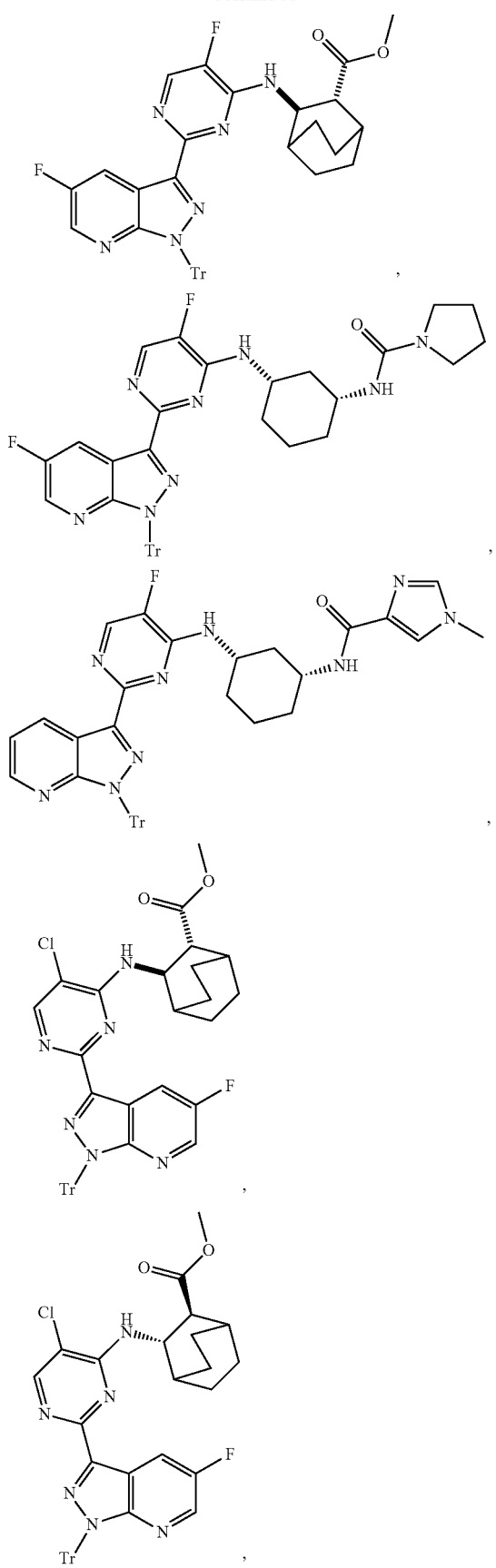
190
-continued
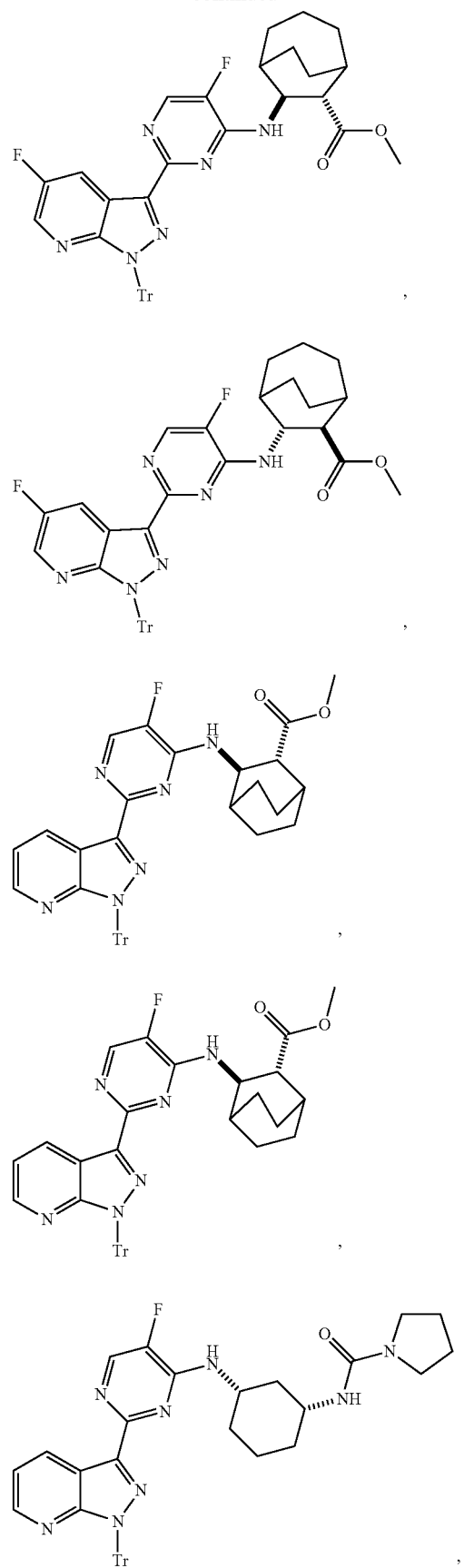

191
-continued
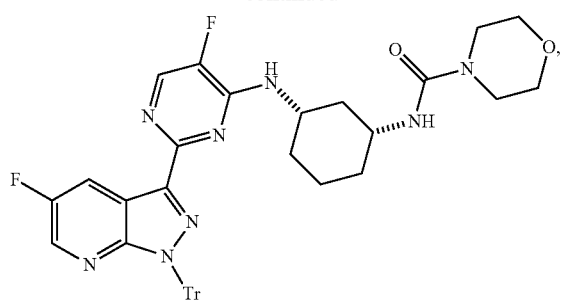
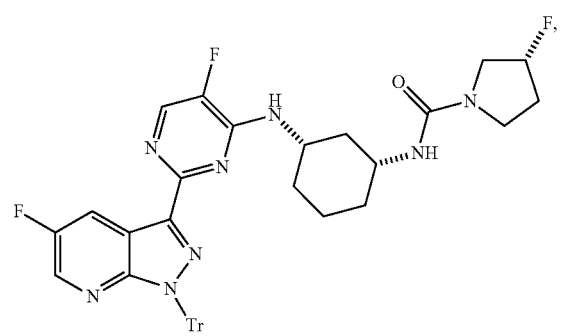
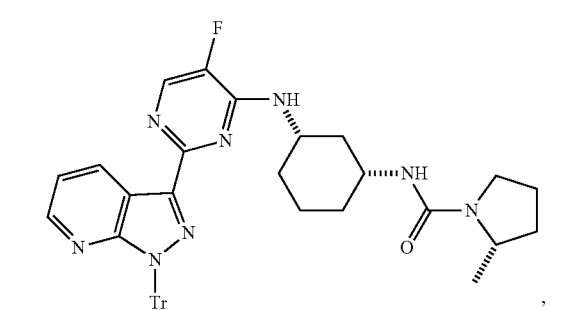
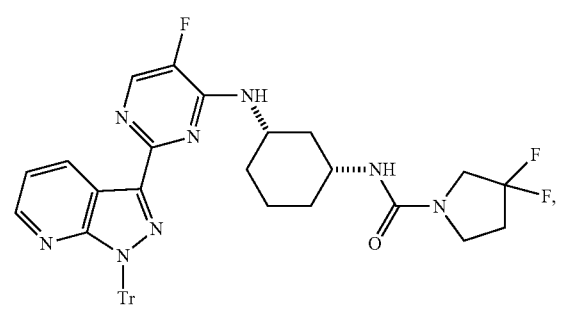
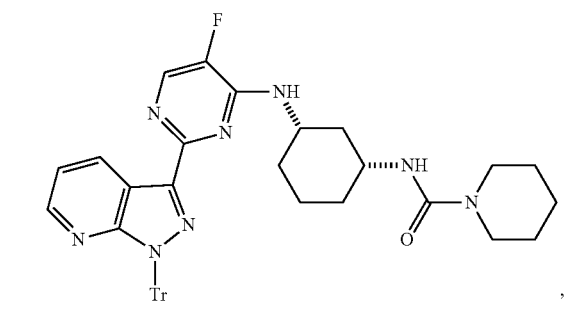
192
-continued
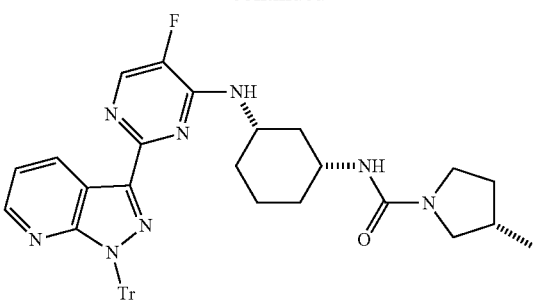
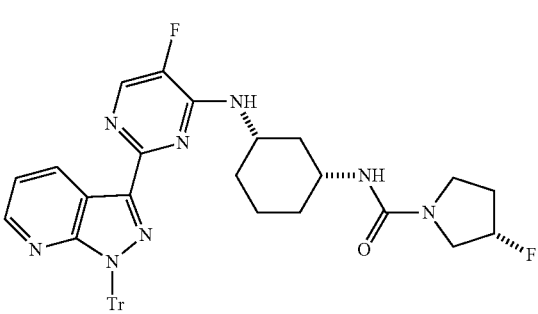
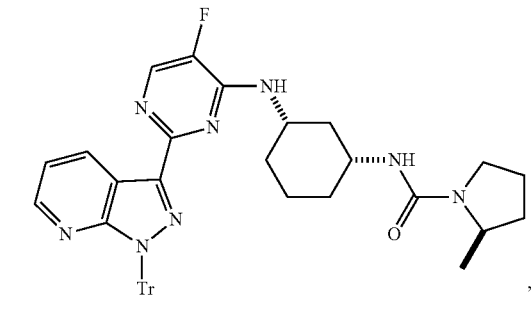
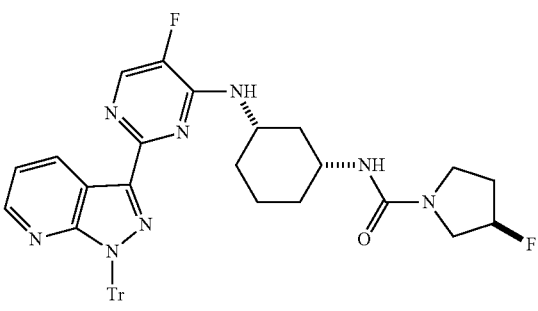
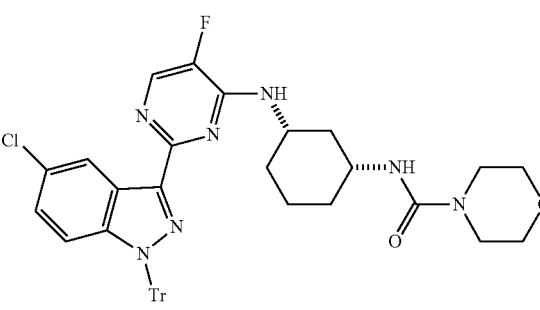

-continued
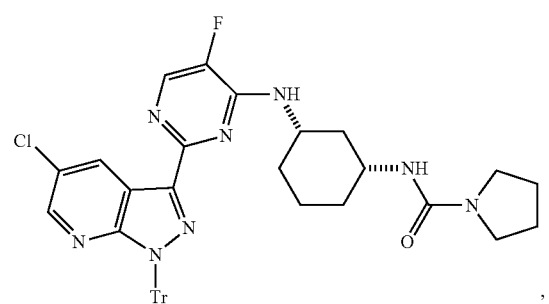
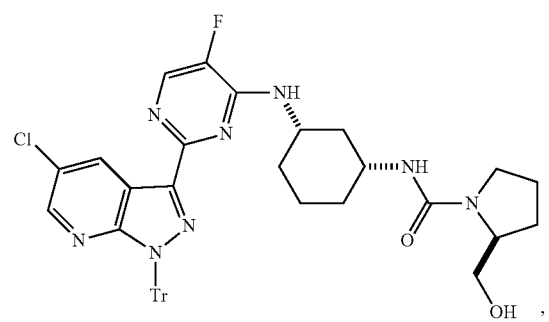
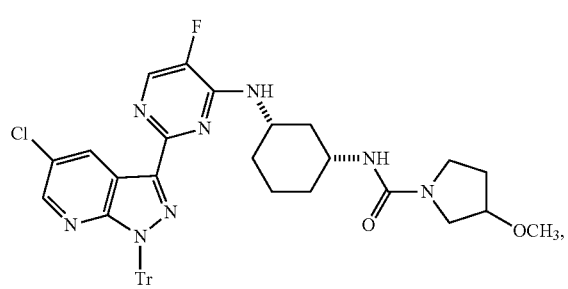
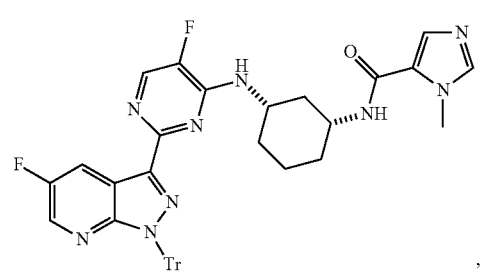
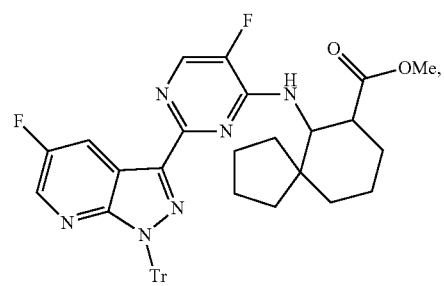
or a pharmaceutically acceptable salt thereof, wherein Tr is trityl.
29. The compound of claim 27, represented by any one of the following structural formulae:
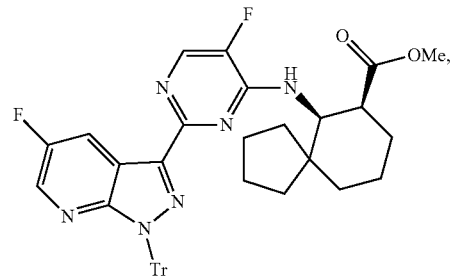
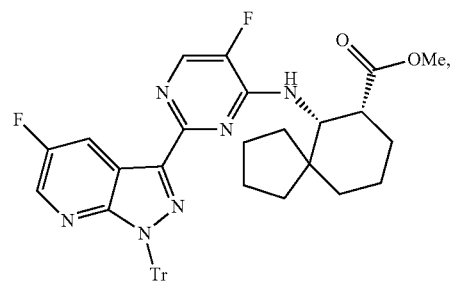
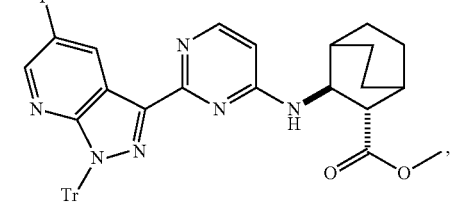
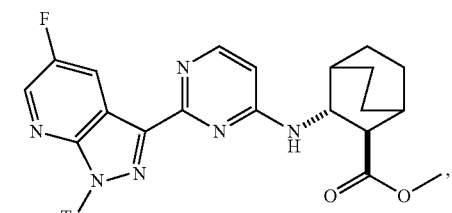
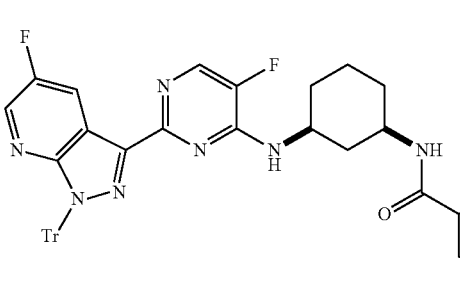

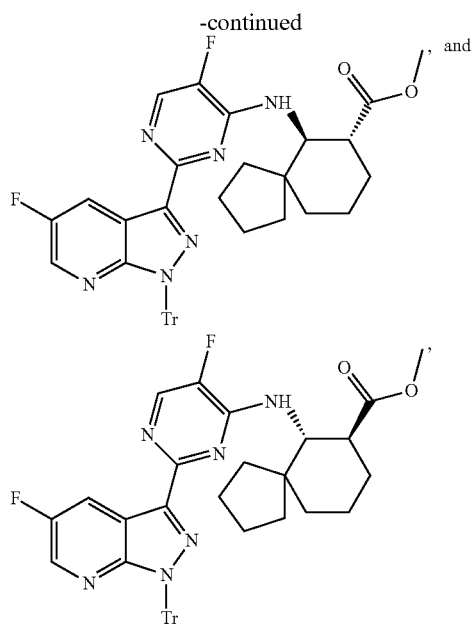
or a pharmaceutically acceptable salt thereof, wherein Tr is trityl.
* * * * *